(12) United States Patent
Widdison

(10) Patent No.: US 10,494,423 B2
(45) Date of Patent: Dec. 3, 2019

(54) MAYTANSINOID DERIVATIVES WITH PEPTIDE LINKER AND CONJUGATES THEREOF

(71) Applicant: ImmunoGen, Inc., Waltham, MA (US)

(72) Inventor: Wayne C. Widdison, Belmont, MA (US)

(73) Assignee: IMMUNOGEN, INC., Waltham, MA (US)

( * ) Notice: Subject to any disclaimer, the term of this patent is extended or adjusted under 35 U.S.C. 154(b) by 0 days.

(21) Appl. No.: 15/019,460

(22) Filed: Feb. 9, 2016

(65) Prior Publication Data

US 2016/0263238 A1 Sep. 15, 2016

Related U.S. Application Data

(63) Continuation of application No. 13/529,349, filed on Jun. 21, 2012, now Pat. No. 9,289,512.

(60) Provisional application No. 61/499,548, filed on Jun. 21, 2011.

(51) Int. Cl.
| | | |
|---|---|---|
| A61K 47/64 | (2017.01) | |
| C07K 16/18 | (2006.01) | |
| C07D 207/416 | (2006.01) | |
| C07K 5/062 | (2006.01) | |
| C07K 16/28 | (2006.01) | |
| A61K 39/00 | (2006.01) | |

(52) U.S. Cl.
CPC .......... *C07K 16/18* (2013.01); *C07D 207/416* (2013.01); *C07K 5/06026* (2013.01); *C07K 5/06052* (2013.01); *C07K 16/2863* (2013.01); *A61K 39/0011* (2013.01); *A61K 2039/505* (2013.01); *C07K 2317/21* (2013.01)

(58) Field of Classification Search
None
See application file for complete search history.

(56) References Cited

U.S. PATENT DOCUMENTS

| | | | |
|---|---|---|---|
| 4,894,348 A | 1/1990 | Ronald et al. | |
| 5,171,666 A | 12/1992 | Gutowski et al. | |
| 5,208,020 A | 5/1993 | Chari et al. | |
| 5,208,324 A * | 5/1993 | Klaveness | A61K 49/085 424/9.35 |
| 9,289,512 B2 | 3/2016 | Widdison | |
| 2003/0134989 A1* | 7/2003 | Aldrich | C07C 213/08 525/333.3 |
| 2008/0175792 A1 | 7/2008 | Lanza et al. | |
| 2008/0226659 A1 | 9/2008 | Erickson et al. | |
| 2013/0011419 A1 | 1/2013 | Chari et al. | |

FOREIGN PATENT DOCUMENTS

| | | | |
|---|---|---|---|
| EP | 0425235 A2 | 5/1991 | |
| EP | 0624377 A2 | 11/1994 | |
| WO | 2001-024763 A2 | 4/2001 | |
| WO | 2003/043583 A2 | 5/2003 | |
| WO | 2005/037992 A2 | 4/2005 | |
| WO | 2005-081711 A2 | 9/2005 | |
| WO | 2005-101017 A1 | 10/2005 | |
| WO | 2006-113623 A2 | 10/2006 | |
| WO | 2009-012256 A1 | 1/2009 | |
| WO | 2010/141566 A1 | 12/2010 | |

OTHER PUBLICATIONS

Doronina, Svetlana O. et al, "Development of potent monoclonal antibody auristatin conjugates for cancer therapy." Nat. Biotech. (2003) 21(7) p. 778-785.*
Choe, Yun H. et al, "Peg prodrugs of 6-mercaptopurine for parenteral administration using benzyl elimination of thiols." Onc. Res. (2004) 14 p. 455-468.*
Dervan, Peter B. et al, "Programmable dna binding oligomers for control of transcription." Curr. Med. Chem. Anti-Cancer Agents (2005) 5 p. 373-387.*
Schmidt, Aaron G. et al, "Peptide inhibitors of dengue-virus entry target a late stated fusion intermediate." PLoS Pathol (2010) 6(4) e1000851.*
Haughland, Richard P., "Handbook of fluorescent probes and research products" (2002) ISBN 0-9710636-0-5.*
Austin, Cary D. et al, "Oxidizing potential of endosomes and lysosomes limits intracellular cleavage of disulfide based antibody drug conjugates." PNAS (2005) 102(50) p. 17987-17992.*
Kellogg, Brenda A. et al, "Disulfide linked antibody maytansinoid conjugates: optimization of in vivo activity by varying the steric hindrance at carbon atoms adjacent to the disulfide linkage." Bioconj. Chem. (2011) 22 p. 717-727.*
Doronina et al., "Novel Peptide Linkers for Highly Potent Antibody—Auristatin Conjugate," Bioconjugate. Chem., 19:1960-1963 (2008).
Ducry and Stump, "Antibody-Drug Conjugates: Linking Cytotoxic Payloads to Monoclonal Antibodies," Bioconjugate. Chem., 21(1):5-13 (2010).
Firer, "Antibody-drug conjugates in cancer therapy—filling in the potholes that lie ahead," OA Cancer, 1(1):8, 2013.
Lam et al., "Recent advances in drug-antibody immunoconjugates for the treatment of cancer," Drugs of the Future, 28(9):905-910 (2003).

(Continued)

*Primary Examiner* — Fred H Reynolds
(74) *Attorney, Agent, or Firm* — McCarter & English, LLP; Xin Zhang; Shama R. Tichkule

(57) ABSTRACT

The invention relates to novel cell-binding agent-cytotoxic agent conjugate having a peptide linkers and more specifically to conjugates of formula (I). The invention also provides novel cytotoxic agents of formula (II), linker compounds represented by formula (III), and drug-linker compounds represented by formula (IV). The invention further provides compositions and methods useful for inhibiting abnormal cell growth or treating a proliferative disorder in a mammal using the compounds or conjugates of the invention.

13 Claims, 23 Drawing Sheets

Specification includes a Sequence Listing.

(56) References Cited

OTHER PUBLICATIONS

Podgorski, et al., "Cathepsin B and its role(s) in cancer progression", Biochem. Soc. Symp., 70:263-276, 2003.
Sanderson et al., "Enhanced in vivo drug-linker stability of an anti-CD70 auristatin immunoconjugate," Proc. Am. Assoc. Cancer Res., 47:469 (2006) XP009151906.
Studer, et al., Influence of a Peptide Linker on Biodistribution and Metabolism of Antibody-Conjugated Benzyl-EDTA. Comparison of Enzymatic Digestion in Vitro and in Vivo, Bioconjug Chem., 3(6):424-429, 1992.
Xie et al., "Pharmacokinetics and Biodistribution of the Antitumor Immunoconjugate, Cantuzumab Mertansine (huC242-DM1), and its Two Components in Mice," J. Pharm. Exper. Ther., 308(3):1073-1082 (2004).
Xie et al., "Selection of a huC242-maytanisinoid conjugate with the highest anti-tumor activity in multiple human tumor xenograft models," Proc. Am. Assoc. Cancer Res., 47:876-877 (2006), p. 876 only.
Wermuth, "Saishin Soyaku Kagaku Joukan", TechnomicInc.1998 pp. 235-271.

\* cited by examiner (A)

R = H or Me
n is an integer from 2 to 100, preferably n is 4, 8, or 24.

(B)

R = H or Me
n is an integer from 2 to 100, preferably n is 4, 8, or 24.

(C)

R = H or Me
n is an integer from 2 to 100, preferably n is 4, 8, or 24.

(D)

R = H or Me
n is an integer from 2 to 100, preferably n is 4, 8, or 24.

A)

B)

A)

B)

A)

B)

huEGFR-7R-(D/L)A(D/L)A-PAB-DM1

MAYTANSINOID DERIVATIVES WITH PEPTIDE LINKER AND CONJUGATES THEREOF

REFERENCE TO RELATED APPLICATION

This application is a continuation of U.S. application Ser. No. 13/529,349, filed Jun. 21, 2012, which claims the benefit of the filing date, under 35 U.S.C. § 119(e), of U.S. Provisional Application No. 61/499,548 filed on Jun. 21, 2011, the entire content of which, including all drawings, is incorporated herein by reference.

SEQUENCE LISTING

This specification incorporates by reference the Sequence Listing submitted via EFS web on Oct. 10, 2012 identified as 121162-00602_Seq_List, which is 803 bytes, and was created on Oct. 10, 2012. The Sequence Listing, electronically filed, does not extend beyond the scope of the specification and does not contain new matter.

BACKGROUND OF THE INVENTION

Antibody-drug conjugates (ADC) are emerging as a powerful class of anti-tumor agents with efficacy across a range of cancers. ADCs are commonly composed of three distinct elements: a cell-binding agent; a linker; and a cytotoxic agent. The linker component of ADC is an important element in developing targeted anti-cancer agents that possess an optimal therapeutic window, i.e., high activity at a low, non-toxic dose.

Therefore, there is a need for ADCs having new class of linker component.

SUMMARY OF THE INVENTION

The present invention is directed to a cell-binding agent-cytotoxic agent conjugate represented by the following structural formula:

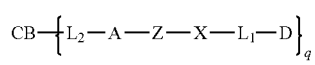

(I)

or a pharmaceutically acceptable salt thereof, wherein:

CB is a cell-binding agent;

$L_2$ is absent or a spacer;

A is an amino acid or a peptide comprising 2 to 20 amino acids;

Z is —NH— or —C(=O)—;

D is a cytotoxic agent;

$L_1$ is absent or a spacer;

X is an aryl or a heteroaryl, either of which is optionally substituted; and q is an integer from 1 to 20.

The present invention is also directed to a compound represented by the following structural formula:

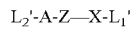

(II), or a salt thereof, wherein:

Z' is —NH$_2$ or —C(=O)—OH; and X, $L_1$ and D are as described above for formula (I).

In another embodiment, the present invention is directed to a compound represented by the following structural formula:

$$L_2'\text{-A-Z}\text{—X-}L_1'$$  (III)

or a salt thereof, wherein:

$L_2'$ is absent or a spacer comprising a reactive moiety that can form a covalent bond with a cell-binding agent;

$L_1'$ is a spacer comprising a reactive moiety that can form a covalent bond with a cytotoxic agent, and A, Z and X are as described above for formula (I).

The present invention is also directed to a compound represented by the following structural formula:

$$L_2'\text{-A-Z}\text{—X-}L_1\text{-D}$$  (IV), wherein:

$L_2'$ is absent or a spacer comprising a reactive moiety that can form a covalent bond with a cell-binding agent; and the remainder of the variables are as described above for formula (I).

In one embodiment, for conjugates of formula (I) and compounds of formula (II), (III) and (IV), when Z is —NH—, $L_1$ does not comprise one of the following moieties directly connected to X:

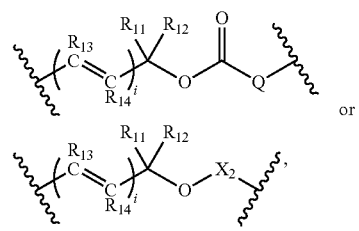

wherein i is 0 or an integer from 1 to 5; Q is —O—, —NR$_{15}$, S or —CR$_{11}$R$_{12}$—; X$_2$ is an aryl or a heteroaryl; and R$_{11}$, R$_{12}$, R$_{13}$, R$_{14}$ and R$_{15}$ are each independently H or an alkyl group.

The present invention also directs to a composition (e.g., a pharmaceutical composition) comprising a conjugate (e.g., a conjugate of formula (I)) or a compound (e.g., a compound of formula (II), (III) or (IV)) and a carrier (a pharmaceutically acceptable carrier). The present invention also includes a composition (e.g., a pharmaceutical composition) comprising a conjugate (e.g., a conjugate of formula (I)) or a compound (e.g., a compound of formula (II), (III) or (IV)) described herein and a carrier (a pharmaceutically acceptable carrier), further comprising a second therapeutic agent. The present compositions are useful for inhibiting abnormal cell growth or treating a proliferative disorder in a mammal (e.g., human). The present compositions are useful for treating conditions such as cancer, rheumatoid arthritis, multiple sclerosis, graft versus host disease (GVHD), transplant rejection, lupus, myositis, infection, immune deficiency such as AIDS, and inflammatory diseases in a mammal (e.g., human).

The present invention also includes a method of inhibiting abnormal cell growth or treating a proliferative disorder in a mammal (e.g., human) comprising administering to said abnormal cell or said mammal a therapeutically effective amount of a conjugate (e.g., a conjugate of formula (I)) or a compound (e.g., a compound of formula (II), (III) or (IV)) or a composition thereof, alone or in combination with a second therapeutic agent.

The present invention also includes a method of synthesizing and using a conjugate (e.g., a conjugate of formula (I)) or a compound (e.g., a compound of formula (II), (III) or (IV)) for in vitro, in situ, and in vivo diagnosis or treatment of mammalian cells, organisms, or associated pathological conditions.

The conjugates (e.g., a conjugate of formula (I)) and the compounds (e.g., a compound of formula (II), (III) or (IV)) of this invention are useful for treating or lessening the severity of disorders, such as, characterized by abnormal growth of cells (e.g., cancer). Other applications for the compounds and the conjugates of this invention include, but are not limited to, treating conditions such as cancer, rheumatoid arthritis, multiple sclerosis, graft versus host disease (GVHD), transplant rejection, lupus, myositis, infection, immune deficiency such as AIDS and inflammatory diseases in a mammal (e.g., human).

DETAILED DESCRIPTION OF THE INVENTION

Definitions

Figure 1:
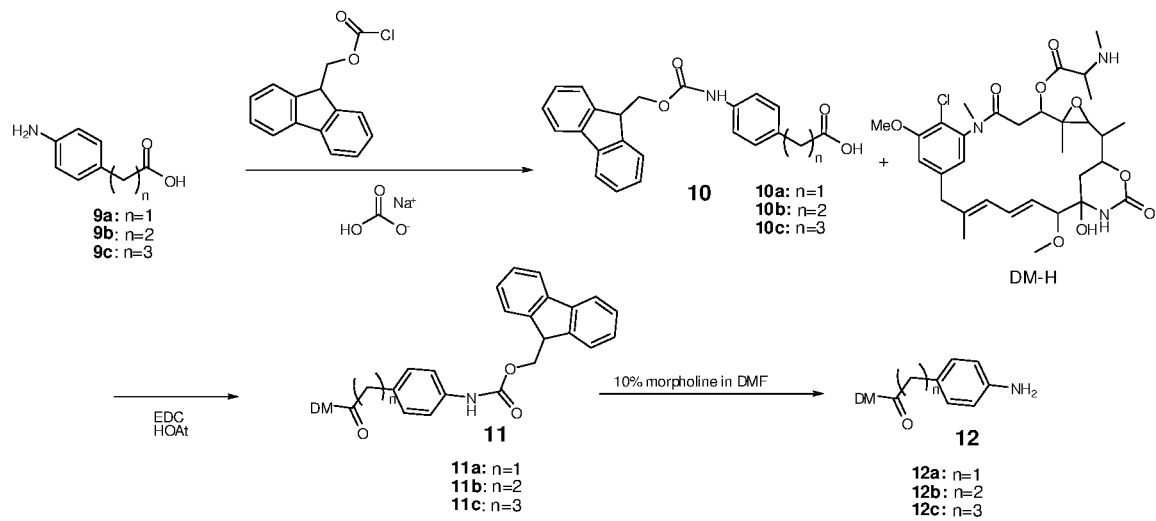
FIGS. 1-4 depict synthetic schemes for preparing representative cytotoxic compounds of the present invention.
Figure 2:
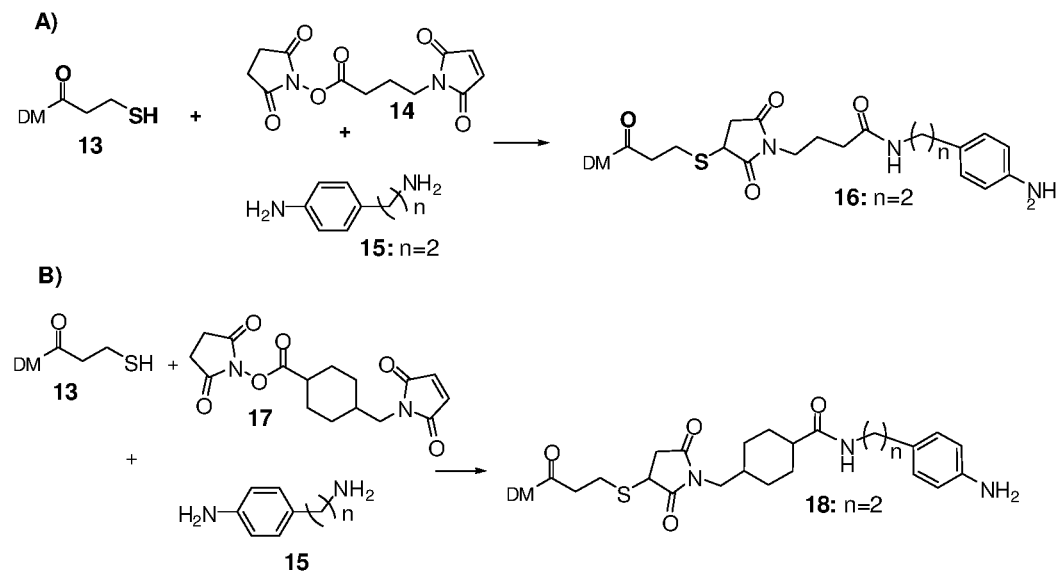
Figure 3:
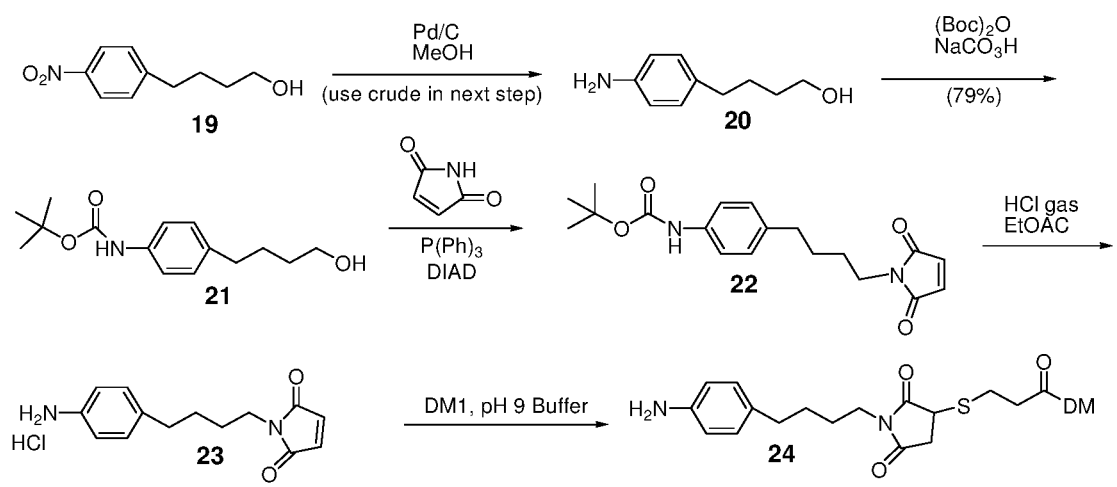
Figure 4:
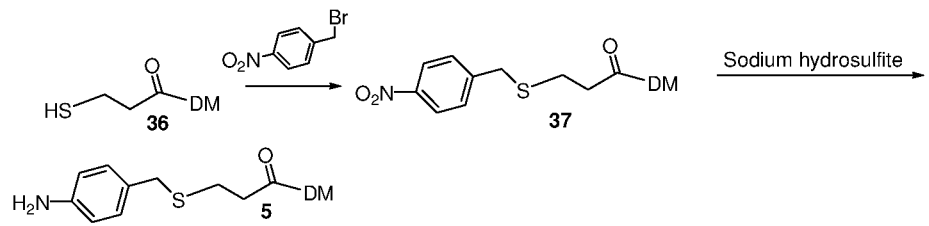
Figure 5:
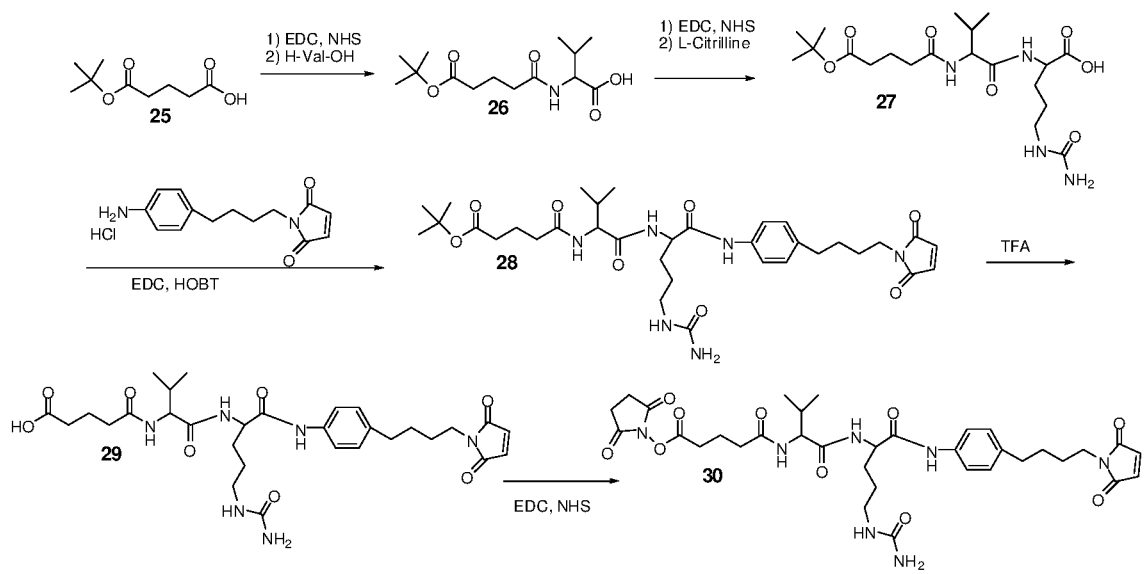
FIGS. 5 and 6 depict synthetic schemes for preparing representative linkers of the present invention.
Figure 6:
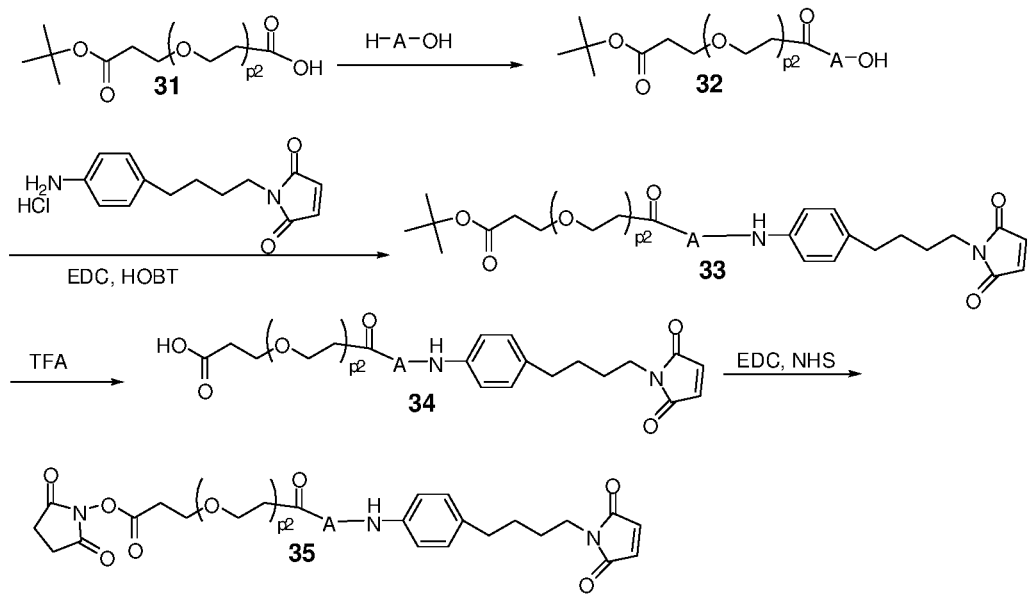
Figure 7:
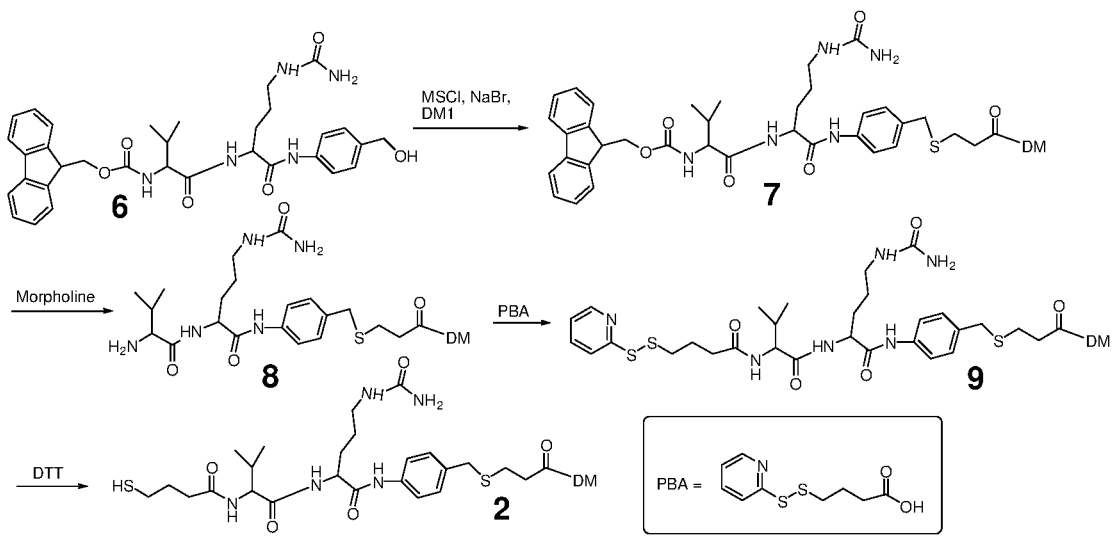
FIGS. 7-9 depict synthetic schemes for preparing representative drug-linker compounds of the present invention.
Figure 8:
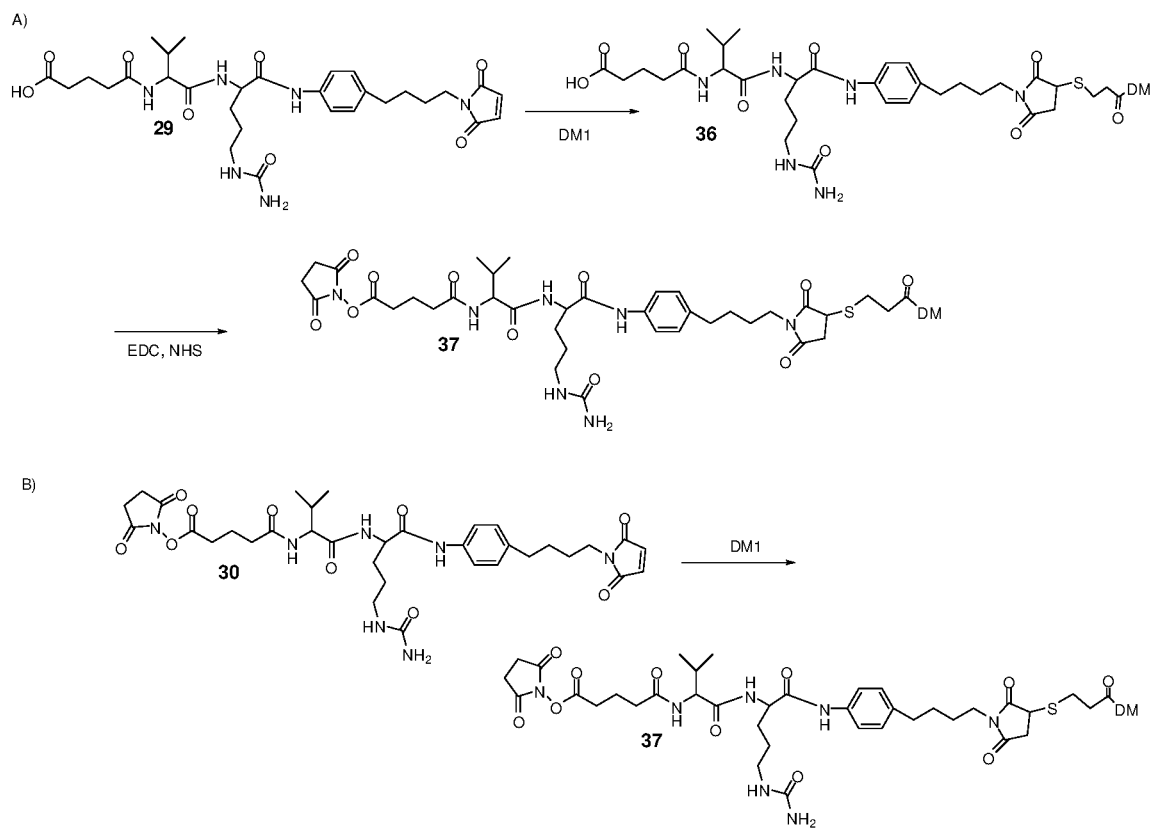
Figure 9:
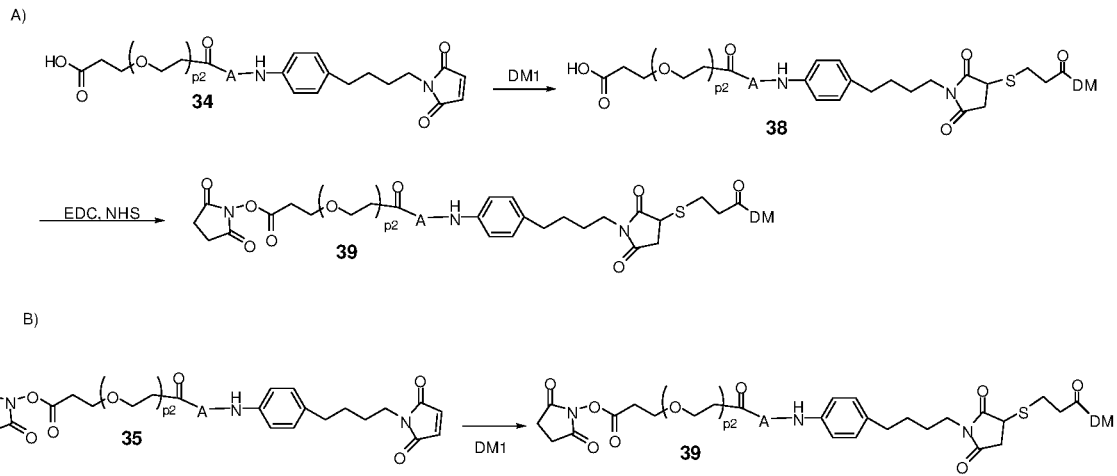

"Alkyl" as used herein refers to a saturated aliphatic linear or branched-chain monovalent hydrocarbon radical having one to twenty carbon atoms. Examples of alkyl include, but are not limited to, methyl, ethyl, 1-propyl, 2-propyl, 1-butyl, 2-methyl-1-propyl, —$CH_2CH(CH_3)_2$, 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Preferably, the alkyl has one to ten carbon atoms, also referred to as "$C_{1-10}$ alkyl." More preferably, the alkyl has one to six carbon atoms, also referred to as "$C_{1-6}$ alkyl." Even more preferably, the alkyl has one to four carbon atoms, also referred to as "$C_{1-4}$ alkyl."

"Alkenyl" as used herein refers to aliphatic linear or branched-chain monovalent hydrocarbon radical of two to twenty carbon atoms with at least one site of unsaturation, i.e., a carbon-carbon, double bond, wherein the alkenyl radical includes radicals having "cis" and "trans" orientations, or by an alternative nomenclature, "E" and "Z" orientations. Examples include, but are not limited to, ethylenyl or vinyl (—CH=$CH_2$), allyl (—$CH_2$CH=$CH_2$), and the like. Preferably, the alkenyl has two to ten carbon atoms, also referred to as "$C_{2-10}$ alkenyl." More preferably, the alkyl has two to four carbon atoms, also referred to as "$C_{2-4}$ alkenyl."

"Alkynyl" as used herein refers to aliphatic linear or branched-chain monovalent hydrocarbon radical of two to twenty carbon atoms with at least one carbon-carbon triple bond. Examples include, but are not limited to ethynyl, propynyl, 1-butynyl, 2-butynyl, 1-pentynyl, 2-pentynyl, 3-pentynyl, hexynyl, and the like. Preferably, the alkynyl has two to ten carbon atoms, also referred to as "$C_{2-10}$ alkynyl." More preferably, the alkynyl has two to four carbon atoms, also referred to as "$C_{2-4}$ alkynyl."

The term "alkylene" refers to a saturated aliphatic linear or branched-chain divalent hydrocarbon radical having one to twenty carbon atoms. Preferably, the alkylene has one to ten carbon atoms. More preferably, the alkylene has one to four carbon atoms.

The term "carbocycle," "carbocyclyl," carbocyclic and "carbocyclic ring" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Examples of monocyclic carbocycles include, but are not limited to, cyclopropyl, cyclobutyl, cyclopentyl, 1-cyclopent-I-enyl, 1-cyclopent-2-enyl, 1-cyclopent-3-enyl, cyclohexyl, 1-cyclohex-I-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The terms "cyclic alkyl" and "cycloalkyl" can be used interchangeably. They refer to a monovalent saturated carbocyclic ring radical. Preferably, the cycloalkyl is 3 to 7 membered monocyclic ring radical. More preferably, the cycloalkyl is cyclohexyl.

The term "cycloalkylalkyl" refers to a cycloalkyl group that is connected to another group by an alkylene group. Examples of cycloalkylalkyls include, but are not limited to, cyclohexylmethyl, cyclohexylethyl, cyclopentylmethyl, cyclopentylethyl, and the like. Preferably, cycloalkylalkyl is cyclohexylmethyl.

"Aryl" as used herein means a monovalent monocyclic or polycyclic (e.g. bicyclic or tricyclic) aromatic hydrocarbon radical of 6-18 carbon atoms derived by the removal of one hydrogen atom from a single carbon atom of a parent aromatic ring system. Some aryl groups are represented in the exemplary structures as "Ar." Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like. Preferably, aryl is phenyl group.

"Arylalkyl" refers to an aryl group that is connected to another group by an alkylene group. Examples of arylalkyl groups include, but are not limited to, benzyl, phenylethyl, naphth-3-yl-methyl, and the like. Preferably, arylalkyl is benzyl.

The terms "heterocycle," "heterocyclyl," heterocyclic and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen, phosphorus, and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl,_dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heterocyclylalkyl" refers to a heterocyclyl that is attached to another group by an alkylene group.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocycicyl can include the oxidized forms such as NO, SO, and $SO_2$.

The term "heteroarylalkyl" refers to a heteroaryl that is attached to another group by an alkylene group.

The term "halo" or "halogen" refers to F, Cl, Br or I.

The alkyl, alkenyl, cycloalkyl, carbocyclyl, aryl, heterocyclyl and heteroaryl described above can be optionally substituted with one more (e.g., 2, 3, 4, 5, 6 or more) suitable substituents. In one embodiment, the alkyl, alkenyl, cycloalkyl, carbocyclyl, aryl, heterocyclyl and heteroaryl described above is unsubstituted. In another embodiment, the alkyl, alkenyl, cycloalkyl, carbocyclyl, aryl, heterocyclyl and heteroaryl described above are substituted with one more (e.g., 2, 3, 4, 5, 6 or more) suitable substituents.

Such suitable substituents, in non-limiting examples, can be selected from an alkyl, alkenyl or alkynyl having from 1 to 10 carbon atoms, cycloalkyl, aryl, heteroaryl, heterocycyclyl, halogen, guanidinium [—NH(C=NH)NH$_2$], —OR$^{100}$, NR$^{101}$R$^{102}$, —NO$_2$, —NR$^{101}$COR$^{102}$, —SR$^{100}$, a sulfoxide represented by —SOR$^{101}$, a sulfone represented by —SO$_2$R$^{101}$, a sulfonate —SO$_3$M, a sulfate —OSO$_3$M, a sulfonamide represented by —SO$_2$NR$^{101}$R$^{102}$, cyano, an azido, —COR$^{101}$, —OCOR$^{101}$, —OCONR$^{101}$R$^{102}$ and a polyethylene glycol unit (—OCH$_2$CH$_2$)$_n$R$^{101}$ wherein M is H or a cation (such as Na$^+$ or K$^+$); R$^{100}$, R$^{101}$, R$^{102}$ and R$^{103}$ are each independently selected from H, alkyl, alkenyl or alkynyl having from 1 to 10 carbon atoms, a polyethylene glycol unit (—OCH$_2$CH$_2$)$_n$—R$^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocycicyl in the groups represented by R$^{100}$, R$^{101}$, R$^{102}$, R$^{103}$ and R$^{104}$ are optionally substituted with one or more (e.g., 2, 3, 4, 5, 6 or more) substituents independently selected from halogen, —OH, CN, NO$_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, CN, NR$^{102}$R$^{103}$, CF$_3$, OR$^{101}$, aryl, heteroaryl, heterocycycl, SR$^{101}$, SOR$^{101}$, SO$_2$R$^{101}$ and —SO$_3$M. Preferably, the suitable substituent is selected from the group consisting of -halogen, —OH, —NO$_2$, —CN, C$_{1-4}$ alkyl, —OR$^{100}$, NR$^{101}$R$^{102}$, —NR$^{101}$COR$^{102}$, —SR$^{100}$, —SO$_2$R$^{101}$, —SO$_2$NR$^{101}$R$^{102}$, —COR$^{101}$, —OCOR$^{101}$ and —OCONR$^{101}$R$^{102}$ wherein R$^{100}$, R$^{101}$, and R$^{102}$ are each independently —H or C$_{1-4}$ alkyl.

The term "compound" and "cytotoxic compound" are used interchangeably. They are intended to include compounds for which a structure or formula or any derivative thereof has been disclosed in the present invention or a structure or formula or any derivative thereof that has been incorporated by reference. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. The term also includes solvates, hydrates, polymorphs or salts (e.g., pharmaceutically acceptable salts) of a compound of all the formulae disclosed in the present invention. The specific recitation of "stereoisomers," "geometric isomers," "tautomers," "solvates," "salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "conjugate" as used herein refers to a compound described herein or a derivative thereof that is linked to a cell binding agent.

The term "linkable to a cell binding agent" as used herein refers to the compounds described herein or derivates thereof comprising at least one reactive group or a precursor thereof suitable to bond these compounds or derivatives thereof to a cell binding agent.

The term "precursor" of a given group refers to any group which may lead to that group by any deprotection, a chemical modification, or a coupling reaction.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The term "prodrug" is also meant to include a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, selinocystiene and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. One amino acid that may be used in particular is citrulline, which is a derivative of arginine and is involved in the formation of urea in the liver. Amino acid mimetics refers to chemical compounds that have a structure that is different from the general chemical structure of an amino acid, but functions in a manner similar to a naturally occurring amino acid. The term "unnatural amino acid" is intended to represent the "D" stereochemical form of the twenty naturally occurring amino acids described above. It is further understood that the term unnatural amino acid includes homologues of the natural amino acids or their D isomers, and synthetically modified forms of the natural amino acids. The synthetically modified forms include, but are not limited to, amino acids having side chains shortened or lengthened by up to two carbon atoms, amino acids comprising optionally substituted aryl groups, and amino acids comprised halogenated groups, preferably halogenated alkyl and aryl groups and also N substitiuted amino acids e.g. N-methyl-alanine. An amino acid or peptide can be attached to a linker/spacer or a cell binding agent through the terminal amine or terminal carboxylic acid of the amino acid or peptide. The amino acid can also be attached to a linker/spacer or a cell-binding agent through a side chain reactive group, such as but not restricted to the thiol group of cysteine, the epsilon amine of lysine or the side chain hydroxyls of serine or threonine.

Amino acids and peptides may be protected by blocking groups. A blocking group is an atom or a chemical moiety that protects the N-terminus of an amino acid or a peptide from undesired reactions and can be used during the synthesis of a drug-ligand conjugate. It should remain attached to the N-terminus throughout the synthesis, and may be removed after completion of synthesis of the drug conjugate by chemical or other conditions that selectively achieve its removal. The blocking groups suitable for N-terminus protection are well known in the art of peptide chemistry. Exemplary blocking groups include, but are not limited to, methyl esters, tert-butyl esters, 9-fluorenylmethyl carbamate (Fmoc) and carbobenzoxy (Cbz).

The term "peptide cleavable by a protease" refers to peptides containing a cleavage recognition sequence of a protease. A cleavage recognition sequence for a protease is a specific amino acid sequence recognized by the protease during proteolytic cleavage. Many protease cleavage sites are known in the art, and these and other cleavage sites can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al, in AMYLOID PROTEIN PRECURSOR IN DEVELOPMENT, AGING, AND ALZHEIMER'S DISEASE, ed. Masters et al. pp. 190-198 (1994).

The peptide sequence is chosen based on its ability to be cleaved by a protease, non-limiting examples of which include cathepsins B, C, D, H, L and S, and furin. Preferably, the peptide sequence is capable of being cleaved by an appropriate isolated protease in vitro, which can be tested using in vitro protease cleavage assays known in the art.

In another embodiment, the peptide sequence is chosen based on its ability to be cleaved by a lysosomal protease. A lysosomal protease is a protease located primarily in the lysosomes, but can also be located in endosomes. Examples of a lysosomal protease include, but are not limited to, cathepsins B, C, D, H, L and S, and furin In another embodiment, the peptide sequence is chosen based on its ability to be cleaved by a tumor-associated protease, such as a protease that is found on the surface of a cancerous cell or extracellularly in the vicinity of tumor cells, non-limiting examples of such proteases include thimet oligopeptidase (TOP), CD10 (neprilysin), a matrix metalloprotease (such as MMP2 or MMP9), a type II transmembrane serine protease (such as Hepsin, testisin, TMPRSS4 or matriptase/MT-SP1), legumain and enzymes described in the following reference (Current Topics in Developmental Biology: Cell Surface Proteases, vol. 54 Zucker S. 2003, Boston, Mass.). The ability of a peptide to be cleaved by tumor-associated protease can be tested using in vitro protease cleavage assays known in the art.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention contains one or more basic moieties, desired pharmaceutically acceptable salts may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention contains one or more acidic moieties, desired pharmaceutically acceptable salts may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound which further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

The term "cytotoxic agent" as used herein refers to any compound that results in the death of a cell, induces cell death, or decreases cell viability. Suitable cytotoxic agents include, for example, maytansinoids and maytansinoid analogs, doxarubicin, taxoids, CC-1065 and CC-1065 analogs, tubulysin, calecheamycin, a duocarycin derivative, dolastatin and dolastatin analogs, e. g. auristatins including auristatin E and auristatin F. In a preferred embodiment of the invention, the cytotoxic agent is a maytansinoid, including maytansinol, maytansinol analogs, ansamitocin and ansamitocin analogs. Maytansinoids are compounds that inhibit microtubule formation and are highly toxic to mammalian cells. Examples of suitable maytansinol analogues include those having a modified aromatic ring and those having modifications at other positions. Such maytansinoids are described in, for example, U.S. Pat. Nos. 4,256,746, 4,294,757, 4,307,016, 4,313,946, 4,315,929, 4,322,348, 4,331,598, 4,361,650, 4,362,663, 4,364,866, 4,424,219, 4,371,533, 4,450,254, 5,475,092, 5,585,499, 5,846,545, and 6,333,410.

The terms "abnormal cell growth" and "proliferative disorder" are used interchangeably in this application.

"Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or over-expression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, acute leukemia, as well as head/brain and neck cancer.

A "therapeutic agent" encompasses both a biological agent such as an antibody, a peptide, a protein, an enzyme or a chemotherapeutic agent.

A "chemotherapeutic agent" is a chemical compound useful in the treatment of cancer.

A "metabolite" is a product produced through metabolism in the body of a specified compound, a derivative thereof, or a conjugate thereof, or salt thereof. Metabolites of a compound, a derivative thereof, or a conjugate thereof, may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds, a derivative thereof, or a conjugate thereof, of the invention, including compounds, a derivative thereof, or a conjugate thereof, produced by a process comprising contacting a compound, a derivative thereof, or a conjugate thereof, of this invention with a mammal for a period of time sufficient to yield a metabolic product thereof.

The phrase "pharmaceutically acceptable" indicates that the substance or composition must be compatible chemically and/or toxicologically, with the other ingredients comprising a formulation, and/or the mammal being treated therewith.

The term "leaving group" refers to a charged or uncharged moiety that departs during a substitution or displacement reaction. Such leaving groups are well known in the art and include, but not limited to, halogens, alkoxy, tosylates, triflates, mesylates, azide, carbamate, one thio moity of a disulfide, thioesters, and diazonium compounds.

A "reactive group" or "reactive moiety" as defined herein refers to a functional group that can form a chemical bond with a cell-binding agent or a cytotoxic agent. Suitable chemical bonds are well known in the art and include disulfide bonds, thioether bonds, acid labile bonds, photo-labile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds.

In one embodiment, the reactive group is selected from the group consisting of a maleimide, a haloacetamido, —SH, —SSR$^f$, —CH$_2$SH, —CH(Me)SH, —C(Me)$_2$SH, —NHR$^g$, —CH$_2$NHR$^g$, —NR$^g$NH$_2$, —COOH, a reactive ester, an amino acid, or a peptide having 2 to 10 amino acids, wherein R$^f$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl) and R$^g$ is H or a C$_{1-4}$ alkyl.

The term "linking moiety" as used herein refers to the remaining chemical moiety of the reactive group after the reactive group is covalently linked to a cell-binding agent or a cytotoxic agent. For example, when the linking group N-hydroxysuccinimide ester is chemically linked with an amine group of the cell-binding agent, the corresponding linking moiety is —C(=O)—. In another example, when the linking group maleimide group is chemically linked to a thio (—SH) group of the cell-binding agent, the linking moiety is

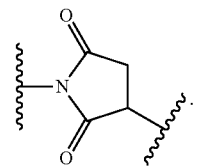 [SMILES: *C1CC(=O)N(*)C1=O]

The "reactive ester" as used herein refers to an ester group having a leaving group that is readily displaced by an amine or a hydroxyl group. Examples of a reactive ester, include, but are not limited to, N-hydroxysuccinimde ester, N-hydroxy sulfosuccinimide ester, nitrophenyl (e.g., 2 or 4-nitrophenyl) ester, dinitrophenyl (e.g., 2,4-dinitrophenyl) ester, sulfo-tetraflurophenyl (e.g., 4-sulfo-2,3,5,6-tetrafluorophenyl) ester and pentafluorophenyl ester.

The term "therapeutically effective amount" means that amount of active compound or conjugate that elicits the desired biological response in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the effective amount is well within the capability of those skilled in the art, especially in light of the detailed disclosure provided herein. Toxicity and therapeutic efficacy of compound I can be determined by standard pharmaceutical procedures in cell cultures and in experimental animals. The effective amount of compound or conjugate of the present invention or other therapeutic agent to be administered to a subject will depend on the stage, category and status of the multiple myeloma and characteristics of the subject, such as general health, age, sex, body weight and drug tolerance. The effective amount of compound or conjugate of the present invention or other therapeutic agent to be administered will also depend on administration route and dosage form. Dosage amount and interval can be adjusted individually to provide plasma levels of the active compound that are sufficient to maintain desired therapeutic effects.

Values and Preferred Values for the Variables

The present invention is directed to novel cytotoxic agents (e.g., compounds of structural formula (II), derivatives thereof (e.g., compounds of structural formula (III) and (IV)) and cell-binding agent-cytotoxic agent conjugates comprising a cell-binding agent covalently linked to the cytotoxic agents or derivative thereof described herein (e.g., conjugates of structural formula (I)).

In one embodiment, values and preferred values for the variables depicted in structural formulas (I), (II), (III) and (IV) are as described below:

Values and Preferred Values for D:

D is a cytotoxic agent. In one embodiment, D is a maytansinoid. In another embodiment, D is represented by the following structural formula:

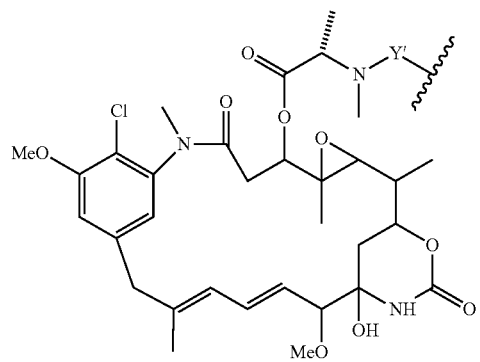

(A')

wherein:

Y' is absent or —C(=O)(CR$_7$R$_8$)$_{l1}$(CR$_9$=CR$_{10}$)$_{p1}$(C≡C)$_{q1}$A'$_{r1}$(CR$_5$R$_6$)$_{m1}$D'$_{u1}$(CR$_{11}$=CR$_{12}$)$_{r1}$(C≡C)$_{s1}$B'$_{t1}$(CR$_3$R$_4$)$_{n1}$CR$_1$R$_2$S—, wherein:

R$_1$ and R$_2$ are each independently H, a linear or branched alkyl or alkenyl having from 1 to 10 carbon atoms, a cycloalkyl or cycloalkenyl having from 3 to 10 carbon atoms, phenyl, substituted phenyl substituted with at least one alkyl having 1-4 carbon atoms, an alkoxy, halogen or nitro, or heteroaryl or heterocyclyl;

A', B', D' are cycloalkyl or cycloalkenyl having 3-10 carbon atoms, optionally substituted aryl, heteroaryl or heterocyclyl;

R$_3$, R$_4$, R$_5$, R$_6$, R$_7$, R$_8$, R$_9$, R$_{11}$, and R$_{12}$ are each independently H, a linear or branched alkyl or alkenyl having from 1 to 10 carbon atoms, a cycloalkyl or cycloalkenyl having from 3 to 10 carbon atoms, phenyl, substituted phenyl substituted with at least one alkyl having 1-4 carbon atoms, an alkoxy, halogen or nitro, or heteroaryl or heterocyclyl;

l1, m1, n1, o1, p1, q1, r1, s1 and t1 are each independently 0 or an integer of from 1 to 5, provided that at least two of l1, m1, n1, o1, p1, q1, r1, s1 and t1 are not zero at any one time.

In another embodiment, D is represented by the following formula:

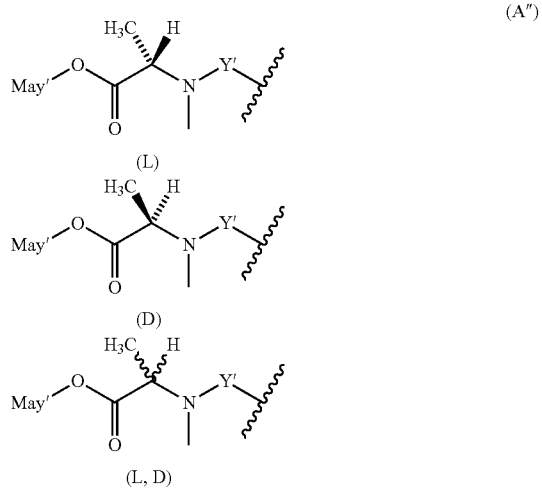

(A")

wherein:

Y' is absent or —C(=O)(CR$_7$R$_8$)$_{l1}$(CR$_5$R$_6$)$_{m1}$(CR$_3$R$_4$)$_{n1}$CR$_1$R$_2$S—, wherein:

R$_1$ and R$_2$ are each independently H, a linear or branched alkyl or alkenyl having from 1 to 10 carbon atoms, a cycloalkyl or cycloalkenyl having from 3 to 10 carbon atoms, phenyl, substituted phenyl substituted with at least one alkyl having 1-4 carbon atoms, an alkoxy, halogen or nitro, or heteroaryl or heterocyclyl;

R$_3$, R$_4$, R$_5$, R$_6$, R$_7$ and R$_8$ are each independently H, linear or branched alkyl or alkenyl having from 1 to 10 carbon atoms, a cycloalkyl or cycloalkenyl having from 3 to 10 carbon atoms, phenyl, substituted phenyl substituted with at least one alkyl having 1-4 carbon atoms, an alkoxy, halogen or nitro, or heteroaryl or heterocyclyl;

l1, m1 and n1 are each independently 0 or an integer of from 1 to 5; and

May'OH represents a maytansinol or a maystansinol analog.

Examples of suitable maytansinol analogs include those having a modified aromatic ring and those having modifications at other positions. Such maytansinoids are described in, for example, U.S. Pat. Nos. 4,256,746, 4,294,757, 4,307,016, 4,313,946, 4,315,929, 4,322,348, 4,331,598, 4,361,650, 4,362,663, 4,364,866, 4,424,219, 4,371,533, 4,450,254, 5,475,092, 5,585,499, 5,846,545, and 6,333,410.

Examples of maytansinol analogs having a modified aromatic ring include: (1) C-19-dechloro (U.S. Pat. No. 4,256,746) (prepared by LAH reduction of ansamytocin P2), (2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH), and (3) C-20-demethoxy, C-20-acyloxy (—OCOR), +/−dechloro (U.S. Pat. No. 4,294,757) (prepared by acylation using acyl chlorides).

Examples of maytansinol analogs having modifications of positions other than an aromatic ring include: (1) C-9-SH (U.S. Pat. No. 4,424,219) (prepared by the reaction of maytansinol with H$_2$S or P$_2$S$_5$), (2) C-14-alkoxymethyl (demethoxy/CH$_2$OR) (U.S. Pat. No. 4,331,598), (3) C-14-hydroxymethyl or acyloxymethyl (CH$_2$OH or CH$_2$OAc) (U.S. Pat. No. 4,450,254) (prepared from Nocardia), (4) C-15-hydroxy/acyloxy (U.S. Pat. No. 4,364,866) (prepared by the conversion of maytansinol by *Streptomyces*), (5) C-15-methoxy (U.S. Pat. Nos. 4,313,946 and 4,315,929) (isolated from Trewia nudiflora), (6) C-18-N-demethyl (U.S. Pat. Nos. 4,362,663 and 4,322,348) (prepared by the demethylation of maytansinol by *Streptomyces*), and (7) 4,5-deoxy (U.S. Pat. No. 4,371,533) (prepared by the titanium trichloride/LAH reduction of maytansinol).

In another embodiment, D is an ansamitocin derivative described in the U.S. Provisional Application No. 61/409,831, filed Nov. 3, 2010, the entiring teaching of which is incorporated herein by its entirety.

In another embodiment, D is represented by the following structural formula:

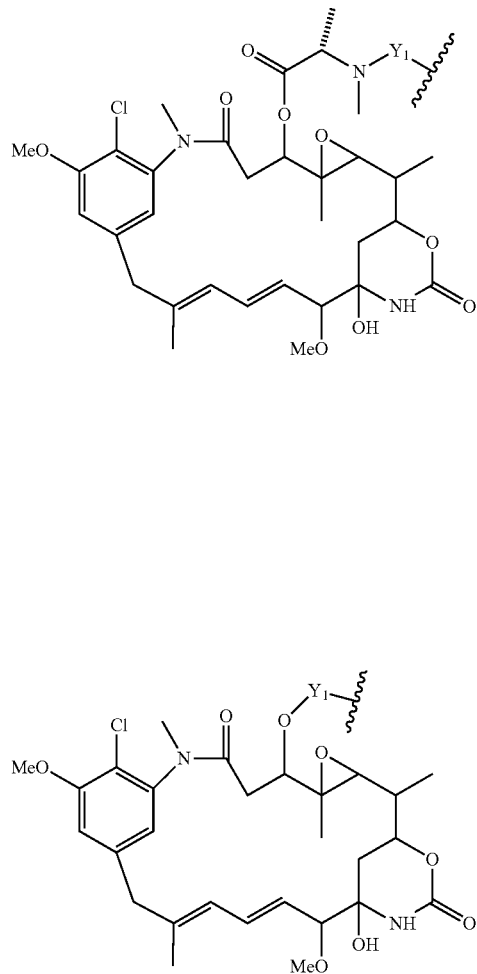

wherein:

$Y_1$ is absent or —C(=O)(CR$_7$R$_8$)$_{l1}$(CR$_5$R$_6$)$_{m1}$(CR$_3$R$_4$)$_{n1}$(CR$_1$R$_2$(S)$_{q1}$)$_{q2}$—, $R_1$, $R_2$, $R_3$, $R_4$, $R_5$, $R_6$, $R_7$ and $R_8$ are each independently H, an alkyl, an alkenyl, a cycloalkyl, a heteroaryl, a heterocyclyl, or an aryl; q1 is 0 or 1; q2 is 0 or 1 and l1, m1 and n1 are each independently 0 or an integer from 1 to 5.

Preferably, q1 and q2 are both 1.

In another embodiment, D is represented by the following structural formula:

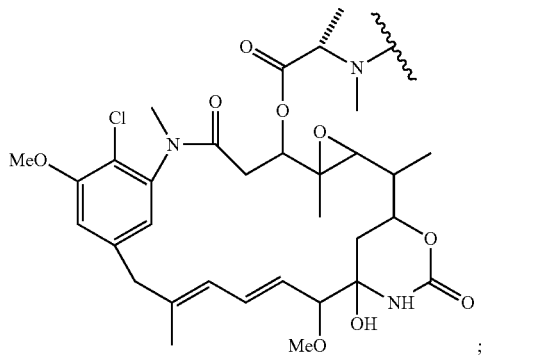

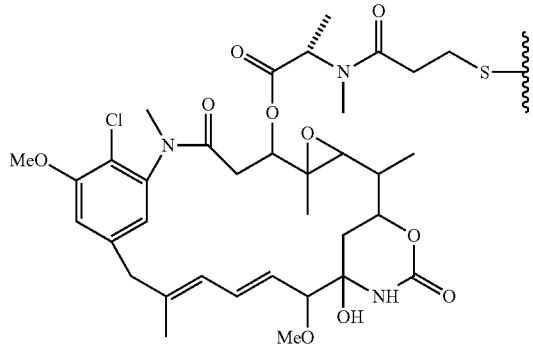

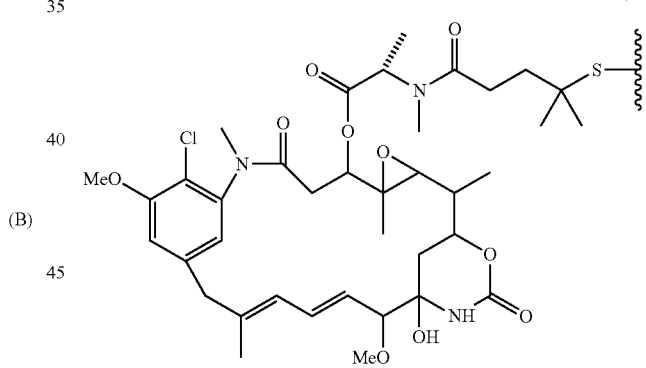

Values and Preferred Values for $L_1$:

In one embodiment, $L_1$ is represented by the following structural formula:

$$-J_x-R^{A1}-V_1-W_1-R^{B1}-V_1'-R^{C1}-J_{D'}-$$

wherein:

$R^{A1}$, $R^{B1}$ and $R^{C1}$ are each absent, an alkyl, an alkenyl, an alkynyl, a cycloalkyl, an aryl, a heteroaryl or a heterocyclyl, wherein the alkyl, alkenyl, alkynyl, cycloalkyl, aryl, heteroaryl, and heterocyclyl are optionally substituted;

$J_x$ and $W_1$ are each independently absent, —O—, —O—C(=O)—, —C(=O)—O—, —S—, —SO—, —SO$_2$—, —SO$_2$NH—, —CR$_{11}$R$_{12}$—S—, —CR$_{11}$R$_{12}$—O—, —CR$_{11}$R$_{12}$NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —SS—, —C(=O)—,

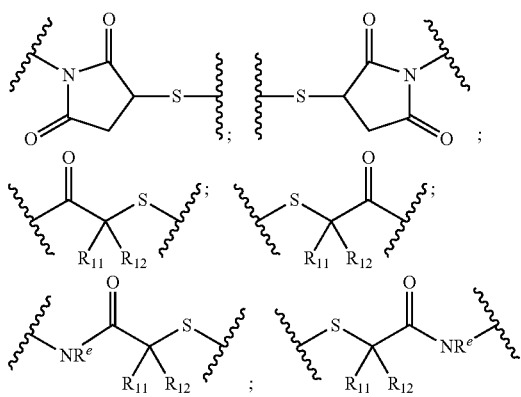

an amino acid, or a peptide having 2 to 8 amino acids, provided that when Z is —NH—, $J_x$ and $V_1$ are absent and $R^{A1}$ is $CR_{11}R_{12}$—, $W_1$ is not —O—C(=O)—.

$J_D$ is absent, —C(=O)—, —S—,

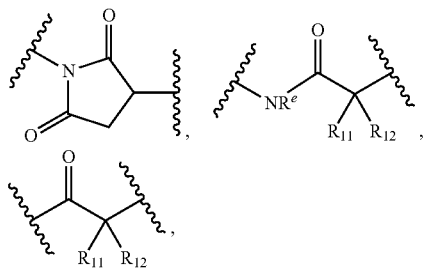

—O—, —O—C(=O)—, —C(=O)—O—, —SO—, —SO$_2$—, —SO$_2$NH—, —O—(C=O)—, —N(R$^e$)—, —N(R$^e$)—C(=O)—, or —N(C(=O)R$^e$)C(=O)—, or —N(C(=O)R$^e$)—;

$V_1$ and $V_1{}'$ are each independently —(O—CH$_2$—CH$_2$)$_{p1}$—, —(CH$_2$—CH$_2$—O)$_{p1}$—, —(NR$^m$—CH$_2$—CH$_2$)$_{p1}$— or —(CH$_2$—CH$_2$—NR$^m$)$_{p1'}$—;

R$^e$ is H, an alkyl, an alkenyl, an alkynyl, or —(CH$_2$—CH$_2$—O)$_{n'}$—R$^k$;

R$^k$ and R$^m$ are each independently H or an alkyl;

$R_{11}$ and $R_{12}$ are each independently H or an alkyl;

n' is an integer from 1 to 24;

p1 is 0 or an integer from 1 to 1000; and p1' is 0 or an integer from 1 to 10.

Preferably, $R_{11}$ and $R_{12}$ are both H.

In another embodiment, $L_1$ is represented by

—(CR$_9$R$_{10}$)$_m$—W$_1$—R$^{B1}$-J$_D$-, wherein:

$R_9$ and $R_{10}$ are each independently H or a $C_{1-4}$ alkyl;

m is an integer from 1 to 10, and $W_1$, $R^{B1}$ and $J_D$ are as described above, provided that when Z is —NH— and m is 1, $W_1$ is not —O—C(=O)—.

In one embodiment, $R^{A1}$, $R^{B1}$ and $R^{C1}$ are each independently absent or an alkyl. Preferably, $R^{A1}$, $R^{B1}$ and $R^{C1}$ are each absent or a $C_{1-6}$ alkyl.

In another embodiment, $R^{A1}$ is absent or an alkyl, preferably a $C_{1-6}$ alkyl; $R^{B1}$ is a cycloalkyl, preferably a cyclohexyl; and $R^{C1}$ is an alkyl, preferably a $C_{1-6}$ alkyl, more preferably, —CH$_2$—.

In one embodiment, $J_x$ is absent.

In one embodiment, $W_1$ is absent, —NH—C(=O)—, —C(=O)NH—, —C(=O)O— or —O—C(=O)—. Preferably, $W_1$ is absent or —NH—C(=O)—.

In one embodiment, $J_D$ is absent, —C(=O)—,

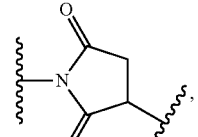

—NH—C(=O)—CH$_2$—, or —S—. Preferably, $J_D$ is absent, —C(=O)— or

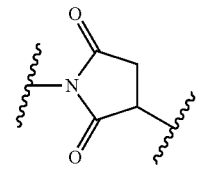

In one embodiment, $R_9$ and $R_{10}$ are both H. Preferably, m is 1, 2 or 3.

In one embodiment, $L_1$ is —CH$_2$—S—R$^{B1}$—C(=O)—, wherein $R^{B1}$ is a $C_{1-10}$ alkyl. Preferably, $R^{B1}$ is —CH$_2$—CH$_2$—.

Values and Preferred Values for X:

X is an optionally substituted aryl or an optionally substituted heteroaryl.

In one embodiment, X is an optionally substituted aryl. In another embodiment, X is an optionally substituted phenyl, such as those represented by the following formula:

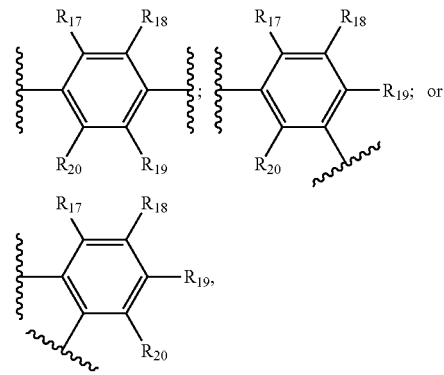

wherein $R_{17}$, $R_{18}$, $R_{19}$ and $R_{20}$ each are independently H, an alkyl, halogen, —OH, —O-alkyl, —NO$_2$, —C(=O)OR$_{30}$, —(C=O)R$_{30}$ or —CN, wherein $R_{30}$ is H or an alkyl, preferably H or a $C_{1-4}$ alkyl. Preferably, $R_{17}$, $R_{18}$, $R_{19}$ and $R_{20}$ are all H.

In another embodiment, X is an optionally substituted six-membered heteroaryl. Preferably, the heteroaryl is selected from the group consisting of pyridine, pyridazine, pyrimidine, pyrazine, a triazine, and tetrazine. In certain embodiments, the heteroaryl is connected to the —NH group and -$L_1$ group at carbon atoms of the heteroaryl.

In another embodiment, X is an optionally substituted five-membered heteroaryl. Preferably, X is selected from the group consisting of:

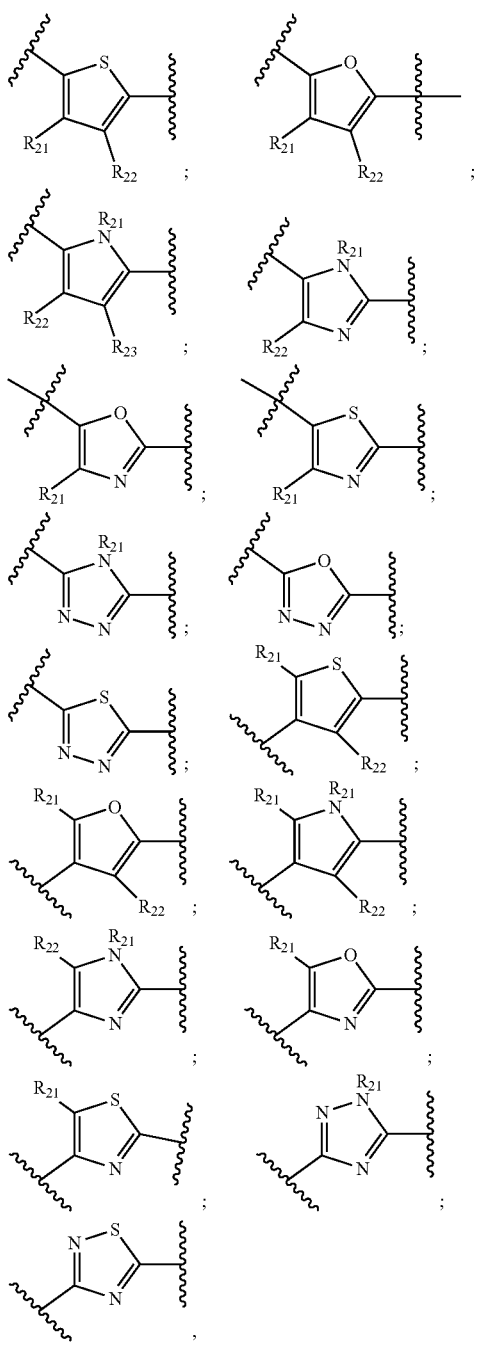

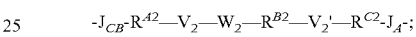

wherein $R_{21}$, $R_{22}$ and $R_{23}$ are each independently H or an alkyl.

Values or Preferred Values for Z and Z':
Z is —NH— or —C(=O)—. Preferably, Z is —NH—.
Z' is —NH$_2$ or —C(=O)OH. Preferably, Z' is —NH$_2$.

Values or Preferred Values for A:

A is an amino acid or a peptide comprising 2 to 20 amino acids. In one embodiment, A is a peptide cleavable by a protease. Preferably, A is a peptide cleavable by a protease expressed in tumor tissue. In another preferred embodiment, A is a peptide cleavable by a lysosomal protease.

In one embodiment, A is a peptide having an amino acid that is covalently linked with —Z—X-L$_1$-D, such as —NH—X-L$_1$-D, selected from the group consisting of Ala, Arg, Asn, Asp, Cit, Cys, selino-Cys, Gln, Glu, Gly, His, Ile, Leu, Lys, Met, Phe, Pro, Ser, Thr, Trp, Tyr and Val each independently as L or D isomers.

In one embodiment, A is a Cys or a peptide comprising a Cys that is covalently linked to L$_2$, wherein the Cys is linked to L$_2$ through the —SH group of Cys side chain.

In another embodiment, A is selected from the group consisting of Val-Cit, Val-Lys, Phe-Lys, Lys-Lys, Ala-Lys, Phe-Cit, Leu-Cit, Lle-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), β-Ala-Leu-Ala-Leu (SEQ ID NO: 2) and Gly-Phe-Leu-Gly (SEQ ID NO: 3), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, D-Ala-Ala, Ala-D-Ala, and D-Ala-D-Ala. Preferably, A is Val-Cit, Val-Lys, Val-D-Cit or Val-D-Lys.

Values and Preferred Values for L2:

L$_2$ is absent or a spacer. In one embodiment, L$_2$ is represented by the following formula:

$$-J_{CB}-R^{A2}-V_2-W_2-R^{B2}-V_2'-R^{C2}-J_{A}-;$$

wherein:

$R^{A2}$, $R^{B2}$ and $R^{C2}$ are each independently absent, an alkyl, an alkenyl, an alkynyl, a cycloalkyl, an aryl, a heteroaryl, a heterocyclyl, a cycloalkylalkyl, an arylalkyl, a heteroarylalkyl or a heterocycloalkyl, wherein the alkyl, alkenyl, alkynyl, cycloalkyl, aryl, heteroaryl, heterocyclyl, cycloalkylalkyl, arylalkyl, heteroarylalkyl and heterocycloalkyl are optionally substituted;

$V_2$ and $V_2'$ are each independently —O—CH$_2$—CH$_2$)$_{p2}$—, —(CH$_2$—CH$_2$—O)$_{p2}$—, —(NR$^m$—CH$_2$—CH$_2$)$_{p2'}$— or —(CH$_2$—CH$_2$—NR$^m$)$_{p2'}$—;

$W_2$ is absent, —O—, —O—C(=O)—, —C(=O)—O—, —S—, —SO—, —SO$_2$—, —CR$_{11}$R$_{12}$—S—, —CR$_{11}$R$_{12}$—O—, —CR$_{11}$R$_{12}$—NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —(O—CH$_2$—CH$_2$)$_{n'}$—, —SS—, —C(=O)—, an amino acid, a peptide having 2 to 8 amino acids,

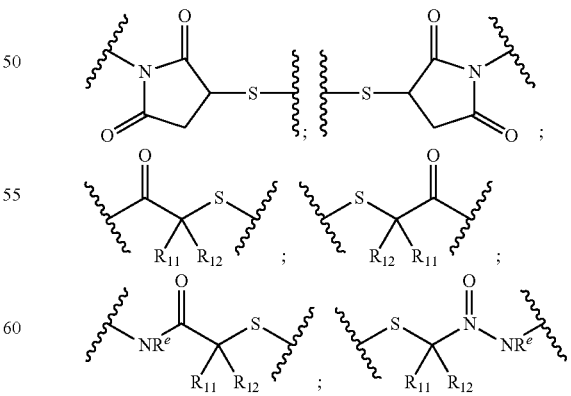

$J_{CB}$ is —C(=O)—, —C(=O)—NR$^e$—, —C(=O)—O—, —C(=NH)—, —C(=NH)—NR$^e$—, —S—, —NR$^e$—, —NH—NR$^e$—,

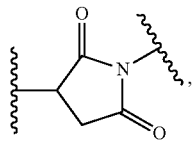 [SMILES: *C1CC(=O)N(*)C1=O]

—C(=NR$^e$)—, =NNR$^e$—, —CH$_2$—C(=O)—, or —CH$_2$—C(=O)—NR$^e$—;
J$_A$ is —NR$^e$—, —C(=O)—, =N—, —NR$^e$—C(=O)—, —O—C(=O)—, —SO$_2$—, —S—

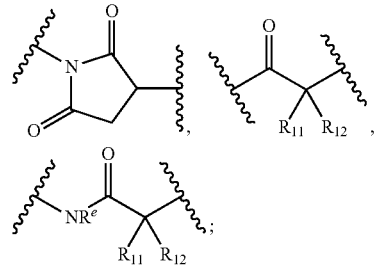

R$_{11}$ and R$_{12}$ are each independently H or an alkyl;
p2 is 0 or an integer from 1 to 1000; and
p2' is 0 or an integer from 1 to 10.
In one embodiment, R$_{11}$ and R$_{12}$ are both H.
In another embodiment, J$_{CB}$ is —C(=O)—,

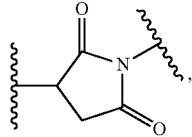 [SMILES: *C1CC(=O)N(*)C1=O]

—CH$_2$—C(=O)— or —CH$_2$—C(=O)—NH—.

In one embodiment, R$^{A2}$ is an alkyl, preferably a C$_{1-6}$ alkyl. In another embodiment, R$^{A2}$ is an optionally substituted phenyl, preferably, unsubstituted phenyl. In another embodiment, R$^{A2}$ is a cycloalkylalkyl. Preferably, R$^{A2}$ is cyclohexylmethyl.

In one embodiment, R$^{B2}$ is absent or an alkyl, preferably a C$_{1-6}$ alkyl.

In one embodiment, R$^{C2}$ is absent or an alkyl, preferably a C$_{1-6}$ alkyl.

In another embodiment, one of R$^{B2}$ and R$^{C2}$ is absent, and the other is an alkyl, preferably a C$_{1-6}$ alkyl.

In another embodiment, both R$^{B2}$ and R$^{C2}$ are absent.

In one embodiment, W$_2$ is absent,

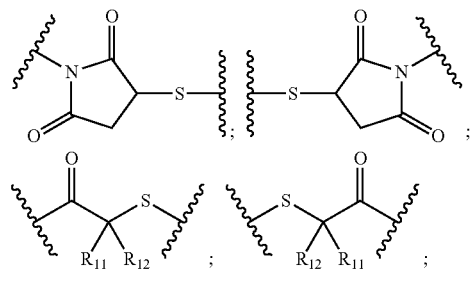

—S—S—, —NH—C(=O)— or —C(=O)—NH—.

In one embodiment, p2 and p2' are 0. In another embodiment, one of p2 and p2' is 0; and the other is an integer from 2 to 24.

In another embodiment, L$_2$ is represented by one of the following formulas:

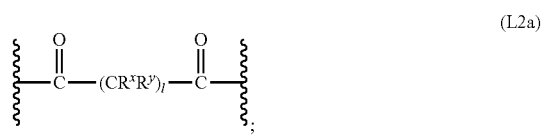
(L2a)

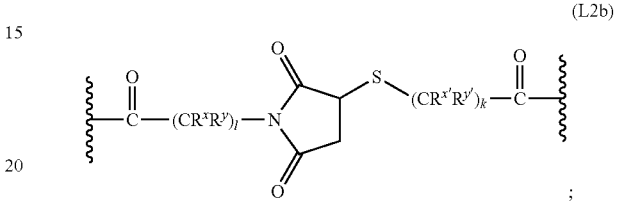
(L2b)

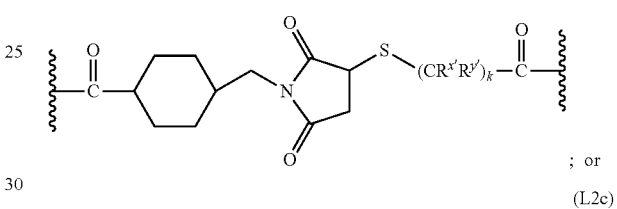
(L2b')

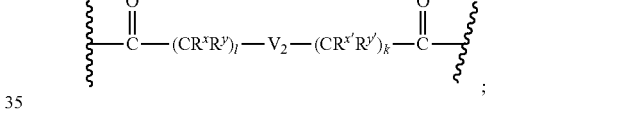
(L2c)

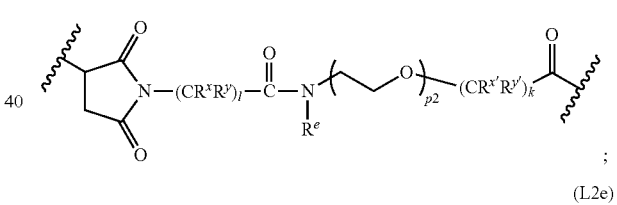
(L2d)

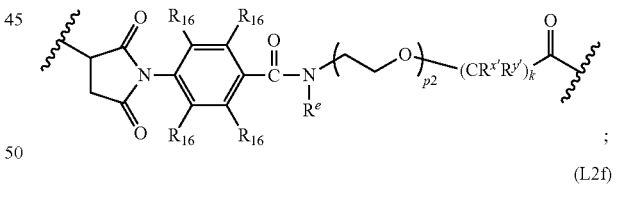
(L2e)

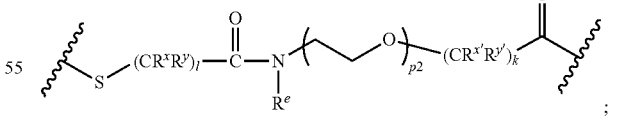
(L2f)

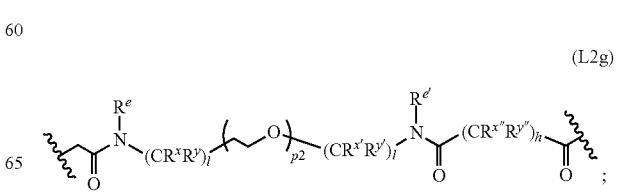
(L2g)

-continued

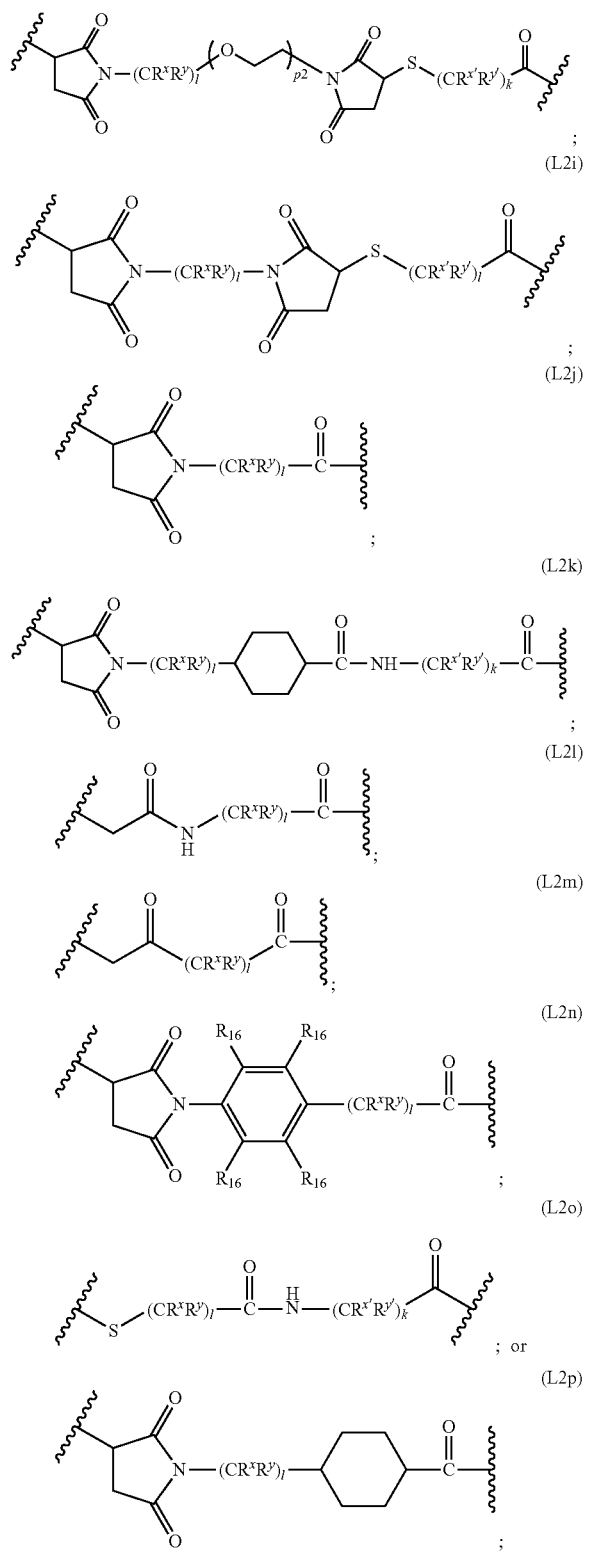

(L2h); (L2i); (L2j); (L2k); (L2l); (L2m); (L2n); (L2o); (L2p)

wherein:

$R^x$, $R^y$, $R^{x'}$, $R^{y'}$, $R^{x''}$ and $R^{y''}$, for each occurrence, are each independently H, —OH, halogen, —O—($C_{1-4}$ alkyl), —$SO_3^-$, —$NR_{40}R_{41}R_{42}^+$, or a $C_{1-4}$ alkyl optionally substituted with —OH, halogen, $SO_3^-$ or $NR_{40}R_{41}R_{42}^+$, wherein $R_{40}$, $R_{41}$ and $R_{42}$ are each independently H or a $C_{1-4}$ alkyl;

$R_{16}$, for each occurrence, is independently H, an alkyl, halogen, —OH, —O-alkyl, —$NO_2$, or —CN;

$V_2$ is —($CH_2$—$CH_2$—O)$_{p2}$— or —(O—$CH_2$—$CH_2$)$_{p2}$—;

l, k and h are each independently an integer from 0 to 10, and p2 is an integer from 1 to 24.

In one embodiment, $R^x$, $R^y$, $R^{x'}$, $R^{y'}$, $R^{x''}$ and $R^{y''}$ are H or $C_{1-4}$ alkyl. Preferably, $R^x$, $R^y$, $R^{x'}$, $R^{y'}$, $R^{x''}$ and $R^{y''}$ are H.

In one embodiment, $R_{16}$ is H or a $C_{1-4}$ alkyl. Preferably, $R_{16}$ is H.

In one embodiment, l and k are each independently an integer from 1 to 6.

In one embodiment, p2 is an integer from 2 to 24.

In one embodiment, $L_2$ is represented by the following structural formula:

-$J_{CB}$-$R^{A2}$—$V_2$—$W_2$—$R^{B2}$—$V_2{'}$—$R^{C2}$-$J_A$-;

wherein:

$J_{CB}$ is

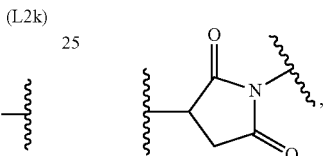

—C(=O)—, —S—, —$CH_2$—C(=O)—, or —$CH_2$—C(=O)—N($R^e$)—;

—$R^{A2}$—$V_2$—$W_2$—$R^{B2}$—$V_2{'}$—$R^{C2}$-$J_A$- is:

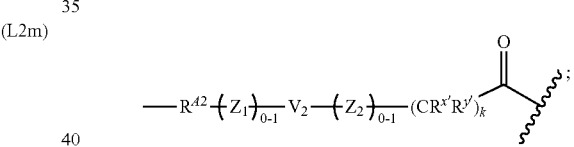

wherein $R^{A2}$ is —($CR^xR^y$)$_l$— or -Cy-($CR^xR^u$)$_l$—;

Cy is a cycloalkyl (e.g., cyclohexyl);

$V_2$ is —($CH_2$—$CH_2$—O)$_{p2}$— or —(O—$CH_2$—$CH_2$)$_{p2}$—;

$Z_1$ is —C(=O)—N($R^e$)—, —N($R^e$)—C(=O)—, or

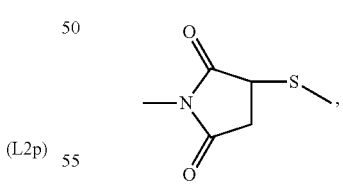

provided that $Z_1$—$V_2$ does not contain an N—O bond;

$Z_2$ is

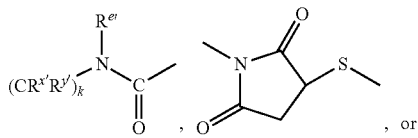

, or

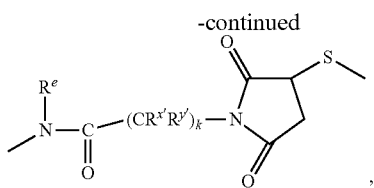

provided that V$_2$—Z$_2$ does not contain an O—N bond;
l is an integer from 0 to 10;
p2 is an integer from 0 to 200;
Z is —NH—.

In one embodiment, L$_2$ is represented by:

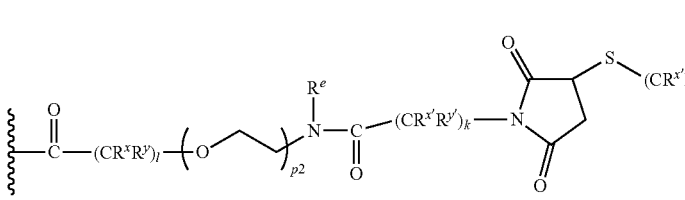
(L2d)

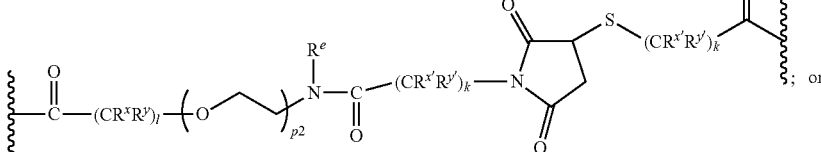
(L2r)

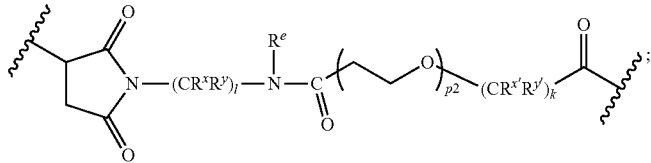
(L2s)

p2 is an integer from 0 to 200.

Values and Preferred Values for L$_1$':

L$_1$' is a spacer comprising a reactive moiety that can form a covalent bond with a cytotoxic agent.

In one embodiment, L$_1$' is represented by the following formula:

-J$_x$-R$^{A1}$—V$_1$—W$_1$—R$^{B1}$—V$_1$'—R$^{C1}$-J$_D$', wherein:

J$_D$' is —C(=O)—OH, —COE, —SH, —S—S(=O)—R$^d$, S—S(=O)$_2$R$^d$, —SSR$^d$,

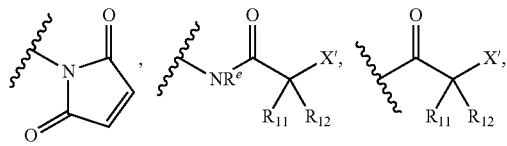

—OH, —O—C(=O)X', —S(=O)X'—, —SO$_2$X', —N(R$^e$)H, —N(R$^e$)—C(=O)—X', or —N(C(=O)R$^e$)C(=O)X', —C(=O)NH(C(=O)R$^e$), or —NH(C(=O)R$^e$), wherein COE represents a reactive ester; X' is a halogen; and R$^d$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl); and values and preferred values for the remainder of the variables are as described for L$_1$ above.

In another embodiment, L$_1$' is represented by the following formula:

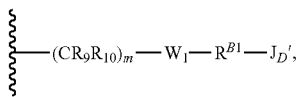

wherein J$_D$' is as described above, and values and preferred values for the remainder of the variables are as described for L$_1$ above.

In one embodiment, J$_D$' is —C(=O)OH, —COE or

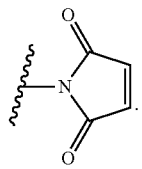

Values and Preferred Values for L2':

L$_2$' is absent or a spacer comprising a reactive moiety that can form a covalent bond with a cell-binding agent.

In one embodiment, L$_2$' is represented by the following formula:

J$_{CB}$'-R$^{A2}$—V$_2$—W$_2$—R$^{B2}$—V$_2$'—R$^{C2}$-J$_A$-, wherein:

J$_{CB}$' is —C(=O)OH, —COE, —N(R$^e$)—C(=O)—X', —O—C(=O)X', —C(=NH)X', —NR$^e$—C(=NH)X', —SH, —SSR$^d$, —NR$^e$H, —NH—NR$^e$H,

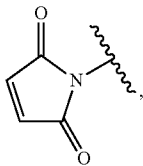

—C(=NR$^e$)X', —NR$^e$NH, X'—CR$_1$R$_2$—C(=O)—, or X'CR$_1$R$_2$—C(=O)—NR$^e$—, wherein COE is a reactive ester, X' is a halogen; and R$^d$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl); and values and preferred values for the remainder of the variables are as described above for L$_2$.

In another embodiment, L$_2$' is represented by a formula selected from the group consisting of formula (L2'a)-(L2'u) described below.

Cell-Binding Agent-Cytotoxic Compound Conjugates

The present invention provides cell-binding agent-cytotoxic compound conjugates comprising a cell-binding agent linked to one or more cytotoxic compounds of the present invention via a peptidase-labile linker.

In one embodiment, the cell-binding agent-cytotoxic compound conjugates are represented by structural formula (I):

$$CB-(L_2-A-Z-X-L_1-D)_q \quad (I)$$

or a pharmaceutically acceptable salt thereof, wherein the values of the variables are as described above for structural formula (I).

In one embodiment, the conjugates of structural formula (I) are as described above provided that when Z is —NH—, L$_1$ does not comprise one of the following moieties directly connected to X:

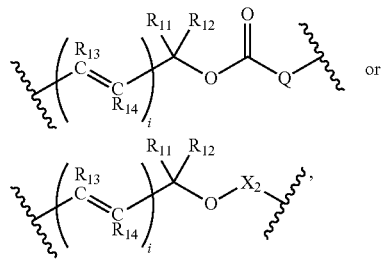

wherein i is 0 or an integer from 1 to 5; Q is —O—, —NR$_{15}$, S or —CR$_{11}$R$_{12}$—; X$_2$ is an aryl or a heteroaryl; and R$_{11}$, R$_{12}$, R$_{13}$, R$_{14}$ and R$_{15}$ are each independently H or an alkyl group. Preferably, i is 0 and R$_{11}$, R$_{12}$, R$_{13}$, R$_{14}$ and R$_{15}$ are all H.

In a 1$^{st}$ specific embodiment, for conjugates represented structural formula (I) or a pharmaceutically acceptable salt thereof described above:

L$_1$ is represented by the following formula:

-J$_x$-R$^{A1}$—V$_1$—W$_1$—R$^{B1}$—V$_1$'—R$^{C1}$-J$_D$-,

L$_2$ is represented by the following formula:

-J$_{CB}$-R$^{A2}$—V$_2$—W$_2$—R$^{B2}$—V$_2$'—R$^{C2}$-J$_A$-;

R$^{A1}$, R$^{B1}$ and R$^{C1}$ are each absent, an alkyl, an alkenyl, an alkynyl, a cycloalkyl, an aryl, a heteroaryl or a heterocyclyl, wherein the alkyl, alkenyl, alkynyl, cycloalkyl, aryl, heteroaryl, and heterocyclyl are optionally substituted;

J$_X$ and W$_1$ are each independently absent, —O—, —O—C(=O)—, —C(=O)—O—, —S—, —SO—, —SO$_2$—, —(CR$_{11}$R$_{12}$)—S—, —(CR$_{11}$R$_{12}$)—O—, —(CR$_{11}$R$_{12}$)—NR$^c$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —SS—, —C(=O)—,

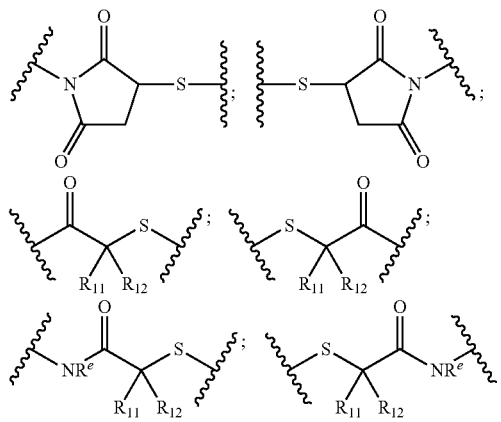

an amino acid, or a peptide having 2 to 8 amino acids, provided that when Z is —NH—, J$_x$ and V$_1$ are absent and R$^{A1}$ is —CR$_{11}$R$_{12}$—, W$_1$ is not —O—C(=O)—;

J$_D$ is absent, —C(=O)—, —S—,

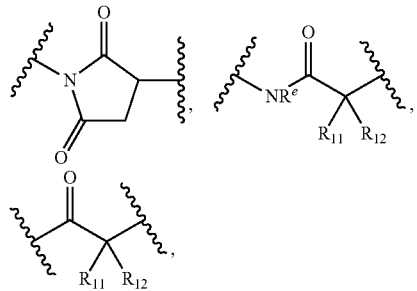

—O—, —O—C(=O)—, —C(=O)—O—, —SO—, —SO$_2$—, —O—(C=O)—, —N(R$^e$)—, —N(R$^e$)—C(=O)—, or —N(C(=O)R$^e$)C(=O)—, or —N(C(=O)R$^e$)—;

V$_1$ and V$_1$' are each independently —(O—CH$_2$—CH$_2$)$_{p1}$—, —(CH$_2$—CH$_2$—O)$_{p1}$—, —(NR$^m$—CH$_2$—CH$_2$)$_{p1'}$— or —(CH$_2$—CH$_2$—NR$^m$)$_{p1'}$—;

R$^e$ is H, an alkyl, an alkenyl, an alkynyl, or —(CH$_2$—CH$_2$—O)$_{n'}$—R$^k$;

R$^k$ and R$^m$ are each independently H or an alkyl;

n' is an integer from 1 to 24;

p1 is 0 or an integer from 1 to 1000;

p1' is 0 or an integer from 1 to 10;

R$^{A2}$, R$^{B2}$ and R$^{C2}$ are each independently absent, an alkyl, an alkenyl, an alkynyl, a cycloalkyl, an aryl, a heteroaryl, a heterocyclyl, a cycloalkylalkyl, an arylalkyl, a heteroarylalkyl, or a heterocyclylalkyl, wherein the alkyl, alkenyl, alkynyl, cycloalkyl, aryl, heteroaryl, heterocyclyl, cycloalkylalkyl, arylalkyl, heteroarylalkyl, and heterocyclylalkyl are optionally substituted;

$V_2$ and $V_2'$ are each independently —(O—CH$_2$—CH$_2$)$_{p2}$—, —(CH$_2$—CH$_2$—O)$_{p2}$—, —(NR$^m$—CH$_2$—CH$_2$)$_{p2'}$— or —(CH$_2$—CH$_2$—NR$^m$)$_{p2'}$—;

$W_2$ is absent, —O—, —O—C(=O)—, —C(=O)—O—, —S—, —SO—, —SO$_2$—, —CR$_{11}$R$_{12}$—S—, —CR$_{11}$R$_{12}$—O—, —CR$_{11}$R$_{12}$—NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —(O—CH$_2$—CH$_2$)$_{n'}$—, —SS—, —C(=O)—, an amino acid, a peptide having 2 to 8 amino acids,

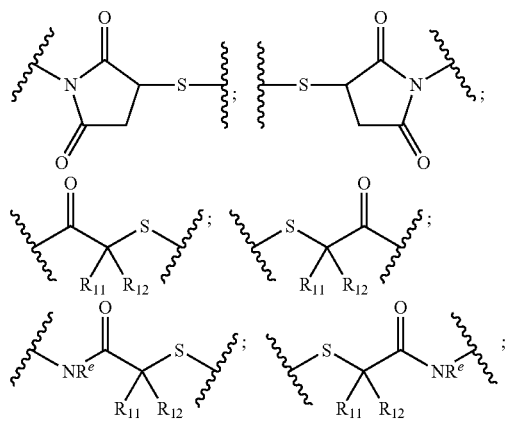

$J_{CB}$ is —C(=O)—, —C(=O)—NR$^e$—, —C(=O)—O—, —C(=NH)—, —C(=NH)—NR$^e$—, —S—, —NR$^e$—, —NH—NR$^e$—,

—C(=NR$^e$)—, =NNR$^e$—, —CH$_2$—C(=O)—, or —CH$_2$—C(=O)—NR$^e$—;

$J_A$ is —NR$^e$—, —C(=O)—, =N—, —NR$^e$—C(=O)—, —O—C(=O)—, —SO$_2$—, —S—

$R_{11}$ and $R_{12}$ are each independently H or an alkyl;
p2 is 0 or an integer from 1 to 1000;
p2' is 0 or an integer from 1 to 10; and, A is peptide cleavable by a peptidase; and values and preferred values for the remainder of the variables are as described for structural formula (I) above.

In a preferred embodiment, D is a maytansinoid; and values and preferred values for the remainder of the variables are as described in the 1$^{st}$ specific embodiment.

In another preferred embodiment, Z is —NH—; and values and preferred values for the remainder of the variables are as described in the 1$^{st}$ specific embodiment. More preferably, D is a maytansinoid.

In another preferred embodiment, $W_2$ is absent,

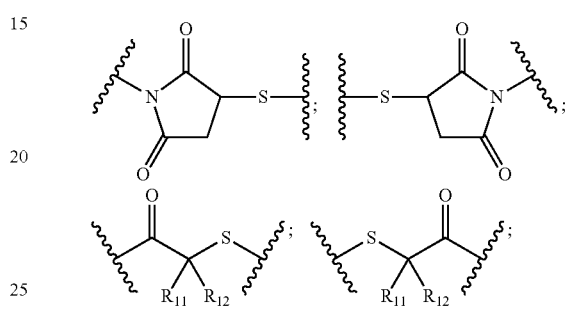

—S—S—, —NH—C(=O)— or —C(=O)—NH—; and values and preferred values for the remainder of the variables are as described in the 1$^{st}$ specific embodiment. More preferably, Z is —NH—; and D is a maytansinoid.

In another preferred embodiment, $V_2$ and $V_2'$ are both absent (i.e., p2 and p2' are both 0); and values and preferred values for the remainder of the variables is as described above in the 1$^{st}$ specific embodiment. More preferably, $W_2$ is absent,

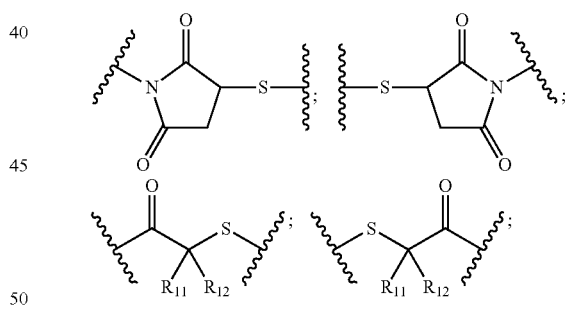

—S—S—, —NH—C(=O)— or —C(=O)—NH—. Even more preferably, Z is —NH— and D is a maytansinoid.

In another preferred embodiment, $R^{42}$ is an alkyl, and values and preferred values for the remainder of the variables is as described above in the 1$^{st}$ specific embodiment. More preferably, $W_2$ is absent,

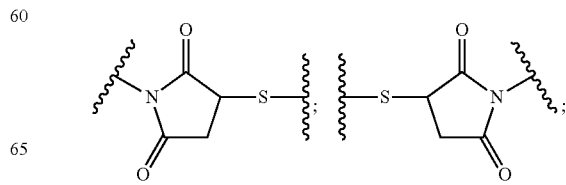

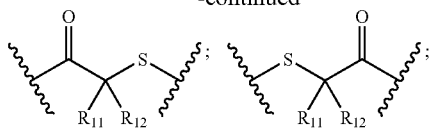

—S—S—, —NH—C(=O)— or —C(=O)—NH—. Even more preferably, Z is —NH— and D is a maytansinoid.

In another preferred embodiment, one of $R^{B2}$ and $R^{C2}$ is absent, and the other is an alkyl; and values and preferred values for the remainder of the variables is as described above in the 1$^{st}$ specific embodiment. More preferably, $W_2$ is absent,

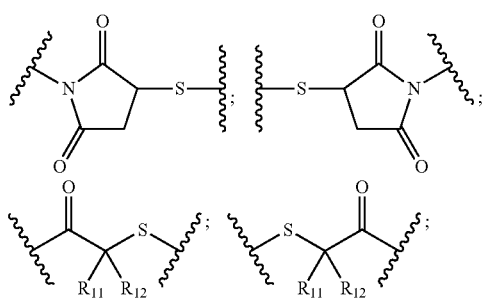

—S—S—, —NH—C(=O)— or —C(=O)—NH—. Even more preferably, Z is —NH— and D is a maytansinoid.

In another preferred embodiment, $R^{B2}$ and $R^{C2}$ are both absent; and values and preferred values for the remainder of the variables is as described above in the 1$^{st}$ specific embodiment. More preferably, $W_2$ is absent,

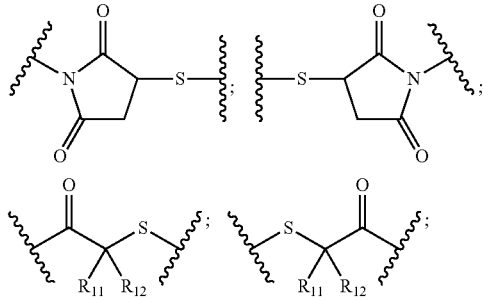

—S—S—, —NH—C(=O)— or —C(=O)—NH—. Even more preferably, Z is —NH— and D is a maytansinoid.

In a 2$^{nd}$ specific embodiment, for the conjugates represented by structural formula (I):

$L_2$ is represented by one of the following structural formulas:

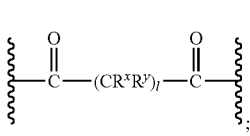 (L2a)

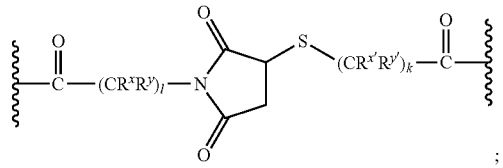 (L2b)

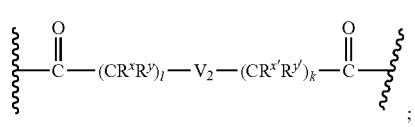 (L2b')

(L2c)

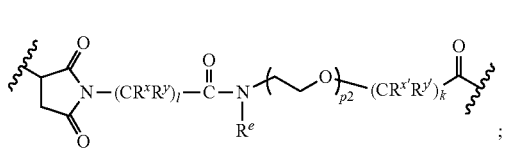 (L2d)

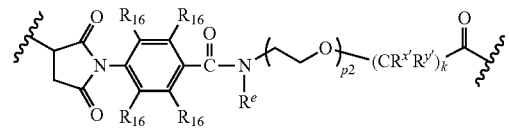 (L2e)

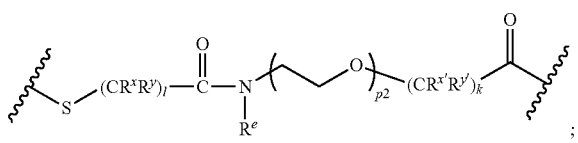 (L2f)

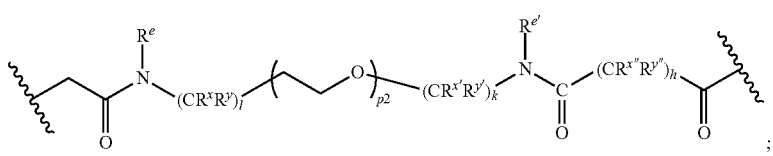 (L2g)

-continued

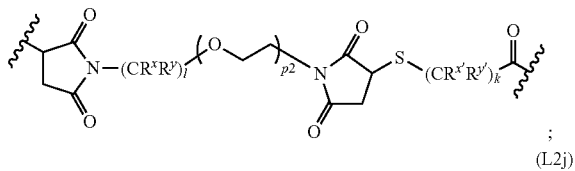

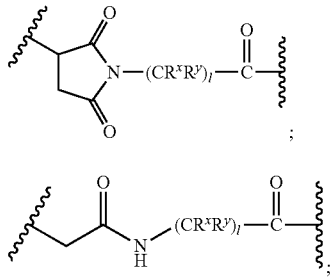

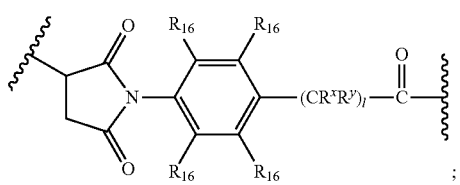

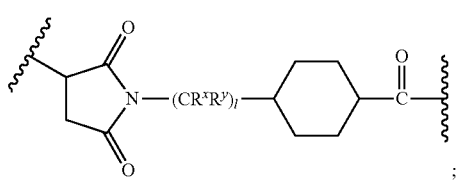

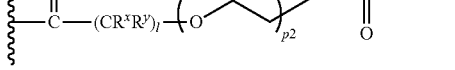

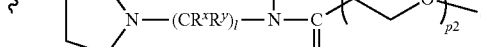

wherein:

$R^x$, $R^y$, $R^{x'}$, $R^{y'}$, $X'''$ and $R^{y'''}$, for each occurrence, are each independently H, —OH, halogen, —O—($C_{1-4}$ alkyl), —$SO_3^-$, —$NR_{40}R_{41}R_{42}^+$, or a $C_{1-4}$ alkyl optionally substituted with —OH, halogen, $SO_3^-$ or $NR_{40}R_{41}R_{42}^+$, wherein $R_{40}$, $R_{41}$ and $R_{42}$ are each independently H or a $C_{1-4}$ alkyl;

$R_{16}$, for each occurrence, is independently H, an alkyl, halogen, —OH, —O-alkyl, —$NO_2$, or —CN;

$V_2$ is —($CH_2$—$CH_2$—O)$_{p2}$— or —(O—$CH_2$—$CH_2$)$_{p2}$—;

l, k and h are each independently an integer from 1 to 10;

Z is —NH—;

A is peptide cleavable by a peptidase; and values and preferred values for the remainder of the variables are as described above in the 1$^{st}$ specific embodiment.

In a preferred embodiment, D is a maytansinoid; and values and preferred values for the remainder of the variables are as described in the 2$^{nd}$ specific embodiment.

In another preferred embodiment, for formulas (L2a)-(L2c), (L2r), and (L2s), $R^x$, $R^y$, $R^{x'}$ and $R^{y'}$ are all H; and for structural formulas (L2d)-(L2p), $R^x$, $R^y$, $R^{x'}$, $R^{y'}$, $R^{x'''}$ and $R^{y'''}$ are all H.

In another preferred embodiment, for formulas (L2a)-(L2c), (L2r), and (L2s), $R^x$, $R^y$, $R^{x'}$ and $R^{y'}$ are all H; p2 is an integer from 2 to 24; and l and k are each independently an integer from 1 to 6. For formulas (L2d)-(L2p), $R^x$, $R^y$, $R^{x'}$, $R^{y'}$, $R^{x'''}$ and $R^{y'''}$ are all H; $R_{16}$ is H; p2 is an integer from 2 to 24; l, k and h are each independently an integer from 1 to 6.

In a related specific embodiment, for the conjugates represented by structural formula (I), $L_2$ is represented by the following structural formula:

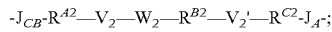

wherein:

$J_{CB}$ is

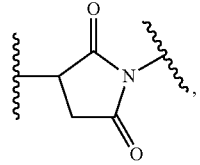 [SMILES: *C1CC(=O)N(*)C1=O]

$—C(=O)—$, $—S—$, $—CH_2—C(=O)—$, or $—CH_2—C(=O)—N(R^e)—$;

$—R^{A2}—V_2—W_2—R^{B2}—V_2{}'—R^{C2}-J_A-$ is:

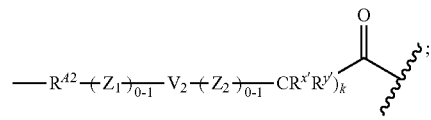

wherein
$R^{A2}$ is $—(CR^xR^y)_l—$ or $-Cy-(CR^xR^y)_l—$;
Cy is a cycloalkyl (e.g., cyclohexyl);
$V_2$ is $—(CH_2—CH_2—O)_{p2}—$ or $—(O—CH_2—CH_2)_{p2}—$;

$Z_1$ is $—C(=O)—N(R^e)—$, $—N(R^e)—C(=O)—$, or

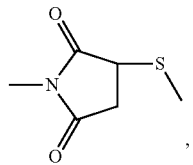

provided that $Z_1—V_2$ does not contain an N—O bond;
$Z_2$ is

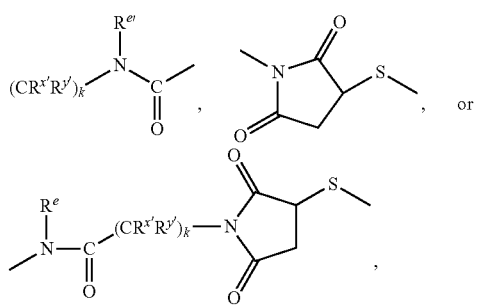

provided that $V_2—Z_2$ does not contain an O—N bond;
l is an integer from 0 to 10;
p2 is an integer from 0 to 200; and,
Z is $—NH—$.

In one embodiment, $L_2$ is represented by:

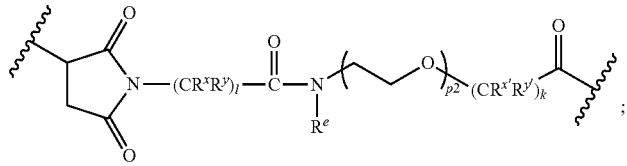

(L2d)

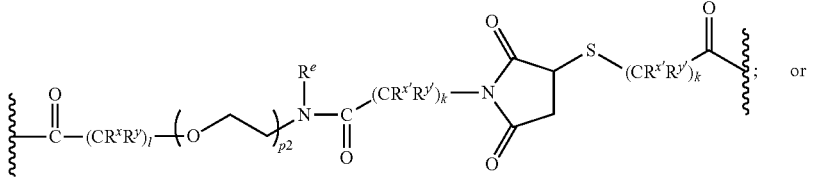

(L2r)

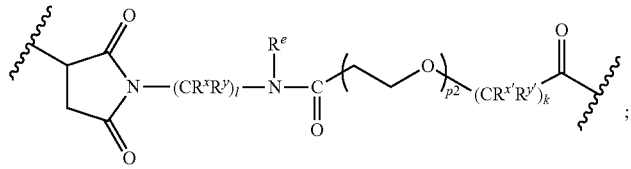

(L2s)

p2 is an integer from 0 to 200.

In a 3rd specific embodiment, for the conjugates represented by structural formula (I), $L_1$ is represented by the following formula:

$$—(CR_9R_{10})_m—W_1—R^{B1}-J_D-\quad (L1)$$

wherein:

$R_9$ and $R_{10}$ are each independently H or a $C_{1-4}$ alkyl;

m is an integer from 1 to 10;

$W_1$ is -absent, —NH—C(=O)—, —C(=O)—NH—, —C(=O)—O— or —O—C(=O)—, provided when Z is —NH— and m is 1, then $W_1$ is not —O—C(=O)—;

$R^{B1}$ is absent or a $C_{1-10}$ alkyl; and $J_D$ is absent, —C(=O)—,

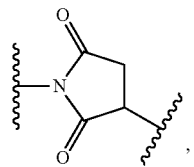 [SMILES: *C1CC(=O)N(*)C1=O],

—NH—C(=O)—CH$_2$—, or —S—;

Z is —NH—;

A is a peptide cleavable by a peptidase; and values and preferred values for the remainder of the variables are as described in the 1st specific embodiment.

In another preferred embodiment, $J_D$ is absent, —C(=O)— or

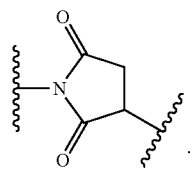 [SMILES: *C1CC(=O)N(*)C1=O].

In another preferred embodiment, $R_9$ and $R_{10}$ are both H; and m is 1, 2 or 3.

In another preferred embodiment, $W_1$ is absent or —NH—C(=O)— and $R^{B1}$ is absent or —(CH$_2$)$_{m'}$—, wherein m' is 1, 2, or 3.

In yet another preferred embodiment, D is a maytansinoid.

In a 4th specific embodiment, the conjugates for the present invention is represented by structural formula (I), wherein:

$L_1$ is represented by formula (L1) described in the 3rd specific embodiment;

$L_2$ is represented by one of the structural formulas (L2a)-(L2s) described in the 2nd specific embodiment;

Z is —NH—;

A is a peptide cleavable by a protease; and

D is a maytansinoid; and values and preferred values for the remainder of the variables are as described above for structural formula (I) in the 2nd and 3rd specific embodiments.

In a 5th specific embodiment, for conjugates represented by formula (I):

$L_2$ is represented by any one of the structural formulas (L2a)-(L2s) described in the 2nd specific embodiment;

A is a peptide cleavable by a protease;

—Z—X-$L_1$-D is represented by the one of the following structural formulas:

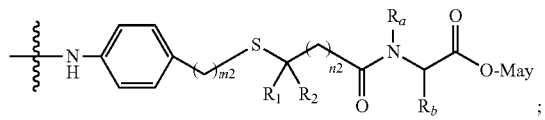

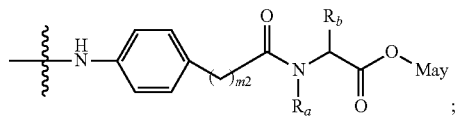

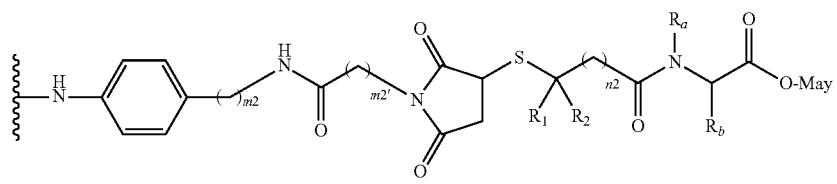

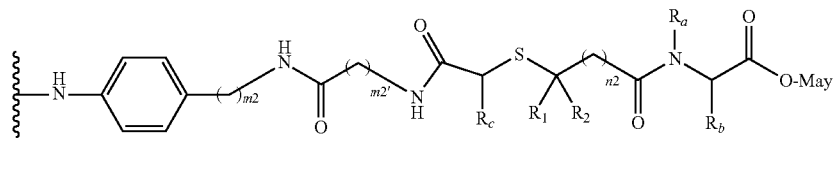

-continued

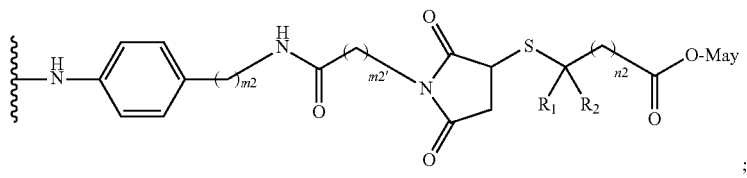
(L1e)

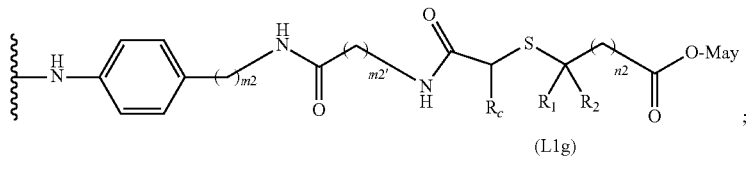
(L1f)

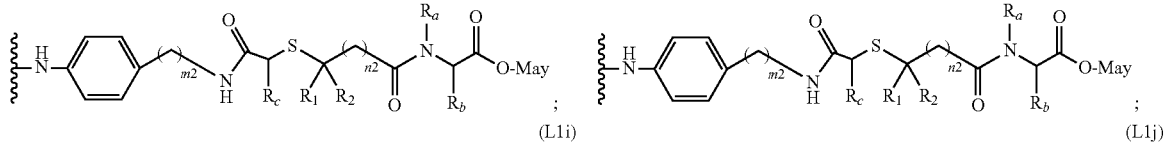
(L1g) ; (L1h)

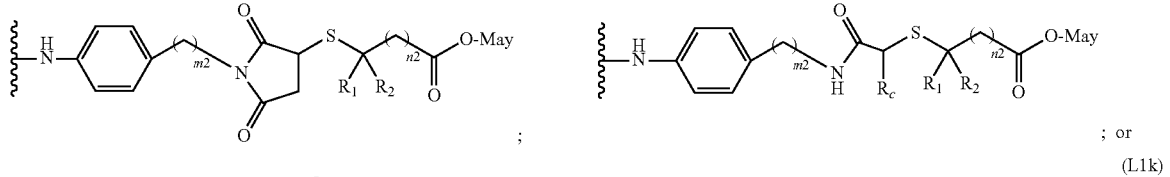
(L1i) ; (L1j)

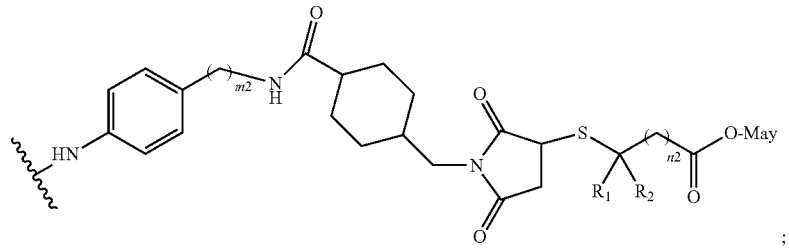
; or (L1k)

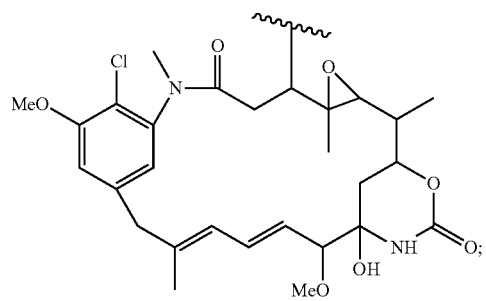 [SMILES: *C1CC(=O)N(C)c2cc(cc(OC)c2Cl)C/C(C)=C/C=C/C(OC)C2(O)CC(OC(=O)N2)C(C)C2OC12C]
;

wherein May is represented by the following structural formula:

$R_1$, $R_2$, $R_a$, $R_b$ and $R_c$ are each independently H or a $C_{1-4}$ alkyl; and m2, m2' and n2 are each independently an integer from 1 to 10; and values and preferred values for the remainder of the variables are as described above for structural formula (I).

In a preferred embodiment, for structural formula (I) described in the $1^{st}$, $2^{nd}$, $3^{rd}$, $4^{th}$ or $5^{th}$ embodiment, including any related specific embodiment, A is a peptide cleavable by a lysosomal protease. In another preferred embodiment, A is a peptide cleavable by a protease expressed in tumor tissue.

In a more preferred embodiment, for structural formula (I) described in the $1^{st}$, $2^{nd}$, $3^{rd}$, $4^{th}$ or $5^{th}$ embodiment, including any related specific embodiment, A is a peptide having an amino acid that is covalent linked with —Z—X-$L_1$-D selected from the group consisting of Ala, Arg, Asn, Asp, Cit, Cys, selino-Cys, Gln, Glu, Gly, His, Ile, Leu, Lys, Met, Phe, Pro, Ser, Thr, Trp, Tyr and Val, each independently as L or D isomer.

In yet another more preferred embodiment, for structural formula (I) described in the $1^{st}$, $2^{nd}$, $3^{rd}$, $4^{th}$ or $5^{th}$ embodiment, including any related specific embodiment, A is selected from the group consisting of Val-Cit, Val-Lys, Phe-Lys, Lys-Lys, Ala-Lys, Phe-Cit, Leu-Cit, Lle-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), β-Ala-Leu-Ala-Leu (SEQ ID NO: 2) and Gly-Phe-Leu-Gly (SEQ ID NO: 3), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, D-Ala-Ala, Ala-D-Ala, and D-Ala-D-Ala.

In an even more preferred embodiment, for structural formula (I) described in the $1^{st}$, $2^{nd}$, $3^{rd}$, $4^{th}$ or $5^{th}$ embodiment, including any related specific embodiment, A is Val-Cit, Val-Lys, Val-D-Cit or Val-D-Lys.

In another preferred embodiment, for structural formula (I) described in the 1st, 2nd, 3rd or 4th embodiment, including any related specific embodiment, D is represented by structural formula (A) or (B):

(A)

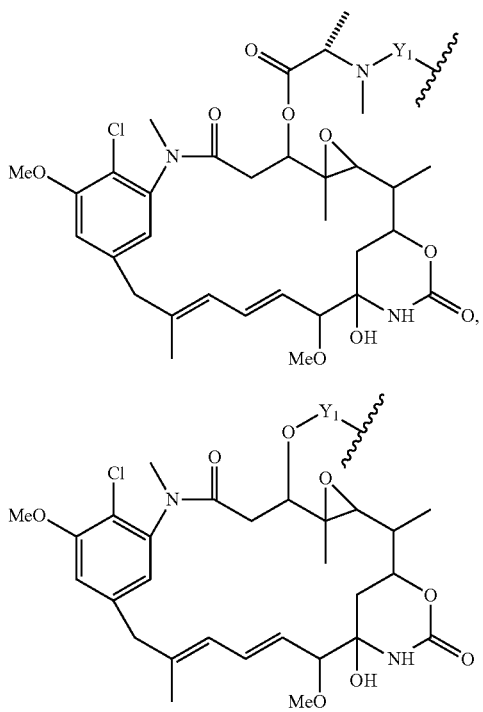

(B)

wherein:

Y₁ is absent or —C(=O)(CR₇R₈)$_{l1}$(CR₅R₆)$_{m1}$(CR₃R₄)$_{n1}$CR₁R₂S—,

R₁, R₂, R₃, R₄, R₅, R₆, R₇ and R₈ are each independently H, an alkyl, an alkenyl, a cycloalkyl, a heteroaryl, a heterocyclyl, or an aryl; and l1, m1 and n1 are each independently 0 or an integer from 1 to 5.

More preferably, for structural formula (I) described in the 1st, 2nd, 3rd or 4th specific embodiment, including any related specific embodiment, D is represented by one of the following structural formulas:

(A1)

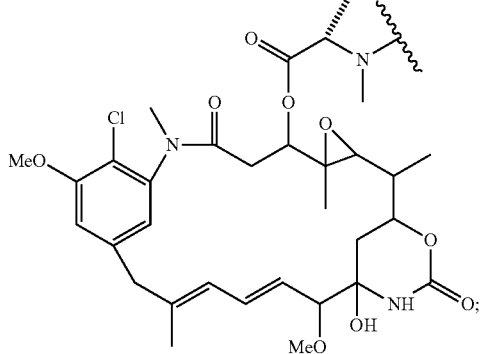

(A2)

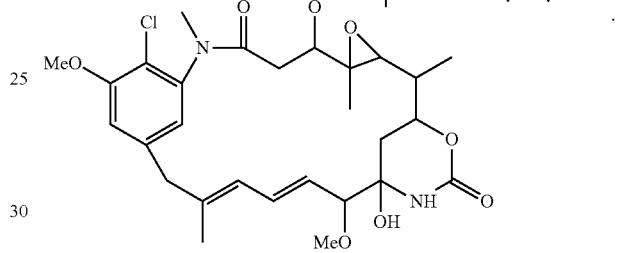

; or (A3)

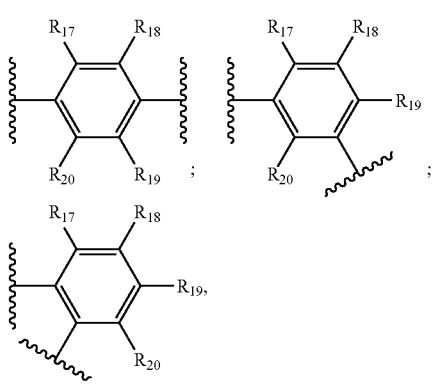

In another preferred embodiment, for structural formula (I), X is an optionally substituted phenyl; and values and preferred values for the remainder of the variables are as described above in the 1st, 2nd, 3rd, 4th or 5th specific embodiment. More preferably, X is represented by any one of the following structural formulas:

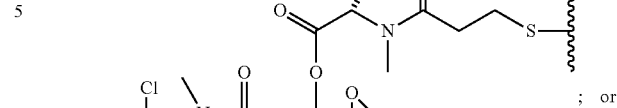

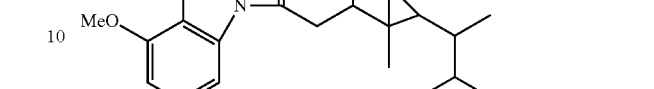

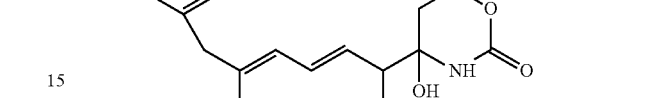

wherein R₁₇, R₁₈, R₁₉ and R₂₀ each are independently H, an alkyl, H, an alkyl, halogen, —OH, —O-alkyl, —NO₂, or —CN. Preferably, R₁₇, R₁₈, R₁₉ and R₂₀ are all H.

In another preferred embodiment, for structural formula (I), X is optionally substituted six-membered heteroaryl selected from the group consisting of pyridine, pyridazine, pyrimidine, pyrazine, a triazine, and tetrazine, wherein the heteroaryl is connected to the —NH group and -L₁ group at the carbon atoms of the heterocycle; and values and preferred values for the remainder of the variables are as described above in the 1st, 2nd, 3rd, 4th or 5th specific embodiment.

In another preferred embodiment, for structural formula (I), X is an optionally substituted five-membered heteroaryl; and preferred values for the remainder of the variables are as described above in the 1$^{st}$, 2$^{nd}$, 3$^{rd}$, 4$^{th}$ or 5$^{th}$ specific embodiment. More preferably, X is selected from the group consisting of:

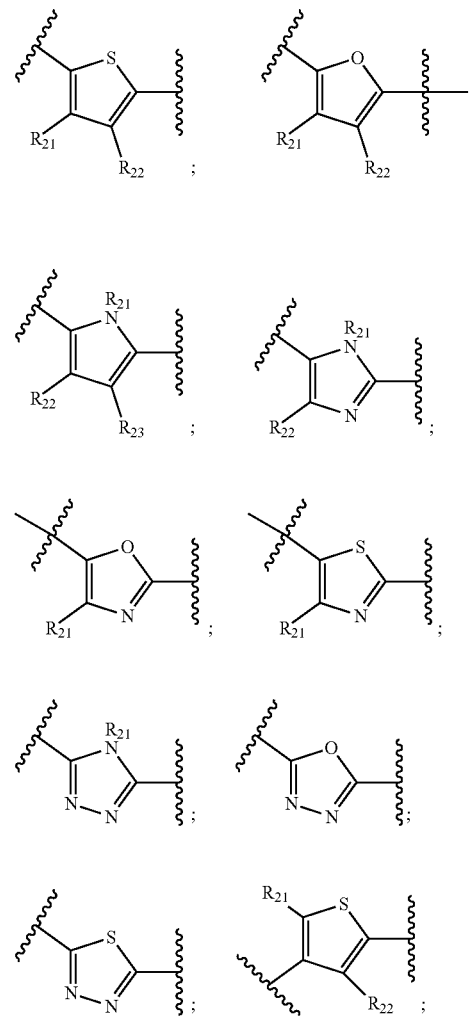

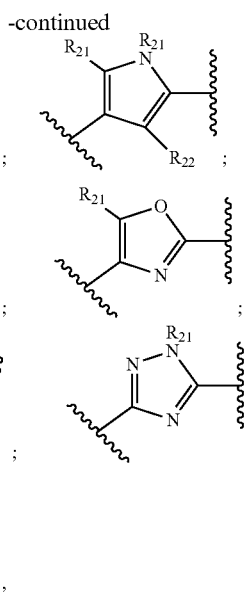

wherein $R_{21}$, $R_{22}$ and $R_{23}$ are each independently H or an alkyl. Preferably, $R_{21}$, $R_{22}$ and $R_{23}$ are all H.

In a 6$^{th}$ specific embodiment, for conjugates represented by structural formula (I):

$L_2$ is represented by any one of the structural formulas (L2a)-(L2s) described in the 2$^{nd}$ specific embodiment;

A is Val-Cit, Val-Lys, Val-D-Cit or Val-D-Lys;

—Z—X-L$_1$-D is represented by the one of the following structural formulas (L1a)-(L1k) described in the 3$^{rd}$ specific embodiment.

In a preferred embodiment, $R_a$ and $R_b$ are both methyl; $R_c$ is H; and the remainder of the variables is as described above in the 6$^{th}$ specific embodiment. More preferably, m2 and m2' are each independently an integer from 1 to 3.

In another preferred embodiment, $R_a$ and $R_b$ are both methyl; $R_c$ is H; $R_1$ and $R_2$ are both H and n is 1; and the remainder of the variables is as described above in the 6$^{th}$ specific embodiment. More preferably, m2 and m2' are each independently an integer from 1 to 3.

In one embodiment, the cell-binding agent-cytotoxic agent conjugates are represented by the following structural formulas:

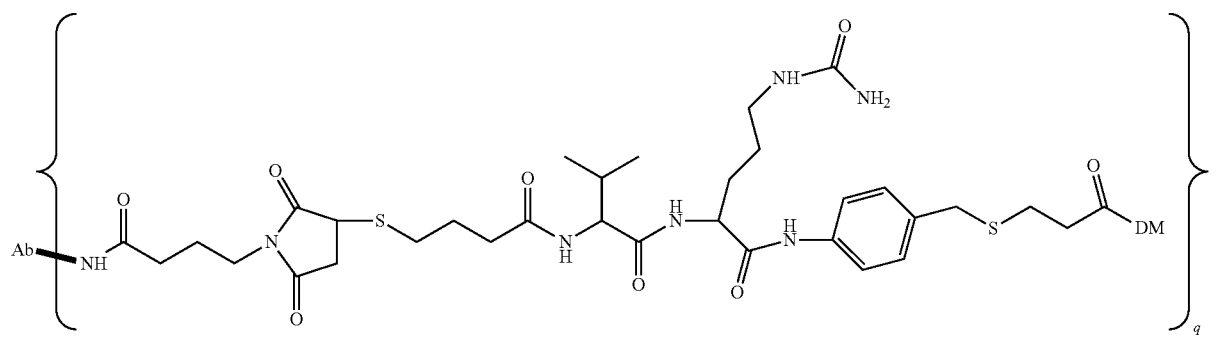

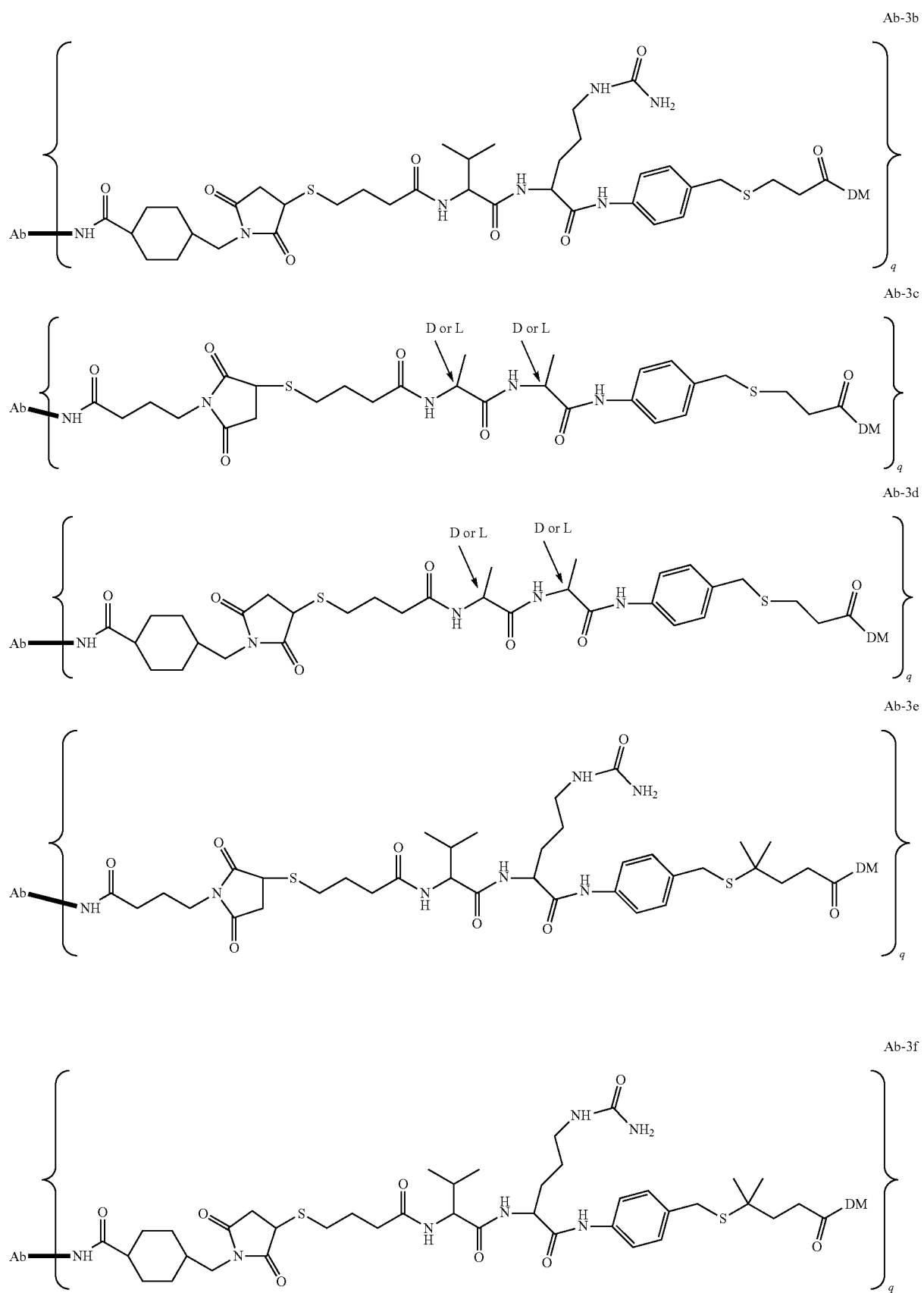

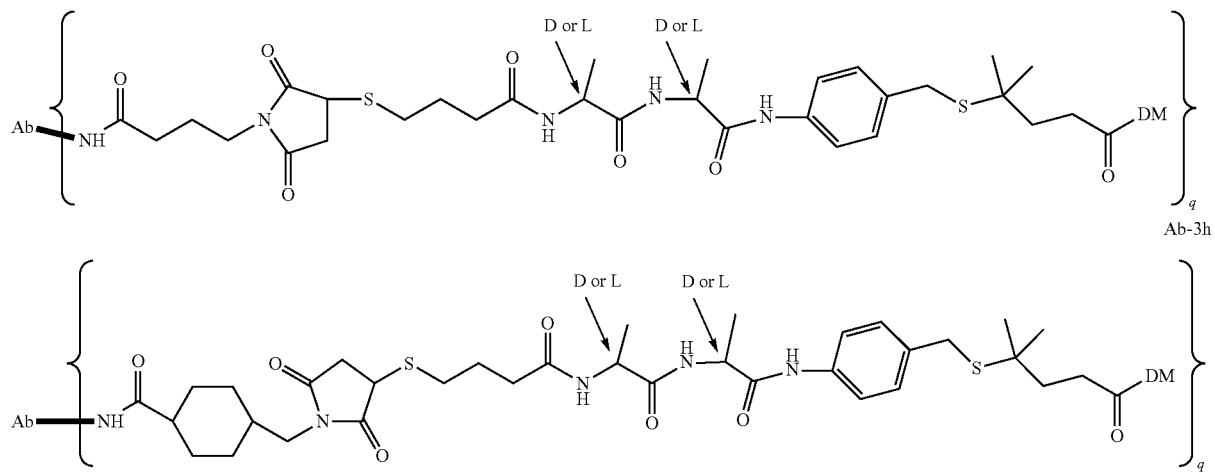

wherein q is an integer from 1-20, from 1-10, from 2-6, from 3-5. In certain embodiments, each conjugated cell binding agent contains on average 3.5, 3-5, 2-6, 1-10, or 1-20 cytotoxic agent molecules.

In one embodiment, the cell-binding agent-cytotoxic agent conjugates of the present invention can be cleaved upon entering cells and/or inside the cells to release the cytotoxic agent, a derivative or a metabolite therefore. The cleavable conjugates may have superior efficacy than the cytotoxic agent due to its ability to deliver the cytotoxic agent to the desired cells (i.e., the tumor cells). In one embodiment, the metabolite compounds can be a compound represented by structural formula (II) described below.

Cytotoxic Compounds

The present invention is also directed to a cytotoxic compound represented by structural formula (II):

$$Z'-X-L_1-D \qquad (II),$$

or a salt (e.g., a pharmaceutically acceptable salt) thereof, wherein values and preferred values are as described above.

In a 7$^{th}$ specific embodiment, for the compound of structural (II), $L_1$ is represented by the following formula:

$$-J_X-R^{A1}-V_1-W_1-R^{B1}-V_1'-R^{C1}-J_D-,$$

wherein:

$R^{A1}$, $R^{B1}$ and $R^{C1}$ are each absent, an alkyl, an alkenyl, an alkynyl, a cycloalkyl, an aryl, a heteroaryl or a heterocyclyl, wherein the alkyl, alkenyl, alkynyl, cycloalkyl, aryl, heteroaryl, and heterocyclyl are optionally substituted;

$J_X$ and $W_1$ are each independently absent, —O—, —O—C(=O)—, —C(=O)—O—, —S—, —SO—, —SO$_2$—, —CR$_{11}$R$_{12}$—S—, —CR$_{11}$R$_{12}$—O—, —CR$_{11}$R$_{12}$NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —SS—, —C(=O)—,

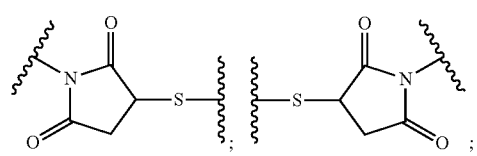

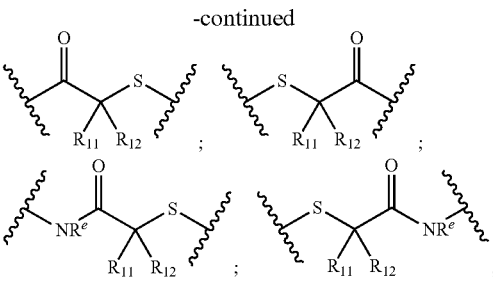

an amino acid, or a peptide having 2 to 8 amino acids, provided that when Z' is NH$_2$, J, and V$_1$ are absent and R$^{41}$ is —CR$_{11}$R$_{12}$—, W$_1$ is not —O—C(=O)—;

$J_D$ is absent, —C(=O)—, —S—,

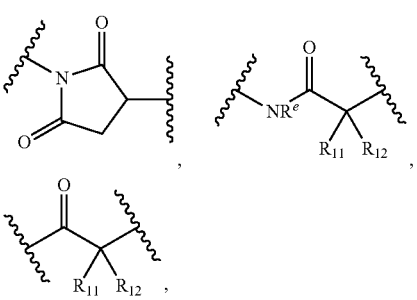

—O—, —O—C(=O)—, —C(=O)—O—, —SO—, —SO$_2$—, —O—(C=O)—, —N(R$^e$)—, —N(R$^e$)—C(=O)—, or —N(C(=O)R$^e$)C(=O)—, or —N(C(=O)R$^e$)—;

V$_1$ and V$_1'$ are each independently —(O—CH$_2$—CH$_2$)$_{p1}$—, —(CH$_2$—CH$_2$—O)$_{p1}$—, —(NR$^m$—CH$_2$—CH$_2$)$_{p1}$— or —(CH$_2$—CH$_2$—NR$^m$)$_{p1}$—;

R$^e$ is H, an alkyl, an alkenyl, an alkynyl, or —(CH$_2$—CH$_2$—O)$_{n'}$—R$^k$;

R$^k$ and R$^m$ are each independently H or an alkyl;

n' is an integer from 1 to 24;

p1 is 0 or an integer from 1 to 1000;

p1' is 0 or an integer from 1 to 10; and values and preferred values for the remainder of the variables are as described above for formula (II).

In an 8th specific embodiment, for compound of structural formula (II), Z' is —NH₂ and the remainder of the variables is as described in the 7th specific embodiment.

In a 9th specific embodiment, for compound of structural formula (II), L₁ is represented by the following formula:

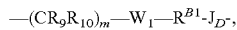

wherein:
R₉ and R₁₀ are each independently H or a C₁₋₄ alkyl;
m is an integer from 1 to 10;
W₁ is absent, —NH—C(=O)—, —C(=O)—NH—, —C(=O)—O— or —O—C(=O)—, provided when Z' is —NH₂, m is 1, W₁ is not —O—C(=O)—;
R^{B1} is absent or a C₁₋₁₀ alkyl; and
J_D is absent, —C(=O)—,

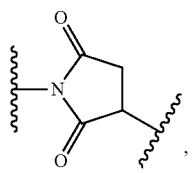 [SMILES: *C1CC(=O)N(*)C1=O]

—NH—C(=O)—CH₂—, or —S—; and values and preferred values are as described above for structural formula (II).

In a preferred embodiment, J_D is absent, —C(=O)— or

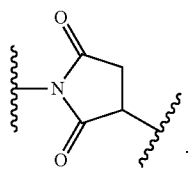 [SMILES: *C1CC(=O)N(*)C1=O]

In another preferred embodiment, R₉ and R₁₀ are both H; and m is 1, 2 or 3.

In another preferred embodiment, W₁ is absent or —NH—C(=O)— and R^{B1} is absent or —(CH₂)_{m'}—, wherein m' is 1, 2, or 3.

In a 10th specific embodiment, Z' is —NH₂ and the remainder of the variables is as described in the 9th specific embodiment.

In a 11th specific embodiment, for compound of structural formula (II), D is represented by structural formula (A) or (B):

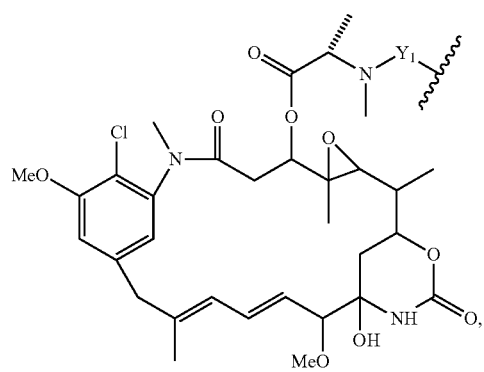

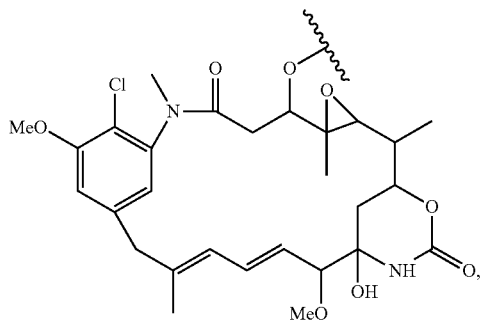

wherein:
Y₁ is absent or —C(=O)(CR₇R₈)_{l1}(CR₅R₆)_{m1}(CR₃R₄)_{n1}CR₁R₂S—,
R₁, R₂, R₃, R₄, R₅, R₆, R₇ and R₈ are each independently H, an alkyl, an alkenyl, a cycloalkyl, a heteroaryl, a heterocyclyl, or an aryl; and
l1, m1 and n1 are each independently 0 or an integer from 1 to 5; and values and preferred values for the remainder of the variables are as described above in the 7th, 8th, 9th, or 10th specific embodiment.

In a preferred embodiment, for structural formula (II), X is an optionally substituted phenyl; and values and preferred values for the remainder of the variables are as described above in the 7th, 8th, 9th, 10th or 11th specific embodiment. More preferably, X is represented by any one of the following structural formulas:

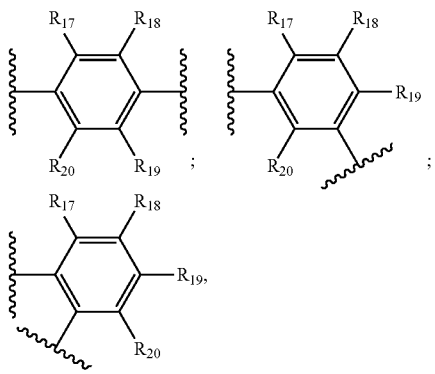

wherein R₁₇, R₁₈, R₁₉ and R₂₀ each are independently H, an alkyl, H, an alkyl, halogen, —OH, —O-alkyl, —C(=O)R₃₀, —C(=O)R₃₀, —NO₂, or —CN, wherein R₃₀ is H or an alkyl, preferably H or a C₁₋₄ alkyl. Preferably, R₁₇, R₁₈, R₁₉ and R₂₀ are all H.

In another preferred embodiment, for structural formula (II), X is optionally substituted six-membered heteroaryl selected from the group consisting of pyridine, pyridazine, pyrimidine, pyrazine, a triazine, and tetrazine, wherein the heteroaryl is connected to the —NH group and -L₁ group at carbon atoms of the heteroaryl; and values and preferred values for the remainder of the variables are as described above in the 7th, 8th, 9th, 10th or 11th specific embodiment.

In another preferred embodiment, for structural formula (II), X is an optionally substituted five-membered heteroaryl; and preferred values for the remainder of the variables are as described above in the 7th, 8th, 9th, 10th or 11th specific embodiment. More preferably, X is selected from the group consisting of:

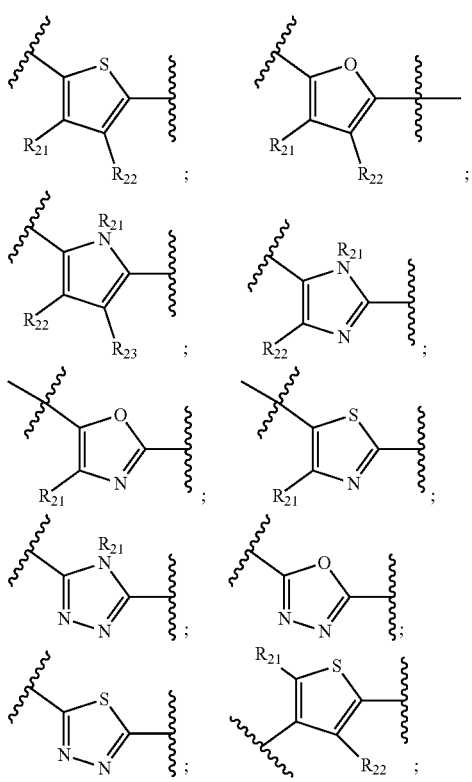
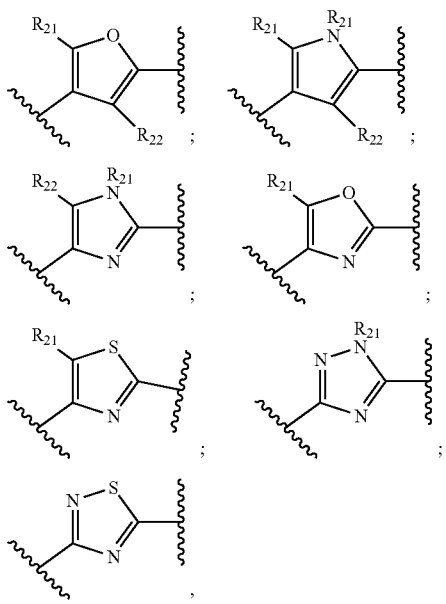
wherein $R_{21}$, $R_{22}$ and $R_{23}$ are each independently H or an alkyl. Preferably, $R_{21}$, $R_{22}$ and $R_{23}$ are all H.
In a 12$^{th}$ specific embodiment, compounds of formula (II) are represented by one of the following structural formulas:
(IIa) 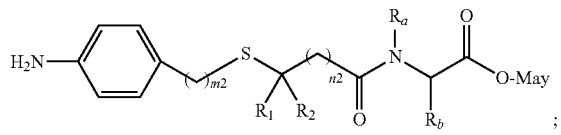 (IIb) 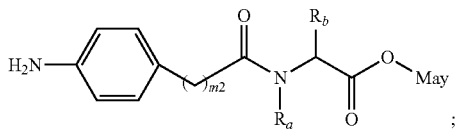
(IIc) 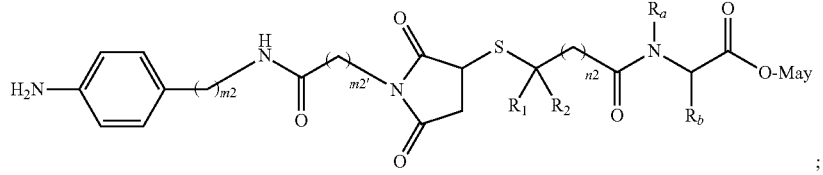
(IId) 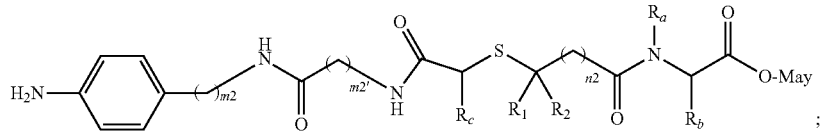
(IIe) 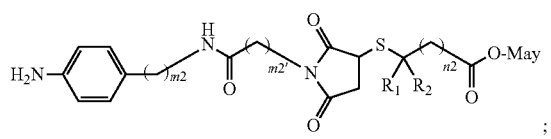 (IIf) 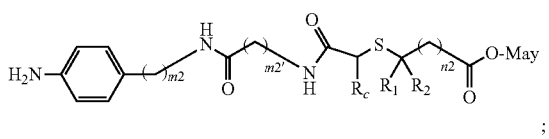
(IIg) 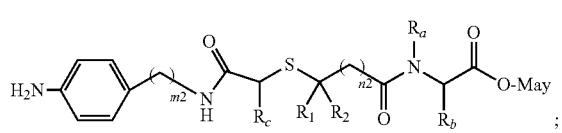 (IIh) 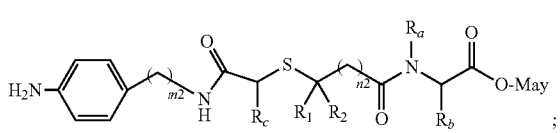

-continued

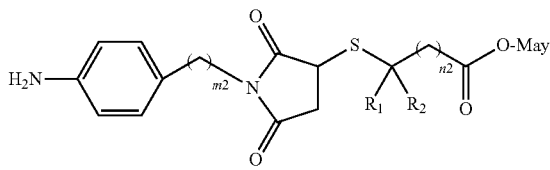
(IIi)

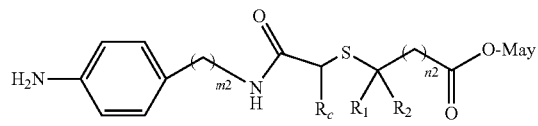
(IIj)

; or

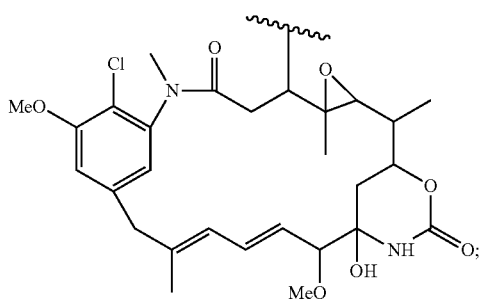 [SMILES: *C1CC(=O)N(C)c2cc(cc(OC)c2Cl)C/C(C)=C/C=C/C(OC)C2(O)CC(OC(=O)N2)C(C)C2OC12C]
(IIk)

;

or a pharmaceutically acceptable thereof, wherein May is represented by the following structural formula:

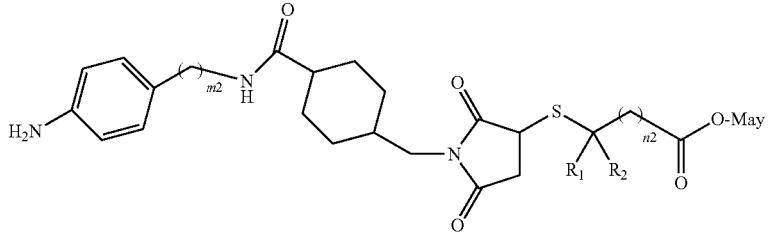

$R_1$, $R_2$, $R_a$, $R_b$ and $R_c$ are each independently H or a $C_{1-4}$ alkyl; and m2, m2' and n2 are each independently an integer from 1 to 10.

In a preferred embodiment, $R_a$ and $R_b$ are both methyl; and $R_c$ is H; and values and preferred values for the remainder of the variables are as described in 12$^{th}$ specific embodiment.

In another preferred embodiment, m2 and m2' are each independently an integer from 1 to 3; and values and preferred values for the remainder of the variables are as described in 12$^{th}$ specific embodiment.

In another preferred embodiment, $R_1$ and $R_2$ are both H and n is 1; and values and preferred values for the remainder of the variables are as described in 12$^{th}$ specific embodiment. More preferably, $R_a$ and $R_b$ are both methyl; and $R_c$ is H. Even more preferably, m2 and m2' are each independently an integer from 1 to 3.

In another preferred embodiment, $R_1$ and $R_2$ are both methyl and n is 2; and values and preferred values for the remainder of the variables are as described in 12$^{th}$ specific embodiment. More preferably, $R_a$ and $R_b$ are both methyl; and $R_c$ is H. Even more preferably, m2 and m2' are each independently an integer from 1 to 3.

Linker Compound

The present invention is also directed to a linker compound that is capable of covalently linking together a cell-binding agent and a cytotoxic agent. In one embedment, the linker compound is represented by formula (III):

$$L_2'\text{-A-Z}-X\text{-}L_1' \quad (III)$$

or a salt thereof, wherein values and preferred values for the variables are as described above.

In one embodiment, when Z is —NH—, $L_1'$ does not comprise one of the following moieties directly connected to X:

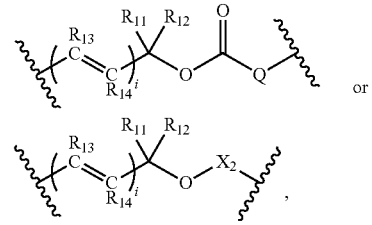

or wherein: i is 0 or an integer from 1 to 5; Q is —O—, —NR$_{15}$, S or —CR$_{11}$R$_{12}$—; $X_2$ is an aryl or a heteroaryl; and R$_{11}$, R$_{12}$, R$_{13}$, R$_{14}$ and R$_{15}$ are each independently H or an alkyl group.

In a 13$^{th}$ specific embodiment, for compounds of structural formula (III):

$L_1'$ is represented by formula (L1')

$$\text{-}J_X\text{-}R^{A1}\text{—}V_1\text{—}W_1\text{—}R^{B1}\text{—}V_1'\text{—}R^{C1}\text{-}J_D' \quad (L1');$$

$L_2'$ is represented by formula (L2'):

$$J_{CB}'\text{-}R^{A2}\text{—}V_2\text{—}W_2\text{—}R^{B2}\text{—}V_2'\text{—}R^{C2}\text{-}J_A\text{-} \quad (L2');$$

$R^{A1}$, $R^{B1}$ and $R^{C1}$ are each absent, an alkyl, an alkenyl, an alkynyl, a cycloalkyl, an aryl, a heteroaryl or a heterocyclyl, wherein the alkyl, alkenyl, alkynyl, cycloalkyl, aryl, heteroaryl, and heterocyclyl are optionally substituted;

$J_X$ and $W_1$ are each independently absent, —O—, —O—C(=O)—, —C(=O)—O—, —S—, —SO—, —SO$_2$—, —CR$_{11}$R$_{12}$—S—, —CR$_{11}$R$_{12}$—O—, —CR$_{11}$R$_{12}$NR$^c$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —SS—, —C(=O)—,

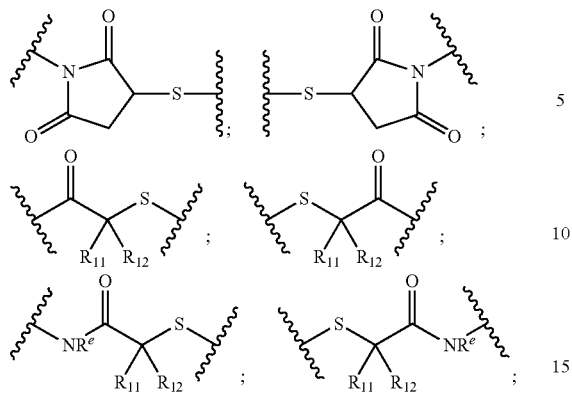

an amino acid, or a peptide having 2 to 8 amino acids, provided that when Z is —NH—, $J_x$ and $V_1$ are absent and $R^{A1}$ is —$CR_{11}R_{12}$—, $W_1$ is not —O—C(=O)—;

$J_D'$ is —C(=O)—OH, —COE, —SH, —S—S(=O)—$R^d$, S—S(=O)$_2R^d$, —$SSR^d$,

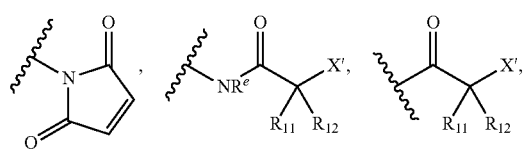

—OH, —O—C(=O)X', —S(=O)X'—, —SO$_2$X', —N($R^e$)H, —N($R^e$)—C(=O)—X', or —N(C(=O)$R^e$)C(=O)X', —C(=O)NH(C(=O)$R^e$), or —NH(C(=O)$R^e$), wherein COE represents a reactive ester; X' is a leaving group (e.g., halogen, mesylate or tosylate); and $R^d$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl);

$V_1$ and $V_1'$ are each independently —(O—CH$_2$—CH$_2$)$_{p1}$—, —(CH$_2$—CH$_2$—O)$_{p1}$—, —(NR$^m$—CH$_2$—CH$_2$)$_{p1'}$— or —(CH$_2$—CH$_2$—NR$^m$)$_{p1'}$—;

$R^e$ is H, an alkyl, an alkenyl, an alkynyl, or —(CH$_2$—CH$_2$—O)$_{n'}$—$R^k$;

$R^k$ and $R^m$ are each independently H or an alkyl;

n' is an integer from 1 to 24;

p1 is 0 or an integer from 1 to 1000;

p1' is 0 or an integer from 1 to 10;

$R^{A2}$, $R^{B2}$ and $R^{C2}$ are each independently absent, an alkyl, an alkenyl, an alkynyl, a cycloalkyl, an aryl, a heteroaryl, a heterocyclyl, a cycloalkylalkyl, an arylalkyl, a heteroarylalkyl or a heterocyclylalkyl;

$V_2$ and $V_2'$ are each independently —(O—CH$_2$—CH$_2$)$_{p2}$—, —(CH$_2$—CH$_2$—O)$_{p2}$—, —(NR$^m$—CH$_2$—CH$_2$)$_{p2'}$— or —(CH$_2$—CH$_2$—NR$^m$)$_{p2'}$—;

$W_2$ is absent, —O—, —O—C(=O)—, —C(=O)—O—, —S—, —SO—, —SO$_2$—, —$CR_{11}R_{12}$—S—, —$CR_{11}R_{12}$—O—, —$CR_{11}R_{12}$—NR$^e$—, —O—(C=O)O—, —O—(C=O)N($R^e$)—, —N($R^e$)—, —N($R^e$)—C(=O)—, —C(=O)—N($R^e$)—, —N($R^e$)—C(=O)O—, —N(C(=O)$R^e$)C(=O)—, —N(C(=O)$R^e$)—, —(O—CH$_2$—CH$_2$)$_{n'}$—, —SS—, —C(=O)—, an amino acid, a peptide having 2 to 8 amino acids, $J_{CB}'$ is —C(=O)OH, —COE, —N($R^e$)—C(=O)—X', —O—C(=O)X', —C(=NH)X', —NR$^e$—C(=NH)X', —SH, —$SSR^d$, —NR$^e$H, —NH—NR$^e$H,

—C(=NR$^e$)X', —NR$^e$NH, X'—$CR_1R_2$—C(=O)—, or X'—$CR_1R_2$—C(=O)—NR$^e$—, wherein COE is a reactive ester, X' is a halogen; and $R^d$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl);

$J_A$ is —NR$^e$—, —C(=O)—, =N—, —NR$^e$—C(=O)—, —O—C(=O)—, —SO$_2$—, —S—, p2 is 0 or an integer from 1 to 1000;

p2' is 0 or an integer from 1 to 10; and

A is a peptide cleavable by a peptidase.

In another preferred embodiment, Z is —NH—; and values and preferred values for the remainder of the variables are as described in the 13$^{th}$ specific embodiment.

In another preferred embodiment, $W_2$ is absent,

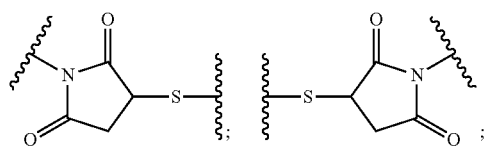

-continued

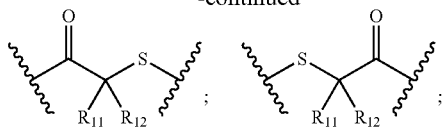

—S—S—, —NH—C(=O)— or —C(=O)—NH—; and values and preferred values for the remainder of the variables are as described above in the 13$^{th}$ specific embodiment. More preferably, Z is —NH—.

In another preferred embodiment, p2 and p2' are both 0; and values and preferred values for the remainder of the variables is as described above in the 13$^{th}$ specific embodiment. More preferably, W$_2$ is absent,

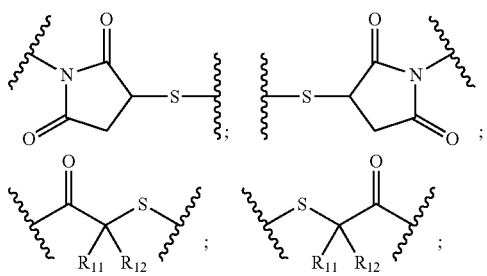

—S—S—, —NH—C(=O)— or —C(=O)—NH—. Even more preferably, Z is —NH—.

In another preferred embodiment, R$^{A2}$ is an alkyl, and values and preferred values for the remainder of the variables is as described above in the 13$^{th}$ specific embodiment. More preferably, W$_2$ is absent,

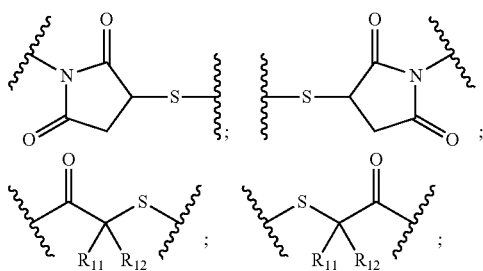

—S—S—, —NH—C(=O)— or —C(=O)—NH—. Even more preferably, Z is —NH—.

In another preferred embodiment, one of R$^{B2}$ and R$^{C2}$ is absent, and the other is an alkyl; and values and preferred values for the remainder of the variables is as described above in the 13$^{th}$ specific embodiment. More preferably, W$_2$ is absent,

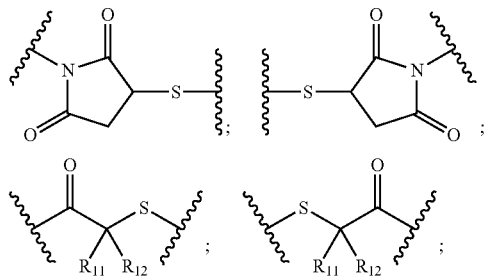

—S—S—, —NH—C(=O)— or —C(=O)—NH—. Even more preferably, Z is —NH—.

In another preferred embodiment, R$^{B2}$ and R$^{C2}$ are both absent; and the remainder of the variables is as described above in the 13$^{th}$ specific embodiment. More preferably, W$_2$ is absent,

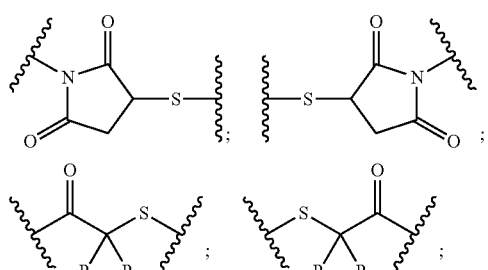

—S—S—, —NH—C(=O)— or —C(=O)—NH—. Even more preferably, Z is —NH— and D is a maytansinoid.

In a 14$^{th}$ specific embodiment, for compounds of structural formula (III), L$_2$' is represented by one of the following structural formulas:

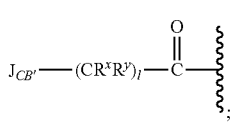
(L2'a)

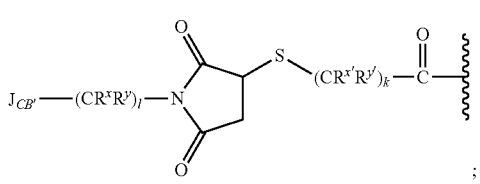
(L2'b)

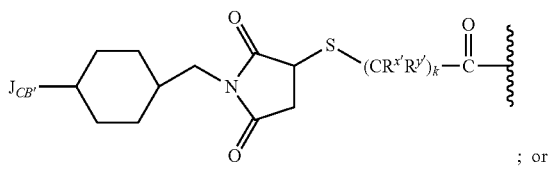
(L2'b')
; or

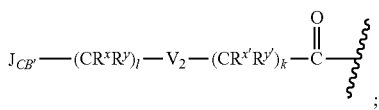
(L2'c)

-continued
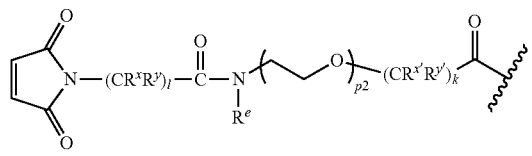
(L2'd)
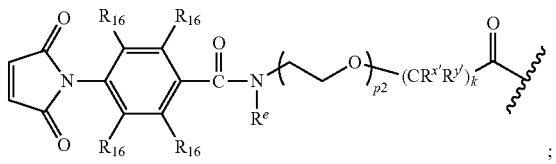
(L2'e)
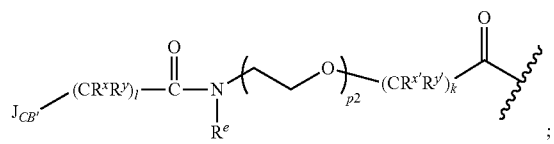
(L2'f)
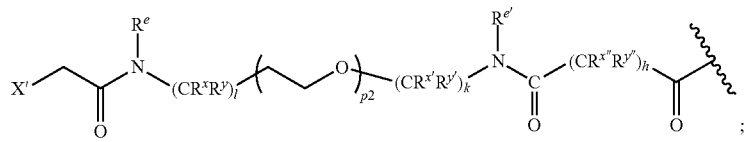
(L2'g)
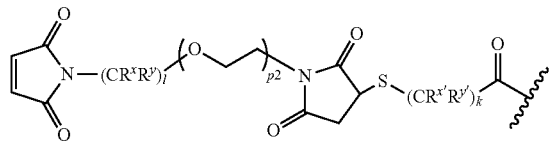
(L2'h)
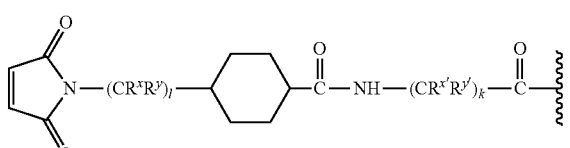
(L2'i)
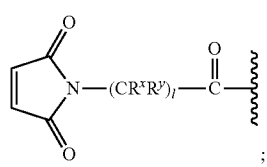
(L2'j)
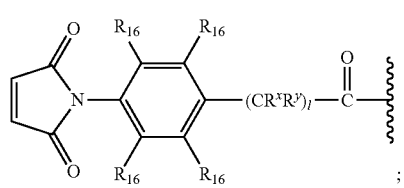
(L2'k)
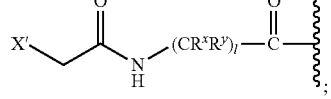
(L2'l)
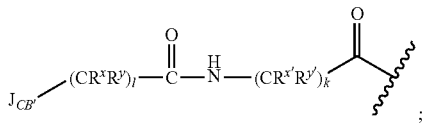
(L2'm)
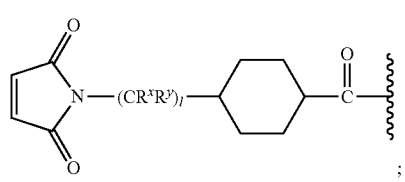
(L2'n)
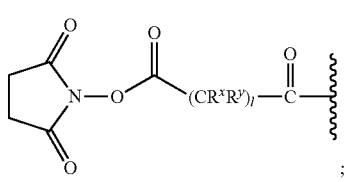
(L2'o)
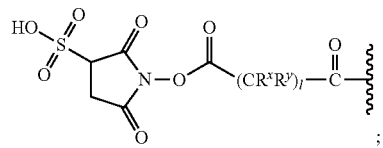
(L2'p)
(L2'q)
(L2'r)
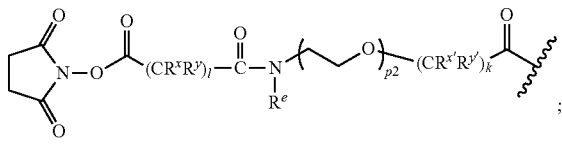
(L2's)

-continued

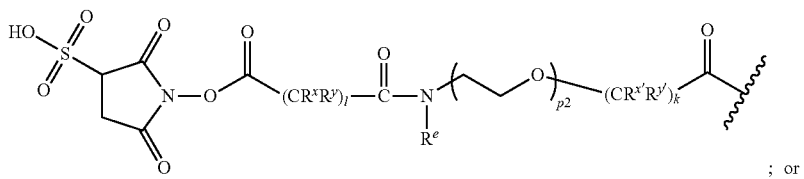
(L2't)

; or

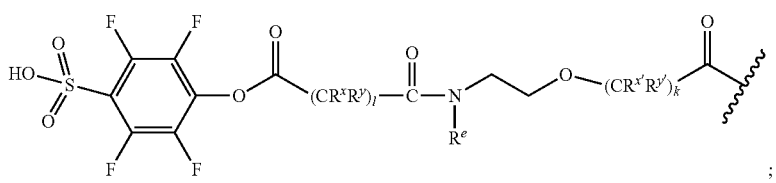
(L2'u)

;

wherein:

$J_{CB}'$ for structural formula (L2'a)-(L2'c) is —COOH or —COE, and $J_{CB}'$ for structural formula (L2'f) and (L2'o) is —SH or —SSR$^d$, wherein —COE is a reactive ester selected from N-hydroxysuccinimde ester, N-hydroxy sulfosuccinimide ester, nitrophenyl (e.g., 2 or 4-nitrophenyl) ester, dinitrophenyl (e.g., 2,4-dinitrophenyl) ester, sulfo-tetrafluorophenyl (e.g., 4-sulfo-2,3,5,6-tetrafluorophenyl) ester, and pentafluorophenyl ester; and phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl);

$R^x$, $R^y$, $R^{x'}$, $R^{y'}$, $R^{x''}$ and $R^{y''}$ for each occurrence, are independently H, —OH, halogen, —O—($C_{1-4}$ alkyl), —SO$_3^-$, —NR$_{40}$R$_{41}$R$_{42}^+$, or a $C_{1-4}$ alkyl optionally substituted with —OH, halogen, SO$_3^-$ or NR$_{40}$R$_{41}$R$_{42}^+$, wherein R$_{40}$, R$_{41}$ and R$_{42}$ are each independently H or a $C_{1-4}$ alkyl;

$V_2$ is —(CH$_2$—CH$_2$—O)$_{p2}$— or —(O—CH$_2$—CH$_2$)$_{p2}$—;

$R_{16}$, for each occurrence, is independently H, an alkyl, halogen, —OH, —O-alkyl, —NO$_2$, or —CN; and l, k and h are each independently 0 or an integer from 1 to 10; and values and preferred values for the remainder of the variables are as described in the 13$^{th}$ specific embodiment.

In another preferred embodiment, for structural formulas (L2'a)-(L2'c), $R^x$, $R^y$, $R^{x'}$ and $R^{y'}$ are all H; and for structural formulas (L2'd)-(L2'p), $R^x$, $R^y$, $R^{x'}$, $R^{y'}$, $R^{x'''}$ and $R^{y'''}$ are all H; and values and preferred values for the remainder of the variables are as described in the 14$^{th}$ specific embodiment.

In another preferred embodiment, for structural formulas (L2'a)-(L2'c), $R^x$, $R^y$, $R^{x'}$ and $R^{y'}$ are all H; p2 is an integer from 2 to 24; and l and k are each independently an integer from 1 to 6. For structural formulas (L2'd)-(L2'p), $R^x$, $R^y$, $R^{x'}$, $R^{y'}$, $R^{x'''}$ and $R^{y'''}$ are all H; $R_{16}$ is H; p2 and p2' are each independently 2 to 24; l, k and h are each independently an integer from 1 to 6; and values and preferred values for the remainder of the variables are as described in the 14$^{th}$ specific embodiment.

In a related specific embodiment, for compounds of structural formula (III), L$_2$' is represented by one of the following structural formulas:

$J_{CB}'$-R$^{A2}$—V$_2$—W$_2$—R$^{B2}$—V$_2'$—R$^{C2}$-J$_4'$;

wherein:

$J_{CB}'$ is

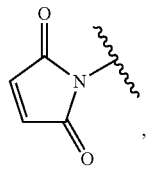 [SMILES: *N1C(=O)C=CC1=O]
,

—C(=O)OH, —COE, —SH, —SSR$^d$, X'—CR$_1$R$_2$—C(=O)—, or X'—CR$_1$R$_2$—C(=O)—NR$^e$—, wherein COE is a reactive ester, X' is a halogen; and R$^d$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl);

—R$^{A2}$—V$_2$—W$_2$—R$^{B2}$—V$_2'$—R$^{C2}$-J$_4'$- is:

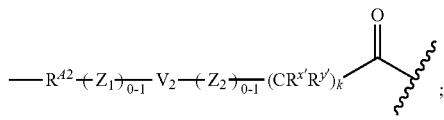
;

wherein

R$^{A2}$ is —(CR$^x$R$^y$)$_l$— or -Cy-(CR$^x$R$^y$)$_l$—;

Cy is a cycloalkyl (e.g., cyclohexyl);

V$_2$ is —(CH$_2$—CH$_2$—O)$_{p2}$— or —(O—CH$_2$—CH$_2$)$_{p2}$—;

Z$_1$ is —C(=O)—N(R$^e$)—, —N(R$^e$)—C(=O)—, or

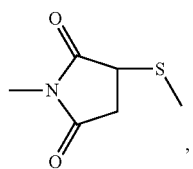
, provided that Z$_1$—V$_2$ does not contain an N—O bond;

$Z_2$ is

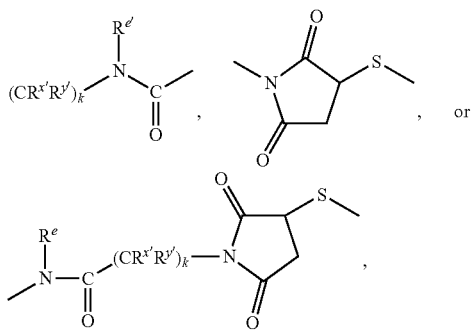

provided that $V_2$—$Z_2$ does not contain an O—N bond;
l is an integer from 0 to 10;
p2 is an integer from 0 to 200;
Z is —NH—.
In one embodiment, $L_2'$ is represented by:

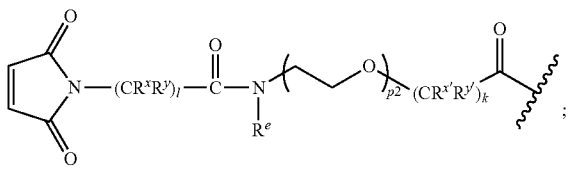
(L2'd)

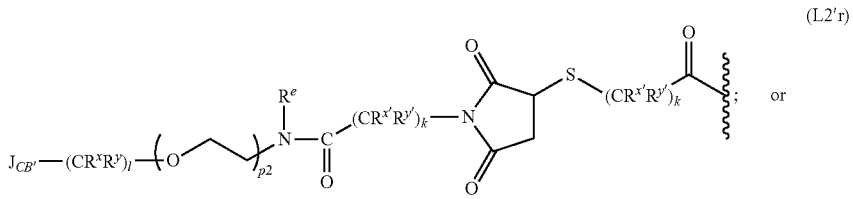
(L2'r)

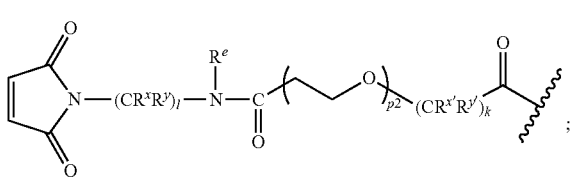
(L2's)

wherein:
p2 is an integer from 0 to 200;
$J_{CB'}$ is —COOH or —COE, wherein —COE is a reactive ester selected from N-hydroxysuccinimde ester, N-hydroxy sulfosuccinimide ester, nitrophenyl (e.g., 2 or 4-nitrophenyl) ester, dinitrophenyl (e.g., 2,4-dinitrophenyl) ester, sulfotetraflurophenyl (e.g., 4-sulfo-2,3,5,6-tetrafluorophenyl) ester, and pentafluorophenyl ester;
$R^x$, $R^y$, $R^{x'}$, and $R^{y'}$, for each occurrence, are each independently H, —OH, halogen, —O—($C_{1-4}$ alkyl), —$SO_3^-$, —$NR_{40}R_{41}R_{42}^+$, or a $C_{1-4}$ alkyl optionally substituted with —OH, halogen, $SO_3^-$ or $NR_{40}R_{41}R_{42}^+$, wherein $R_{40}$, $R_{41}$ and $R_{42}$ are each independently H or a $C_{1-4}$ alkyl;
l and k, for each occurrence, are independently an integer from 1 to 10.

In a 15$^{th}$ specific embodiment, for compounds of formula (III), $L_1'$ is represented by the following formula:

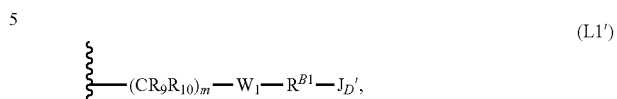
(L1')

wherein:
$R_9$ and $R_{10}$ are each independently H or a $C_{1-4}$ alkyl;
m is an integer from 1 to 10;
$W_1$ is absent, —NH—C(=O)—, —C(=O)—NH—, —C(=O)—O— or —O—C(=O)—, provided that when Z is —NH—, $J_x$ and $V_1$ are absent and $R^{41}$ is —$CR_{11}R_{12}$—, $W_1$ is not —O—C(=O)—;
$R^{B1}$ is absent or a $C_{1-10}$ alkyl; and
$J_D'$ is absent, —C(=O)OH, COE,

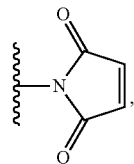 [SMILES: *N1C(=O)C=CC1=O]

—NH—C(=O)—$CH_2$—X', —SH, or —$SSR^d$;

X' is a leaving group (e.g., halogen); and values and preferred values for the remainder of the variables are as describe above in the 13$^{th}$ specific embodiment.

In a preferred embodiment, $J_D'$ is —C(=O)OH, —COE or

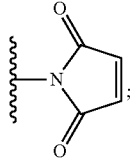

and values and preferred values for the remainder of the variables are as described in the 15th specific embodiment.

In another preferred embodiment, $R_9$ and $R_{10}$ are both H; and m is 1, 2 or 3.

In another preferred embodiment, $W_1$ is absent or —NH—C(=O)— and $R^{B1}$ is absent or —(CH$_2$)$_{m'}$—, wherein m' is 1, 2, or 3; and values and preferred values for the remainder of the variables are as described in the 15th specific embodiment.

In a 16th specific embodiment, for compounds represented by formula (III), $L_1$ is represented by formula (L1') described in the 15th specific embodiment;

$L_2$ is represented by one of the structural formulas (L2'a)-(L2'p) described in the 14th specific embodiment;

Z is —NH—;

A is a peptide cleavable by a protease; and values and preferred values for the remainder of the variables are as described above for structural formula (III) in the 14th and 15th specific embodiment.

In a 17th specific embodiment, for compounds of formula (III):

$L_2'$ is represented by any one of the structural formulas (L2'a)-(L2'p) described in the 14th specific embodiment;

A is a peptide cleavable by a protease;

—Z—X-$L_1'$ is represented by the one of the following structural formulas:

(L1'a)
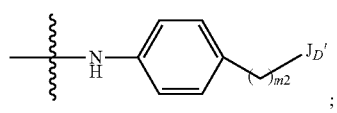

(L1'b)
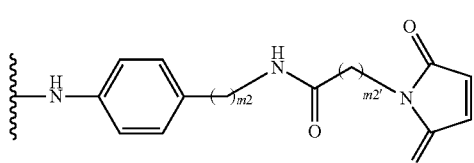

(L1'c)
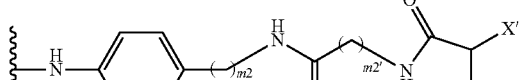
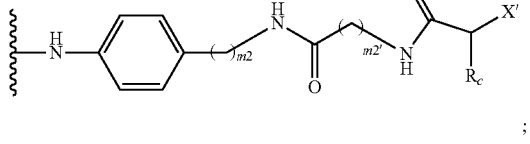

-continued (L1'd)
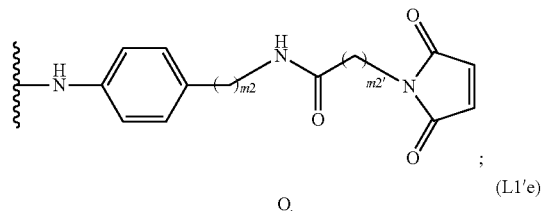

(L1'e)
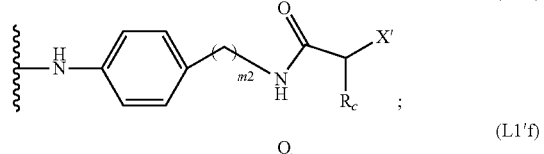

(L1'f)
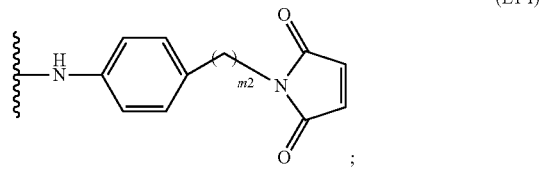

(L1'g)
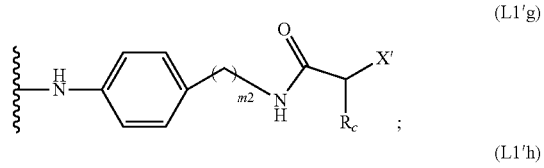

(L1'h)
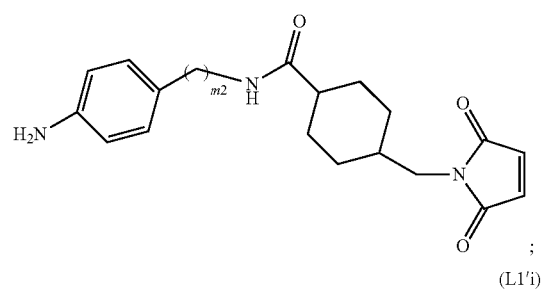

(L1'i)
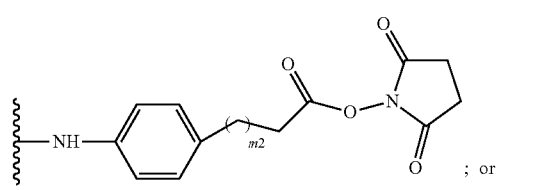
; or (L1'j)
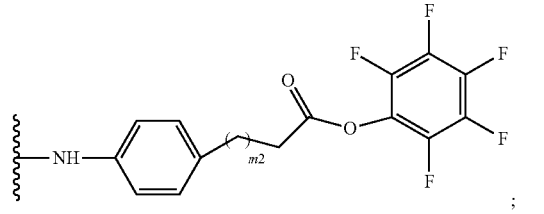
;

wherein $R_c$ is H or a $C_{1-4}$ alkyl; and m2 and m2' are each independently an integer from 1 to 10. Preferably, $R_c$ is H. In another preferred embodiment, m2 and m2' are each independently an integer from 1 to 3.

In a preferred embodiment, for formula (III) described in the 13th, 14th, 15th, 16th or 17th embodiment, including any related specific embodiment, A is a peptide cleavable by a lysosomal protease. In another preferred embodiment, A is a peptide cleavable by a protease expressed in tumor tissue.

In a more preferred embodiment, for formula (III) described in the 13th, 14th, 15th, 16th or 17th embodiment, including any related specific embodiment, A is a peptide having an amino acid that is covalent linked with —Z—X-L$_1$-D selected from the group consisting of Ala, Arg, Asn, Asp, Cit, Cys, selino-Cys, Gln, Glu, Gly, His, Ile, Leu, Lys, Met, Phe, Pro, Ser, Thr, Trp, Tyr and Val, each independently as L or D isomer.

In yet another more preferred embodiment, for formula (I) described in the 13th, 14th, 15th, 16th or 17th embodiment, including any related specific embodiment, A is selected from the group consisting of Val-Cit, Val-Lys, Phe-Lys, Lys-Lys, Ala-Lys, Phe-Cit, Leu-Cit, Lle-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), β-Ala-Leu-Ala-Leu (SEQ ID NO: 2) and Gly-Phe-Leu-Gly (SEQ ID NO: 3), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, D-Ala-Ala, Ala-D-Ala, and D-Ala-D-Ala.

In an even more preferred embodiment, for formula (III) described in the 13th, 14th, 15th, 16th or 17th embodiment, including any related specific embodiment, A is Val-Cit, Val-Lys, Val-D-Cit or Val-D-Lys.

In another preferred embodiment, for formula (III) described in the 13th, 14th, 15th or 16th embodiment, including any related specific embodiment, X is an optionally substituted phenyl. More preferably, X is represented by any one of the following structural formulas:

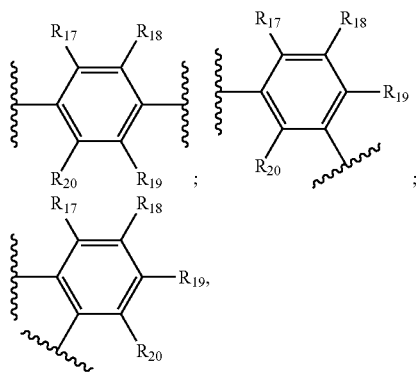

wherein R$_{17}$, R$_{18}$, R$_{19}$ and R$_{20}$ each are independently H, an alkyl, H, an alkyl, halogen, —OH, —O-alkyl, —NO$_2$, or —CN. Preferably, R$_{17}$, R$_{18}$, R$_{19}$ and R$_{20}$ are all H.

In another preferred embodiment, for structural formula (III), X is optionally substituted six-membered heteroaryl selected from the group consisting of pyridine, pyridazine, pyrimidine, pyrazine, a triazine, and tetrazine, wherein the heteroaryl is connected to the —NH group and -L$_1$ group at a carbon atom of the heteroaryl; and values and preferred values for the remainder of the variables are as described above in the 13th, 14th, 15th or 16th specific embodiment.

In another preferred embodiment, for structural formula (III), X is an optionally substituted five-membered heteroaryl; and preferred values for the remainder of the variables are as described above in the 13th, 14th, 15th or 16th specific embodiment. More preferably, X is selected from the group consisting of:

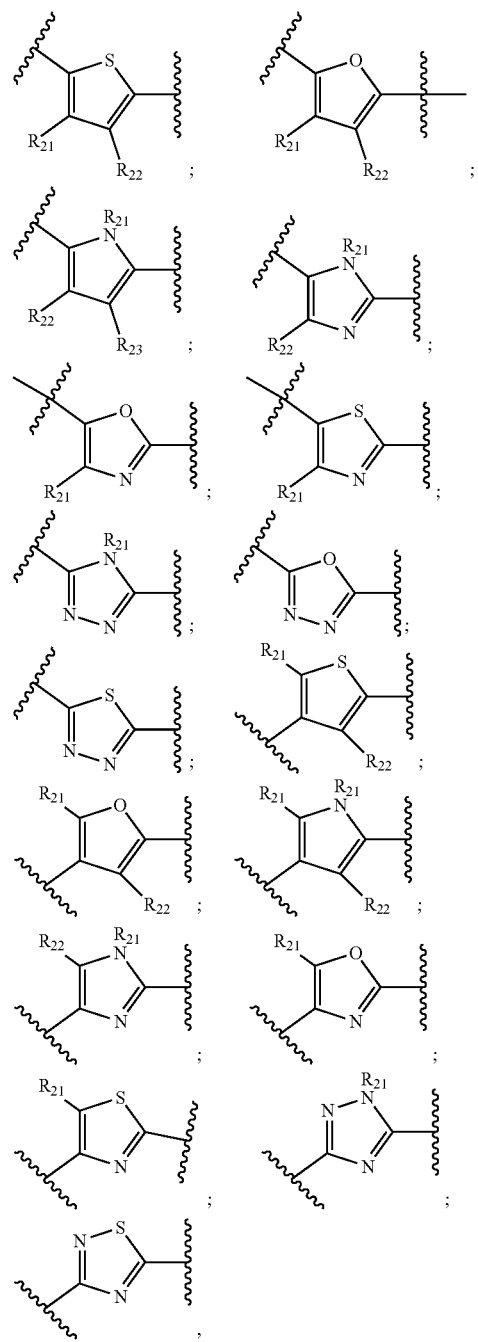

wherein R$_{21}$, R$_{22}$ and R$_{23}$ are each independently H or an alkyl. Preferably, R$_{21}$, R$_{22}$ and R$_{23}$ are all H.

Drug-Linker Compounds

The present invention is also directed to a drug-linker compound represented by formula (IV):

L$_2$'-A-Z—X-L$_1$-D     (IV), wherein:

L$_2$' is a spacer comprising a reactive moiety that can form a covalent bond with a cell-binding agent, H or —OH;

A is an amino acid or a peptide comprising 2 to 20 amino acids;

Z is —NH— or C(=O)—;

D is a cytotoxic agent;

$L_1$ is absent or a spacer,

X is an optionally substituted aryl or a heteroaryl.

In one embodiment, for compounds of formula (IV), when X is —NH—, $L_1$ does not comprise one of the following moieties directly connected to X:

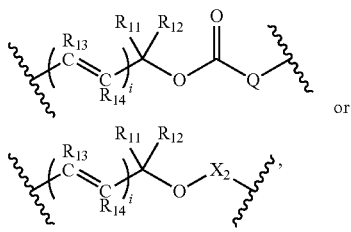

or wherein i is 0 or an integer from 1 to 5; Q is —O—, —NR$_{15}$, S or —CR$_{11}$R$_{12}$—; $X_2$ is an aryl or a heteroaryl; and R$_{11}$, R$_{12}$, R$_{13}$, R$_{14}$ and R$_{15}$ are each independently H or an alkyl group.

In a 18$^{th}$ specific embodiment, for compounds of formula (IV):

$L_1$ is represented by the following formula:

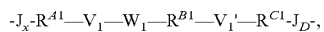

$L_2'$ is represented by the following formula:

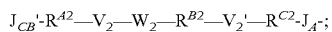

wherein:

$R^{A1}$, $R^{B1}$ and $R^{C1}$ are each absent, an alkyl, an alkenyl, an alkynyl, a cycloalkyl, an aryl, a heteroaryl or a heterocyclyl, wherein the alkyl, alkenyl, alkynyl, cycloalkyl, aryl, heteroaryl, and heterocyclyl are optionally substituted;

$J_X$ and $W_1$ are each independently absent, —O—, —O—C(=O)—, —C(=O)—O—, —S—, —SO—, —SO$_2$—, —CR$_{11}$R$_{12}$—S—, —CR$_{11}$R$_{12}$—O—, —CR$_{11}$R$_{12}$NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —SS—, —C(=O)—,

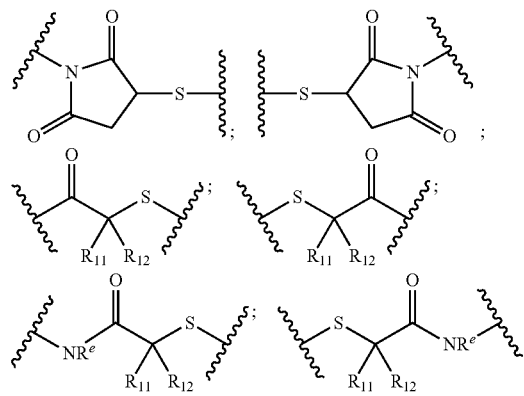

an amino acid, or a peptide having 2 to 8 amino acids, provided that when Z is —NH—, $J_x$ and $V_1$ are absent and $R^{A1}$ is —CR$_{11}$R$_{12}$—, $W_1$ is not —O—C(=O)—;

$J_D$ is absent, —C(=O)—, —S—,

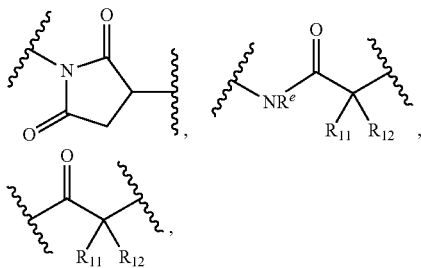

—O—, —O—C(=O)—, —C(=O)—O—, —SO—, —SO$_2$—, —O—(C=O)—, —N(R$^e$)—, —N(R$^e$)—C(=O)—, or —N(C(=O)R$^e$)C(=O)—, or —N(C(=O)R$^e$)—;

$V_1$ and $V_1'$ are each independently —(O—CH$_2$—CH$_2$)$_{p1}$—, —(CH$_2$—CH$_2$—O)$_{p1}$—, —(NR$^m$—CH$_2$—CH$_2$)$_{p1}$— or —(CH$_2$—CH$_2$—NR$^m$)$_{p1}$—;

$R^e$ is H, an alkyl, an alkenyl, an alkynyl, or —(CH$_2$—CH$_2$—O)$_{n'}$—R$^k$;

$R^k$ and $R^m$ are each independently H or an alkyl;

n' is an integer from 1 to 24;

p1 is 0 or an integer from 1 to 1000;

p1' is 0 or an integer from 1 to 10;

$R^{A2}$, $R^{B2}$ and $R^{C2}$ are each independently absent, an alkyl, an alkenyl, an alkynyl, a cycloalkyl, an aryl, a heteroaryl, a heterocyclyl, a cycloalkyl, an arylalkyl, a heteroarylalkyl, or a heterocyclylalkyl;

$V_2$ and $V_2'$ are each independently —(O—CH$_2$—CH$_2$)$_{p2}$—, —(CH$_2$—CH$_2$—O)$_{p2}$—, —(NR$^m$—CH$_2$—CH$_2$)$_{p2'}$— or —(CH$_2$—CH$_2$—NR$^m$)$_{p2'}$—;

$W_2$ is absent, —O—, —O—C(=O)—, —C(=O)—O—, —S—, —SO—, —SO$_2$—, —CR$_{11}$R$_{12}$—S—, —CR$_{11}$R$_{12}$—O—, —CR$_{11}$R$_{12}$—NR$^e$—, —O—(C=O)O—, —O—(C=O)N(R$^e$)—, —N(R$^e$)—, —N(R$^e$)—C(=O)—, —C(=O)—N(R$^e$)—, —N(R$^e$)—C(=O)O—, —N(C(=O)R$^e$)C(=O)—, —N(C(=O)R$^e$)—, —(O—CH$_2$—CH$_2$)$_{n'}$—, —SS—, —C(=O)—, an amino acid, a peptide having 2 to 8 amino acids,

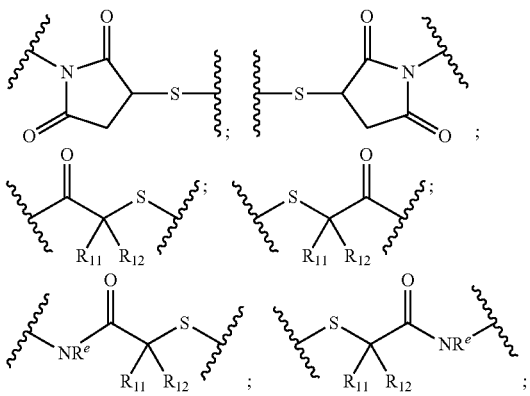

$J_{CB}'$ is —C(=O)OH, —COE, —N(R$^e$)—C(=O)—X', —O—C(=O)X', —C(=NH)X', —NR$^e$—C(=NH)X', —SH, —SSR$^d$, —NR$^e$H, —NH—NR$^e$H,

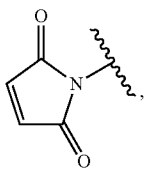 [SMILES: *N1C(=O)C=CC1=O]

—C(=NR$^e$)X', —NR$^e$NH, X'—CR$_1$R$_2$—C(=O)—, or X'—CR$_1$R$_2$—C(=O)—NR$^e$—, wherein —COE is a reactive ester, X' is a halogen; and R$^d$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl);

J$_A$ is —NR$^e$—, —C(=O)—, =N—, —NR$^e$—C(=O)—, —O—C(=O)—, —SO$_2$—, —S—,

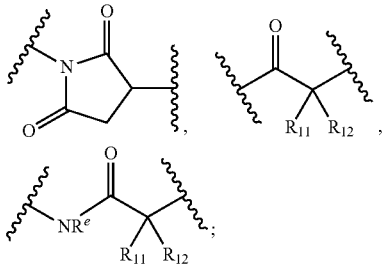

p2 is 0 or an integer from 1 to 1000;

p2' is 0 or an integer from 1 to 10; and values and preferred values for the remainder of the variables are as described above for formula (IV).

In a preferred embodiment, D is a maytansinoid; and values and preferred values for the remainder of the variables are as described in the 18$^{th}$ specific embodiment.

In another preferred embodiment, Z is —NH—; and values and preferred values for the remainder of the variables are as described in the 18$^{th}$ specific embodiment. More preferably, D is a maytansinoid.

In another preferred embodiment, W$_2$ is absent,

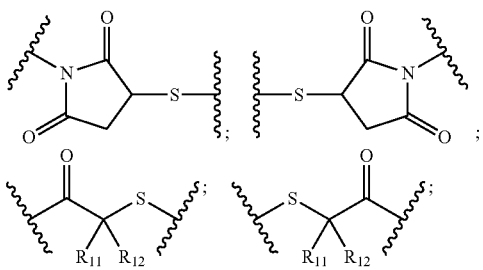

—S—S—, —NH—C(=O)— or —C(=O)—NH—; and values and preferred values for the remainder of the variables are as described in the 18$^{th}$ specific embodiment. More preferably, Z is —NH—; and D is a maystansinoid.

In another preferred embodiment, p2 for both V$_2$ and V$_2$' are 0; and values and preferred values for the remainder of the variables is as described above in the 18$^{th}$ specific embodiment. More preferably, W$_2$ is absent,

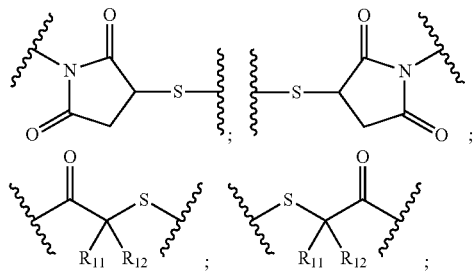

—S—S—, —NH—C(=O)— or —C(=O)—NH—. Even more preferably, Z is —NH— and D is a maytansinoid.

In another preferred embodiment, R$^{A2}$ is an alkyl, and values and preferred values for the remainder of the variables is as described above in the 18$^{th}$ specific embodiment. More preferably, W$_2$ is absent,

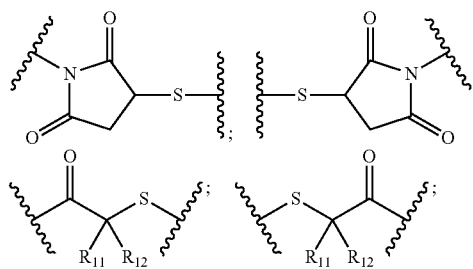

—S—S—, —NH—C(=O)— or —C(=O)—NH—. Even more preferably, Z is —NH— and D is a maytansinoid.

In another preferred embodiment, one of R$^{B2}$ and R$^{C2}$ is absent, and the other is an alkyl; and values and preferred values for the remainder of the variables is as described above in the 18$^{th}$ specific embodiment. More preferably, W$_2$ is absent,

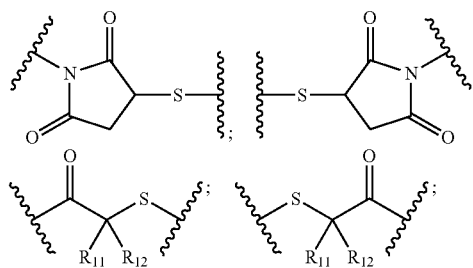

—S—S—, —NH—C(=O)— or —C(=O)—NH—. Even more preferably, Z is —NH— and D is a maytansinoid.

In another preferred embodiment, R$^{B2}$ and R$^{C2}$ are both absent; and values and preferred values for the remainder of the variables is as described above in the 18$^{th}$ specific embodiment. More preferably, W$_2$ is absent,

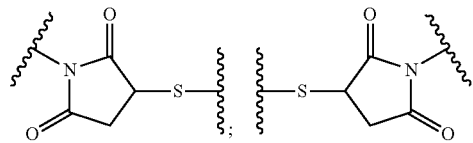

-continued
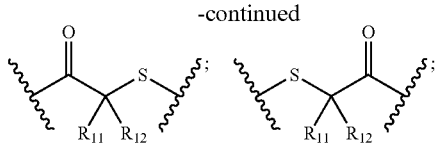
—S—S—, —NH—C(=O)— or —C(=O)—NH—. Even more preferably, Z is —NH— and D is a maytansinoid.
In a 19$^{th}$ specific embodiment, for compounds of formula (IV), $L_2'$ is represented by one of the following structural formulas:
(L2'a)
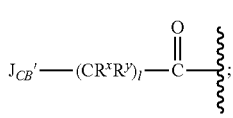
(L2'b)
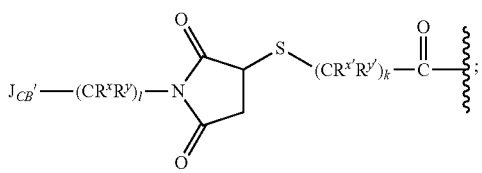
(L2'b')
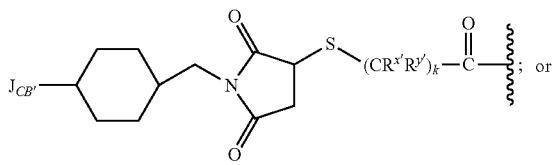
(L2'c)
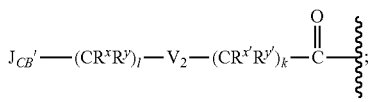
(L2'd)
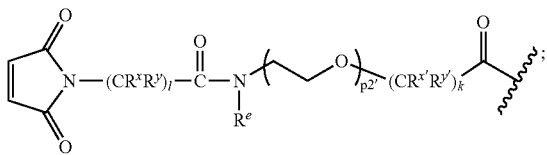
(L2'e)
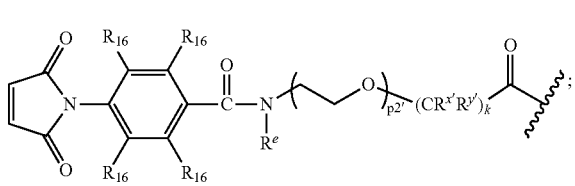
(L2'f)
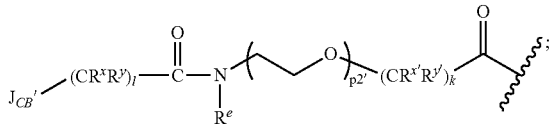
(L2'g)
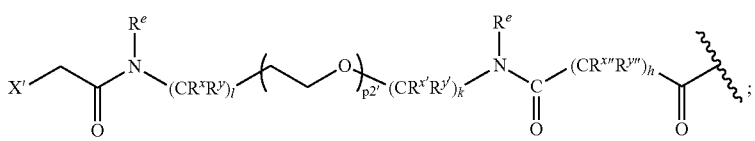
(L2'h)
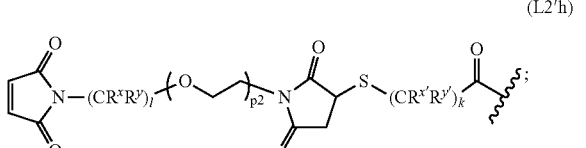
(L2'i)
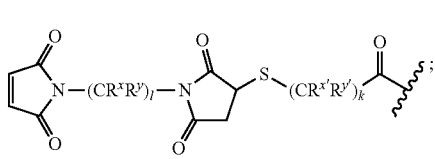
(L2'j)
(L2'k)
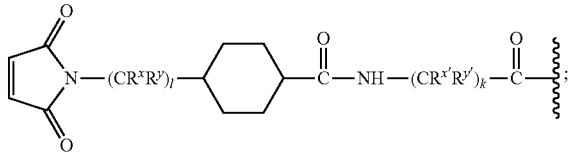
(L2'l)
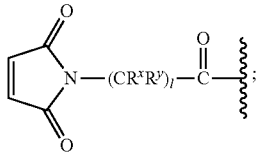
(L2'm)
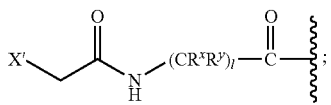

-continued

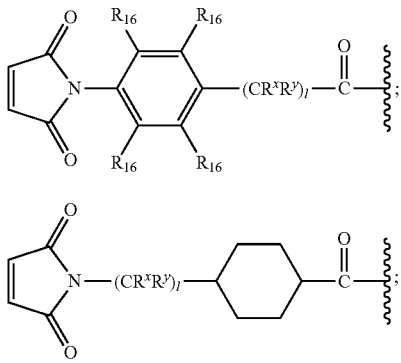 (L2'n)

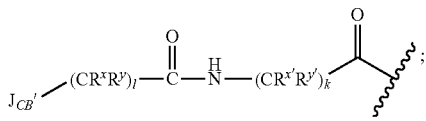 (L2'o)

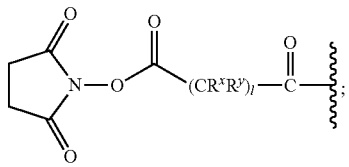 (L2'q)

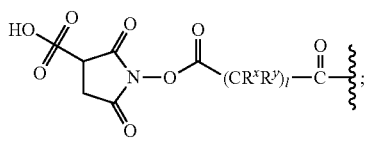 (L2'p)

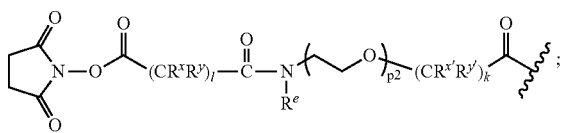 (L2's)

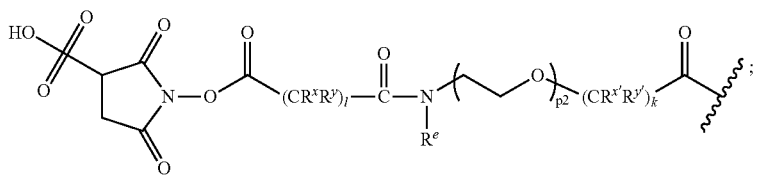 (L2'r)

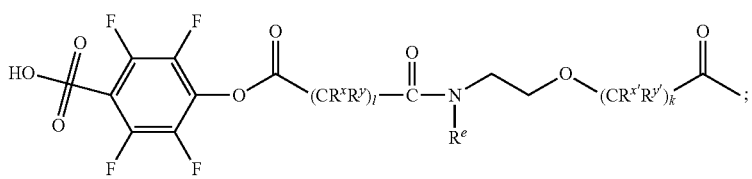 (L2't)

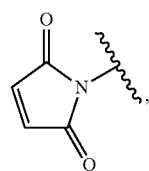 (L2'u)

wherein:

$R^x$, $R^y$, $R^{x'}$, $R^{y'}$, $R^{x''}$, and $R^{y''}$, for each occurrence, are each independently H, —OH, halogen, —O—($C_{1-4}$ alkyl), —$SO_3^-$, —$NR_{40}R_{41}R_{42}^+$, or a $C_{1-4}$ alkyl optionally substituted with —OH, halogen, $SO_3^-$ or $NR_{40}R_{41}R_{42}^+$, wherein $R_{40}$, $R_{41}$ and $R_{42}$ are each independently H or a $C_{1-4}$ alkyl;

$R_{16}$, for each occurrence, is independently H, an alkyl, halogen, —OH, —O-alkyl, —$NO_2$, or —CN;

$V_2$ is —($CH_2$—$CH_2$—O)$_{p2}$— or —(O—$CH_2$—$CH_2$)$_{p2}$—;

l, k and h are each independently an integer from 1 to 10;

Z is —NH—;

A is peptide cleavable by a peptidase; and values and preferred values for the remainder of the variables are as described above in the 18$^{th}$ specific embodiment.

In a preferred embodiment, D is a maytansinoid; and values and preferred values for the remainder of the variables are as described in the 19$^{th}$ specific embodiment.

In another preferred embodiment, for structural formulas (L2'a)-(L2'c) and (L2'p)-(L2'u), $R^x$, $R^y$, $R^{x'}$ and $R^{y'}$ are all H; and for structural formulas (L2'd)-(L2'p), $R^x$, $R^y$, $R^{x'}$, $R^{y'}$, $R^{x''}$ and $R^{y''}$ are all H.

In another preferred embodiment, for structural formulas (L2'a)-(L2'c) and (L2'p)-(L2'u), $R^x$, $R^y$, $R^{x'}$ and $R^{y'}$ are all H;

p2 is an integer from 2 to 24; and l and k are each independently an integer from 1 to 6. For structural formulas (L2'd)-(L2'p), $R^x$, $R^y$, $R^{x'}$, $R^{y'}$, $R^{x''}$ and $R^{y''}$ are all H; $R_{16}$ is H; p2 for each occurrence is independently 2 to 24; l, k and h are each independently an integer from 1 to 6.

In a related embodiment, for compounds of formula (IV), $L_{2'}$ is represented by one of the following structural formulas:

$$J_{CB'}\text{-}R^{A2}\text{—}V_2\text{—}W^2\text{—}R^{B2}\text{—}V_{2'}\text{—}R^{C2}\text{-}J_{A'};$$

wherein:

$J_{CB'}$ is

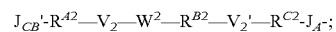

—C(=O)OH, —COE, —SH, —$SSR^d$, X'—$CR_1R_2$—C(=O)—, or X'—$CR_1R_2$—C(=O)—$NR^e$—, wherein COE is a reactive ester, X' is a halogen; and $R^d$ is selected from phenyl, nitrophenyl (e.g., 2 or 4-nitrophenyl), dinitrophenyl (e.g., 2 or 4-nitrophenyl), carboxynitrophenyl (e.g., 3-carboxy-4-nitrophenyl), pyridyl or nitropyridyl (e.g., 4-nitropyridyl);

—$R^{A2}$—$V_2$—$W_2$—$R^{B2}$—$V_{2'}$—$R^{C2}$-$J_A$- is:

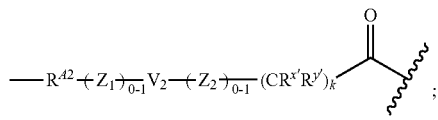

wherein
$R^{A2}$ is —$(CR^xR^y)_l$— or -Cy-$(CR^xR^y)_l$—;
Cy is a cycloalkyl (e.g., cyclohexyl);

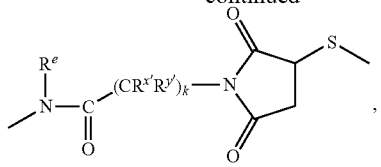

provided that $V_2$—$Z_2$ does not contain an O—N bond;
l is an integer from 0 to 10;
p2 is an integer from 0 to 200;
Z is —NH—.

In one embodiment, $L_2'$ is represented by:

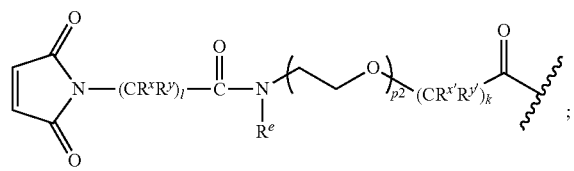
(L2′d)

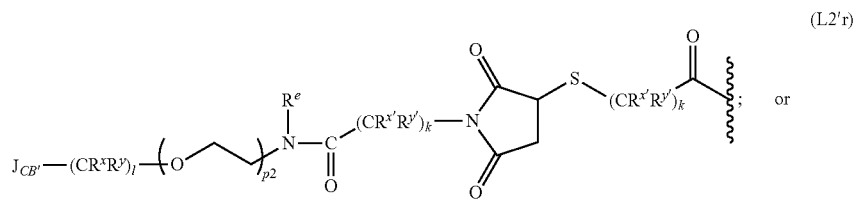
(L2′r)

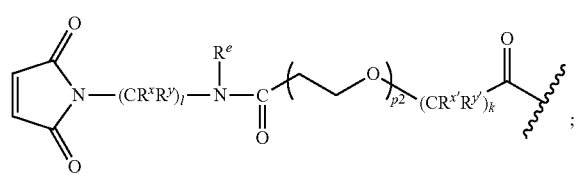
(L2′s)

$V_2$ is —$(CH_2—CH_2—O)_{p2}$— or —$(O—CH_2—CH_2)_{p2}$—;

$Z_1$ is —C(=O)—N($R^e$)—, —N($R^e$)—C(=O)—, or

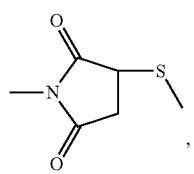

provided that $Z_1$—$V_2$ does not contain an N—O bond;

$Z_2$ is

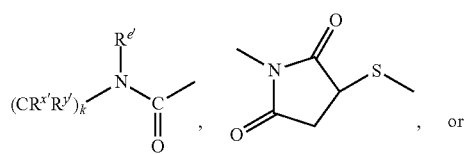, or wherein:
p2 is an integer from 0 to 200;
$J_{CB'}$ is —COOH or —COE, wherein —COE is a reactive ester selected from N-hydroxysuccinimde ester, N-hydroxy sulfosuccinimide ester, nitrophenyl (e.g., 2 or 4-nitrophenyl) ester, dinitrophenyl (e.g., 2,4-dinitrophenyl) ester, sulfo-tetraflurophenyl (e.g., 4-sulfo-2,3,5,6-tetrafluorophenyl) ester, and pentafluorophenyl ester;
$R^x$, $R^y$, $R^{x'}$, and $R^{y'}$, for each occurrence, are each independently H, —OH, halogen, —O—($C_{1-4}$ alkyl), —$SO_3^-$, —$NR_{40}R_{41}R_{42}^+$, or a $C_{1-4}$ alkyl optionally substituted with —OH, halogen, $SO_3^-$ or $NR_{40}R_{41}R_{42}^+$, wherein $R_{40}$, $R_{41}$ and $R_{42}$ are each independently H or a $C_{1-4}$ alkyl;
l and k, for each occurrence, are independently an integer from 1 to 10.

In a 20$^{th}$ specific embodiment, for compounds of formula (IV), $L_1$ is represented by the following formula:

—$(CR_9R_{10})_m$—$W_1$—$R^{B1}$-$J_D$-  (L1)

wherein:
$R_9$ and $R_{10}$ are each independently H or a $C_{1-4}$ alkyl;
m is an integer from 1 to 10;
$W_1$ is absent, —NH—C(=O)—, —C(=O)—NH—, —C(=O)—O— or O—C(=O)—, provided when Z is —NH— and m is 1, $W_1$ is not —O—C(=O)—;
$R^{B1}$ is absent or a $C_{1-10}$ alkyl; and $J_D$ is absent, —C(=O)—,

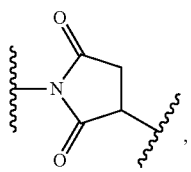 [SMILES: *C1CC(=O)N(*)C1=O]

—NH—C(=O)—CH$_2$—, or —S—;

Z is —NH—;

A is a peptide cleavable by a peptidase; and values and preferred values for the remainder of the variables are as described in the 18$^{th}$ specific embodiment.

In a preferred embodiment, $J_D$ is absent, —C(=O)— or

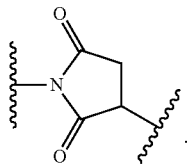 [SMILES: *C1CC(=O)N(*)C1=O]

In another preferred embodiment, $R_9$ and $R_{10}$ are both H; and m is 1, 2 or 3.

In another preferred embodiment, $W_1$ is absent or —NH—C(=O)— and $R^{B1}$ is absent or —(CH$_2$)$_{m'}$—, wherein m' is 1, 2, or 3.

In yet another preferred embodiment, D is a maytasinoid.

In a 21$^{st}$ specific embodiment, for compounds represented by formula (IV), wherein:

$L_1$ is represented by formula (L1) described in the 20$^{th}$ specific embodiment;

$L_2'$ is represented by one of the structural formulas (L2'a)-(L2'o) described in the 19$^{th}$ specific embodiment;

Z is —NH—;

A is a peptide cleavable by a protease; and

D is a maytansinoid; and values and preferred values for the remainder of the variables are as described above for structural formula (I) in the 19$^{th}$ and 20$^{th}$ specific embodiment.

In a 22$^{nd}$ specific embodiment, for compounds of formula (IV):

$L_2'$ is represented by any one of the structural formulas (L2'a)-(L2'p) described in the 19$^{th}$ specific embodiment;

A is a peptide cleavable by a protease;

—Z—X-$L_1$-D is represented by the one of the following structural formulas:

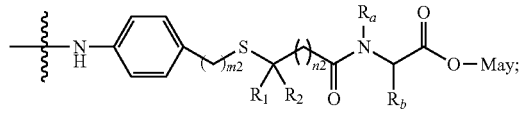

(L1a)

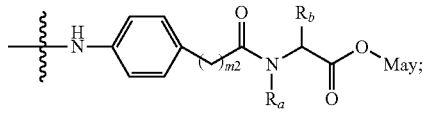

(L1b)

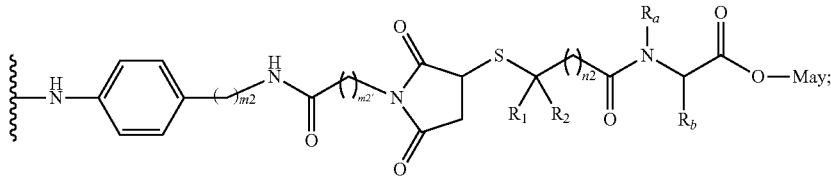

(L1c)

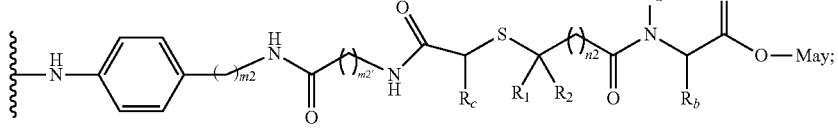

(L1d)

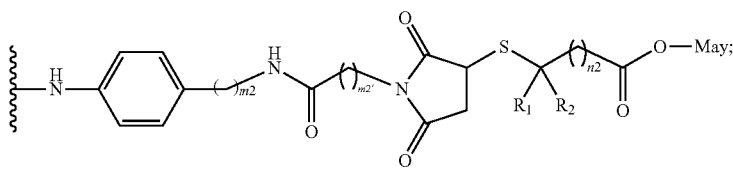

(L1e)

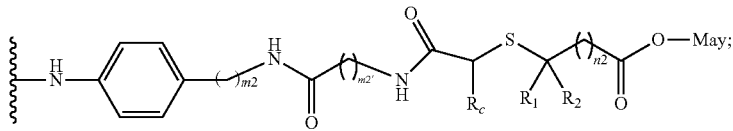

(L1f)

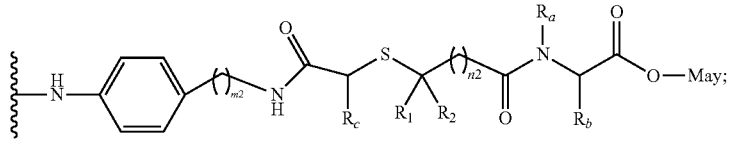

(L1g)

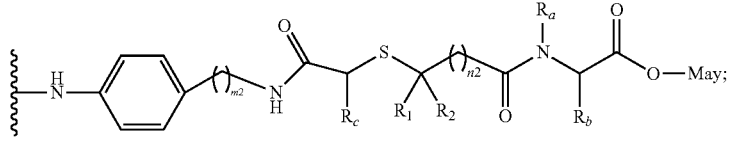

(L1h)

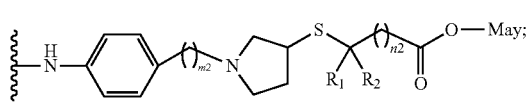

(L1i)

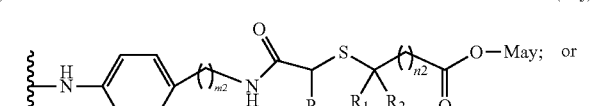

(L1j)  or

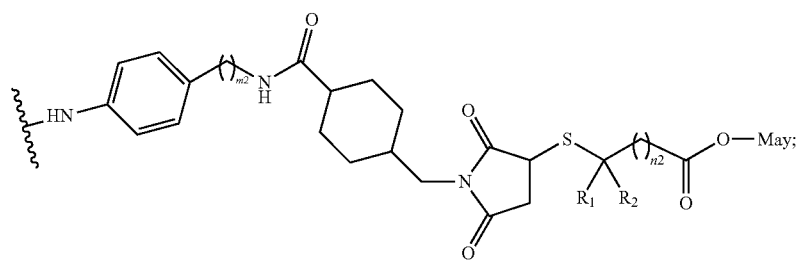

(L1k)

wherein May is represented by the following structural formula:

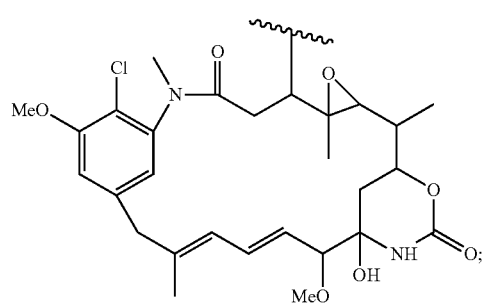 [SMILES: *C1CC(=O)N(C)c2cc(cc(OC)c2Cl)C/C(C)=C/C=C/C(OC)C2(O)CC(OC(=O)N2)C(C)C2OC12C]

$R_1$, $R_2$, $R_a$, $R_b$ and $R_c$ are each independently H or a $C_{1-4}$ alkyl; and m2, m2' and n2 are each independently an integer from 1 to 10; and values and preferred values for the remainder of the variables are as described above for formula (IV).

In a preferred embodiment, for formula (IV) described in the $18^{th}$, $19^{th}$, $20^{th}$, $21^{st}$ or $22^{nd}$, embodiment, including any related specific embodiment, A is a peptide cleavable by a lysosomal protease. In another preferred embodiment, A is a peptide cleavable by a protease expressed in tumor tissue.

In a more preferred embodiment, for formula (IV) described in the $18^{th}$, $19^{th}$, $20^{th}$, $21^{st}$ or $22^{nd}$ embodiment, including any related specific embodiment, A is a peptide having an amino acid that is covalent linked with —Z—X-$L_1$-D selected from the group consisting of Ala, Arg, Asn, Asp, Cit, Cys, selino-Cys, Gln, Glu, Gly, His, Ile, Leu, Lys, Met, Phe, Pro, Ser, Thr, Trp, Tyr and Val, each independently as L or D isomer.

In yet another more preferred embodiment, for formula (IV) described in the $18^{th}$, $19^{th}$, $20^{th}$, $21^{st}$ or $22^{nd}$ embodiment, including any related specific embodiment, A is selected from the group consisting of Val-Cit, Val-Lys, Phe-Lys, Lys-Lys, Ala-Lys, Phe-Cit, Leu-Cit, Lle-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), β-Ala-Leu-Ala-Leu (SEQ ID NO: 2) and Gly-Phe-Leu-Gly (SEQ ID NO: 3), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, D-Ala-Ala, Ala-D-Ala, and D-Ala-D-Ala.

In an even more preferred embodiment, for formula (IV) described in the $18^{th}$, $19^{th}$, $20^{th}$, $21^{st}$ or $22^{nd}$ embodiment, including any related specific embodiment, A is Val-Cit, Val-Lys, Val-D-Cit or Val-D-Lys.

In a $23^{rd}$ specific embodiment, for compounds for formula (IV):

$L_2'$ is represented by any one of the structural formulas (L2'a)-(L2'p) described in the $19^{th}$ specific embodiment;

A is Val-Cit, Val-Lys, Val-D-Cit or Val-D-Lys;

—Z—X-$L_1$-D is represented by the one of the following structural formulas (L1a)-(L1k) described in the $22^{nd}$ specific embodiment.

In a preferred embodiment, $R_a$ and $R_b$ are both methyl; $R_c$ is H; and the remainder of the variables is as described above in the $23^{rd}$ specific embodiment. More preferably, m2 and m2' are each independently an integer from 1 to 3.

In another preferred embodiment, $R_a$ and $R_b$ are both methyl; $R_c$ is H; $R_1$ and $R_2$ are both H and n is 1; and the remainder of the variables is as described above in the $23^{rd}$ specific embodiment. More preferably, m2 and m2' are each independently an integer from 1 to 3.

In another preferred embodiment, for compounds of formula (IV) described in the 18$^{th}$, 19$^{th}$, 20$^{th}$ or 21$^{st}$ embodiment, including any related specific embodiment, D is represented by structural formula (A) or (B):

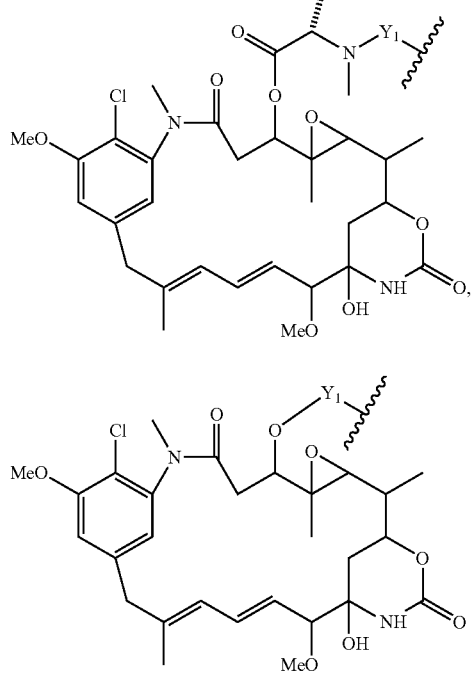

(A)

, or (B)

wherein:

Y$_1$ is absent or —C(=O)(CR$_7$R$_8$)$_{l1}$(CR$_5$R$_6$)$_{m1}$(CR$_3$R$_4$)$_{n1}$CR$_1$R$_2$S—, R$_1$, R$_2$, R$_3$, R$_4$, R$_5$, R$_6$, R$_7$ and R$_8$ are each independently H, an alkyl, an alkenyl, a cycloalkyl, a heteroaryl, a heterocyclyl, or an aryl; and l1, m1 and n1 are each independently 0 or an integer from 1 to 5.

More preferably, for structural formula (IV) described in the 18$^{th}$, 19$^{th}$, 20$^{th}$ or 21$^{st}$ specific embodiment, including any related specific embodiment, D is represented by one of the following structural formulas:

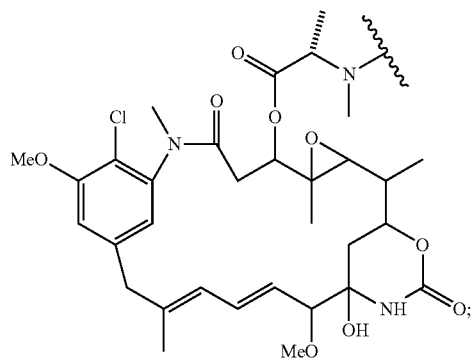

(A1)

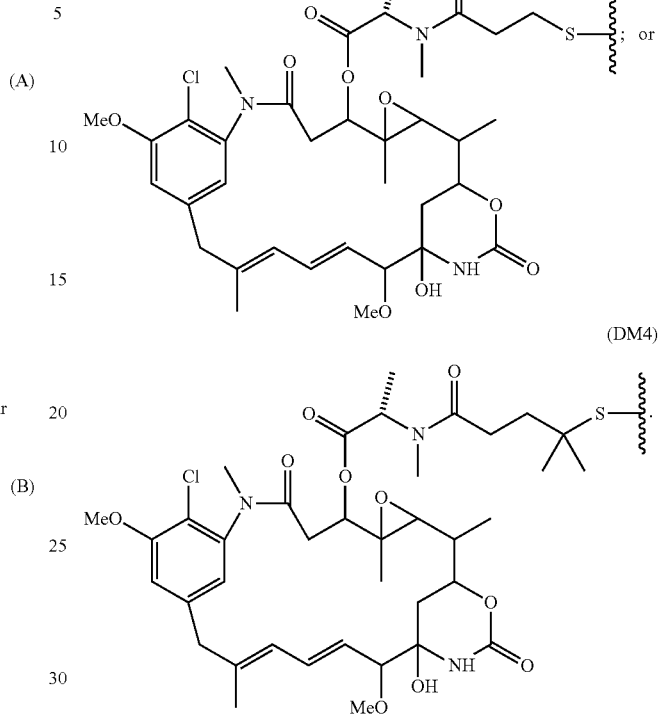

(DM1)

; or (DM4)

In another preferred embodiment, for formula (IV) described in the 18$^{th}$, 19$^{th}$, 20$^{th}$ or 21$^{st}$ embodiment, including any related specific embodiment, X is an optionally substituted phenyl. More preferably, X is represented by any one of the following structural formulas:

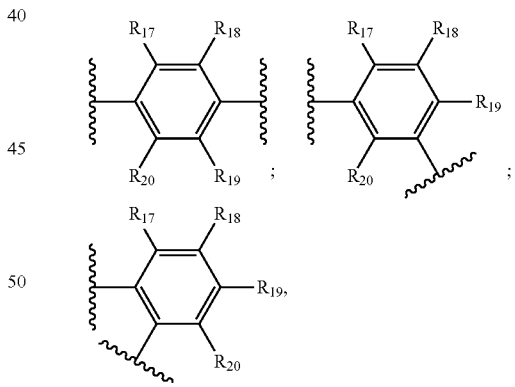

;

;

, wherein R$_{17}$, R$_{18}$, R$_{19}$ and R$_{20}$ each are independently H, an alkyl, H, an alkyl, halogen, —OH, —O-alkyl, —C(=O)OR$_{30}$, —C(=O)R$_{30}$, —NO$_2$, or —CN, wherein R$_{30}$ is H or an alkyl. Preferably, R$_{17}$, R$_{18}$, R$_{19}$ and R$_{20}$ are all H.

In another preferred embodiment, for structural formula (IV), X is optionally substituted six-membered heteroaryl selected from the group consisting of pyridine, pyridazine, pyrimidine, pyrazine, a triazine, and tetrazine, wherein the heteroaryl is connected to the —NH group and -L$_1$ group at the carbon atoms of the heteroaryl; and values and preferred values for the remainder of the variables are as described above in the 18$^{th}$, 19$^{th}$, 20$^{th}$ or 21$^{st}$ specific embodiment.

In another preferred embodiment, for structural formula (IV), X is an optionally substituted five-membered heteroaryl; and preferred values for the remainder of the variables are as described above in the 18$^{th}$, 19$^{th}$, 20$^{th}$ or 21$^{st}$ specific embodiment. More preferably, X is selected from the group consisting of:

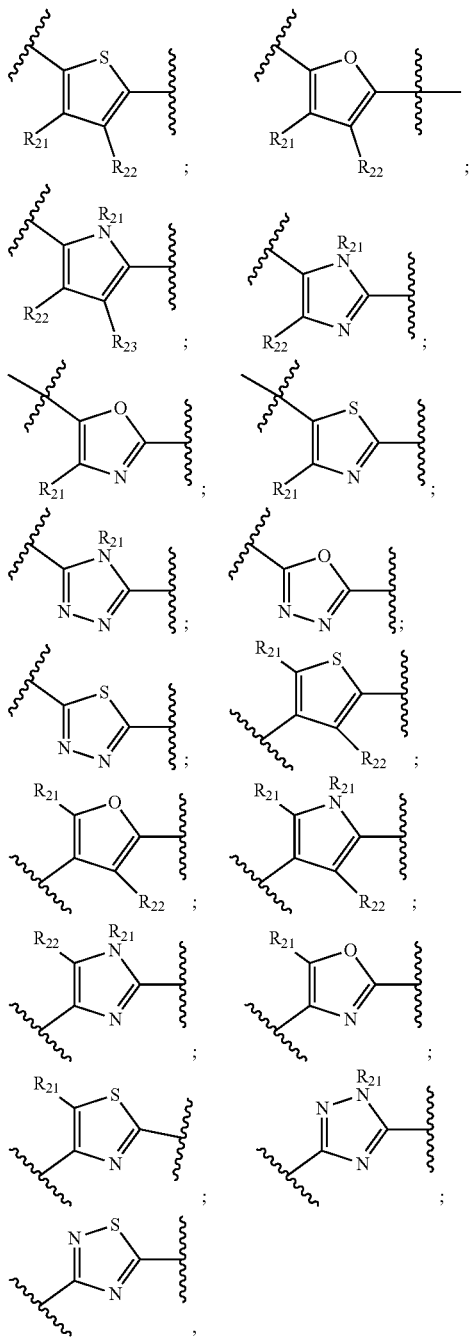

wherein $R_{21}$, $R_{22}$ and $R_{23}$ are each independently H or an alkyl. Preferably, $R_{21}$, $R_{22}$ and $R_{23}$ are all H.

Cell-Binding Agents

The effectiveness of the conjugates of the invention as therapeutic agents depends on the careful selection of an appropriate cell-binding agent. Cell-binding agents may be of any kind presently known, or that become known and includes peptides and non-peptides. Generally, these can be antibodies (especially monoclonal antibodies), lymphokines, hormones, growth factors, vitamins (such as folate etc., which may bind to a cell surface receptor thereof, e.g., a folate receptor), nutrient-transport molecules (such as transferrin), or any other cell-binding molecule or substance.

In certain embodiments, the cell-binding agents are proteins or polypeptides, or compounds comprising proteins or polypeptides. Preferably, the proteins or polypeptides comprise one or more Lys residues with side chain —NH$_2$ groups. Alternatively or in addition, the proteins or polypeptides comprise one or more Cys residues. The side chain —SH groups of the Cys residues may be intact, or may be in a disulfide bond that can be reduced. Preferably, reduction of the disulfide bond(s) does not significantly negatively impact the cell-binding function of the proteins or polypeptides (e.g., in the case of antibody or antigen-binding portion thereof, reduction of the disulfide bonds does not substantially increase the dissociation of light chains/heavy chains).

The Lys side chain —NH$_2$ groups and/or the Cys side chain —SH groups may be covalently linked to the linkers, which are in turn linked to the compounds of the invention, thus conjugating the cell-binding agents to the compounds of the invention. Each protein-based cell-binding agents may contain multiple Lys side chain —NH$_2$ groups and/or the Cys side chain —SH groups available for linking the compounds of the invention.

More specific examples of cell-binding agents that can be used include:

polyclonal antibodies;
monoclonal antibodies;
fragments of antibodies such as Fab, Fab', and F(ab')$_2$, Fv, minibodies, diabodies, tribodies, tetrabodies, nanobodies, probodies, domain bodies, unibodies and the like (Parham, *J. Immunol.* 131:2895-2902 (1983); Spring et al. *J. Immunol.* 113:470-478 (1974); Nisonoff et al. *Arch. Biochem. Biophys.* 89:230-244 (1960), Kim et al., Mol, Cancer Ther., 7: 2486-2497 (2008), Carter, Nature Revs., 6: 343-357 (2006), R. Kontermann & S. Dubel, 2001 Antibody Engineering, Springer-Verlag, Heidelberg-New York);
bispecific antibodies (Morrison, S L *Nature biotechnology* 25 (11): 1233-4 (2007));
nanobody, probody, diabody, minibody, centyrins;
ankyrin repeat proteins (DARPins; Zahnd et al., *J. Biol. Chem.*, 281, 46, 35167-35175, (2006); Binz, H. K., Amstutz, P. & Pluckthun, A. (2005) *Nature Biotechnology*, 23, 1257-1268) or ankyrin-like repeats proteins or synthetic peptides described, for example, in U.S. Patent Publication Number 20070238667; U.S. Pat. No. 7,101,675; and WO/2007/147213; WO/2007/062466);
interferons (e.g. α, β, γ);
lymphokines such as IL-2, IL-3, IL-4, IL-6;
hormones such as insulin, TRH (thyrotropin releasing hormone), MSH (melanocyte-stimulating hormone), steroid hormones, such as androgens and estrogens;
growth factors and colony-stimulating factors such as EGF, TGF-alpha, FGF, VEGF, G-CSF, M-CSF and GM-CSF (Burgess, *Immunology Today* 5:155-158 (1984));
transferrin (O'Keefe et al. *J. Biol. Chem.* 260:932-937 (1985)); and
vitamins, such as folate.

Protein scaffolds based on a consensus sequence of fibronectin type III (FN3) repeats (also known as Centyrins; See U.S. Patent Publication 2010/0255056, incorporated herein by reference);

Designer Ankyrin Repeat Proteins (DARPins; U.S. Patent Application Nos. 20040132028; 20090082274;

20110118146; 20110224100, incorporated herein by reference), C. Zahnd et al. 2010, Cancer Res., 70; 1595-1605, incorporated herein by reference); and, Fibronectin domain scaffold proteins (Adnectins: US Patent Application Nos. 20070082365; 20080139791, incorporated herein by reference).

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969,108; McCafferty et al., WO 92/01047; Liming et al., WO 99/06587). In addition, resurfaced antibodies disclosed in U.S. Pat. No. 5,639,641 may also be used, as may chimeric antibodies and humanized antibodies. Selection of the appropriate cell-binding agent is a matter of choice that depends upon the particular cell population that is to be targeted, but in general human monoclonal antibodies are preferred if an appropriate one is available.

For example, the monoclonal antibody MY9 is a murine $IgG_1$ antibody that binds specifically to the CD33 Antigen {J. D. Griffin et al 8 Leukemia Res., 521 (1984)} and can be used if the target cells express CD33 as in the disease of acute myelogenous leukemia (AML). The cell-binding agent may be any compound that can bind a cell, either in a specific or non-specific manner. Generally, these can be antibodies (especially monoclonal antibodies and antibody fragments), interferons, lymphokines, hormones, growth factors, vitamins, nutrient-transport molecules (such as transferrin), or any other cell-binding molecule or substance.

Where the cell-binding agent is an antibody, it binds to an antigen that is a polypeptide and may be a transmembrane molecule (e.g. receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; fibroblast growth factor receptor 2 (FGFR2), epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins, EpCAM, GD3, FLT3, PSMA, PSCA, MUC1, MUC16, STEAP, CEA, TENB2, EphA receptors, EphB receptors, folate receptor, FOLR1, mesothelin, cripto, $alpha_v beta_6$, integrins, VEGF, VEGFR, EGFR, tarnsferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CD152 or an antibody which binds to one or more tumor-associated antigens or cell-surface receptors disclosed in US Publication No. 20080171040 or US Publication No. 20080305044 and are incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as HER2, HER3 or HER4 receptor; endoglin, c-Met, c-kit, 1GF1R, PSGR, NGEP, PSMA, PSCA, LGR5, B7H4, TAG72 (tumor-associated glycoprotein 72) and fragments of any of the above-listed polypeptides.

Additionally, GM-CSF, which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Folic acid can be used to target the folate receptor expressed on ovarian and other tumors. Epidermal growth factor can be used to target squamous cancers such as lung and head and neck. Somatostatin can be used to target neuroblastomas and other tumor types.

Cancers of the breast and testes can be successfully targeted with estrogen (or estrogen analogues) or androgen (or androgen analogues) respectively as cell-binding agents.

In one embodiment, the cell-binding agent is humanized monoclonal antibodies. In another embodiment, the cell-binding agent is huMy9-6, or other related antibodies, which are described in U.S. Pat. Nos. 7,342,110 and 7,557,189 (incorporated herein by reference). In another embodiment, the cell-binding agent is an anti-folate receptor antibody described in U.S. Provisional Application Nos. 61/307,797, 61/346,595, 61/413,172 and U.S. application Ser. No. 13/033,723 (published as US 2012-0009181 A1). The teachings of all these applications are incorporated herein by reference in its entirety.

In certain embodiments, the cell-binding agent may be a monoclonal antibody or antigen-binding portions thereof sharing sequences critical for antigen-binding with an antibody disclosed herein, such as huMy9-6 or its related antibodies described in U.S. Pat. Nos. 7,342,110 and 7,557, 189 (incorporated herein by reference). These derivative antibodies may have substantially the same or identical (1) light chain and/or heavy chain CDR3 regions; (2) light chain and/or heavy chain CDR1, CDR2, and CDR3 regions; or (3) light chain and/or heavy chain regions, compared to an antibody described herein. Sequences within these regions may contain conservative amino acid subsitutions, including substitutions within the CDR regions. Preferably, there is no more than 1, 2, 3, 4, or 5 conservative substitutions. In certain embodiments, the derivative antibodies have a light chain region and/or a heavy chain region that is at least about 90%, 95%, 99% or 100% identical to an antibody described herein. These derivative antibodies may have substantially the same binding specificity and/or affinity to the target antigen compared to an antibody described herein. Preferably, the $K_d$ and/or $k_{off}$ values of the derivative antibodies are within 10-fold (either higher or lower), 5-fold (either higher or lower), 3-fold (either higher or lower), or 2-fold (either higher or lower) of an antibody described herein. These derivative antibodies may be fully human antibodies, or humanized antibodies, or chimeric antibodies. The derivative antibodies may be produced according to any art-recognized methods.

In another embodiment, the cell-binding agent is anti-EGFR antibodies or fragments therefore. Preferably, the anti-EGFR antibodies or fragments thereof are as described in U.S. Provisional Application Nos. 61/408,500, filed on Oct. 29, 2010; 61/436,012, filed on Jan. 25, 2011; 61/408, 497, filed on Oct. 29, 2010, and 61/477,086, filed on Apr. 19, 2011, the entire teachings of which are incorporated herein by reference in its entirety. In a preferred embodiment, the anti-EGFR antibody is huML66. In another preferred embodiment, the anti-EGFR antibody is huEGFR-7. Even more preferably, the anti-EGFR antibody is huEGFR-7R, wherein the heavy chain of the antibody comprising the amino acid sequence of the huEGFR-7 $V_H$ sequence and the light chain of the antibody comprising the amino acid sequence of the huEGFR-7R $V_L$ v.1.0 sequence.

In one embodiment, the cell binding agent is anti-CD20 antibodies. Preferably, the anti-CD20 antibodies are as described in the US2011/0195021 (e.g., huCD20-7), the entire teachings of which are incorporated herein by reference in its entirety.

Production of Cell-Binding Agent-Drug Conjugates

Figure 10:
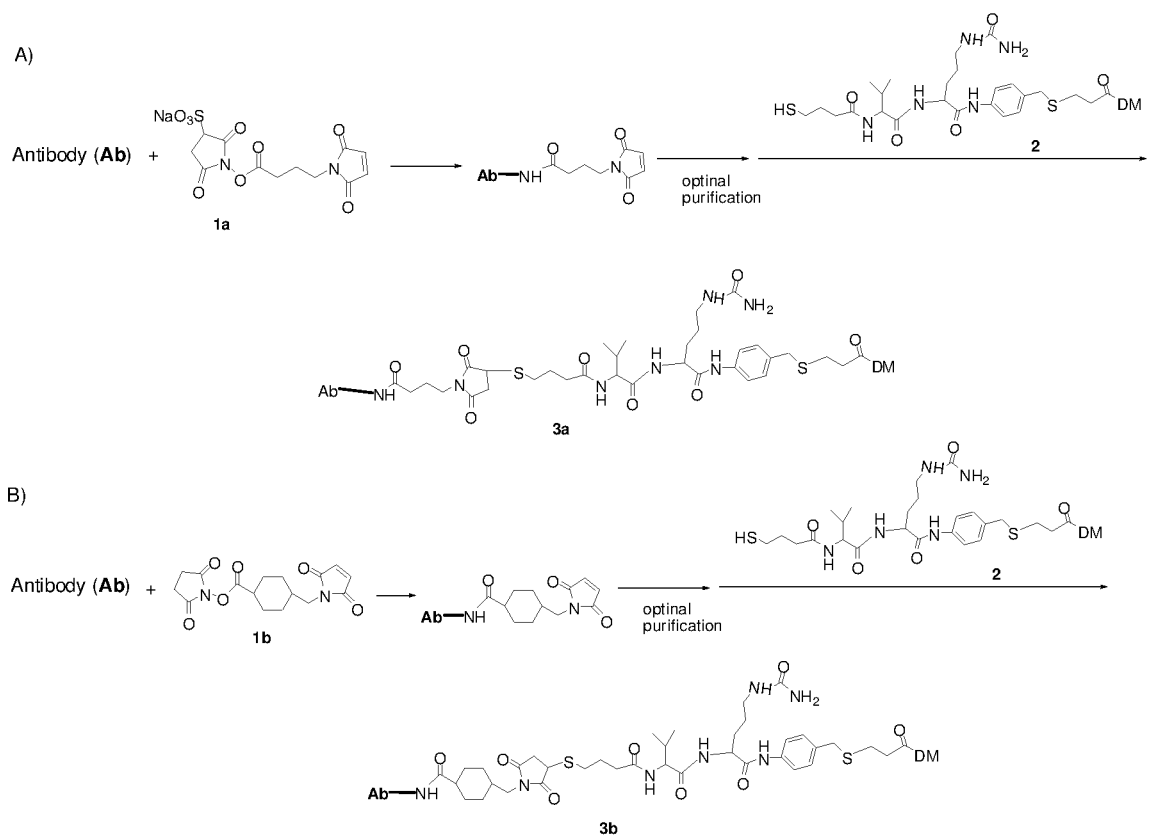
FIG. 10 depicts a two-step and a one-pot process for preparing representative conjugates of the present invention.
Figure 20:
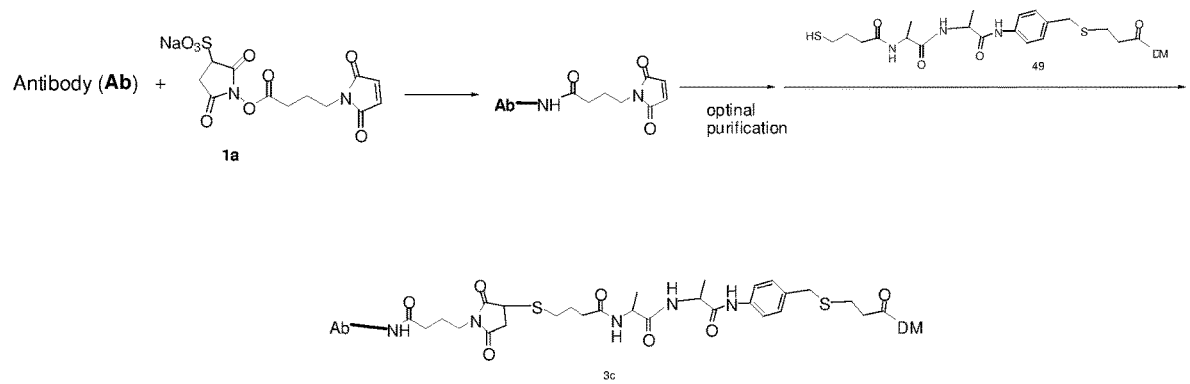
FIG. 20-22 show various synthetic schemes for making antibody conjugates Ab-3c and Ab-3d comprising the Ala-Ala-PAB-DM1 moiety.
Figure 20:
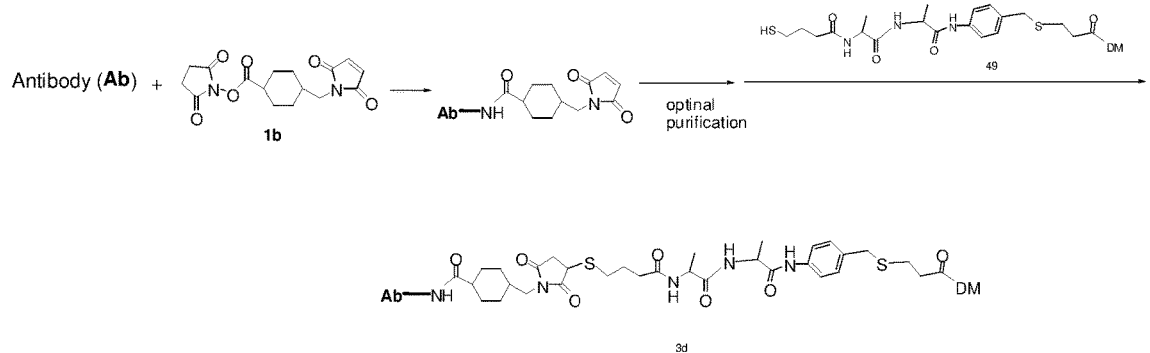

The conjugates of the present invention can be prepared according to any known method in the art. See, for example, WO 2009/134977, U.S. Pat. Nos. 7,811,572, 6,441,163, U.S 2006/0182750, and Widdison, W. C. et. al. Semisynthetic maytansine analogues for the targeted treatment of cancer. *J Med Chem* 2006, 49 (14), 4392-4408, In one embodiment, the conjugates of the present invention can be prepared by: a) reacting a cell-binding agent with a linker compound (e.g., compounds of formula III) to form a modified cell-binding agent having the linkers covalently bound thereto; b) optionally purifying the modified cell-binding agent; c) conjugating a cytotoxic agent to the modified cell-binding agent to form a cell-binding agent-cytotoxic agent conjugate; and d) purifying the cell-binding agent-cytotoxic agent conjugate. Representative processes are shown in FIGS. 10 and 20.

In one embodiment, conjugates of compounds of the invention with cell binding agents can be produced by methods described in the art. For example, U.S. Pat. No. 7,855,275 describes the method of conjugation with an antibody bearing engineered cysteine residues. Alternatively, thiol groups can be generated by controlled reduction of interchain disulfides of antibodies, followed by treatment with a cytotoxic agent bearing a maleimido group, as described in U.S. Pat. No. 7,659,241. Thiol groups can also be introduced into antibodies by reaction with a crosslinking agent such as 2-iminothiolane (see for example Goff and Carroll *Bioconjugate Chem.*, 1990, 1 (6), pp 381-386) followed by reaction with a cytotoxic agent bearing a maleimido group to provide a conjugate. Methods to produce conjugate through lysine residues on an antibody are described in the art (see for example U.S. Pat. No. 7,851, 432).

Figure 11:
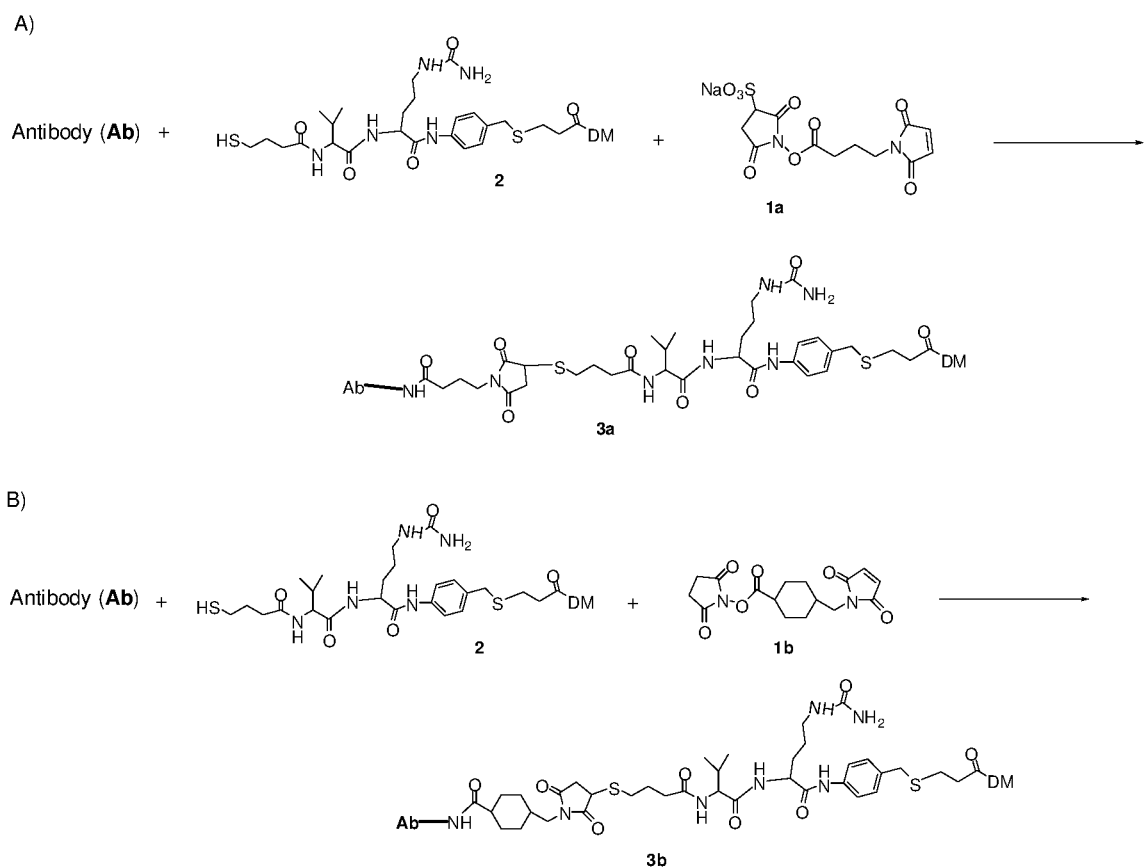
FIG. 11 depicts a one-step process for preparing representative conjugates of the present invention.
Figure 21:
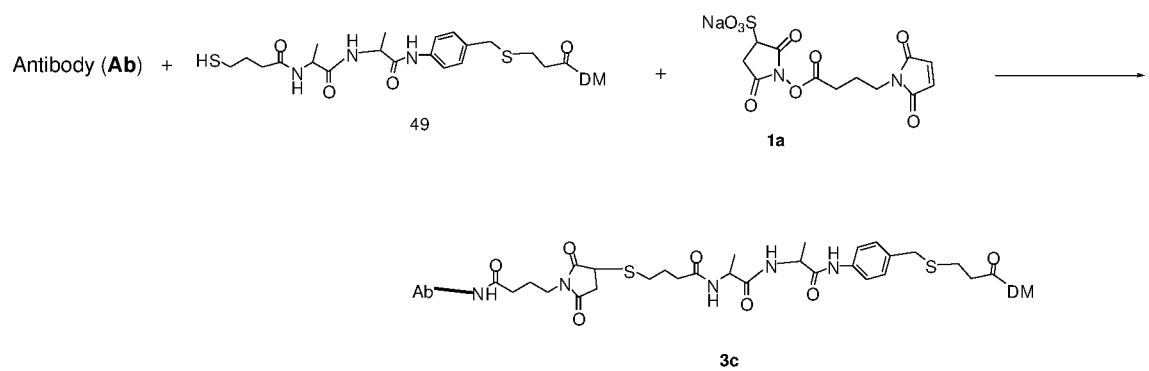
Figure 21:
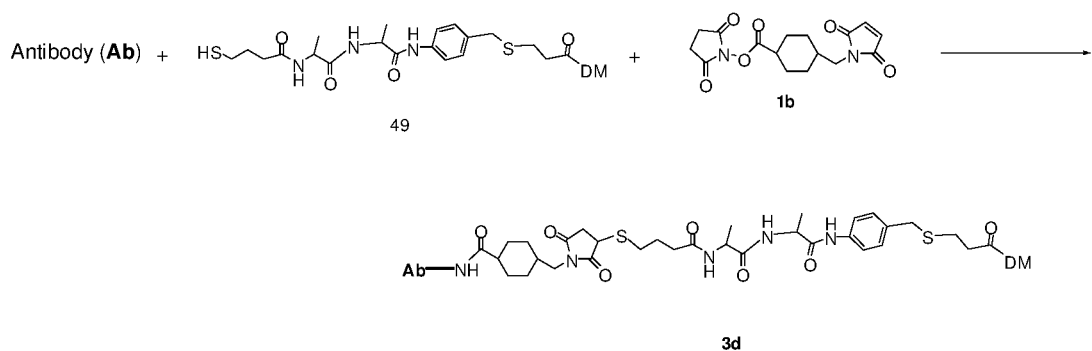

In another embodiment, the conjugate of the present invention can be prepared by mixing together a cell-binding agent, a cytotoxic agent and a linker compound. Preferably, the cell-binding agent is contacted with a cytotoxic agent first to form a mixture comprising the cell-binding agent and the cytotoxic agent, followed by contacting the mixture with a linker compound (e.g., compounds of formula (III)) to form the cell-binding agent-cytotoxic agent conjugate. The conjugate can then be purified. Representative processes are shown in FIGS. 11 and 21.

Figure 12:
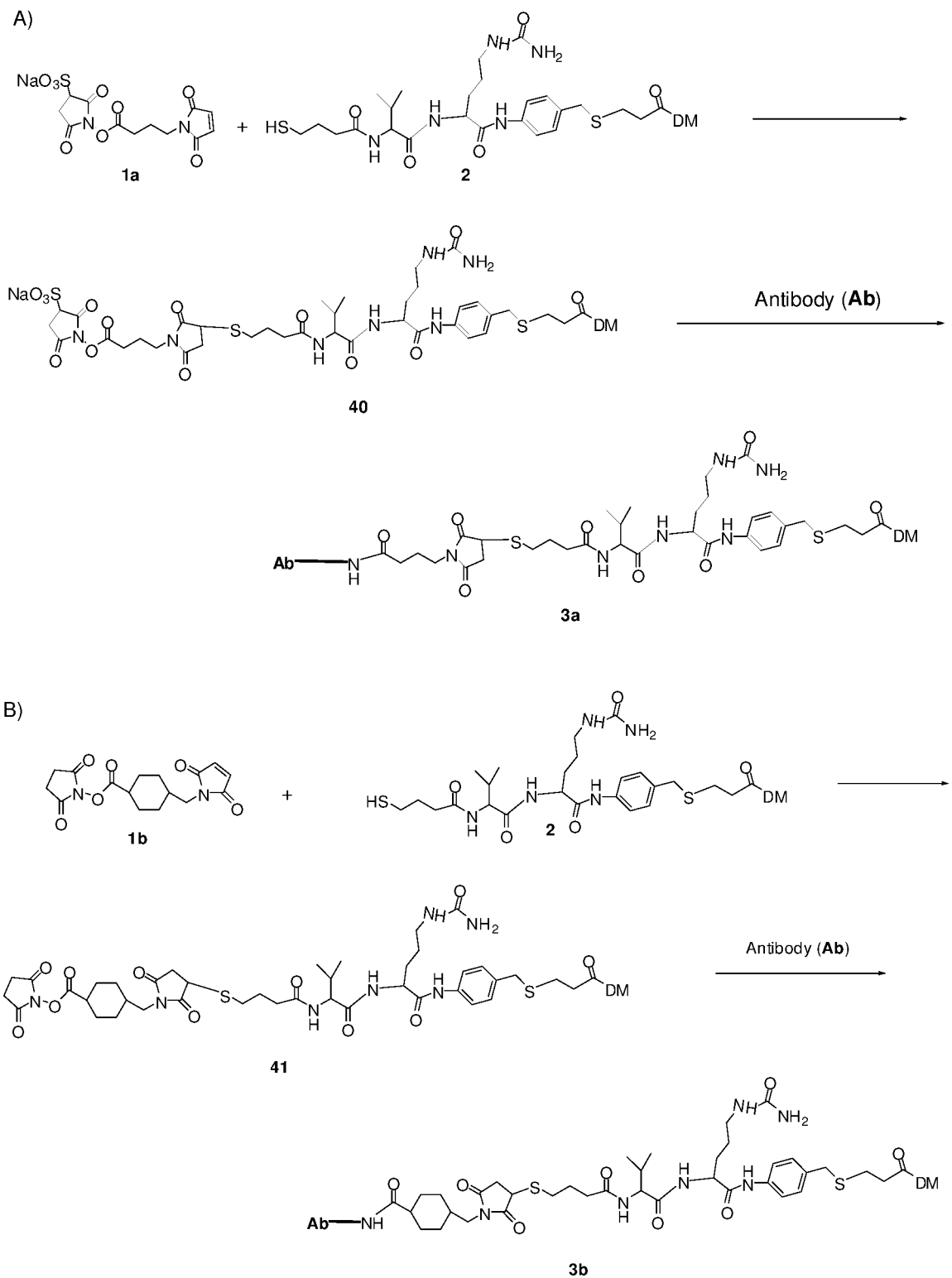
FIG. 12 depicts a one-step process for preparing representative conjugates for the present invention involving pre-forming the drug-linker compounds.
Figure 13:
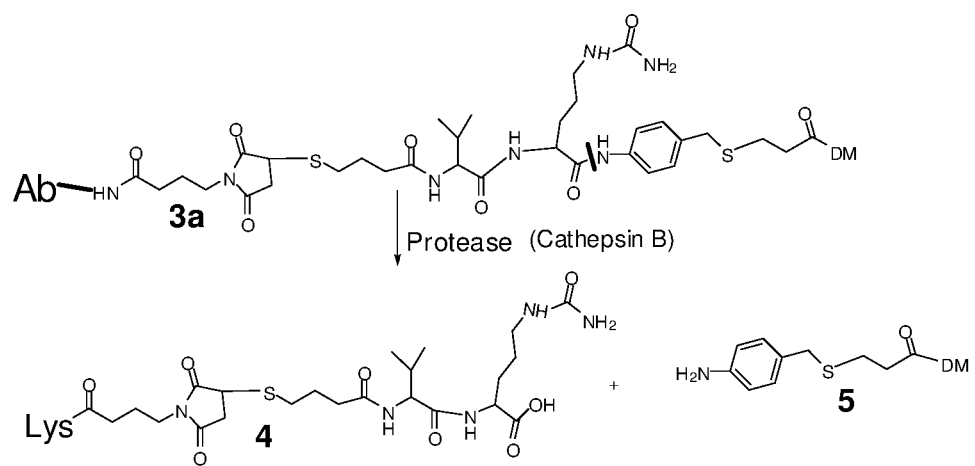
FIG. 13 shows a scheme for cleavage of conjugate 3a by protease cathepsin B.
Figure 22:
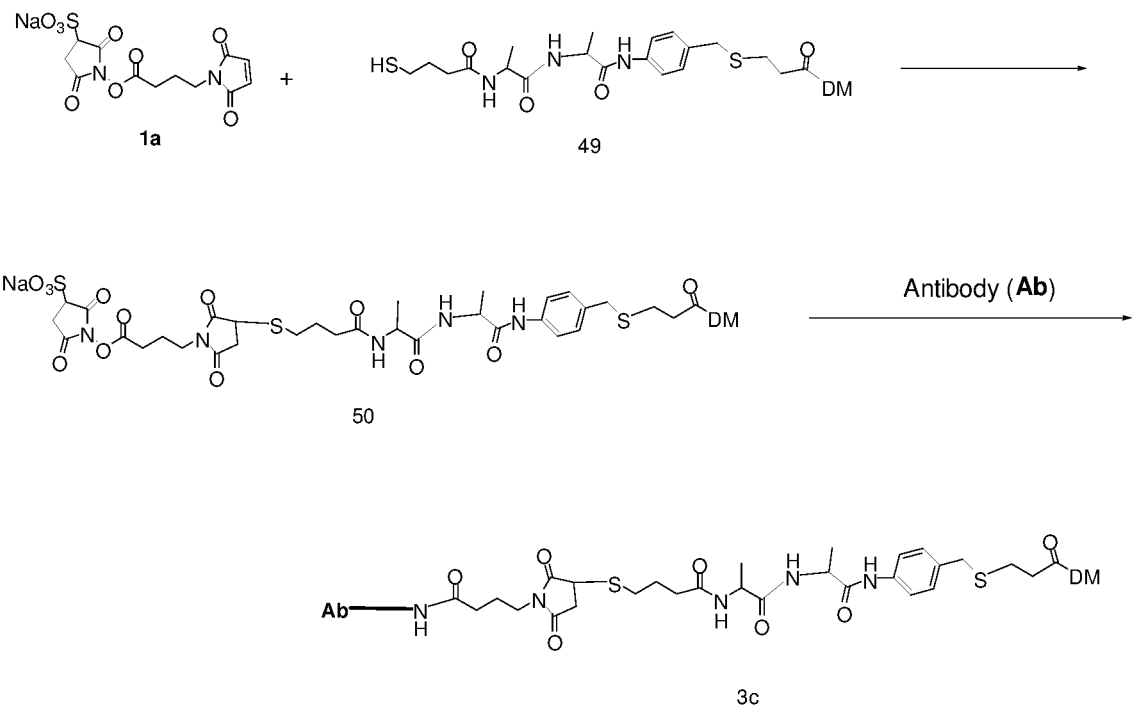
Figure 22:
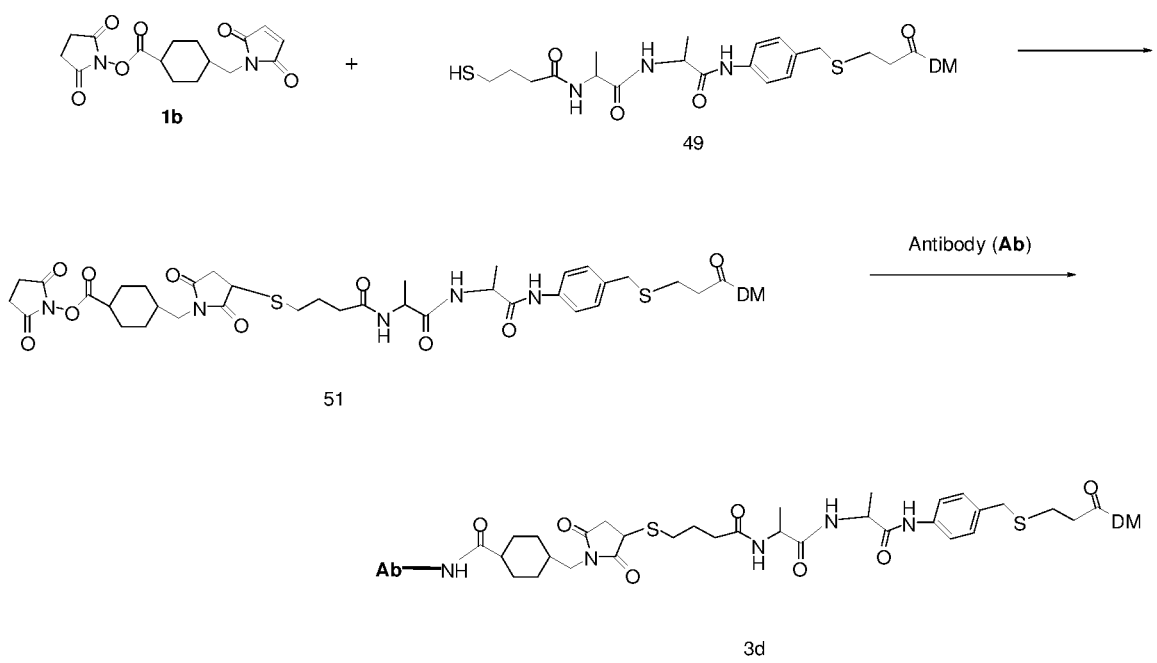
Figure 23:
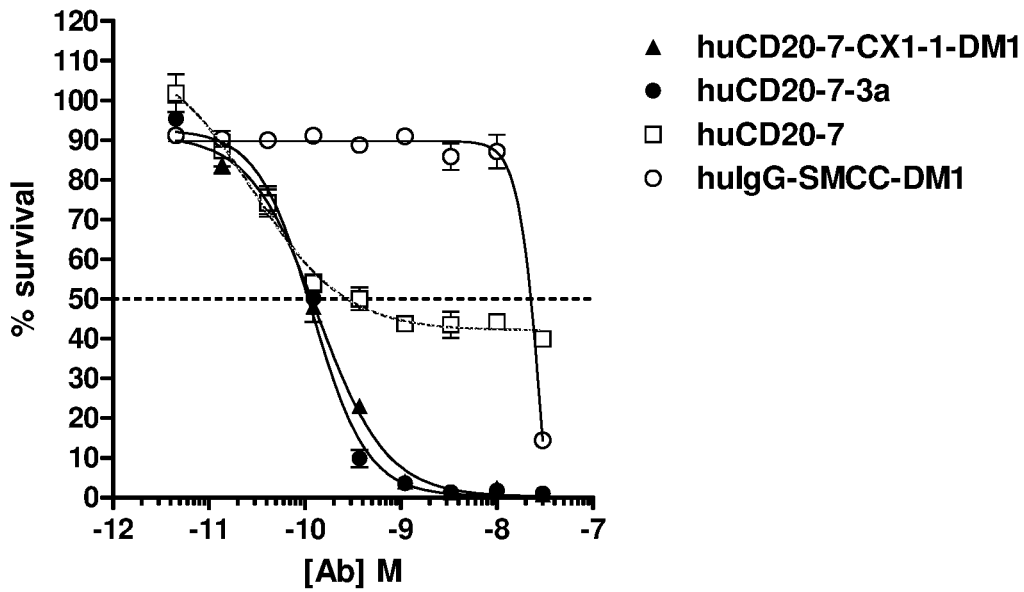
FIG. 23 shows in vitro cytotoxicity data for huCD20-7-3a conjugate as compared to naked antibody and conjugates with other linkers. "huCD20-7 (Ab)" is the human anti-CD20 antibody without conjugated cytotoxic agent DM1. "huIgG-SMCC-DM1" is a negative control conjugate with a human IgG (not specific for CD20) conjugated with DM1 through an SMCC type linker moiety. Grante 519 is a mantle cell lymphoma cell line, and Farage is a diffuse large cell non-Hodgkin's lymphoma (DLCL) cell line.
Figure 23:
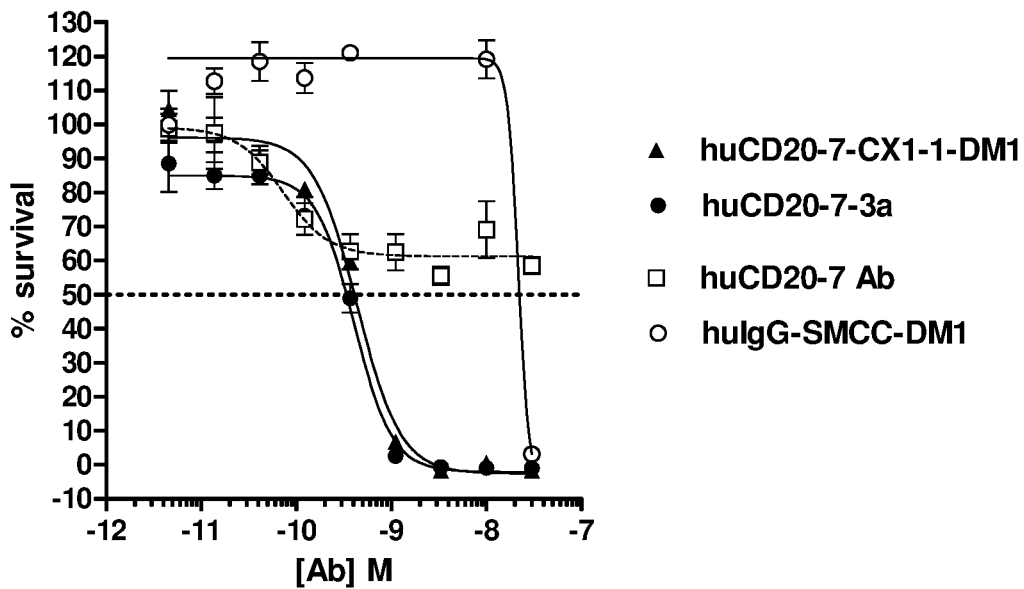

In another embodiment, the conjugates of the present invention can be prepared by reacting a cell-binding agent with a drug-linker compound (e.g., compounds of formula (IV)) having a reactive moiety capable of forming a covalent bond with the cell-binding agent to form a cell-binding agent-cytotoxic agent conjugate. The conjugate can then be purified. The drug-linker compound can be generated in situ and used to react with the antibody without purification. Representative processes are shown in FIGS. 12 and 22.

The number of cytotoxic compound molecule bound per cell-binding agent (e.g., antibody) molecule can be determined spectroscopically by measuring the ratio of the absorbance at 280 nm and 252 nm. An average of 1-20 cytotoxic compounds/antibody molecule(s) can be linked by the methods described herein. The preferred average number of linked cytotoxic compounds per antibody molecule is 1-10, more preferably 2-5, and even more preferably is 2.5-4.0.

Cytotoxicity of Compounds and Conjugates of the Invention

Figure 14:
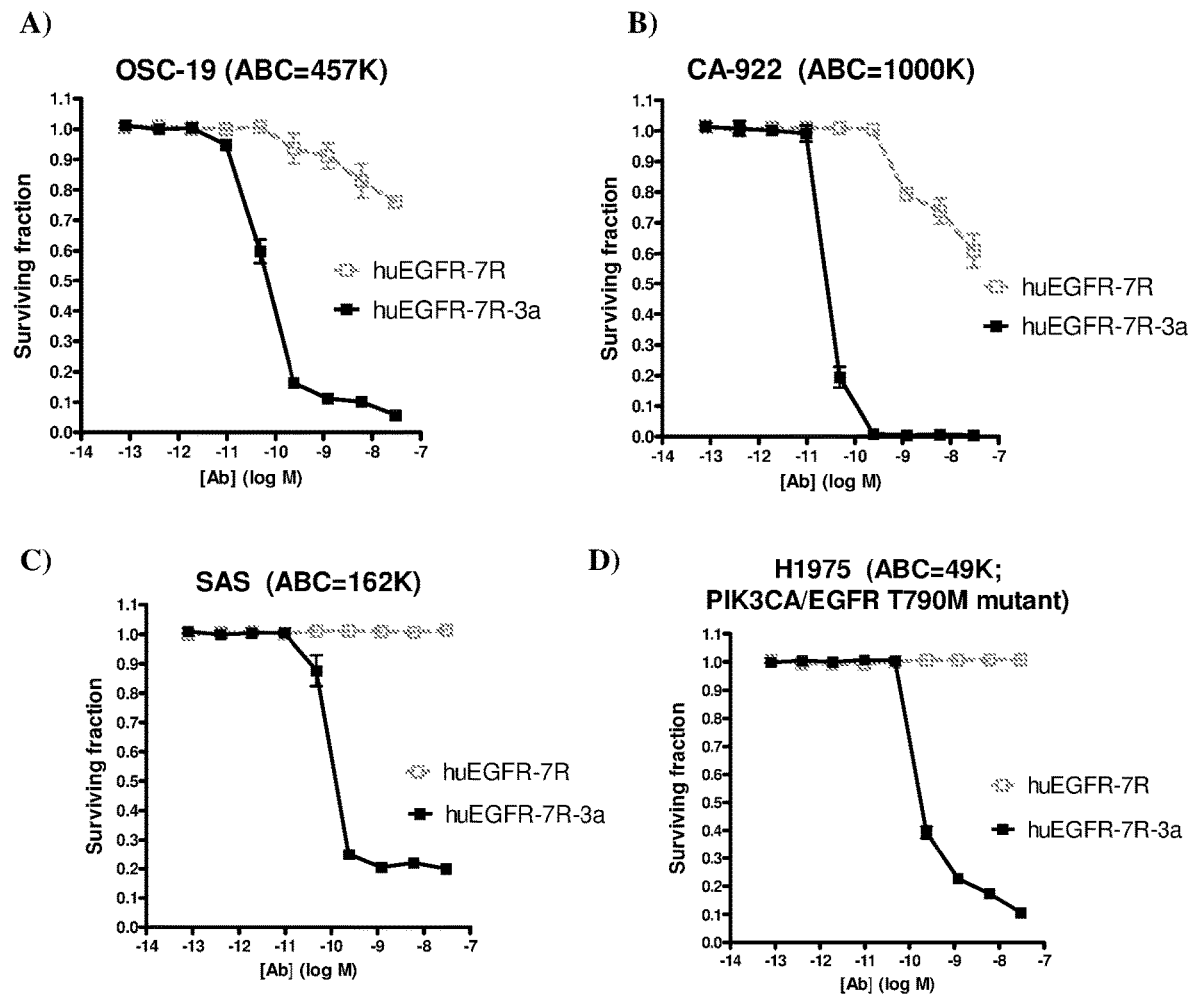
FIG. 14 shows in vitro cytotoxicity of EGFR-7R-3a conjugate compared to the naked antibody.

The cytotoxic compounds and cell-binding agent-drug conjugates of the invention can be evaluated for their ability to suppress proliferation of various cancer cell lines in vitro. The in vitro cytotoxicity assays can be conducted using methods known in the art (e.g., Widdison, W. C. et. al. Semisynthetic maytansine analogues for the targeted treatment of cancer. *J Med Chem* 2006, 49 (14), 4392-408). For example, cells to be evaluated can be exposed to the compounds or conjugates for 1-5 days and the surviving fractions of cells measured in direct assays by known methods. $IC_{50}$ values can then be calculated from the results of the assays. Examples of in vitro potency of antibody-cytotoxic agent conjugates of the present invention are shown in FIG. 14. As shown in FIG. 14, the maytansinoid conjugate huEGFR-7R-3a significantly enhanced anti-tumor activity of the huEGFR-7R naked antibody. In addition, the conjugate is highly potent against various cancer cell lines, even the low antigen expressing cell line.

Figure 15:
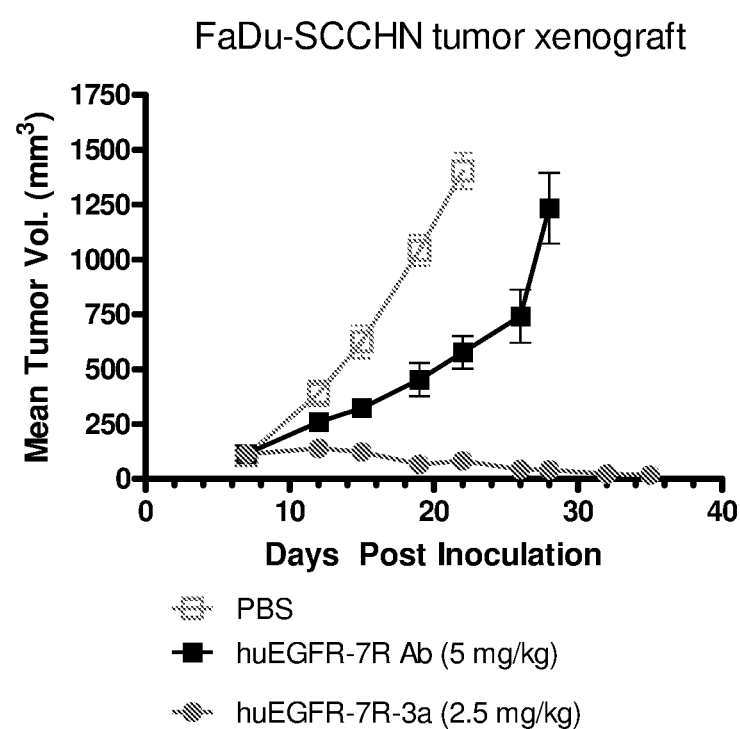
FIG. 15 shows in vivo antitumor activity EGFR-7R-3a conjugate as compared to the naked antibody.
Figure 16:
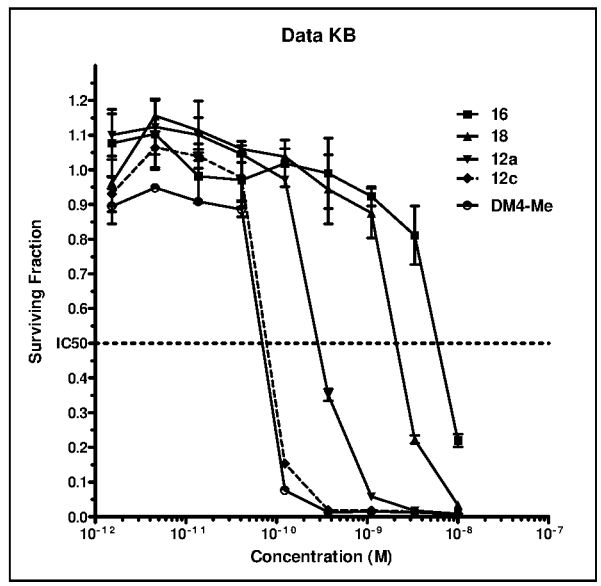
FIG. 16 shows in vitro cytotoxicity of representative cytotoxic compounds of the present invention as compared to DM4-Me.
Figure 17:
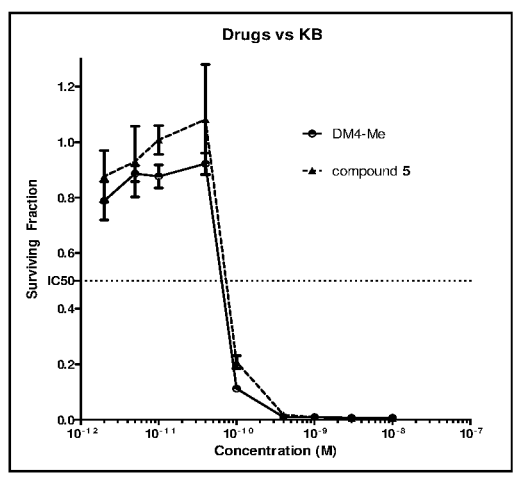
FIG. 17 shows in vitro cytotoxicity of compound 5 (protease cleavage product of EGFR-7R-3a conjugate) as compared to DM4-Me.

The conjugates of the present invention are also effective in inhibiting tumor growth in tumor bearing nude mice. Examples of in vivo efficacy are shown in FIG. 15. FIG. 15 shows that the huEGFR-7R-3a conjugate is significantly more active than the naked antibody, with 3 out of 6 mice had complete response and 7% T/C.

Compositions and Methods of Use

The present invention includes a composition (e.g., a pharmaceutical composition) comprising conjugates (e.g., conjugates of formula (I)) or cytotoxic compounds described herein (e.g., compounds of formula (II)), and a carrier (a pharmaceutically acceptable carrier). The present invention also includes a composition (e.g., a pharmaceutical composition) comprising conjugates (e.g., conjugates of formula (I)) or cytotoxic compounds described herein (e.g., compounds of formula (II)), and a carrier (a pharmaceutically acceptable carrier), further comprising a second therapeutic agent. The present compositions are useful for inhibiting abnormal cell growth or treating a proliferative disorder in a mammal (e.g., human). The present compositions are also useful for treating depression, anxiety, stress, phobias, panic, dysphoria, psychiatric disorders, pain, and inflammatory diseases in a mammal (e.g., human).

The present invention includes a method of inhibiting abnormal cell growth or treating a proliferative disorder in a mammal (e.g., human) comprising administering to said mammal a therapeutically effective amount of conjugates (e.g., conjugates of formula (I)) or cytotoxic compounds described herein (e.g., compounds of formula (II)), or a composition thereof, alone or in combination with a second therapeutic agent.

The present invention also provides methods of treatment comprising administering to a subject in need of treatment an effective amount of any of the conjugates described above.

Similarly, the present invention provides a method for inducing cell death in selected cell populations comprising contacting target cells or tissue containing target cells with an effective amount of the conjugates of the present invention. The target cells are cells to which the cell-binding agent of the conjugates can bind.

If desired, other active agents, such as other anti-tumor agents, may be administered along with the conjugate.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/ml to 25 mg/ml human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

Examples of in vitro uses include treatments of autologous bone marrow prior to their transplant into the same patient in order to kill diseased or malignant cells: treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 µM to 1 µM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent or conjugates of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 1000 ml of normal saline to which 5 to 10 ml of human serum albumin can be added. Dosages will be 10 µg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of inducing cell death in selected cell populations include malignancy of any type including, for example, cancer of the lung (small cell and non-small cell), breast, colon, brain, prostate, kidney, pancreas, ovary, head and neck, skin (melanoma), Merkel cell carcinoma, glioblastoma, neuroblastoma, and cancers of lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; and parasite infections, such as giardiasis, amoebiasis, schistosomiasis, and others as determined by one of ordinary skill in the art.

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. One of skill in the art can review the PDR, using one or more of the following parameters, to determine dosing regimen and dosages of the chemotherapeutic agents and conjugates that can be used in accordance with the teachings of this invention. These parameters include: Comprehensive index; Manufacturer; Products (by company's or trademarked drug name); Category index; Generic/chemical index (non-trademark common drug names); Color images of medications; Product information, consistent with FDA labeling; Chemical information; Function/action; Indications & Contraindications; Trial research, side effects, warnings.

Analogues and Derivatives

One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

All references cited herein and in the examples that follow are expressly incorporated by reference in their entireties.

EXAMPLES

Material and Methods

All reagents were obtained from Sigma-Aldrich chemical Co., unless otherwise stated. All synthetic reactions were conducted under an argon atmosphere with magnetic stirring unless otherwise stated. Compound 6 was prepared as described by Dubowchick et al and is also described here (Dubowchik, G. M et. al. Cathepsin B-labile dipeptide linkers for lysosomal release of doxorubicin from internalizing immunoconjugates: model studies of enzymatic drug release and antigen-specific in vitro anticancer activity. *Bioconjug Chem* 2002, 13 (4), 855-69). Solutions of $N^{2'}$-deacetyl-$N^{2'}$—(N-methyl-alanyl)-maytansine in ethyl acetate were prepared as described in (U.S. Pat. No. 7,598,375 B2). Proton magnetic resonance ($^1$H NMR) and carbon magnetic resonance spectra ($^{13}$C NMR) were obtained on a Bruker Avance spectrometer operating at 400 MHz and 100 MHz respectively. The NMR chemical shifts are reported in δ values relative to the sample solvent. Preparative high performance liquid chromatography was performed on a Varian instrument and analytical HPLC was performed on an Agilent 1100 HPLC. DM1 and DM4 compounds were prepared by established methods (U.S. Pat. Nos. 7,301,019 B2, 7,598,375 B2).

The Following Lists Preparative HPLC Methods:

Preparative C18 HPLC Method 1:
Column: 50 mm×250 mm, Kromasil, 10 um, C18
Flow rate: 100 mL/min
Detection: Typically 220 nm, 252 nm or 280 nm
Solvent A: deionized water containing 0.2% formic acid
Solvent B: acetonitrile

| Gradient conditions | |
|---|---|
| Time | % B |
| 0 | 20 |
| 7 | 20 |
| 27 | 95 |
| 32 | 95 |
| 33 | 20 |

With 6 min of re-equilibration between purifications

Preparative C18 HPLC Method 2:
Column: 21.4 mm×100 mm C18, 5 um, Varian Dynamax OmniSphere
Flow rate: 20 mL/min
Detection: 282 nm
Solvent A: Deionized water containing 0.2% formic acid
Solvent B: Acetonitrile

| Gradient conditions | |
|---|---|
| Time | % B |
| 0 | 20 |
| 5 | 20 |
| 25 | 95 |
| 28 | 95 |
| 29 | 20 |
| 36 | 20 |

Preparative C18 HPLC Method 3:
Column: 22 mm×150 mm, Kromasil, 10 um, C18
Flow rate: 20 mL/min
Detection: Typically 220 nm, 252 nm or 280 nm
Solvent A: deionized water containing 0.2% formic acid
Solvent B: acetonitrile

| Gradient conditions | |
|---|---|
| Time | % B |
| 0 | 10 |
| 20 | 95 |
| 20.5 | 10 |
| 25 | 10 |

As used herein, abbreviations May, DM, DM1, DM4, and DM4-Me are represented by the following structures:

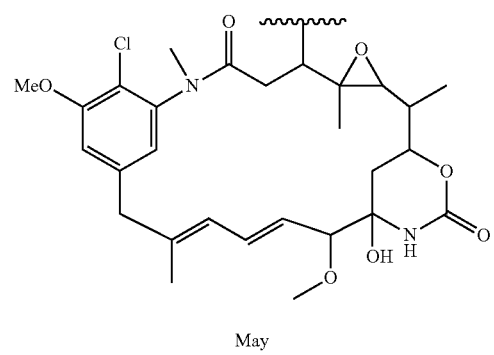

May

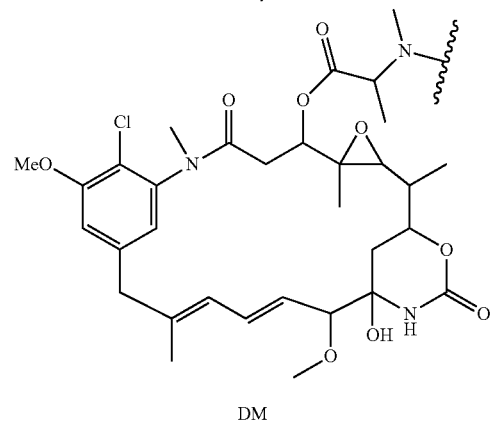

DM

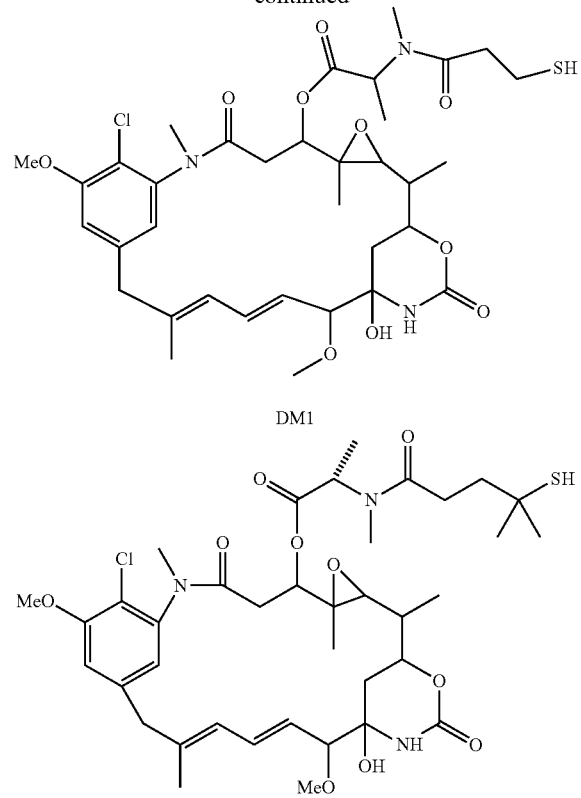
DM1
DM4
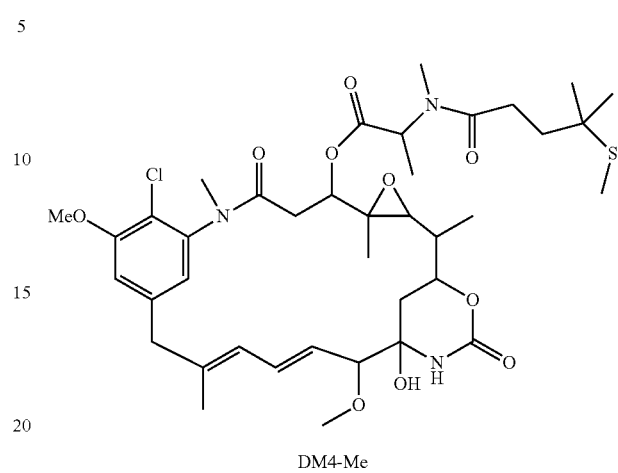
DM4-Me
Example 1. Synthesis of Compound 2
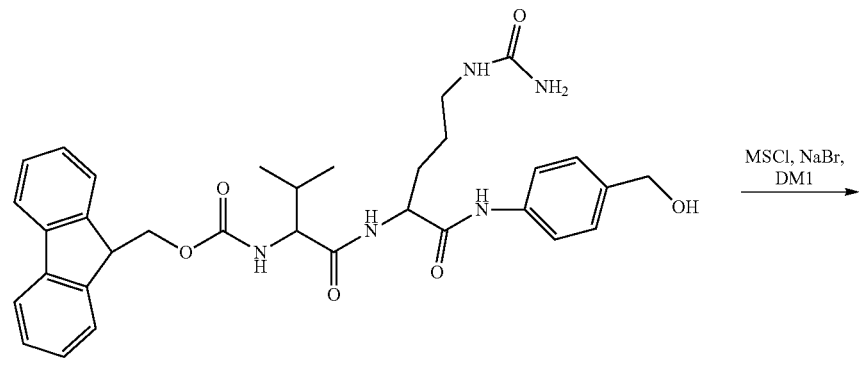
6
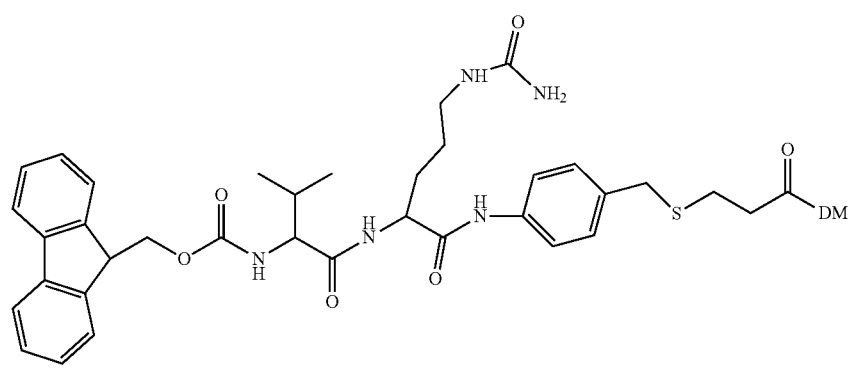
7

Compound 6:

To a suspension of compound 6 (0.96 g, 1.6 mmol) in anhydrous dimethylformamide (9.0 mL) was added triethylamine (0.36 mL, 2.6 mmol) followed by mesyl chloride (0.19 mL, 2.4 mmol). After 20 min sodium brimide (0.98 g, 9.6 mmol) was added. After an additional 4 h a solution of DM1 (490 mg, 0.67 mmol) in dimethyl acetamide (12 mL) was added and the reaction was stirred for 2 h. The reaction mixture was purified by preparative C 18 HPLC method 1 ($R_f$=23 min). Fractions containing desired pure product were combined and solvent was evaporated under vacuum to give 450 mg of compound 7 (50% yield). $^1$H NMR (400 MHz, CDCl$_3$) δ 10.00 (s, 1H), 8.10 (d, J=7.4 Hz, 1H), 7.86 (d, J=7.4 Hz, 2H), 7.74 (t, J=7.4 Hz, 2H), 7.53 (d, J=8.1 Hz, 2H), 7.46-7.38 (m, 2H), 7.38-7.30 (m, 3H), 7.14-7.07 (m, 2H), 6.80 (s, 1H), 6.68-6.47 (m, 3H), 6.09-5.90 (m, 1H), 5.63 (dd, J=14.9, 9.1 Hz, 1H), 5.46-5.33 (m, 2H), 4.63-4.45 (m, 2H), 4.41-4.32 (m, 1H), 4.32-4.21 (m, 2H), 4.14 (t, J=11.4 Hz, 1H), 4.01 (d, J=6.7 Hz, 1H), 3.97 (s, 3H), 3.67-3.55 (m, 2H), 3.54-3.34 (m, 4H), 3.31 (s, 3H), 3.17-3.08 (m, 5H), 3.07-2.95 (m, 1H), 2.85 (d, J=9.5 Hz, 1H), 2.73 (s, 3H), 2.70-2.63 (m, 1H), 2.59 (s, 2H), 2.57-2.50 (m, 3H), 2.44 (dd, J=14.9, 7.4 Hz, 1H), 2.12-1.98 (m, 2H), 1.84-1.72 (m, 1H), 1.63 (s, 3H), 1.56-1.29 (m, 5H), 1.23 (d, J=6.6 Hz, 3H), 1.19 (d, J=6.1 Hz, 3H), 0.98-0.86 (m, 6H), 0.81 (s, 3H). $^{13}$C NMR (101 MHz, CDCl$_3$) δ 169.54, 168.83, 168.80, 168.70, 166.40, 157.40, 154.42, 153.69, 149.69, 142.16, 142.03, 139.62, 139.50, 139.05, 139.03, 136.64, 135.95, 131.37, 130.92, 127.16, 126.63, 125.84, 125.28, 123.56, 123.47, 119.92, 118.20, 117.40, 115.72, 112.05, 86.74, 78.31, 75.94, 71.56, 65.11, 64.09, 58.55, 58.19, 54.76, 54.46, 51.28, 49.98, 45.10, 43.93, 38.89, 36.17, 34.79, 33.47, 31.75, 30.27, 28.87, 28.06, 27.90, 25.04, 24.35, 17.57, 16.49, 13.37, 12.74, 11.39, 9.84. HRMS (M+Na)$^+$ calcd for C$_{68}$H$_{85}$ClN$_8$O$_{15}$S, 1343.5441; found 1343.5378.

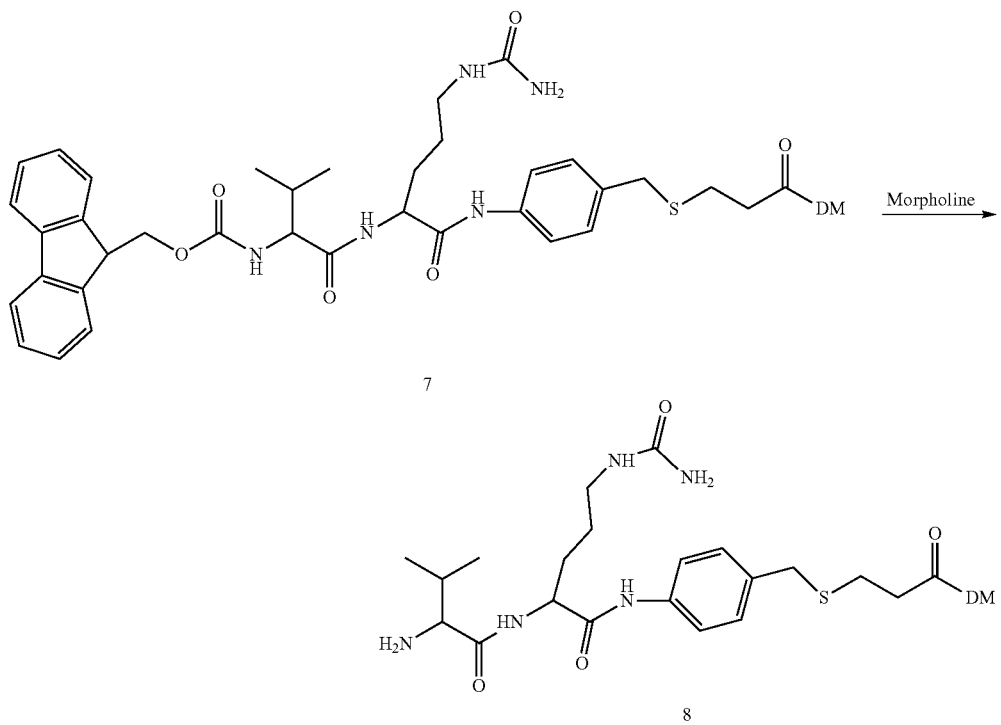

Compound 8:

To a solution of compound 7 (440 mg, 0.33 mmol) in anhydrous dimethylformamide (4 mL) was added morpholine (0.5 mL, 5.7 mmol). After 40 min the reaction was purified by preparative C18 HPLC Method 1 ($R_f$=20 min), fractions containing pure desired product were combined, frozen in a dry ice/acetone bath then lyophilized to give 180 mg of (49% yield) compound 8. $^1$H NMR (400 MHz, DMSO) δ 10.10 (s, 1H), 8.69 (d, J=7.8 Hz, 1H), 8.18-8.07 (m, 2H), 7.49 (d, J=8.5 Hz, 2H), 7.06 (d, J=8.1 Hz, 2H), 6.71 (s, 1H), 6.63-6.43 (m, 3H), 5.58 (dd, J=15.0, 9.1 Hz, 1H), 5.32 (dd, J=13.4, 6.6 Hz, 1H), 4.64-4.49 (m, 2H), 4.16-4.05 (m, 1H), 3.93 (s, 3H), 3.78-3.36 (m, 2H), 3.27 (s, 3H), 3.07 (s, 3H), 3.06-2.96 (m, 1H), 2.80 (d, J=9.6 Hz, 1H), 2.67 (s, 3H), 2.66-2.58 (m, 1H), 2.43-2.30 (m, 1H), 2.18-2.05 (m, 1H), 1.99 (d, J=11.8 Hz, 1H), 1.84-1.71 (m, 1H), 1.71-1.60 (m, 1H), 1.58 (s, 2H), 1.55-1.24 (m, 5H), 1.18 (d, J=6.8 Hz, 3H), 1.14 (d, J=6.3 Hz, 3H), 0.97 (s, 3H), 0.95 (s, 3H), 0.76 (s, 3H). HRMS (M+Na)$^+$ calcd for C$_{53}$H$_{75}$ClN$_8$O$_{13}$S, 1121.4761; found 1121.4717.

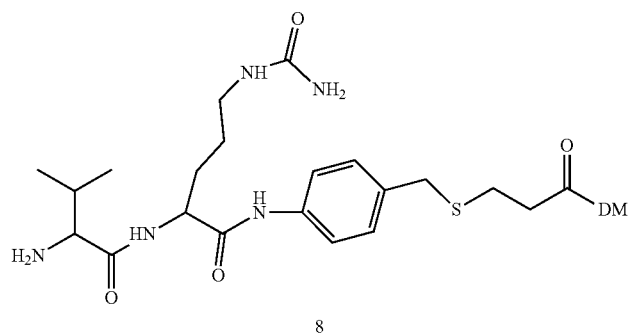 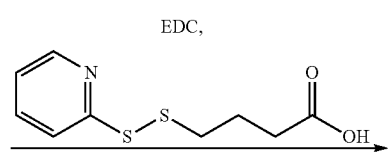

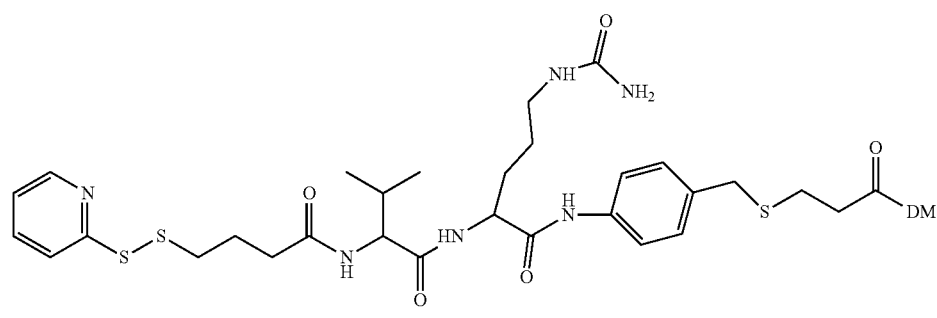

Compound 9:

To a solution of compound 8 (160 mg, 0.14 mmol) and PBA (4-(pyridin-2-yldisulfanyl)butanoic acid) (97 mg, 0.42 mmol) in anhydrous dimethylformamide (2 mL) was added EDC (108 mg, 0.56 mmol) and HOBT (43 mg, 0.28 mmol). After min the reaction was purified by preparative C18 HPLC method 2 ($R_f$=23), fractions containing pure desired product were combined, frozen in a dry ice/acetone bath and lyophilized to give 75 mg (40% yield) of compound 9. $^1$H NMR (400 MHz, CD$_3$CN) δ 8.43-8.35 (m, 3H), 7.87-7.58 (m, 6H), 7.50-7.01 (m, 10H), 6.61-6.40 (m, 2H), 5.59 (dd, J=14.1, 9.1 Hz, 1H), 5.32 (q, J=6.8 Hz, 1H), 4.55 (dd, J=12.1, 3.0 Hz, 1H), 4.39 (dd, J=9.3, 4.7 Hz, 1H), 4.16-4.04 (m, 2H), 3.92 (s, 3H), 3.59 (d, J=2.9 Hz, 2H), 3.53-3.41 (m, 2H), 3.28 (s, 3H), 3.08 (s, 3H), 3.07-2.99 (m, 3H), 2.91-2.76 (m, 5H), 2.68 (s, 3H), 2.66-2.50 (m, 4H), 2.36 (dt, J=7.6, 6.5 Hz, 5H), 1.91-1.87 (m, 2H), 1.58 (s, 3H), 1.49-1.31 (m, 4H), 1.19 (d, J=6.9 Hz, 3H), 1.15 (d, J=6.4 Hz, 3H), 0.88 (d, J=5.0 Hz, 3H), 0.86 (d, J=5.0 Hz, 3H), 0.75 (s, 3H). HRMS (M+Na)$^+$ calcd for C$_{62}$H$_{84}$ClN$_9$O$_{14}$S$_3$, 1332.4886; found 1332.4828.

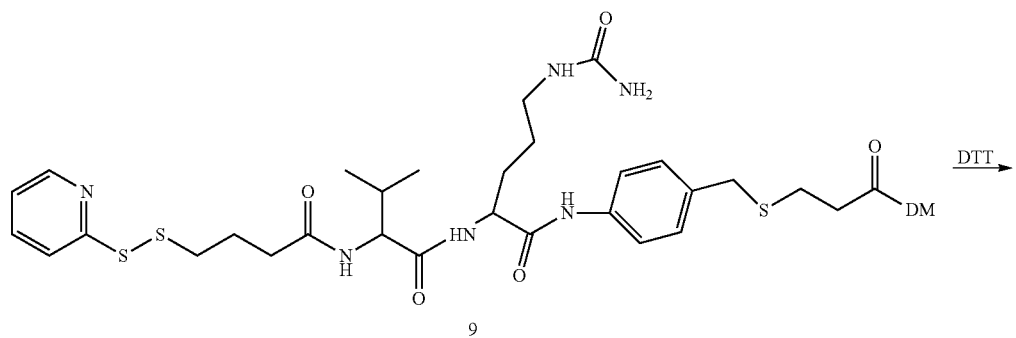

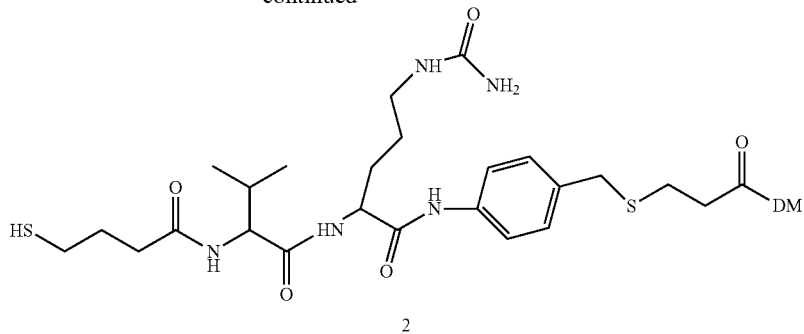

2

Compound 2:

To a solution of compound 9 (70 mg, 0.053 mmol) in 2:1 dimethoxyethane:100 mM potassium phosphate pH 7.5 buffer was added dithiothreitol (41 mg, 0.26 mmol). After 30 min the reaction was purified by semi preparative C18 HPLC method 2 ($R_t$=21 min). Fractions containing pure desired product were combined and frozen in a dry ice/acetone bath then lyophilized to give 11 mg (17%) of compound 2. $^1$H NMR (400 MHz, DMSO) δ 9.88 (s, 1H), 8.04 (d, J=7.6 Hz, 1H), 7.85 (d, J=8.7 Hz, 1H), 7.48 (d, J=8.2 Hz, 1H), 7.11-7.04 (m, 2H), 6.78 (s, 1H), 6.61-6.45 (m, 2H), 6.02-5.96 (m, 2H), 5.91 (s, 1H), 5.57 (dd, J=14.8, 8.8 Hz, 2H), 5.37 (s, 2H), 5.32 (dd, J=12.6, 5.7 Hz, 1H), 4.53 (dd, J=11.7, 2.1 Hz, 1H), 4.41 (dd, J=13.3, 7.8 Hz, 1H), 4.23-4.16 (m, 1H), 4.13-4.04 (m, 1H), 3.93 (s, 3H), 3.57 (d, J=7.4 Hz, 2H), 3.46 (d, J=9.0 Hz, 3H), 3.26 (s, 3H), 3.12 (s, 1H), 3.09 (s, 3H), 3.07-2.93 (m, 2H), 2.80 (d, J=9.6 Hz, 1H), 2.77-2.70 (m, 1H), 2.68 (s, 3H), 2.69-2.53 (m, 2H), 2.47-2.24 (m, 4H), 2.10-1.95 (m, 2H), 1.83-1.69 (m, 2H), 1.62 (d, J=3.5 Hz, 1H), 1.58 (s, 3H), 1.48-1.35 (m, 4H), 1.30-1.21 (m, 2H), 1.17 (d, J=6.7 Hz, 3H), 1.13 (d, J=6.2 Hz, 3H), 0.87 (d, J=6.7 Hz, 3H), 0.85 (d, J=6.8 Hz, 3H), 0.76 (s, 3H). HRMS $(M+Na)^+$ calcd for $C_{57}H_{81}ClN_8O_{14}S_2$, 1223.4790; found 1223.4900.

Example 2. Procedures for the Preparation of FMoc Protected Anilines

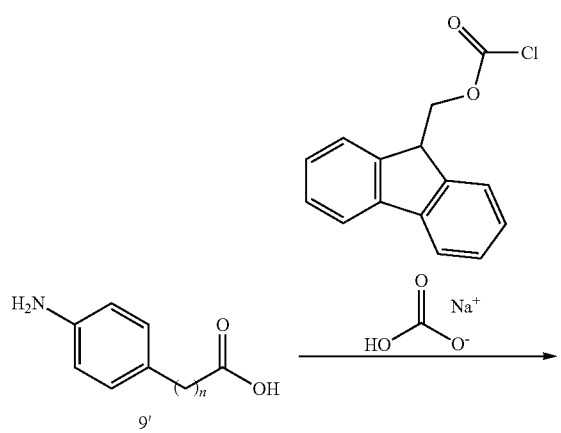

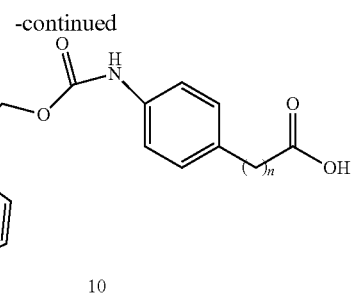

10

FMoc-4-aminophenyl acetic acid 10a (n=1)

4-aminophenyl acetic acid (204 mg, 1.35 mmol) in a 10 mL flask was dissolved in a mixture of 10% aqueous sodium bicarbonate (0.29 mL) and tetrahydrofuran (2.3 mL) then cooled in an ice/water bath. 9-fluorenylmethyl chloroformate (367 mg, 1.42 mmol) was added in small portions over 3 min. After 4 h the cooling bath was removed. After additional 4 h at room temperature, the reaction was extracted with deionized water (2 mL) and ethyl ether (2 mL) and the aqueous layer was brought to pH 4 with dilute HCl and placed in a refrigerator. After 1 h solid was collected by vacuum filtration and washed with deionized water then dried under vacuum to give 284 mg of product (56% yield). Mass spectrum $(M+Na)^+$ calcd for $C_{23}H_{19}NO_4$, 396.1; found 396.1.

FMoc-3-(4-aminophenyl)propionic acid 10b (n=2)

3-(4-aminophenyl)propionic acid (250 mg, 1.5 mmol) in a 10 mL flask was dissolved in a mixture of 10% aqueous sodium bicarbonate (0.32 mL) and tetrahydrofuran (2.2 mL) then cooled in an ice/water bath. 9-fluorenylmethyl chloroformate (422 mg, 1.5 mmol) was added in small portions over 3 min. After 4 h the cooling bath was removed. After additional 4 h at room temperature, the reaction was extracted with deionized water (2 mL) and ethyl ether (2 mL) and the aqueous layer was brought to pH 4 with dilute HCl and placed in a refrigerator. After 1 h solid was collected by vacuum filtration and washed with deionized water then dried under vacuum to give 470 mg of product (80% yield). Mass spectrum $(M+Na)^+$ calcd for $C_{24}H_{21}NO_4$, 400.1; found 410.0.

FMoc-4-(4-aminophenyl)butanoic acid 10c (n=3)

4-(4-aminophenyl)butanoic acid (250 mg, 1.4 mmol) in a 10 mL flask was dissolved in a mixture of 10% aqueous sodium bicarbonate (0.29 mL) and tetrahydrofuran (2.1 mL) then cooled in an ice/water bath. 9-fluorenylmethyl chloroformate (390 mg, 1.4 mmol) was added in small portions over 3 min. After 4 h the cooling bath was removed. After additional 4 h at room temperature, the reaction was extracted with deionized water (2 mL) and ethyl ether (2 mL) and the aqueous layer was brought to pH 4 with dilute HCl and placed in a refrigerator. After 1 h solid was collected by vacuum filtration and washed with deionized water then dried under vacuum to give 290 mg of product (52% yield). Mass spectrum $C_{25}H_{23}NO_4$ (M+Na)$^+$ calcd for 424.1; found 424.0.

Example 3. Procedures for the Coupling of Carboxylic Acids to $N^2$-deacetyl-$N^2$—(N-methyl-alanyl)-maytansine

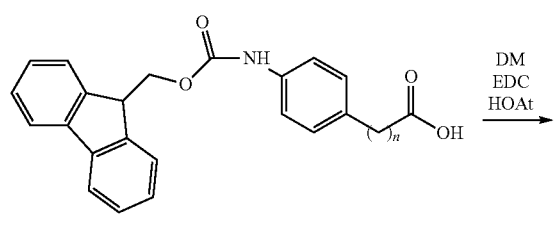

$N^{2'}$-deacetyl-$N^{2'}$-(FMoc-4-aminophenyl acetyl)-Maytansine 11a (n=1)

FMoc-4-aminophenyl acetic acid (compound 10a) (50 mg, 0.13 mmol), EDC (84 mg, 0.44 mmol), and HOAT (59 mg, 44 mmol) were dissolved in a minimum volume of dimethylformamide and added to an ethyl acetate solution of $N^{2'}$-deacetyl-$N$-$^{2'}$(N-methyl-alanyl)-maytansine. After 3 h solvent was evaporated under vacuum and residue was taken up in a minimum volume of dimethyl sulfoxide and purified by preparative HPLC method 3. Fractions containing pure product ($R_t$=16 min) were combined and solvent was evaporated under vacuum to give 12 mg (14% yield) of desired product. Mass spectrum (M+Na)$^+$ calcd for $C_{55}H_{61}ClN_4O_{12}$, 1027.4; found 1027.3.

$N^{2'}$-deacetyl-$N$-$^{2'}$[FMoc-3-(4-aminophenyl)propionyl]-maytansine 11b (n=2)

FMoc-3-(4-aminophenyl)propionic acid (compound 10b) (51 mg, 0.13 mmol), EDC (84 mg, 0.44 mmol), and HOAT (60 mg, 0.44 mmol) were dissolved in a minimum volume of dimethylformamide and added to an ethyl acetate solution of $N^{2'}$-deacetyl-$N$-$^{2'}$(N-methyl-alanyl)-maytansine. After 3 h solvent was evaporated under vacuum and residue was taken up in a minimum volume of dimethyl sulfoxide and purified by preparative HPLC method 3. Fractions containing pure product ($R_t$=16.5 min) were combined and solvent was evaporated under vacuum to give 20 mg (22% yield) of desired product. Mass spectrum (M+Na)$^+$ calcd for $C_{56}H_{63}ClN_4O_{12}$, 1041.4; found 1041.0.

$N^{2'}$-deacetyl-$N$-$^{2'}$[FMoc-4-(4-aminophenyl)butyrl]-maytansine 11c (n=3)

FMoc-4-(4-aminophenyl)butanoic acid (compound 10c) (53 mg, 0.13 mmol), EDC (85 mg, 0.45 mmol), and HOAT (57 mg, 0.44 mmol) were dissolved in a minimum volume of dimethylformamide and added to an ethyl acetate solution of $N^{2'}$-deacetyl-$N$-$^{2'}$(N-methyl-alanyl)-maytansine. After 3 h solvent was evaporated under vacuum and residue was taken up in a minimum volume of dimethyl sulfoxide and purified by preparative HPLC method 3. Fractions containing pure product ($R_t$=16.5 min) were combined and solvent was evaporated under vacuum to give 14 mg (15% yield) of desired product. ($R_t$=17 min) Mass spectrum (M+Na)$^+$ calcd for $C_{57}H_{65}ClN_4O_{12}$, 1055.4; found 1055.3.

Example 4. Procedures for FMoc Deprotection

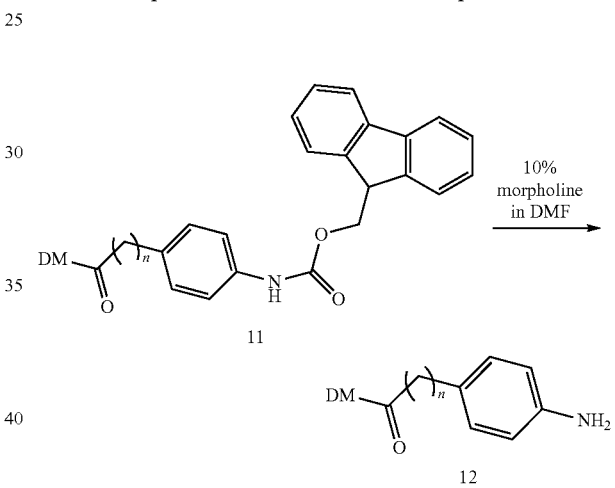

$N^{2'}$-deacetyl-$N$-$^{2'}$(4-aminophenyl acetyl)-Maytansine 12a (n=1)

$N^{2'}$-deacetyl-$N^{2'}$-(FMoc-4-aminophenyl acetyl)-Maytansine (12 mg, 0.012 mmol) was dissolved in a solution of 10% morpholine in dimethylformamide (0.3 mL). After 1 hr the sample was purified by preparative HPLC method 3 and the fraction containing pure material ($R_t$=8.2 min) was transferred to a flask then solvent was removed under vacuum to give 7.5 mg (80% yield) or desired product. HRMS (M+Na)$^+$ calcd for C40H51ClN4O10, 805.3135; found 805.3192.

$N^{2'}$-deacetyl-$N$-$^{2'}$[3-(4-aminophenyl) propionyl]-maytansine 12b (n=2)

$N^2$-deacetyl-$N^{2'}$-[FMoc-3-(4-aminophenyl)propionyl]-maytansine (20 mg, 0.2 mmol) was dissolved in a solution of 10% morpholine in dimethylformamide (0.3 mL). After 1 hr the sample was purified by preparative HPLC method 3 and the fraction containing pure material ($R_t$=8.4 min) was transferred to a flask then solvent was removed under vacuum to give 5.0 mg (31% yield) or desired product. HRMS (M+Na)$^+$ calcd for $C_{41}H_{53}ClN_4O_{10}$, 819.3298; found 819.3348.

N$^{2'}$-deacetyl-N-$^{2'}$[4-(4-aminophenyl)butyrf]-maytansine 12c (n=3)

N$^{2'}$-deacetyl-N$^{2'}$-[FMoc-4-(4-aminophenyl)butyrl]-maytansine (14 mg, 0.14 mmol) was dissolved in a solution of 10% morpholine in dimethylformamide (0.3 mL). After 1 hr the sample was purified by preparative HPLC method 3 and the fraction containing pure material ($R_t$=8.5 min) was transferred to a flask then solvent was removed under vacuum to give 5.1 mg (46% yield) or desired product. HRMS (M+Na)$^+$ calcd for $C_{42}H_{55}ClN_4O_{10}$, 833.3505; found 833.3434.

Example 5. Synthesis of Compound 16

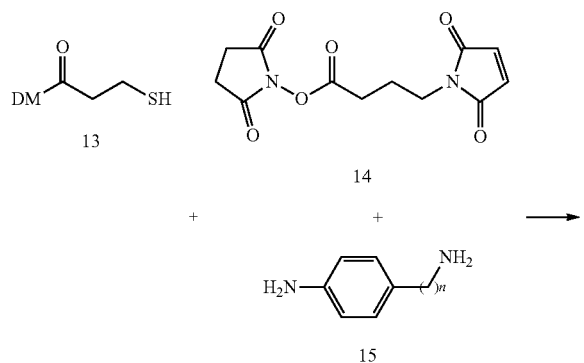

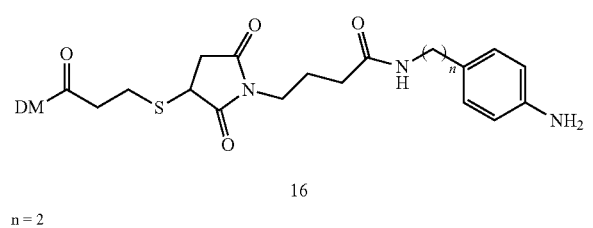

n = 2

Compound 13 (DM1) (25 mg, 0.034 mmol) and 4-(2-aminoethyl)aniline (compound 15, n=2) (9.22 mg, 0.068 mmol) were dissolved in a solution of dimethylacetamide (1.0 mL) and 100 mM potassium phosphate pH 8 buffer (1.0 mL) to which was added compound 14 (9.5 mg, 0.034 mg). After 2 hr the mixture was purified by preparative HPLC method 3. Fractions containing pure product were combined in a flask then the flask was cooled in a dry/ice acetone bath until the solvent was frozen. Then the sample was lyophilized to give 29 mg (97% yield) of desired product. Mass spectrum (M+Na)$^+$ calcd for $C_{51}H_{67}ClN_6O_{13}S$; 1061.4; found 1061.1.

Example 6. Synthesis of Compound 18

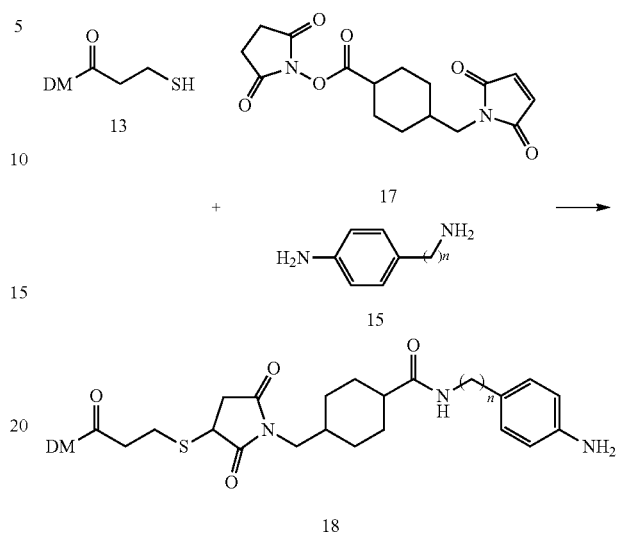

n = 2

DM1 (25 mg, 0.034 mmol) and 4-(2-aminoethyl)aniline (compound 15) (9.22 mg, 0.068 mmol) were dissolved in a solution of dimethylacetamide (1.0 mL) and 100 mM potassium phosphate pH 8 buffer (1.0 mL) to which was added compound 17 (11.32 mg, 0.034 mmol). After 2 hr the mixture was purified by preparative HPLC method 3. Fractions containing pure product were combined in a flask then the flask was cooled in a dry/ice acetone bath until the solvent was frozen. Then the sample was lyophilized to give 26 mg (92% yield) of desired product. Mass spectrum (M+K)$^+$ calcd for $C_{55}H_{73}ClN_6O_{13}S$, 1131.4; found 1131.3.

Example 7. Synthesis of Compound 24

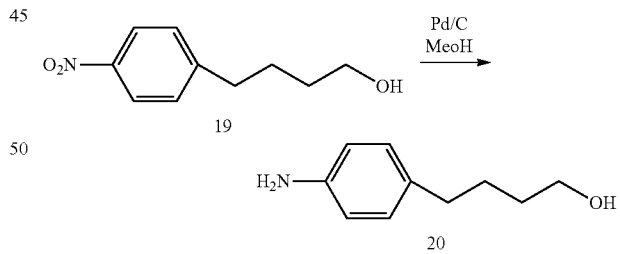

4-(4-aminophenyl)butanol (compound 20)

4-(4-nitrophenyl)butanol (compound 19, 1.7 mL, 10.2 mmol) was dissolved in methanol (20 mL) to which 10% Palladium on carbon (0.2 g) was added and the mixture was hydrogenated using hydrogen gas (30 psi) at ambient temperature for 1 hr. The mixture was filtered through celite filter aid and solvent was evaporated from the filtrate under vacuum to give 1.3 g (77% yield) of crude product. Mass spectrum (M+H)$^+$ calcd for $C_{10}H_{15}NO$ 166.1; found 166.1.

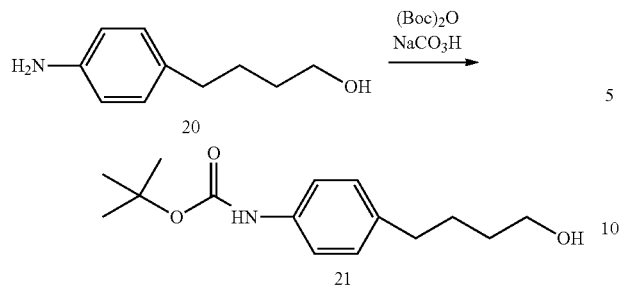

4-(Boc-4-aminophenyl)butanol (compound 21)

Crude 4-(4-aminophenyl)butanol (1.2 g, 7.6 mmol) was dissolved in tetrahydrofuran (10.9 mL) to which was added a solution of sodium bicarbonate (2.4 g, 29 mmol) dissolved in deionized water (10.9 mL). To the resulting solution was added Boc anhydride (1.78 g, 7.6 mmol) at ambient temperature. After 3 hr the reaction was extracted with deionized water and ethyl acetate (mL). The organic layer was dried over anhydrous sodium sulfate, filtered and solvent was removed from the filtrate under vacuum. The residue was taken up in a minimum volume of ethyl acetate and purified by silica chromatography using hexanes with a linear gradient of ethyl acetate 0-100% using an combiflash system. Fractions containing pure product were combined and solvent was evaporated under vacuum to give 1.5 g (79% yield) of desired product. HRMS (M+Na)$^+$ calcd for $C_{15}H_{23}NO_3$, 288.1576 found 288.1557.

4-(Boc-4-aminophenyl)butanemaleimide (compound 22)

4-(Boc-4-aminophenyl)butanol (241 mg, 2.5 mmol) and triphenylphosphine (641 mg, 2.4 mmol) were dissolved in anhydrous tetrahydrofuran (11.6 mL). 4-(Boc-aminophenyl) butanol (600 mg, 2.26 mmol) was then added followed by diisopropylazodicarboxylate (0.53 mL, 2.7 mmol). After 12 hours the reaction mixture was purified by silica chromatography using dichloromethane and a linear 0-100% gradient of ethyl acetate. Fractions containing pure product were combined and solvent was evaporated under vacuum to give (602 mg) 77% yield of desired product. $^1$H NMR (400 MHz, CDCl$_3$) δ 7.27 (d, J=10.0 Hz, 2H), 7.10 (d, J=8.3 Hz, 2H), 6.70 (s, 2H), 3.55 (t, J=6.6 Hz, 2H), 2.60 (t, J=7.0 Hz, 2H), 1.68-1.55 (m, 4H), 1.53 (s, 9H). HRMS (M+Na)$^+$ calcd for $C_{19}H_{24}N_2O_4$, 367.1634, found 367.1606.

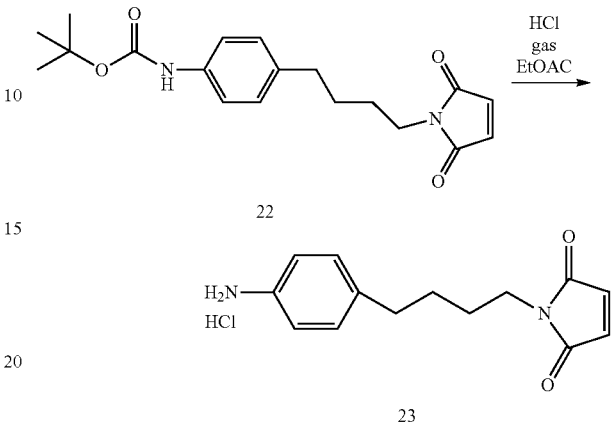

4-aminophenylbutanemaleimide (compound 23)

A 1M solution of HCl in ethyl acetate was prepared by bubbling HCl gas into a pre-tared 25 mL flask containing ethyl acetate (10 mL) for approximately 1 min and adding ethyl acetate. To this solution was added 4-(Boc-4-aminophenyl)butanemaleimide (50 mg, 0.15 mmol). After 1 hr the solvent was removed under vacuum to give 38 mg (95% yield) of desired product which was used without purification. HRMS (M+H)$^+$ calcd for $C_{14}H_{17}ClN_2O_2$ 281.1059, found 281.1060.

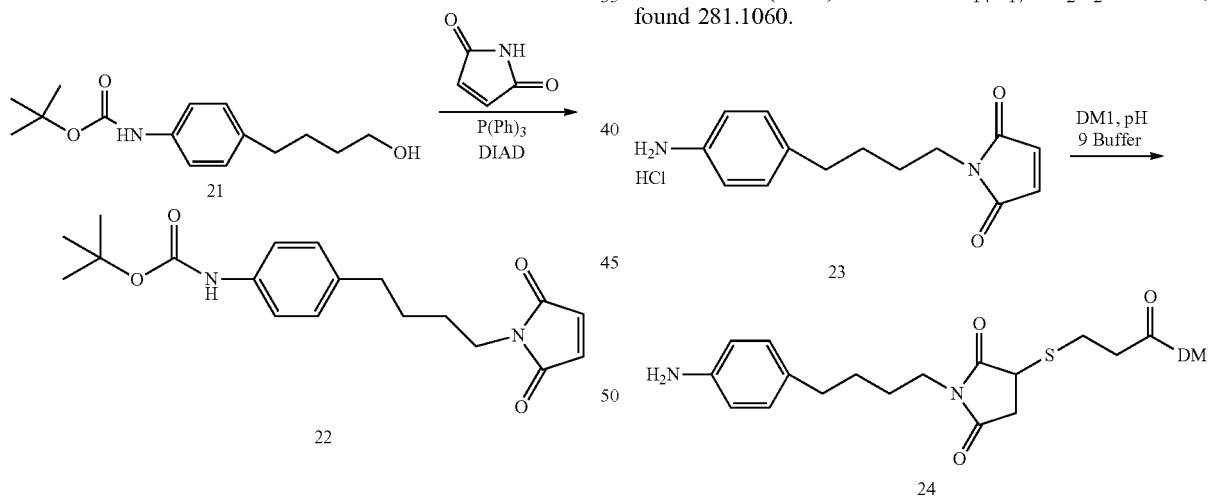

$N^{2'}$-deacetyl-$N$-$^{2'}$3-(1-(4-(4-aminophenyl)butyl)-2,5-dioxopyrrolidin-3-ylthio)-propanionyl-maytansine (compound 24)

DM1 (25 mg, 0.034 mmol) was dissolved in dimthyl acetamide (1.0 mL) to which was added 100 mM potassium phosphate pH 8.0 buffer (1.0 mL) and 4-aminophenylbutanemaleimide (9.5 mg, 0.034 mmol). After 3 hr the reaction mixture was purified by preparative reverse phase HPLC method 3. Fractions containing pure product were combined and solvent was removed under vacuum to give 9.5 mg (22% yield) of desired product. HRMS (M+H)$^+$ calcd for $C_{49}H_{64}ClN_5O_{12}S$, 982.4041; found 982.4034.

Example 8. Synthesis of Compound 5

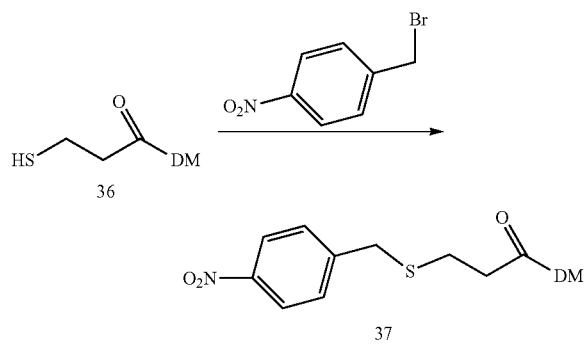

Synthesis of Compound 37

1-(bromomethyl)-4-nitrobenzene (300 mg, 1.4 mmol) was dissolved in a solution of DM1 (35 mg, 0.047 mmol) in dimethylformamide (3.5 mL) and 50 mM potassium phosphate buffer pH 7.5 (1 mL). After 30 min the reaction mixture was purified by direct load onto a preparative HPLC using preparative HPLC method 2. Pure fractions of desired product ($R_t$=25 min) were combined and solvent was removed under vacuum to give 30 mg (72% yield) of desired product. $^1$H NMR (400 MHz, CDCl$_3$) δ 8.09-8.03 (m, 2H), 7.37 (d, J=8.6 Hz, 2H), 6.77 (d, J=1.5 Hz, 1H), 6.63 (d, J=11.1 Hz, 1H), 6.54 (d, J=1.5 Hz, 1H), 6.40 (dd, J=15.2, 11.1 Hz, 1H), 6.27 (s, 1H), 5.61 (dd, J=15.3, 9.1 Hz, 1H), 5.33 (q, J=6.7 Hz, 1H), 4.73 (dd, J=12.0, 2.9 Hz, 1H), 4.23 (dd, J=16.5, 6.0 Hz, 1H), 3.98 (s, 3H), 3.72 (d, J=2.8 Hz, 2H), 3.52-3.43 (m, 2H), 3.33 (s, 3H), 3.14 (s, 3H), 3.02-2.94 (m, 2H), 2.79 (s, 3H), 2.77-2.39 (m, 5H), 2.14 (dd, J=14.3, 3.0 Hz, 1H), 1.62 (d, J=8.6 Hz, 3H), 1.53 (d, J=13.5 Hz, 1H), 1.44 (td, J=10.0, 6.5 Hz, 1H), 1.27 (t, J=7.3 Hz, 7H), 0.76 (s, 3H). $^{13}$C NMR (101 MHz, CDCl$_3$) δ 170.64, 168.79, 156.08, 152.31, 147.03, 146.06, 142.16, 141.04, 139.36, 133.39, 129.61, 127.70, 125.32, 123.80, 122.02, 118.87, 113.06, 88.58, 80.91, 78.15, 74.18, 67.17, 60.03, 56.73, 56.67, 52.46, 46.55, 38.93, 36.42, 36.23, 35.51, 33.63, 32.47, 30.82, 26.68, 15.57, 14.66, 13.45, 12.22. HRMS (M+Na)$^+$ calcd for $C_{42}H_{53}ClN_4O_{12}S$, 895.2967; found 895.2875.

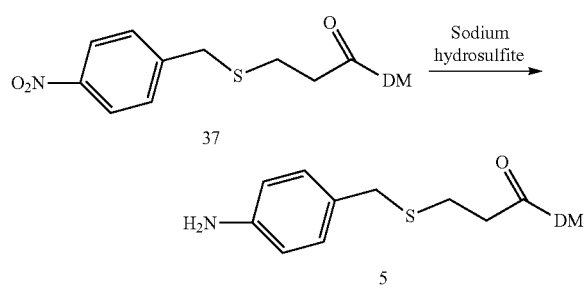

Synthesis of Compound 5

Compound 37 (20 mg, 0.023 mmol) was dissolved in a solution of tetrahydrofuran (0.8 mL) and deionized water (0.5 mL) in a 10 mL flask and sodium hydrosulfite (30 mg, 0.17 mmol) was added. Stirring was continued over night. Desired product was purified by reverse phase HPLC method 2. The desired fractions ($R_t$=20) were combined and solvent was removed under vacuum to give 8 mg (41% yield) of desired product. HRMS (M+Na)$^+$ calcd for $C_{42}H_{55}ClN_4O_{10}S$, 865.3225; found 865.3165.

Example 9. Synthesis of Compounds 43a and 43b

Figure 18:
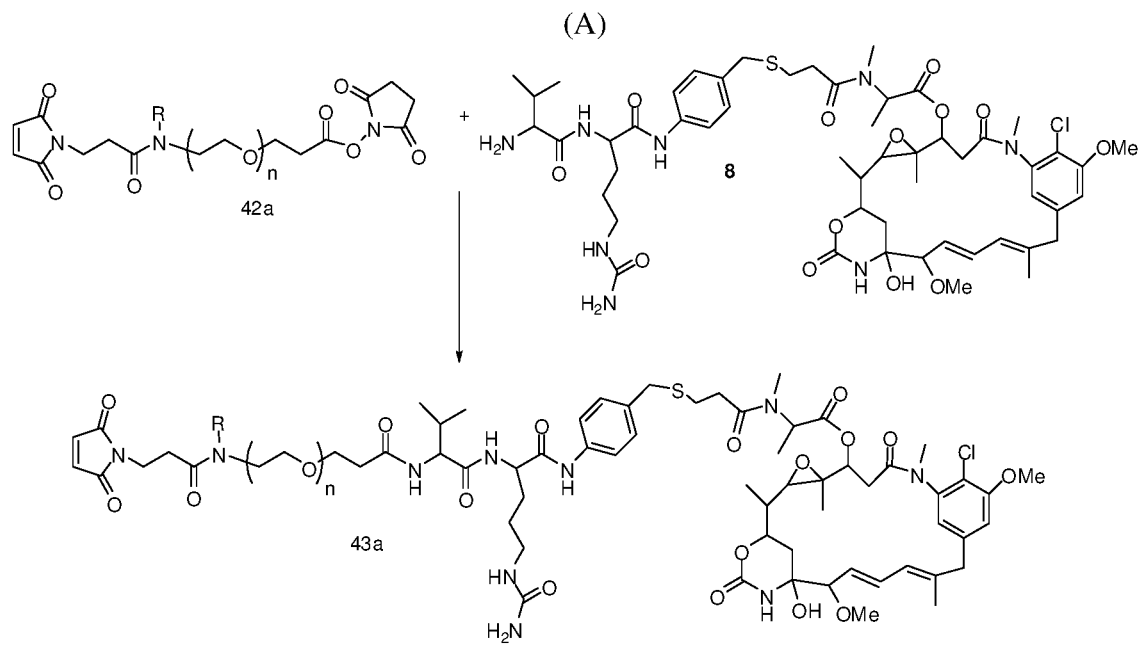
FIG. 18 shows the synthesis scheme for representative drug-linker compounds of the present invention and the corresponding conjugates.
Figure 18:
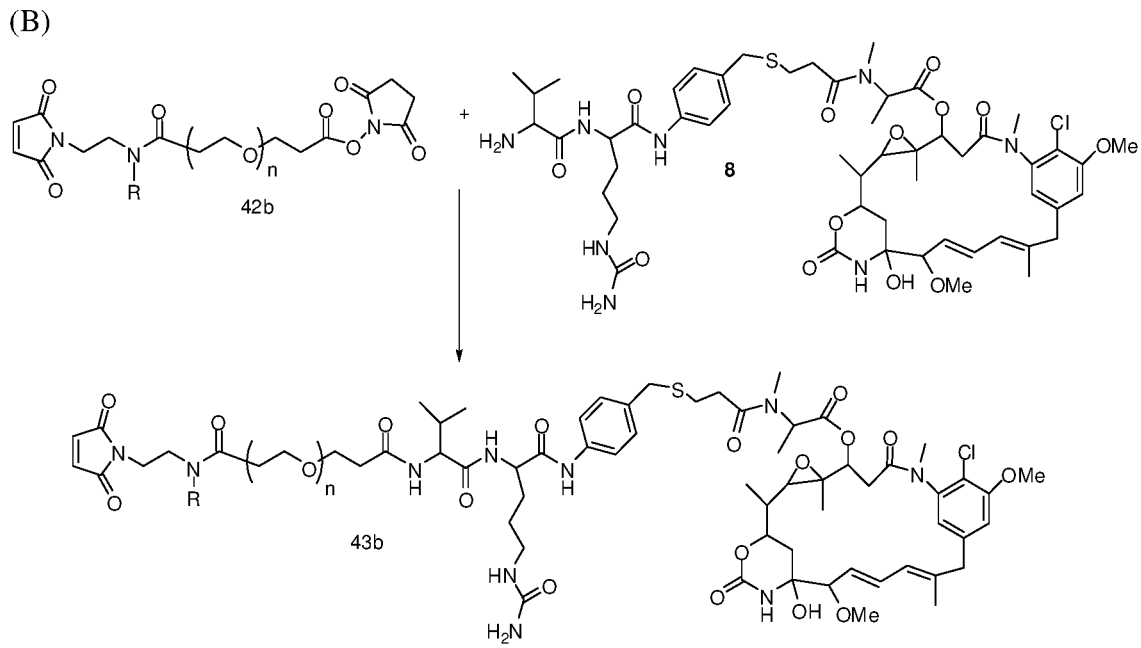
Figure 18:
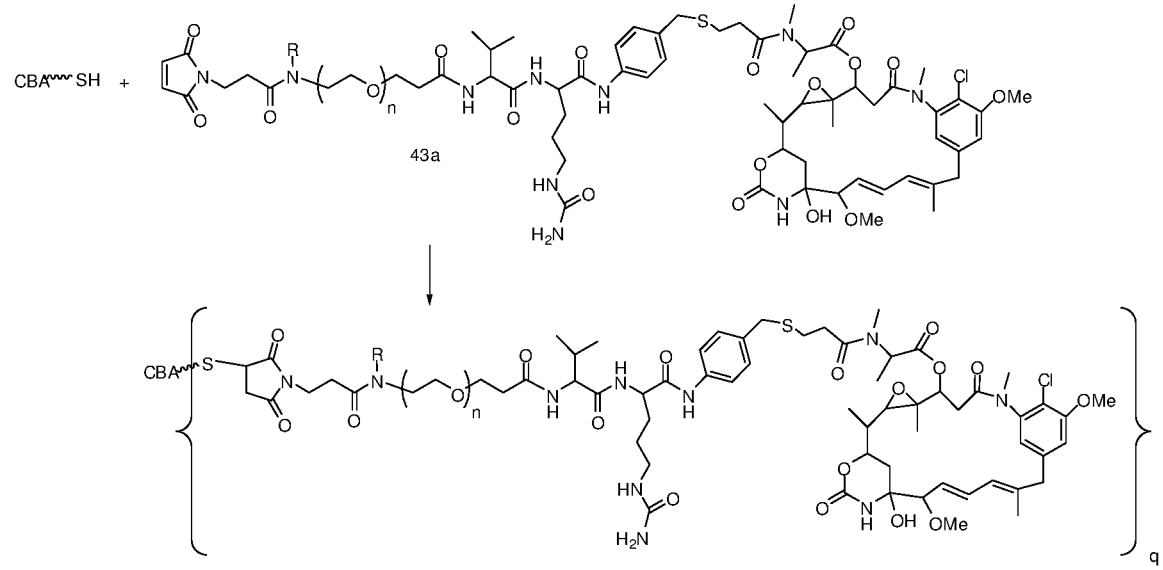
Figure 18:
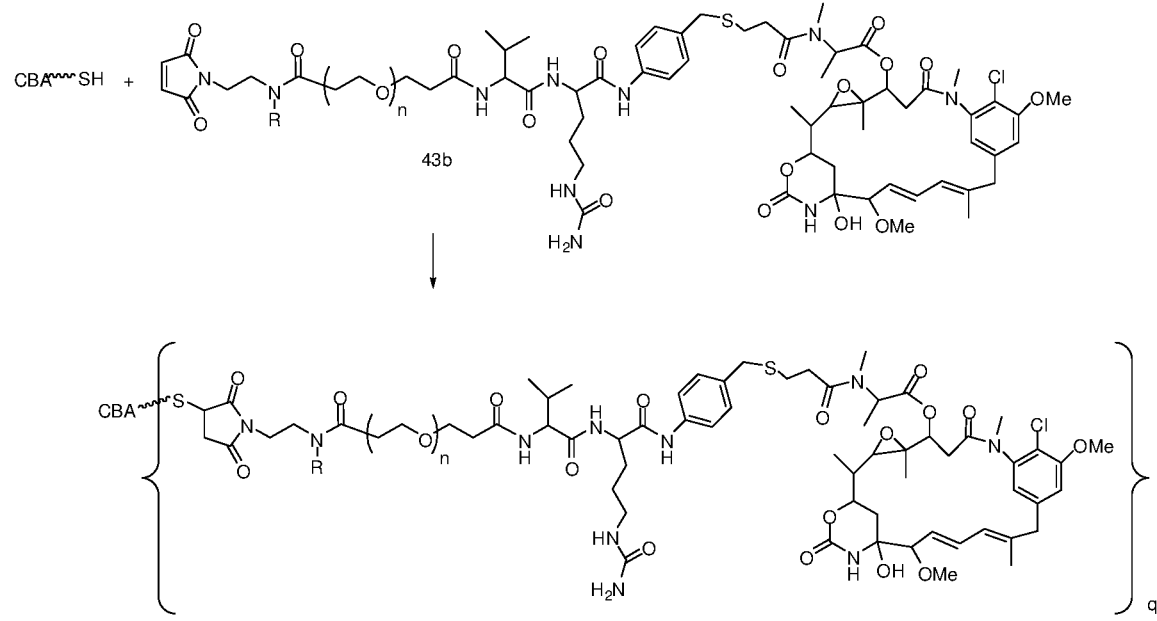

The synthesis scheme for Compounds 43a and 43b is provided in FIG. 18. Specifically, to a magnetically stirred solution of Compound 8 in dimethylformamide is added Compound 42a or 42b. After stirring, the reaction mixture is purified by C18 preparative method. Fractions containing pure 43a or 43b are combined frozen in a dry ice/acetone bath then lyophilized to give the desired compound.

Figure 19:
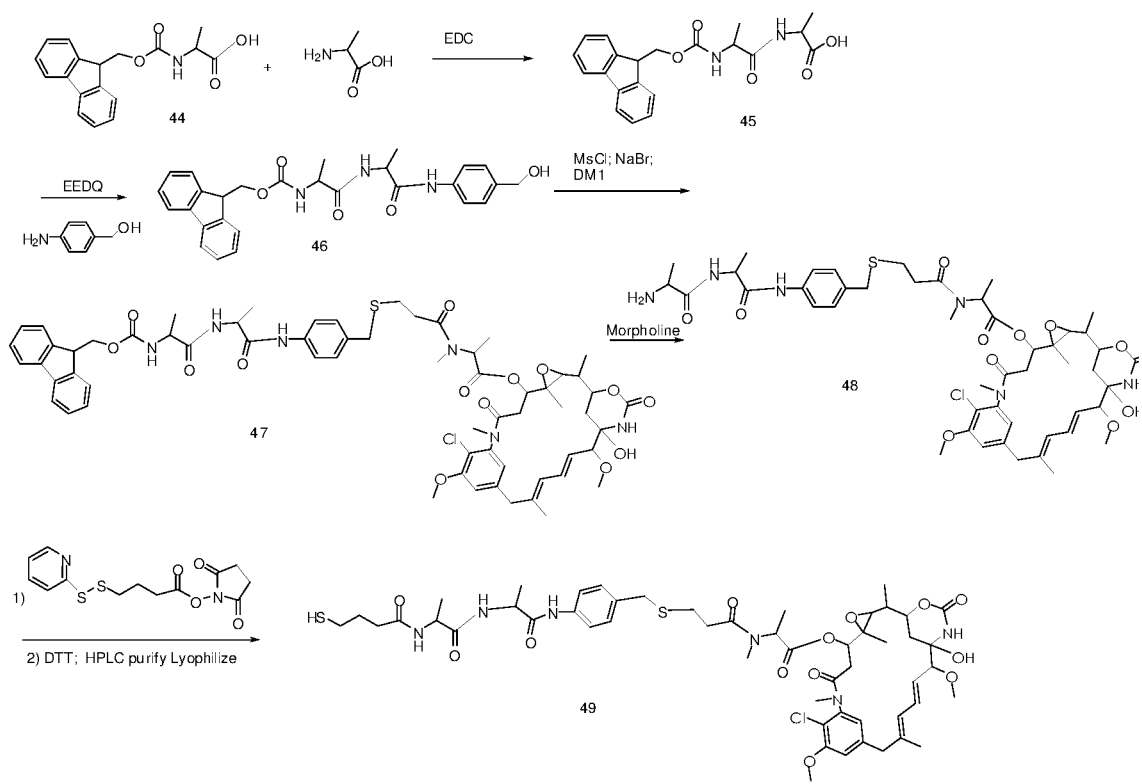
FIG. 19 shows the synthesis scheme for the Ala-Ala-PAB-DM1 compounds containing natural (L-Ala) and/or non-natural (D-Ala) amino acids, e.g., D-amino acid on either of the two positions in the Ala-Ala dipeptide.

Example 10. Synthesis of Ala-Ala-PAB-DM1 Compounds that May Contain Non-Natural Di-Peptides The synthesis scheme for linkers containing one or both non-natural amino acids (e.g., D-amino acid) is provided in FIG. 19. As an example, L- or D-Ala were used in the synthesis scheme. However, any L- or D-amino acids can be used in substantially the same way.

In all, all four combination of di-peptides, namely Ala-Ala (L, L), Ala-D-Ala (L, D), D-Ala-Ala (D, L), and D-Ala-D-Ala (D, D), were prepared for the Ala-Ala-PAB-DM1 compound. The example demonstrates that maytansinoid-peptides using non-natural amino aicds in either potition of the di-peptide linker can be made. Representative general synthesis schemes are provided below.

Also see FIGS. 20-22, which provides several synthesis schemes for making antibody conjugates using the Ala-Ala-PAB-DM1 compounds.

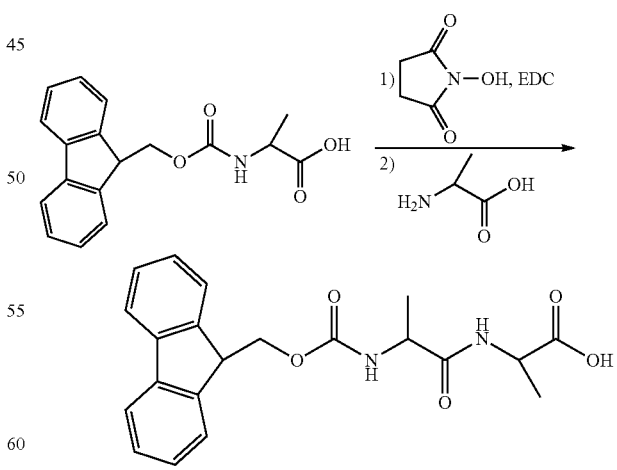

General Procedure to Prepare (FMoc-D-Ala-D-Ala-OH) and Isomers:

FMoc-D-Ala-OH (3.0 g, 9.6 mmol), N-hydroxysuccinimide (1.6 g, 14.4 mmol) and 1-ethyl-3-(3-dimethylaminopropyl)carbodiimide (EDC,1.85 g, 9.64 mmol) were weighed into a 200 mL flask equipped with a magnetic stir bar. Dimethyl formamide (25 mL) was added and the reaction was stirred at ambient temperature for 1 hr to give crude activated succinimide ester. D-alanine (2.5 g, 28 mmol) was dissolved in a solution of dimethyl formamide (6 mL) and deionized water (20 mL) in a 200 mL capacity beaker equipped with a magnetic stir bar. The mixture was stirred and the pH was monitored with a pH meter. The pH was adjusted to pH 8.5 by addition of 1 M NaOH then crude activated ester solution (1.5 mL) was added in a slow stream. After addition the pH was adjusted to pH 8.5 by addition of 1 M NaOH. This alternate addition of crude activated ester solution followed by 1M NaOH to give a pH of 8.5 was repeated until all of the crude activated ester solution was added. Then the pH was adjusted to pH 8.5 and the reaction was allowed to stir for 1 hr. A 1200 g, 30 micron, C18 Interchem cartridge was equilibrated at 85 mL/min with 75:25 deionized water 0.2% formic acid: acetonitrile (1.5 L). Dimethyl sulfoxide (6 mL) was loaded onto the column followed by the entire reaction mixture. The column was then run with a gradient elution at 85 mL/min with deionized water containing 0.2% formic acid and acetonitrile at 25% from time 0-5.0 min., then a linear gradient of acetonitrile from 25% to 95% from 5.0-40 min. Fractions containing pure desired product were combined and solvent was evaporated under vacuum to give 2.0 g (54% yield) of white solid. $^1$H NMR (400 MHz, DMSO-d6) δ 1.19 (dt, J=7.2, 1.9 Hz, 3H), 1.24 (dt, J=7.3, 2.0 Hz, 3H), 2.01 (t, J=2.1 Hz, 1H), 4.10-4.22 (m, 2H), 4.23 (d, J=6.1 Hz, 2H), 7.31 (td, J=7.7, 2.3 Hz, 2H), 7.39 (td, J=7.6, 2.5 Hz, 2H), 7.62-7.71 (m, 2H), 7.79-7.88 (m, 2H), 8.11 (t, J=2.0 Hz, 1H), 8.10-8.17 (m, 1H). $^{13}$C NMR (101 MHz, DMSO) δ 174.74, 173.26, 163.88, 156.38, 144.31, 144.18, 141.20, 128.34, 127.76, 125.82, 125.79, 120.65, 66.28, 50.32, 48.12, 47.12, 18.53, 17.53. HRMS (m/z): [M+Na]$^+$ calcd for $C_{21}H_{22}N_2O_5Na$ 405.1427; found 405.1409.

FMoc-L-Ala-L-Ala-OH $^1$H NMR (400 MHz, DMSO-d6) δ 1.23 (d, J=7.1 Hz, 3H), 1.28 (d, J=7.3 Hz, 3H), 4.02-4.15 (m, 1H), 4.16-4.32 (m, 4H), 7.33 (td, J=7.4, 1.2 Hz, 2H), 7.37-7.46 (m, 2H), 7.50 (d, J=7.8 Hz, 1H), 7.73 (t, J=7.4 Hz, 2H), 7.89 (d, J=7.5 Hz, 2H), 8.13 (d, J=7.3 Hz, 1H), 12.53 (s, 1H). $^{13}$C NMR (101 MHz, DMSO) δ 174.04, 172.32, 155.64, 143.93, 143.80, 140.71, 127.63, 127.07, 125.33, 125.30, 120.10, 65.60, 49.69, 47.43, 46.66, 18.19, 17.18.

FMoc-L-Ala-D-Ala-OH $^1$H NMR (400 MHz, DMSO-d6) δ 1.24 (d, J=7.2 Hz, 3H), 1.27 (d, J=7.3 Hz, 3H), 4.14 (t, J=7.5 Hz, 1H), 4.19-4.35 (m, 3H), 7.32 (t, J=7.5 Hz, 2H), 7.41 (t, J=7.5 Hz, 2H), 7.48 (d, J=8.1 Hz, 1H), 7.74 (t, J=7.5 Hz, 2H), 7.87 (d, J=7.5 Hz, 2H), 8.13 (t, J=8.2 Hz, 1H), 11.97-13.16 (m, 1H). $^{13}$C NMR (101 MHz, DMSO) δ 174.02, 172.25, 155.64, 143.95, 143.83, 140.75, 127.67, 127.11, 125.39, 125.34, 120.12, 65.71, 49.93, 47.53, 46.70, 18.62, 17.51.

FMoc-D-Ala-L-Ala-OH

MS (m/z): [M+H]$^+$ calcd for $C_{21}H_{23}N_2O_5$ 383.1; found 383.0.

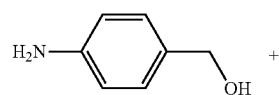

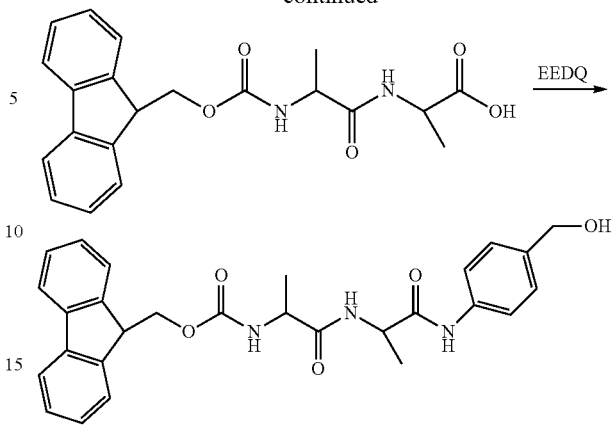

General Procedure to Prepare (FMoc-D-Ala-D-Ala-PAB-OH) and Isomers:

FMoc-d-Ala-d-Ala-OH (1.5 g, 3.92 mmol) and 4-aminobenzylalcohol (0.97 g, 7.86 mmol) were weighed into a 200 mL capacity flask equipped with a magnetic stir bar to which 1:1 dichloromethane:methanol (60 mL) was added followed by 2-ethoxy-1-ethoxy carbonyl-1,2-dihydroquinoline (EEDQ, 1.94 g, 7.84 mmol) and the reaction was magnetically stirred at ambient temperature for 48 hr. Precipitate formed and solvent was removed under vacuum. Ethyl ether (90 mL) was added and mixed vigorously for 5 min followed by sonication for 5 min. The mixture was transferred in portions to 20 mL vials, capped then centrifuged until the fine precipitate sediment at the bottom of the vials then supernatant was decanted. Ethyl ether (40 mL) was added, mixed vigorously for 5 min and the mixture was sedimented as described with removal of supernatant. A stream of nitrogen was passed over the moist solid for 2 min then the solid residue was placed under vacuum to removed residual solvent giving 1.4 g (73% yield) of desired product as a white solid. $^1$H NMR (400 MHz, DMSO-d6) δ 1.24 (d, J=7.0 Hz, 3H), 1.31 (d, J=7.0 Hz, 3H), 4.11 (q, J=7.1 Hz, 1H), 4.19-4.33 (m, 3H), 4.36-4.51 (m, 4H), 5.10 (t, J=5.6 Hz, 1H), 7.23 (d, J=8.1 Hz, 2H), 7.33 (t, J=7.4 Hz, 2H), 7.42 (t, J=7.4 Hz, 2H), 7.55 (dd, J=7.8, 4.9 Hz, 3H), 7.72 (t, J=8.1 Hz, 2H), 7.89 (d, J=7.5 Hz, 2H), 8.10 (d, J=7.2 Hz, 1H), 9.88 (s, 1H). HRMS (m/z): [M+Na]$^+$ calcd for $C_{28}H_{29}N_3O_5Na$; 510.2005 found 510.1985.

FMoc-L-Ala-L-Ala-PAB-OH $^1$H NMR (400 MHz, DMSO-d6) δ 1.24 (d, J=7.1 Hz, 3H), 1.31 (d, J=7.0 Hz, 3H), 4.11 (q, J=7.1 Hz, 1H), 4.17-4.32 (m, 3H), 4.42 (dd, J=11.9, 6.3 Hz, 3H), 5.10 (t, J=5.7 Hz, 1H), 7.24 (d, J=8.3 Hz, 2H), 7.33 (t, J=7.4 Hz, 2H), 7.41 (t, J=7.5 Hz, 2H), 7.55 (dd, J=7.7, 4.2 Hz, 3H), 7.72 (t, J=8.2 Hz, 2H), 7.89 (d, J=7.5 Hz, 2H), 8.11 (d, J=7.3 Hz, 1H), 9.88 (s, 1H). $^{13}$C NMR (101 MHz, DMSO) δ 171.02, 170.57, 170.53, 168.09, 155.24, 151.21, 143.85, 143.75, 141.25, 141.23, 140.68, 139.39, 138.30, 137.59, 133.23, 132.56, 128.93, 128.89, 128.45, 127.60, 127.25, 127.05, 125.25, 125.13, 121.35, 120.07, 119.99, 119.02, 117.11, 113.90, 109.69, 88.19, 79.97, 78.62, 77.62, 73.14, 66.74, 59.99, 56.53, 56.09, 51.64, 49.99, 49.96, 48.96, 46.64, 45.40, 37.68, 36.33, 35.16, 34.86, 33.32, 31.91, 29.68, 25.97, 18.14, 15.01, 14.39, 13.04, 11.35.

FMoc-L-Ala-D-Ala-PAB-OH

MS (m/z): [M+NH]+ calcd for $C_{28}H_{30}N_3O_5$; 487.2 found 487.0.

FMoc-D-Ala-L-Ala-PAB-OH $^1$H NMR (400 MHz, DMSO-d6) δ 1.27 (d, J=7.1 Hz, 3H), 1.34 (d, J=7.0 Hz, 3H), 4.14 (t, J=7.0 Hz, 1H), 4.22 (t, J=6.9 Hz, 1H), 4.31 (d, J=6.2 Hz, 2H), 4.46 (q, J=4.4, 3.2 Hz, 3H), 5.14 (d, J=5.4 Hz, 1H), 7.25 (d, J=8.3 Hz, 2H), 7.33 (t, J=7.4 Hz, 2H), 7.40 (td, J=7.4, 4.6 Hz, 2H), 7.62 (d, J=8.3 Hz, 2H), 7.64-7.77 (m, 3H), 7.87 (dd, J=7.5, 2.8 Hz, 2H), 8.33 (d, J=7.5 Hz, 1H), 9.75 (s, 1H). $^{13}$C NMR (101 MHz, DMSO) δ 172.53, 170.86, 156.00, 143.87, 143.74, 140.74, 137.64, 137.40, 127.65, 127.09, 126.89, 125.29, 125.24, 120.10, 119.12, 65.77, 62.65, 50.25, 48.95, 46.68, 18.17, 17.93.

gradient to 98% acetonitrile from 5.0-30 min. The desired fraction eluted at 27 min. and was collected in a 250 mL flask which was placed in a dry ice acetone bath to freeze the solvent. The flask was removed from the bath then frozen solvent was removed by lyophilization to give 130 mg (59% yield) of desired product as a white solid.

FMoc-L-Ala-L-Ala-PAB-DM1

$^1$H NMR (400 MHz, DMSO-d6) δ 0.76 (s, 3H), 1.12 (d, J=6.5 Hz, 3H), 1.16 (d, J=6.8 Hz, 3H), 1.24 (d, J=7.2 Hz, 3H), 1.31 (dd, J=6.8, 2.4 Hz, 3H), 1.40-1.49 (m, 2H), 1.58

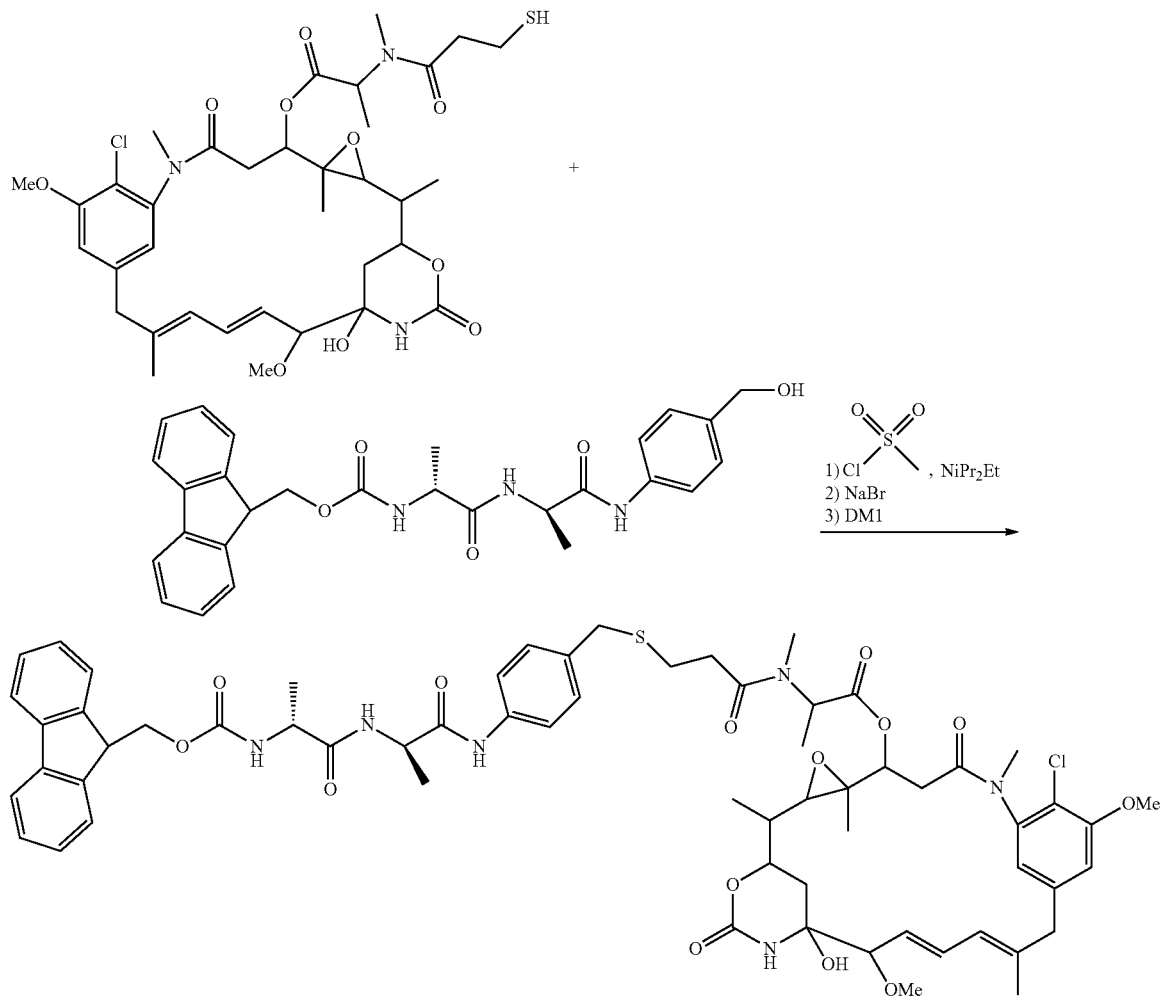

General Procedure to Prepare (FMoc-D-Ala-D-Ala-PAB-DM1) and Isomers:

FMoc-d-Ala-d-Ala-PAB-OH (135 mg, 0.18 mmol) was dissolved in dimethyl formamide (0.8 mL) in a vial containing a magnetic stir bar. Methanesulfonyl chloride (34 μL, 0.44 mmol) was added with stirring followed by diisopropyl ethyl amine (77 μL, 0.44 mmol). After 30 min sodium bromide (263 mg, 2.5 mmol) was added and the mixture was vigorously stirred for 30 min. The vial was centrifuged for 5 min then supernatant was added to a vial containing DM1 120 mg). After 1 hr, the material was purified without workup by preparative HPLC at 100 mL/min using a 250 mm×50 mm C18 column with gradient elution. The column was eluted with deionized water containing 0.2% formic acid with 20% acetonitrile from time 0-5.0 min then a linear (s, 3H), 2.03 (dd, J=14.5, 2.8 Hz, 1H), 2.37 (ddd, J=16.3, 8.2, 5.8 Hz, 1H), 2.59-2.65 (m, 1H), 2.67 (s, 3H), 2.69-2.76 (m, 1H), 2.78 (d, J=9.7 Hz, 1H), 3.07 (s, 3H), 3.13 (d, J=12.7 Hz, 1H), 3.24 (d, J=3.1 Hz, 3H), 3.47 (dd, J=9.0, 3.1 Hz, 1H), 3.55-3.65 (m, 2H), 3.93 (d, J=2.4 Hz, 3H), 4.03-4.12 (m, 2H), 4.22 (d, J=6.8 Hz, 1H), 4.27 (d, J=8.1 Hz, 1H), 4.41 (q, J=7.1, 6.6 Hz, 1H), 4.52 (dd, J=11.9, 2.8 Hz, 1H), 5.30 (q, J=6.8 Hz, 1H), 5.55 (dd, J=13.6, 9.1 Hz, H), 5.93 (s, 1H), 6.49-6.59 (m, 3H), 6.87 (s, 1H), 7.07-7.12 (m, 2H), 7.15 (d, J=1.8 Hz, 1H), 7.30-7.37 (m, 2H), 7.41 (t, J=7.5 Hz, 2H), 7.47 (dd, J=8.5, 2.7 Hz, 2H), 7.55 (d, J=7.5 Hz, 1H), 7.72 (t, J=8.1 Hz, 2H), 7.84 (d, J=7.4 Hz, 1H), 7.88 (d, J=7.5 Hz, 2H), 8.14 (d, J=7.2 Hz, 1H), 9.94 (s, 1H). $^{13}$C NMR (101 MHz, DMSO) δ 171.02, 170.57, 170.53, 168.09, 155.76, 155.24, 151.21, 143.85, 143.75, 141.25, 141.23, 140.68, 139.39, 138.30, 137.59, 133.23, 132.56, 128.93, 128.89, 128.45, 127.60, 127.25, 127.05, 125.25, 125.13, 121.58, 121.35, 120.07, 119.99, 119.02, 117.11, 113.90, 109.69, 88.18, 79.97, 78.62, 77.62, 73.14, 66.74, 65.64, 59.99, 56.53, 56.09, 51.64, 49.99, 49.96, 48.96, 46.64, 45.40, 37.68, 36.33, 35.16, 34.86, 33.32, 31.91, 29.67, 25.97, 18.14, 15.00, 14.39, 13.04, 11.35. HRMS (m/z): [M+Na]$^+$ calcd for $C_{63}H_{75}ClN_6O_{14}SNa$, 1229.4649; found 1229.4614.

FMoc-L-Ala-D-Ala-PAB-DM1

$^1$H NMR (400 MHz, DMSO-d6) δ 0.73 (s, 3H), 1.12 (d, J=6.3 Hz, 3H), 1.15 (d, J=6.7 Hz, 3H), 1.24 (t, J=4.9 Hz, 5H), 1.31 (d, J=6.9 Hz, 4H), 1.40 (dd, J=18.2, 10.5 Hz, 3H), 1.56 (s, 3H), 1.98-2.04 (m, 1H), 2.37 (dt, J=15.2, 7.5 Hz, 1H), 2.59-2.64 (m, 1H), 2.66 (s, 3H), 2.78 (d, J=9.5 Hz, 1H), 3.06 (s, 3H), 3.18 (s, 2H), 3.54-3.64 (m, 2H), 4.01-4.14 (m, 2H), 4.20 (d, J=6.9 Hz, 2H), 4.26 (t, J=5.8 Hz, 2H), 4.41 (q, J=7.0, 6.6 Hz, 1H), 4.51 (dd, J=12.2, 2.9 Hz, 1H), 5.29 (q, J=6.4 Hz, 1H), 5.53 (dd, J=14.7, 9.0 Hz, 1H), 5.91 (s, 1H), 6.50 (d, J=10.6 Hz, 2H), 6.56 (d, J=11.0 Hz, 1H), 6.85 (d, J=11.0 Hz, 1H), 7.04-7.09 (m, 2H), 7.12-7.16 (m, 1H), 7.31 (t, J=7.4 Hz, 2H), 7.39 (q, J=7.0 Hz, 3H), 7.48 (d, J=7.6 Hz, 2H), 7.64 (d, J=6.7 Hz, 1H), 7.70 (t, J=7.8 Hz, 3H), 7.86 (dd, J=7.6, 3.7 Hz, 3H), 8.33 (t, J=7.9 Hz, 1H), 9.77 (d, J=10.6 Hz, 1H). $^{13}$C NMR (101 MHz, DMSO) δ 172.47, 170.89, 170.52, 168.06, 155.22, 151.21, 143.82, 143.63, 141.25, 141.20, 140.66, 138.38, 133.29, 132.51, 128.86, 127.59, 127.03, 125.26, 125.19, 121.50, 120.04, 119.15, 117.08, 113.86, 88.17, 79.94, 77.61, 77.57, 73.12, 66.71, 65.72, 59.95, 56.51, 56.00, 51.60, 50.12, 48.98, 46.60, 37.67, 36.32, 35.13, 34.85, 33.26, 31.87, 29.64, 25.90, 18.07, 17.99, 14.98, 14.39, 13.03, 11.33. HRMS (m/z): [M+Na]$^+$ calcd for $C_{63}H_{75}ClN_6O_{14}SNa$, 1229.4649; found 1229.4622.

FMoc-D-Ala-L-Ala-PAB-DM1

$^1$H NMR (400 MHz, DMSO-d6) δ 0.72 (d, J=6.5 Hz, 3H), 1.12 (d, J=6.3 Hz, 3H), 1.15 (d, J=6.8 Hz, 3H), 1.24 (dd, J=7.0, 3.7 Hz, 3H), 1.29-1.33 (m, 3H), 1.38-1.46 (m, 2H), 1.56 (d, J=2.5 Hz, 3H), 2.02 (d, J=14.5 Hz, 1H), 2.32-2.41 (m, 1H), 2.59-2.64 (m, 1H), 2.67 (s, 3H), 2.78 (d, J=9.6 Hz, 1H), 3.06 (d, J=1.4 Hz, 2H), 3.11 (s, 1H), 3.19 (s, 1H), 3.24 (s, 1H), 3.32 (s, 5H), 3.43 (dd, J=12.3, 9.1 Hz, 1H), 3.55-3.64 (m, 2H), 3.93 (s, 3H), 4.02-4.14 (m, 2H), 4.21 (t, J=6.2 Hz, 1H), 4.24-4.29 (m, 2H), 4.42 (t, J=6.8 Hz, 1H), 4.51 (dd, J=11.9, 2.5 Hz, 1H), 5.29 (q, J=6.7 Hz, 1H), 5.54 (ddd, J=13.7, 8.9, 3.9 Hz, 1H), 5.91 (s, 1H), 6.45-6.52 (m, 2H), 6.56 (d, J=11.1 Hz, 1H), 6.86 (d, J=10.8 Hz, 1H), 7.07 (dd, J=8.3, 2.6 Hz, 2H), 7.14 (dd, J=8.1, 1.7 Hz, 1H), 7.32 (td, J=7.5, 5.7, 3.9 Hz, 3H), 7.39 (q, J=7.1 Hz, 3H), 7.49 (dd, J=8.3, 5.3 Hz, 2H), 7.62 (d, J=6.9 Hz, 1H), 7.70 (td, J=12.1, 10.2, 5.1 Hz, 2H), 7.87 (dd, J=7.5, 3.5 Hz, 2H), 8.27-8.32 (m, 1H), 9.75 (d, J=11.1 Hz, 1H). $^{13}$C NMR (101 MHz, DMSO) δ 172.48, 172.43, 171.09, 170.89, 170.53, 168.08, 155.87, 155.22, 151.21, 143.84, 143.79, 143.71, 143.64, 141.23, 140.67, 138.34, 137.42, 133.35, 132.54, 129.40, 128.89, 128.85, 128.42, 127.61, 127.05, 125.26, 125.20, 121.53, 120.08, 119.15, 117.08, 113.91, 88.16, 82.95, 79.95, 77.60, 73.13, 66.72, 65.69, 59.98, 56.53, 56.08, 51.62, 50.10, 48.89, 46.60, 45.38, 37.67, 36.33, 35.15, 34.84, 33.27, 31.89, 29.66, 25.95, 18.12, 18.02, 14.99, 14.39, 13.04, 11.32. HRMS (m/z): [M+Na]$^+$ calcd for $C_{63}H_{75}ClN_6O_{14}SNa$, 1229.4649; found 1229.4615.

FMoc-D-Ala-D-Ala-PAB-DM1

$^1$H NMR (400 MHz, DMSO-d6) δ 0.76 (s, 3H), 1.12 (d, J=6.3 Hz, 3H), 1.16 (d, J=6.8 Hz, 3H), 1.21-1.26 (m, 6H), 1.31 (dd, J=7.3, 3.0 Hz, 5H), 1.44 (dd, J=15.3, 9.9 Hz, 2H), 1.57 (s, 3H), 2.03 (dd, J=14.7, 2.4 Hz, 1H), 2.37 (ddd, J=16.0, 7.6, 3.5 Hz, 1H), 2.67 (s, 3H), 2.78 (d, J=9.7 Hz, 1H), 3.07 (s, 3H), 3.13 (d, J=12.5 Hz, 1H), 3.24 (s, 3H), 3.37 (d, J=12.4 Hz, 1H), 3.47 (d, J=9.0 Hz, 1H), 3.55-3.66 (m, 2H), 3.93 (s, 3H), 4.02-4.14 (m, 3H), 4.19-4.30 (m, 4H), 4.42 (d, J=9.4 Hz, 3H), 4.52 (dd, J=11.9, 2.8 Hz, 1H), 5.30 (q, J=6.7 Hz, 1H), 5.56 (dd, J=13.7, 9.0 Hz, 1H), 6.49-6.60 (m, 3H), 6.87 (s, 1H), 7.09 (d, J=8.2 Hz, 2H), 7.15 (d, J=1.8 Hz, 1H), 7.23 (d, J=8.2 Hz, 1H), 7.33 (t, J=7.5 Hz, 3H), 7.41 (t, J=7.6 Hz, 2H), 7.46 (d, J=8.2 Hz, 2H), 7.54 (dd, J=8.0, 2.9 Hz, 3H), 7.72 (t, J=8.1 Hz, 2H), 7.89 (d, J=7.6 Hz, 2H), 8.10 (t, J=6.4 Hz, 1H), 9.89 (d, J=11.6 Hz, 1H). HRMS (m/z): [M+Na]$^+$ calcd for $C_{63}H_{75}ClN_6O_{14}SNa$, 1229.4649; found 1229.4584.

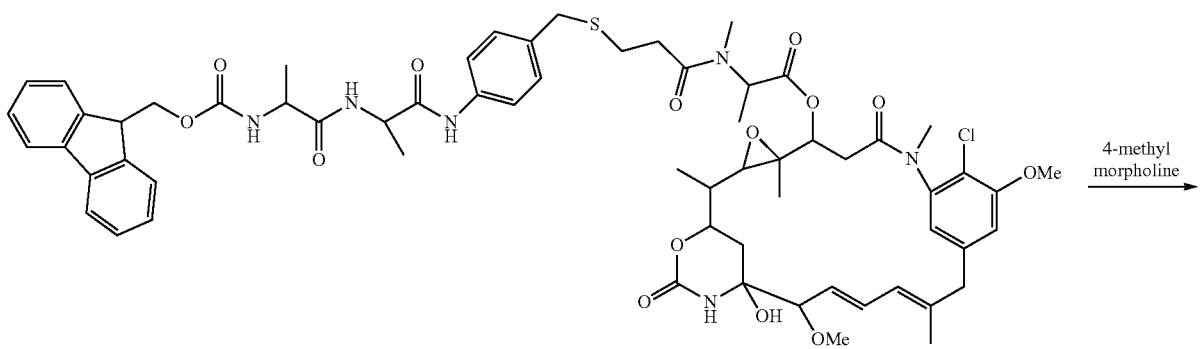

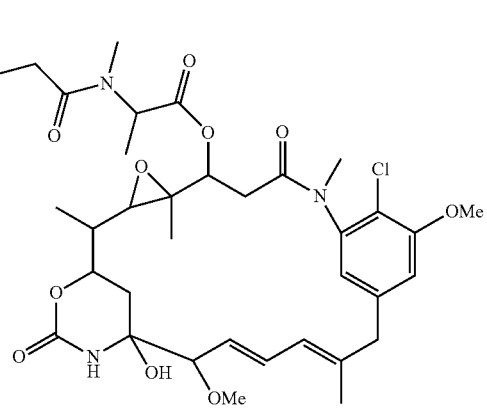

General Procedure to Prepare of (H-Ala-Ala-PAB-DM1) and Isomers:

FMoc-D-Ala-D-Ala-PAB-DM1 (120 mg, 0.099 mmol) was dissolved in dimethyl formamide (1.5 mL) to which 4-methyl morpholine (250 µL, 2.5 mmol) was added and the reaction was magnetically stirred at ambient temperature for 2 hr. The mixture without workup was purified without workup by preparative HPLC at 40 mL/min using a 250 mm×30 mm C18 column with gradient elution. The column was eluted with deionized water containing 0.2% formic acid with 20% acetonitrile from time 0-5.0 min then a linear gradient to 98% acetonitrile from 5.0-30 min. The desired product eluted at 21 min and was collected in a 50 mL flask which was placed in a dry ice/acetone bath to freeze the solvent. The flask was removed from the bath and frozen solvent was removed by lyophilization to give 80 mg (82% yield) of desired material as a white solid.

H-L-Ala-L-Ala-PAB-DM1

$^1$H NMR (400 MHz, DMSO-d6) δ 0.77 (s, 3H), 1.12 (d, J=6.3 Hz, 3H), 1.16 (d, J=6.8 Hz, 3H), 1.24 (d, J=12.2 Hz, 1H), 1.28 (d, J=6.9 Hz, 3H), 1.33 (d, J=7.0 Hz, 3H), 1.40-1.50 (m, 2H), 1.58 (s, 3H), 2.03 (dd, J=14.5, 2.8 Hz, 1H), 2.37 (ddd, J=16.1, 8.1, 5.8 Hz, 1H), 2.54 (d, J=2.3 Hz, 1H), 2.62 (dd, J=13.8, 6.1 Hz, 1H), 2.67 (s, 3H), 2.68-2.75 (m, 1H), 2.78 (d, J=9.8 Hz, 1H), 2.86 (t, J=4.8 Hz, 0H), 3.06 (s, 3H), 3.14 (d, J=12.6 Hz, 1H), 3.25 (s, 3H), 3.39 (d, J=12.5 Hz, 1H), 3.48 (d, J=9.1 Hz, 1H), 3.60 (d, J=7.6 Hz, 2H), 3.63-3.71 (m, 1H), 3.93 (s, 3H), 4.02-4.10 (m, 1H), 4.45 (t, J=6.5 Hz, 1H), 4.51 (dd, J=12.1, 2.8 Hz, 1H), 5.30 (q, J=6.8 Hz, 1H), 5.51-5.59 (m, 1H), 6.50-6.59 (m, 3H), 6.88 (s, 1H), 7.10 (d, J=8.4 Hz, 2H), 7.16 (d, J=1.8 Hz, 1H), 7.46-7.50 (m, 2H), 8.29 (s, 2H), 8.62 (d, J=7.3 Hz, 1H), 10.13 (s, 1H). $^{13}$C NMR (101 MHz, DMSO) δ 170.78, 170.62, 170.58, 170.47, 168.14, 165.07, 155.28, 151.27, 141.30, 141.27, 138.34, 137.63, 133.37, 132.60, 128.98, 128.52, 125.19, 121.63, 119.13, 117.16, 113.94, 88.22, 80.01, 77.67, 73.19, 66.79, 64.39, 60.03, 56.57, 56.13, 51.69, 49.23, 48.30, 45.46, 43.26, 37.73, 36.38, 35.19, 34.91, 33.39, 31.96, 29.72, 26.04, 18.23, 18.00, 17.96, 15.05, 14.43, 13.09, 11.38. HRMS (m/z): [M+H]$^+$ calcd for $C_{48}H_{66}ClN_6O_{12}S$, 985.4148; found 985.4131.

H-L-Ala-D-Ala-PAB-DM1

$^1$H NMR (400 MHz, DMSO-d6) δ 0.76 (s, 3H), 1.12 (d, J=6.3 Hz, 3H), 1.16 (d, J=6.8 Hz, 3H), 1.21 (d, J=6.9 Hz, 3H), 1.32 (d, J=7.0 Hz, 3H), 1.38-1.50 (m, 2H), 1.58 (s, 3H), 2.03 (dd, J=14.4, 2.9 Hz, 1H), 2.38 (ddd, J=16.0, 8.1, 5.9 Hz, 1H), 2.54 (d, J=2.4 Hz, 1H), 2.58-2.8 (m, 1H), 2.67 (s, 3H), 2.79 (d, J=9.6 Hz, 1H), 3.07 (s, 3H), 3.14 (d, J=12.3 Hz, 1H), 3.25 (s, 3H), 3.38 (d, J=12.4 Hz, 1H), 3.48 (d, J=8.9 Hz, 1H), 3.48-3.60 (m, 2H), 3.60 (d, J=7.5 Hz, 1H), 3.94 (s, 3H), 4.01-4.12 (m, 1H), 4.13-4.38 (m, 2H), 4.43 (d, J=6.4 Hz, 1H), 4.52 (dd, J=11.9, 2.8 Hz, 1H), 5.30 (q, J=6.7 Hz, 1H), 5.56 (dd, J=13.5, 9.2 Hz, 1H), 6.48-6.61 (m, 3H), 6.89 (s, 1H), 7.10 (d, J=8.4 Hz, 2H), 7.16 (d, J=1.9 Hz, 1H), 7.49 (dd, J=8.6, 2.5 Hz, 2H), 8.43 (s, 1H), 8.45-8.55 (m, 1H), 10.14 (s, 1H). $^{13}$C NMR (101 MHz, DMSO) δ 173.48, 171.02, 170.58, 170.55, 168.11, 155.27, 151.27, 141.26, 138.32, 137.57, 133.33, 132.58, 128.91, 128.47, 125.15, 121.59, 119.24, 117.14, 113.90, 88.22, 79.99, 77.63, 73.17, 66.77, 66.27, 60.00, 56.55, 56.11, 51.66, 49.39, 48.96, 45.44, 44.99, 37.71, 36.36, 35.17, 34.88, 33.36, 31.92, 29.70, 25.97, 20.05, 18.48, 15.03, 14.40, 13.06, 11.38. HRMS (m/z): [M+H]$^+$ calcd for $C_{48}H_{66}ClN_6O_{12}S$, 985.4148; found 985.4134.

H-D-Ala-L-Ala-PAB-DM1

MS (m/z): [M+H]$^+$ calcd for $C_{48}H_{66}ClN_6O_{12}S$, 984.4; found 984.2.

H-D-Ala-D-Ala-PAB-DM1

HRMS (m/z): [M+H]$^+$ calcd for $C_{48}H_{65}ClN_6O_{12}SNa$, 1007.3968; found 1007.3938.

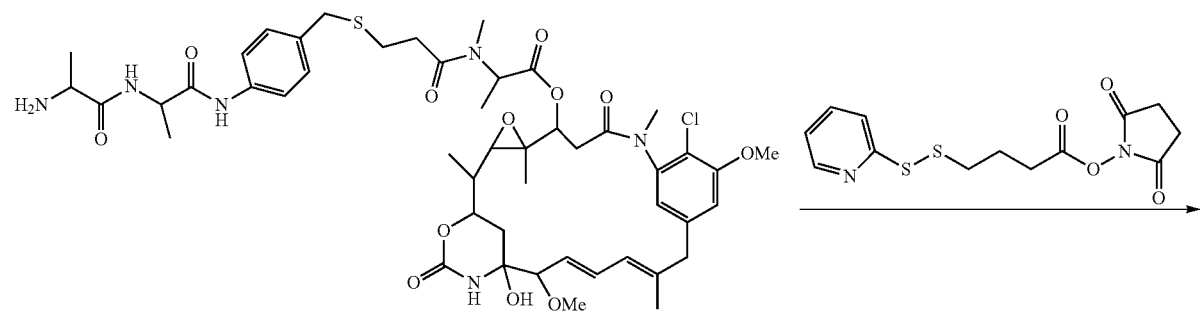

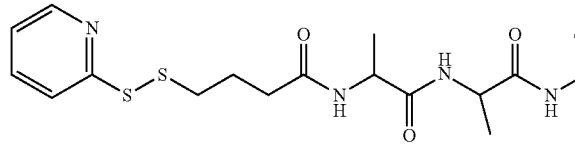
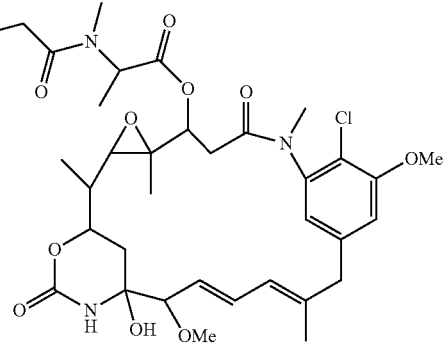

General Procedure to the Prepare of (SPDB-Ala-Ala-PAB-DM1) and Isomers

The H-L-Ala-L-Ala-PAB-DM1 compound (64 mg, 0.065 mmol) was dissolved in dimethyl formamide (1 mL) to each was added SPDB (50 mg, 0.153 mmol). After magnetically stirring for 1 hr the sample was purified without workup by preparative HPLC at 40 mL/min using a 250 mm×30 mm C18 column with gradient elution. The column was eluted with deionized water containing 0.2% formic acid with 20% acetonitrile from time 0-4.0 min then a linear gradient to 95% acetonitrile from 4.0-21 min. The desired product which eluted at 17 min. was collected in a 50 mL flask and the contents were frozen by placing the flask in a dry ice acetone bath. Frozen solvent was then removed by lyophilization to give 68 mg (85% yield) of desired product as a white solid. $^1$H NMR (400 MHz, DMSO-d6) δ 0.77 (s, 3H), 1.12 (d, J=6.3 Hz, 3H), 1.16 (d, J=6.8 Hz, 3H), 1.20 (d, J=7.0 Hz, 3H), 1.30 (d, J=7.0 Hz, 3H), 1.40-1.50 (m, 3H), 1.58 (s, 3H), 1.86 (p, J=7.2 Hz, 2H), 2.03 (dd, J=14.4, 2.9 Hz, 1H), 2.27 (t, J=7.2 Hz, 2H), 2.38 (ddd, J=16.2, 8.2, 5.9 Hz, 1H), 2.62 (dd, J=14.8, 7.1 Hz, 2H), 2.67 (s, 3H), 2.70-2.77 (m, 2H), 2.79 (d, J=9.7 Hz, 1H), 2.83 (t, J=7.3 Hz, 2H), 3.07 (s, 3H), 3.13 (d, J=12.6 Hz, 1H), 3.25 (s, 3H), 3.38 (d, J=12.3 Hz, 2H), 3.48 (d, J=8.9 Hz, 1H), 3.55-3.66 (m, 2H), 3.93 (s, 3H), 4.02-4.12 (m, 1H), 4.25 (p, J=7.0 Hz, 1H), 4.38 (p, J=7.0 Hz, 1H), 4.52 (dd, J=11.9, 2.9 Hz, 1H), 5.27-5.34 (m, 1H), 5.56 (dd, J=13.6, 9.0 Hz, 1H), 5.93 (s, 1H), 6.49-6.64 (m, 2H), 6.87 (s, 1H), 7.09 (d, J=8.4 Hz, 2H), 7.15 (d, J=1.7 Hz, 1H), 7.21 (ddd, J=7.0, 4.7, 1.2 Hz, 1H), 7.48-7.53 (m, 2H), 7.73-7.84 (m, 2H), 8.10 (dd, J=7.1, 3.6 Hz, 2H), 8.41-8.47 (m, 1H), 9.85 (s, 1H). $^{13}$C NMR (101 MHz, DMSO) δ 172.43, 171.75, 170.93, 170.56, 168.10, 159.28, 155.25, 151.24, 149.50, 141.25, 138.33, 137.69, 137.45, 133.33, 132.59, 128.86, 128.46, 125.14, 121.57, 121.04, 119.21, 119.09, 117.12, 113.89, 88.20, 79.99, 77.63, 73.16, 66.76, 60.00, 56.53, 56.10, 51.65, 48.96, 48.92, 48.74, 45.43, 37.70, 37.38, 36.35, 35.17, 34.87, 33.33, 33.28, 31.92, 29.69, 25.98, 24.51, 17.89, 17.53, 15.02, 14.41, 13.06, 11.37. HRMS (m/z): [M+H]$^+$ calcd for C$_{57}$H$_{74}$ClN$_7$O$_{13}$S$_3$Na, 1218.4093; found 1218.4062.

SPDB-L-Ala-D-Ala-PAB-DM1

$^1$H NMR (400 MHz, DMSO-d6) δ 0.76 (s, 3H), 1.12 (d, J=6.2 Hz, 3H), 1.16 (d, J=6.8 Hz, 3H), 1.20 (d, J=7.1 Hz, 3H), 1.24 (d, J=13.6 Hz, 1H), 1.31 (d, J=7.2 Hz, 3H), 1.39-1.51 (m, 3H), 1.58 (d, J=5.7 Hz, 3H), 1.86 (p, J=7.2 Hz, 3H), 2.00-2.08 (m, 1H), 2.27 (t, J=7.2 Hz, 2H), 2.38 (ddd, J=15.8, 8.0, 5.8 Hz, 1H), 2.63 (dd, J=13.8, 6.4 Hz, 1H), 2.67 (s, 3H), 2.76-2.86 (m, 4H), 3.07 (s, 3H), 3.24 (s, 3H), 3.48 (d, J=8.9 Hz, 1H), 3.54-3.66 (m, 2H), 3.93 (s, 3H), 4.02-4.11 (m, 1H), 4.22 (dt, J=13.9, 6.8 Hz, 1H), 4.32-4.40 (m, 1H), 4.52 (dd, J=11.9, 2.9 Hz, 1H), 5.31 (q, J=6.8 Hz, 2H), 5.56 (dd, J=13.7, 9.0 Hz, 1H), 5.93 (s, 1H), 6.48-6.61 (m, 2H), 6.89 (d, J=6.9 Hz, 1H), 7.10 (dd, J=8.6, 2.1 Hz, 2H), 7.18-7.25 (m, 1H), 7.56 (m, 2H), 7.70-7.83 (m, 2H), 8.21 (d, J=6.2 Hz, 2H), 8.38 (d, J=7.6 Hz, 1H), 8.41-8.46 (m, 1H), 9.68 (s, 1H). $^{13}$C NMR (101 MHz, DMSO) δ 172.43, 171.75, 170.93, 170.56, 168.10, 159.28, 155.25, 151.24, 149.50, 141.25, 138.33, 137.69, 137.45, 133.33, 132.59, 128.86, 128.46, 125.14, 121.57, 121.04, 119.21, 119.09, 117.12, 113.89, 88.20, 79.99, 77.63, 73.16, 66.76, 60.00, 56.53, 56.10, 51.65, 48.96, 48.92, 48.74, 45.43, 37.70, 37.38, 36.35, 35.17, 34.87, 33.33, 33.28, 31.92, 29.69, 25.98, 24.51, 17.89, 17.53, 15.02, 14.41, 13.06, 11.37. HRMS (m/z): [M+H]$^+$ calcd for C$_{57}$H$_{74}$ClN$_7$O$_{13}$S$_3$Na, 1218.4093; found 1218.4058.

SPDB-D-Ala-L-Ala-PAB-DM1

$^1$H NMR (400 MHz, DMSO-d6) δ 0.76 (s, 3H), 1.12 (d, J=6.4 Hz, 3H), 1.16 (d, J=6.8 Hz, 3H), 1.20 (d, J=7.0 Hz, 3H), 1.22-1.27 (m, 1H), 1.31 (d, J=7.1 Hz, 3H), 1.40-1.50 (m, 2H), 1.57 (s, 3H), 1.85 (p, J=7.3 Hz, 2H), 2.03 (dd, J=14.4, 2.9 Hz, 1H), 2.27 (t, J=7.2 Hz, 2H), 2.32-2.44 (m, 1H), 2.63 (dd, J=13.7, 6.5 Hz, 1H), 2.67 (s, 3H), 2.69-2.77 (m, 1H), 2.80 (td, J=9.5, 8.8, 4.1 Hz, 3H), 3.07 (s, 3H), 3.12 (dd, J=12.9, 4.1 Hz, 1H), 3.24 (s, 3H), 3.48 (d, J=9.1 Hz, 1H), 3.54-3.66 (m, 2H), 3.93 (s, 3H), 4.02-4.11 (m, 1H), 4.22 (t, J=6.8 Hz, 1H), 4.36 (td, J=7.4, 1.6 Hz, 1H), 4.52 (dd, J=11.9, 2.9 Hz, 1H), 5.30 (q, J=6.8 Hz, 1H), 5.56 (dd, J=13.4, 9.1 Hz, 1H), 5.93 (s, 1H), 6.48-6.54 (m, 2H), 6.57 (d, J=11.3 Hz, 2H), 6.87 (s, 1H), 7.10 (dd, J=8.6, 2.1 Hz, 2H), 7.12-7.17 (m, 1H), 7.20 (dd, J=7.2, 4.8 Hz, 1H), 7.56 (dd, J=8.5, 2.6 Hz, 2H), 7.70-7.83 (m, 2H), 8.22 (d, J=6.3 Hz, 1H), 8.38 (dd, J=7.6, 3.9 Hz, 1H), 8.41-8.45 (m, 1H), 9.69 (d, J=3.5 Hz, 1H). $^{13}$C NMR (101 MHz, DMSO) δ 172.44, 172.42, 171.75, 170.95, 170.59, 170.56, 168.11, 159.28, 155.25, 151.24, 149.51, 141.26, 138.33, 137.71, 137.47, 133.35, 133.34, 132.59, 128.89, 128.87, 128.47, 125.15, 121.58, 121.06, 119.22, 119.10, 117.13, 113.90, 88.20, 79.99, 77.64, 73.16, 66.77, 60.01, 56.54, 56.11, 51.65, 48.96, 48.93, 48.74, 45.43, 37.70, 37.38, 36.35, 35.18, 34.87, 33.34, 33.29, 31.92, 29.69, 26.00, 24.51, 17.90, 17.54, 15.03, 14.41, 13.06, 11.37. HRMS (m/z): [M+H]$^+$ calcd for C$_{57}$H$_{74}$ClN$_7$O$_{13}$S$_3$Na, 1218.4093; found 1218.4062.

SPDB-D-Ala-D-Ala-PAB-DM1

$^1$H NMR (400 MHz, DMSO-d6) δ 0.76 (s, 3H), 1.12 (d, J=6.3 Hz, 3H), 1.16 (d, J=6.8 Hz, 3H), 1.20 (d, J=7.1 Hz, 3H), 1.30 (d, J=7.1 Hz, 3H), 1.44 (dd, J=15.0, 8.8 Hz, 2H), 1.57 (s, 3H), 1.79-1.92 (m, 2H), 2.03 (d, J=11.9 Hz, 1H), 2.26 (t, J=7.2 Hz, 2H), 2.31-2.43 (m, 1H), 2.67 (s, 5H), 2.75-2.89 (m, 4H), 3.07 (s, 3H), 3.13 (d, J=12.5 Hz, 1H), 3.24 (s, 3H), 3.48 (d, J=9.0 Hz, 1H), 3.60 (d, J=6.9 Hz, 2H), 3.93 (s, 3H), 4.06 (t, J=10.5 Hz, 1H), 4.19-4.29 (m, 1H), 4.31-4.43 (m, 1H), 4.51 (dd, J=12.0, 2.6 Hz, 1H), 5.30 (q, J=6.6 Hz, 1H), 5.55 (dd, J=13.5, 9.7 Hz, 1H), 5.92 (s, 1H), 6.47-6.61 (m, 3H), 6.87 (s, 1H), 7.09 (d, J=8.5 Hz, 2H), 7.15 (d, J=1.4 Hz, 1H), 7.22 (ddd, J=7.2, 4.8, 1.2 Hz, 1H), 7.48 (d, J=8.5 Hz, 2H), 7.72-7.86 (m, 2H), 8.09 (d, J=7.0 Hz, 2H), 8.42-8.50 (m, 1H), 9.82 (s, 1H). HRMS (m/z): [M+H]$^+$ calcd for $C_{57}H_{74}ClN_7O_{13}S_3Na$, 1218.4093; found 1218.4061.

$^1$H NMR (400 MHz, DMSO-d6) δ 0.77 (s, 3H), 1.12 (d, J=6.3 Hz, 3H), 1.16 (d, J=6.8 Hz, 3H), 1.21 (d, J=7.2 Hz, 3H), 1.31 (d, J=7.0 Hz, 3H), 1.44 (td, J=10.5, 9.9, 4.8 Hz, 2H), 1.58 (s, 3H), 1.76 (p, J=7.2 Hz, 2H), 2.03 (dd, J=14.4, 2.7 Hz, 1H), 2.19-2.28 (m, 3H), 2.38 (ddd, J=15.9, 8.1, 5.9 Hz, 1H), 2.43-2.48 (m, 1H), 2.62 (q, J=7.8, 6.5 Hz, 1H), 2.67 (s, 3H), 2.79 (d, J=9.6 Hz, 1H), 3.07 (s, 3H), 3.13 (d, J=12.5 Hz, 1H), 3.25 (s, 3H), 3.30-3.42 (m, 3H), 3.48 (d, J=9.0 Hz, 1H), 3.54-3.66 (m, 2H), 3.94 (s, 3H), 4.02-4.12 (m, 1H),

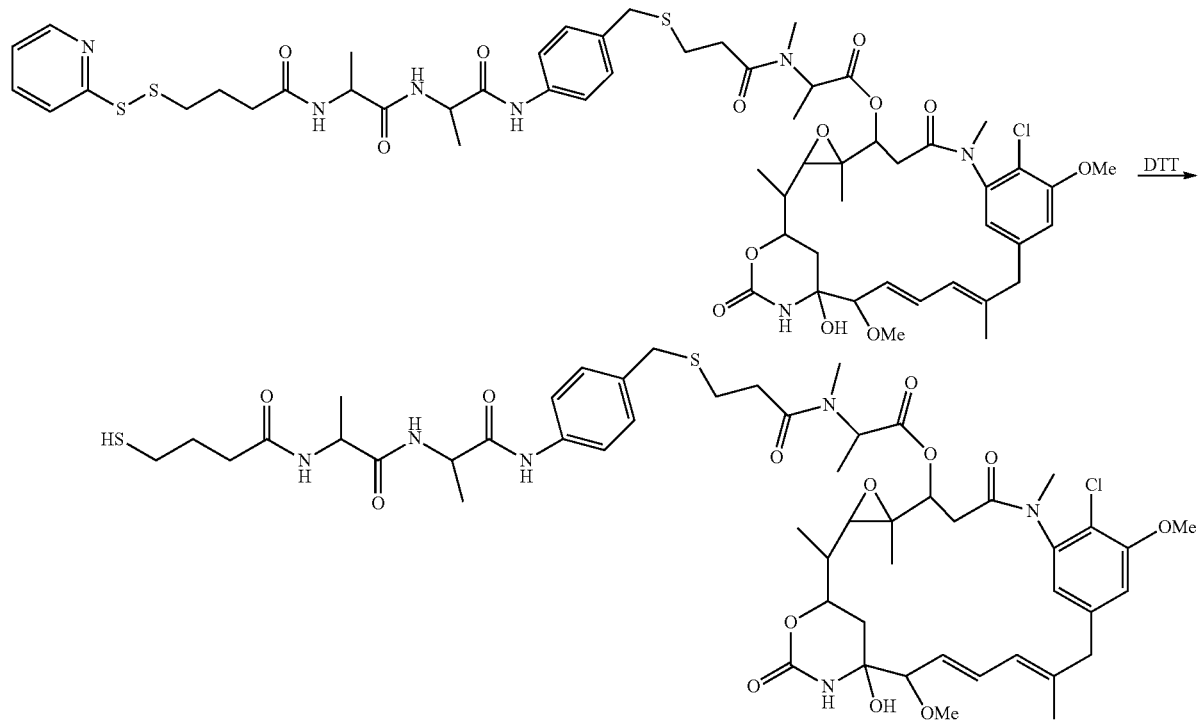

General Procedure to Prepare (HS-D-Ala-D-Ala-PAB-DM1) and Isomers:

To SPDB-D-Ala-D-Ala-PAB-DM1 (65 mg, 0.054 mmol) in dimethyl sulfoxide (350 μL) was added 50 mM potassium phosphate buffer pH 7.4 (100 μL) followed by dithiothreitol (DTT, 35 mg, 0.227 mmol). The mixtures were stirred magnetically for 1 h then purified without workup by preparative HPLC at 40 mL/min using a 250 mm×30 mm C18 column with gradient elution. The column was eluted with deionized water containing 0.2% formic acid with 20% acetonitrile from time 0-4.0 min then a linear gradient to 95% acetonitrile from 4.0-21 min. The desired product eluted at 16 min and was collected in a 50 mL flask. The flask was quickly placed in a dry ice acetone bath until the contents were frozen then frozen solvent was removed under vacuum by lyophilization to give 40 mg (67% yield) of desired product as a white solid. $^1$H NMR (400 MHz, DMSO-d6) δ 3.69 (d, J=5.8 Hz, 2H), 3.78 (d, J=5.4 Hz, 2H), 3.89 (d, J=5.7 Hz, 2H), 4.23 (d, J=6.2 Hz, 1H), 4.29 (d, J=7.0 Hz, 2H), 4.42 (d, J=4.3 Hz, 2H), 5.10 (d, J=5.0 Hz, 1H), 7.23 (d, J=8.3 Hz, 2H), 7.32 (t, J=7.4 Hz, 2H), 7.41 (t, J=7.4 Hz, 2H), 7.55 (d, J=8.3 Hz, 2H), 7.57-7.64 (m, 1H), 7.71 (d, J=7.4 Hz, 2H), 7.89 (d, J=7.5 Hz, 2H), 8.24 (t, J=5.4 Hz, 2H), 9.76 (s, 1H). HRMS (m/z): [M+H]$^+$ calcd for $C_{52}H_{71}ClN_6O_{13}S_2Na$, 1109.4107; found 1109.4073.

HS-L-Ala-L-Ala-PAB-DM1

4.27 (p, J=7.1 Hz, 1H), 4.38 (p, J=7.1 Hz, 1H), 4.52 (dd, J=11.9, 2.8 Hz, 1H), 5.31 (q, J=6.8 Hz, 1H), 5.56 (dd, J=13.5, 9.1 Hz, 1H), 5.92 (s, 1H), 6.48-6.60 (m, 3H), 6.87 (s, 1H), 7.09 (d, J=8.3 Hz, 2H), 7.15 (s, 1H), 7.50 (d, J=8.3 Hz, 2H), 8.08 (dd, J=10.2, 7.1 Hz, 2H), 9.85 (s, 1H). $^{13}$C NMR (101 MHz, DMSO) δ 172.23, 171.71, 171.00, 170.57, 170.54, 168.09, 155.25, 151.23, 141.26, 141.23, 138.30, 137.59, 133.22, 132.58, 128.92, 128.45, 125.14, 121.58, 119.03, 117.14, 113.89, 88.20, 79.98, 77.63, 73.15, 66.76, 59.98, 56.53, 56.10, 51.64, 48.94, 48.27, 45.42, 37.70, 36.34, 35.17, 34.88, 33.68, 33.33, 31.91, 29.68, 29.52, 25.97, 23.44, 18.04, 17.90, 15.02, 14.40, 13.05, 11.37. HRMS (m/z): [M+H]$^+$ calcd for $C_{52}H_{71}ClN_6O_{13}S_2Na$, 1109.4107; found 1109.4082.

HS-L-Ala-D-Ala-PAB-DM1

$^1$H NMR (400 MHz, DMSO-d6) δ 0.76 (s, 3H), 1.12 (d, J=6.3 Hz, 3H), 1.16 (d, J=6.7 Hz, 3H), 1.21 (d, J=7.1 Hz, 3H), 1.31 (d, J=7.0 Hz, 3H), 1.39-1.50 (m, 2H), 1.58 (s, 3H), 1.75 (p, J=7.2 Hz, 2H), 2.03 (dd, J=14.4, 2.8 Hz, 1H), 2.19 (t, J=6.0 Hz, 1H), 2.24 (t, J=7.3 Hz, 2H), 2.33-2568 (m, 3H), 2.59-2.71 (m, 1H), 2.79 (d, J=9.8 Hz, 1H), 3.08 (s, 3H), 3.12 (d, J=12.7 Hz, 1H), 3.25 (s, 3H), 3.32-3.42 (m, 2H), 3.48 (d, J=9.0 Hz, 1H), 3.54-3.66 (m, 2H), 3.93 (s, 3H), 4.06 (t, J=11.4 Hz, 1H), 4.23 (p, J=6.9 Hz, 1H), 4.36 (p, J=7.2 Hz, 1H), 4.52 (dd, J=11.9, 2.9 Hz, 1H), 5.30 (q, J=6.8 Hz, 1H), 5.56 (dd, J=13.5, 9.2 Hz, 1H), 5.92 (s, 1H), 6.48-6.54 (m, 2H), 6.56 (s, 2H), 6.87 (s, 1H), 7.10 (d, J=8.3 Hz, 2H), 7.12-7.17 (m, 1H), 7.56 (dd, J=8.6, 2.6 Hz, 2H), 8.18 (d, J=6.4 Hz, 1H), 8.36 (t, J=6.5 Hz, 1H), 9.68 (s, 1H). $^{13}$C NMR (101 MHz, DMSO) δ 172.48, 172.01, 171.99, 170.93, 170.55, 168.09, 155.25, 151.23, 141.25, 138.34, 137.45, 133.32, 132.59, 128.87, 128.84, 128.44, 125.12, 121.57, 119.23, 117.13, 113.88, 88.22, 79.98, 77.62, 73.16, 66.76, 59.98, 56.52, 56.10, 51.64, 48.95, 48.74, 45.43, 37.71, 36.35, 35.17, 34.86, 33.45, 33.34, 31.91, 29.68, 29.50, 25.96, 23.39, 17.89, 17.53, 15.02, 14.40, 13.06, 11.38. HRMS (m/z): [M+H]$^+$ calcd for $C_{52}H_{71}ClN_6O_{13}S_2Na$, 1109.4107; found 1109.4078.

HS-D-Ala-L-Ala-PAB-DM1

$^1$H NMR (400 MHz, DMSO-d6) δ 0.77 (s, 3H), 1.12 (d, J=6.4 Hz, 3H), 1.16 (d, J=6.8 Hz, 3H), 1.21 (d, J=7.0 Hz, 3H), 1.31 (d, J=7.1 Hz, 3H), 1.44 (td, J=10.7, 9.9, 5.6 Hz, 2H), 1.58 (s, 3H), 1.75 (p, J=7.1 Hz, 2H), 2.03 (dd, J=14.5, 2.9 Hz, 1H), 2.24 (t, J=7.3 Hz, 2H), 2.31-2.49 (m, 2H), 2.58-2.72 (m, 1H), 2.67 (s, 3H), 2.78 (d, J=9.6 Hz, 1H), 3.07 (s, 3H), 3.09-3.16 (m, 2H), 3.25 (s, 3H), 3.36-3.43 (m, 3H), 3.48 (d, J=9.0 Hz, 1H), 3.53-3.67 (m, 2H), 3.93 (s, 3H), 4.01-4.12 (m, 1H), 4.24 (q, J=6.7 Hz, 1H), 4.36 (qd, J=7.8, 5.9 Hz, 1H), 4.52 (dd, J=12.0, 2.9 Hz, 1H), 5.30 (q, J=6.7 Hz, 1H), 5.56 (dd, J=13.4, 9.0 Hz, 1H), 5.92 (s, 1H), 6.47-6.61 (m, 4H), 6.87 (s, 1H), 7.10 (dd, J=8.5, 2.3 Hz, 2H), 7.14-7.18 (m, 1H), 7.56 (dd, J=8.6, 2.4 Hz, 2H), 8.17 (d, J=6.4 Hz, 1H), 8.36 (dd, J=7.5, 5.1 Hz, 1H), 9.68 (d, J=4.7 Hz, 1H). $^{13}$C NMR (101 MHz, DMSO) δ 172.42, 171.95, 170.91, 170.53, 168.08, 155.23, 151.20, 141.23, 138.31, 137.42, 133.35, 132.56, 128.86, 128.44, 125.11, 121.56, 119.20, 117.10, 113.88, 99.50, 88.19, 79.96, 77.61, 73.14, 66.74, 59.98, 56.52, 56.09, 51.62, 48.91, 48.68, 37.68, 35.17, 34.83, 33.44, 31.91, 29.67, 29.48, 25.98, 23.36, 17.90, 17.56, 15.01, 14.39, 13.04, 11.35. HRMS (m/z): [M+H]$^+$ calcd for $C_{52}H_{71}ClN_6O_{13}S_2Na$, 1109.4107; found 1109.4078.

HS-D-Ala-D-Ala-PAB-DM1

$^1$H NMR (400 MHz, DMSO-d6) δ 3.69 (d, J=5.8 Hz, 2H), 3.78 (d, J=5.4 Hz, 2H), 3.89 (d, J=5.7 Hz, 2H), 4.23 (d, J=6.2 Hz, 1H), 4.29 (d, J=7.0 Hz, 2H), 4.42 (d, J=4.3 Hz, 2H), 5.10 (d, J=5.0 Hz, 1H), 7.23 (d, J=8.3 Hz, 2H), 7.32 (t, J=7.4 Hz, 2H), 7.41 (t, J=7.4 Hz, 2H), 7.55 (d, J=8.3 Hz, 2H), 7.57-7.64 (m, 1H), 7.71 (d, J=7.4 Hz, 2H), 7.89 (d, J=7.5 Hz, 2H), 8.24 (t, J=5.4 Hz, 2H), 9.76 (s, 1H). HRMS (m/z): [M+H]$^+$ calcd for $C_{52}H_{71}ClN_6O_{13}S_2Na$, 1109.4107; found 1109.4073.

Example 11. Conjugate Preparation

Preparation of huML66-3a Conjugate

A 22 mM stock solution of sulfo-GMBS linker (1a, from Pierce) in dimethylacetamide and a 3.7 mM stock of compound 2 in dimethylacetamide were prepared. The linker (1.5 mM) and maytansinoid thiol (2.0 mM) were reacted in 60% dimethylacetamide, 40% 10 mM succinate, pH 5 for 5 min at ambient temperature. Thioether formation was confirmed by loss of ~290 nm absorbance in the UV-VIS spectrum, corresponding to complete reaction of the maleimide group on the linker.

Addition of 8 molar equivalents of the in situ prepared compound 40 to 10 mg huML66 antibody (2.5 mg/ml) buffered in 50 mM EPPS (4-(2-hydroxyethyl)piperazine-1-propanesulfonic acid), pH 8 was carried out at a final dimethylacetamide v/v of 10%. Reaction proceeded overnight at room temperature followed by desalting in NAP columns (Illustra Sephadex G-25 DNA Grade, GE Healthcare) equilibrated in PBS pH 7.4 to remove unconjugated maytansinoid. Dialysis of conjugate into 10 mM histidine, 250 mM glycine, 1% sucrose pH 5.5 was then carried out at 4° C. using Slide-a-Lyzer dialysis cassettes (ThermoScientific, 20,000 MWCO).

The purified conjugate was found to have an average of 4.5 maytansinoid molecules linked per antibody (by UV-VIS using molar extinction coefficients $\varepsilon_{252\ nm}$=33,874 cm$^{-1}$M$^{-1}$ and $\varepsilon_{280\ nm}$=9230 cm$^{-1}$M$^{-1}$ for 5, and $\varepsilon_{280\ nm}$=205,520 cm$^{-1}$M$^{-1}$ and $\varepsilon_{252\ nm}$=72,754 cm$^{-1}$M$^{-1}$ for huML66 antibody), 97% monomer (by size exclusion chromatography), 1.4% unconjugated maytansinoid (by HISEP mixed mode chromatography), a final protein concentration of 1.1 mg/ml, and an overall 66% protein yield.

Preparation of huC242-3b 18 mM stock solution of SMCC linker (Pierce) in dimethylacetamide and 3.5 mM stock of 2 in dimethylacetamide were prepared. The linker (1.5 mM) and maytansinoid thiol (2.0 mM) were reacted in 60% dimethylacetamide, 40% 10 mM succinate, pH 5 for 5 min at rt. Thioether formation was confirmed by loss of ~302 nm absorbance in the UV-VIS spectrum, corresponding to complete reaction of the maleimide group on the linker.

Addition of 8 molar equivalents of the in situ prepared compound 41 to 10 mg huC242 antibody (2.5 mg/ml) buffered in 50 mM EPPS (4-(2-hydroxyethyl)piperazine-1-propanesulfonic acid), pH 8 was carried out at a final dimethylacetamide v/v of 20%. Reaction proceeded overnight at room temperature followed by desalting in NAP columns (Illustra Sephadex G-25 DNA Grade, GE Healthcare) equilibrated in PBS pH 7.4 to remove unconjugated maytansinoid. Dialysis of conjugate into 10 mM histidine, 250 mM glycine, 1% sucrose pH 5.5 was then carried out at 4° C. using Slide-a-Lyzer dialysis cassettes (ThermoScientific, 20,000 MWCO).

The purified conjugate was found to have an average of 3.3 maytansinoid molecules linked per antibody (by UV-VIS using molar extinction coefficients $\varepsilon_{252\ nm}$=33,874 cm$^{-1}$M$^{-1}$ and $\varepsilon_{280\ nm}$=9230 cm$^{-1}$M$^{-1}$ for compound 5, and $\varepsilon_{280\ nm}$=217,560 cm$^{-1}$M$^{-1}$ and $\varepsilon_{252\ nm}$=80,062 cm$^{-1}$M$^{-1}$ for huML66 antibody), 95% monomer (by size exclusion chromatography), <1% unconjugated maytansinoid (by HISEP mixed mode chromatography), a final protein concentration of 0.9 mg/ml, and an overall 54% protein yield.

Preparation of huEGFR-7R-3a 20 mM stock solution of sulfo-GMBS linker (Pierce) in dimethylacetamide and 2.3 mM stock of HS-VC-PAB-DM1 in dimethylacetamide were prepared. The linker (1.5 mM) and maytansinoid thiol (2.0 mM) were reacted in 60% dimethylacetamide, 40% 10 mM succinate, pH 5 for 5 min at rt. Thioether formation was confirmed by loss of ~290 nm absorbance in the UV-VIS spectrum, corresponding to complete reaction of the maleimide group on the linker.

Addition of 6 molar equivalents (based on linker) of the in situ prepared 89 to 7.5 mg huEGFR-7R antibody (2.5 mg/ml) buffered in 50 mM EPPS (4-(2-hydroxyethyl)piperazine-1-propanesulfonic acid), pH 8 was carried out at a final dimethylacetamide v/v of 15%. Reaction proceeded 4 h at room temperature followed by desalting in NAP columns (Illustra Sephadex G-25 DNA Grade, GE Healthcare) equilibrated in PBS pH 7.4 to remove unconjugated maytansinoid. Dialysis of conjugate into 10 mM succinate, 250 mM glycine, 0.5% sucrose, 0.01% TWEEN-20 pH 5.5 was then carried out at 4° C. using Slide-a-Lyzer dialysis cassettes (ThermoScientific, 20,000 MWCO).

The purified conjugate was found to have an average of 4.2 maytansinoid molecules linked per antibody (by UV-VIS using molar extinction coefficients $\varepsilon_{252\ nm}$=33,874 cm$^{-1}$M$^{-1}$ and $\varepsilon_{280\ nm}$=9230 cm$^{-1}$M$^{-1}$ for 5, and $\varepsilon_{280\ nm}$=213,445 cm$^{-1}$M$^{-1}$ and $\varepsilon_{252\ nm}$=72,521 cm$^{-1}$M$^{-1}$ for huML66 antibody), 95.5% monomer (by size exclusion chromatography), 1.4% unconjugated maytansinoid (by HISEP mixed mode chromatography), a final protein concentration of 0.96 mg/ml, and an overall 60% protein yield.

Example 12. In Vitro Cleavage of huC242-3b Conjugate by Cathepsin B huC242-3b conjugate (4.6 µM) was incubated with 0.9 µM cathepsin B (bovine spleen; EMD Biosciences) in pH 6.0 buffer containing 0.6 mM CaCl$_2$/MgCl$_2$ and 2 mM DTT (dithiothreitol) at 37° C. 100 µl aliquots were taken at various time points (0, 1, 3, 8, 17, and 26 h) and free maytansinoids were quantified using a mixed-mode chromatography method (Fleming, et al, *Analytical Biochemistry*, 2005, 340, 272). Briefly, a HISEP shielded hydrophobic phase column (5 µm particle size, 4.6×250 mm length, Supelco, Bellefonte, Pa., USA) was used for analyzing Ab-DM1 conjugates. Detection was at 252 and 280 nm (extracted from PDA spectra). The flow rate was 0.7 ml/min. Mobile phase A consisted of 100 mM ammonium acetate (pH 7.0). Mobile phase B was 100% acetonitrile. The column was equilibrated at 25% B followed by a linear gradient over 25 min to 40% B after sample injection. Intact conjugate elutes between 2-5 min while the sole released metabolite 5 was detected at a retention time of 21 min. Subsequent analysis of the 21 min peak fraction by mass spectroscopy showed a major ion 865 m/z corresponding to the (M+Na)$^+$ for $C_{42}H_{55}ClN_4O_{10}S$. Synthesized compound 5 had the same retention time and mass spectrum as this metabolite.

Example 13. In Vitro Cytotoxic Assay on Tumor Cells

Activity of the linker of the invention was tested using anti human EGFR antibody (huEGFR-7R (see U.S. Provisional Patent Application Nos. 61/408,497, filed on Oct. 29, 2010, and 61/477,086, filed on Apr. 19, 2011)) in in vitro cytotoxicity assay. Briefly, target cells were plated at 1,500 to 3,000 cells per well in 100 µL complete RPMI media containing 10% FBS. Test articles were diluted in complete RPMI media using 5-fold dilution series and 100 µL were added per well. The final concentration typically ranged from 3×10$^{-8}$ M to 8×10$^{-14}$ M. Cells were incubated at 37° C. in a humidified 5% CO$_2$ incubator for 5 days. Viability of the remaining cells was determined by colorimetric WST-8 assay and the absorbance at 450 nm (A450) was measured in a multiwell plate reader. The surviving fraction was calculated by dividing each treated sample value by the average value of untreated controls. The surviving fraction value was plotted against the antibody-conjugate concentration in a semi-log plot for each treatment. The in vitro cytotoxicity of antibody-maytansinoid conjugates of the invention was compared to the activity of the naked antibody. The results from a typical cytotoxicity assay are shown in FIG. 14.

In OSC-19 squamous cell carcinoma of head and neck (SCCHN) cell line (FIG. 14A) that expressed 0.457 million EGFR antigen per cell (ABC), the maytansinoid conjugates significantly enhanced anti-tumor activity of the huEGFR-7R naked antibody.

Similarly, in CA-922 and SAS SCCHN cell lines that expressed 1 and 0.162 million ABC respectively (FIGS. 14B and 14C), huEGFR-7R conjugate with 3a linker was highly potent with EC$_{50}$ of 0.034 and 0.086 nM, respectively. Even in the low antigen expressing cell line such as H1975 non-small cell lung cancer (NSCLC) that expressed 49,000 ABC (FIG. 14D), the huEGFR-7R-3a conjugate was very potent with EC$_{50}$ of 0.18 nM. Altogether, these results show that the 3a linker is highly potent in SCCHN and NSCLC cancer cell lines that are relatively resistant to other maytansinoid conjugates.

Example 14. In Vitro Cytotoxic Assay of Conjugates with Non-Natural Amino Acid Linkers In vitro cytotoxicity of EGFR-7R-Ala-Ala-PAB-DM1 (EGFR-7R-3c) conjugate was compared to that of EGFR-7R-3a and EGFR-7R-SPDB-DM4 conjugates. FIGS. 26A-26F show that stereochemistry does seem to affect potency to certain degree, and that the (L,L) isomer seems to be the most potent, followed by the (D,L) isomer, and then the (L,D) isomer, and lastly the (D,D) isomer.

The D-amino acid containing peptide linkers, and peptide linkers containing just L isomers but with natural or non-natural side chains may be better tolerated in vivo. Thus conjugates with such linkers have may have improved tolerability while retaining most (if not all) of the tumor cell cytotoxicity seen in the mAb-L-Ala-L-Ala-PAB-DM1 or mAb-L-Val-L-Cit-PAB-DM1 (Ab-3a) conjugates.

Example 15. In Vivo Efficacy Study

To further test the activity of huEGFR-7R-3a conjugate, the conjugate was compared with the huEGFR-7R naked antibody in EGFR expressing FaDu squamous cell carcinoma of head and neck xenograft (FIG. 15). About 1×10$^7$ tumor cells were injected subcutaneously into SCID mice. Animals were randomized by tumor volume into treatment groups when tumors reached a mean tumor volume of approximately 100 mm$^3$ and injected once with the indicated dosage of naked antibody or antibody-maytansinoid conjugates. Mean tumor volume of each treatment groups is plotted against time post tumor cell inoculation (FIG. 15). Table 1 shows the number of mice with complete response (CR) (no palpable tumor) and percent of tumor growth inhibition (% T/C) which corresponds to the median of tumor volume of each treated group divided by the median tumor volume of control group when the tumor volume of the control group reaches a predetermined size. A treatment with a % T/C value of below 42% is considered active, while a treatment with a % T/C value of below 12% is considered highly active.

The huEGFR-7R-3a conjugate was significantly more active than the huEGFR-7R naked antibody, with 3 out of 6 mice had complete response and 7% T/C. This result demonstrates the high potency of huEGFR-7R-3a conjugate in inhibiting the FaDu tumor growth in vivo.

TABLE 1

| Activity of EGFR Ab and maytansinoid conjugates in FaDu tumor xenograft | | |
|---|---|---|
| Ab and conjugate | % T/C | CR |
| huEGFR-7R Ab 5 mg/kg | 44% | 0/6 |
| huEGFR-7R-3a 2.5 mg/kg | 7% | 3/6 |

Figure 24:
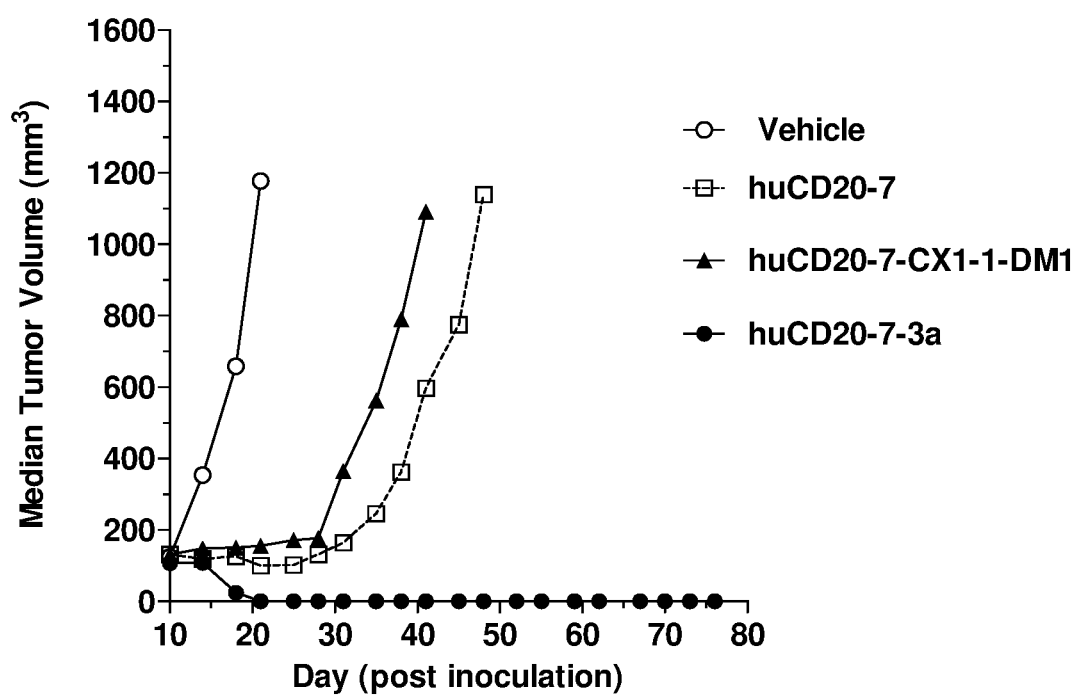
FIG. 24 shows in vivo cytotoxicity data for the huCD20-7-3a conjugate as compared to naked antibody and conjugates with other linkers. Medium tumor volume is plotted against days post tumor cell inoculation. See Example 11 for the preparation of several conjugates with 3a, including using the "huEGFR-7R" human anti-EGFR antibody as the cell binding agent.
Figure 25:
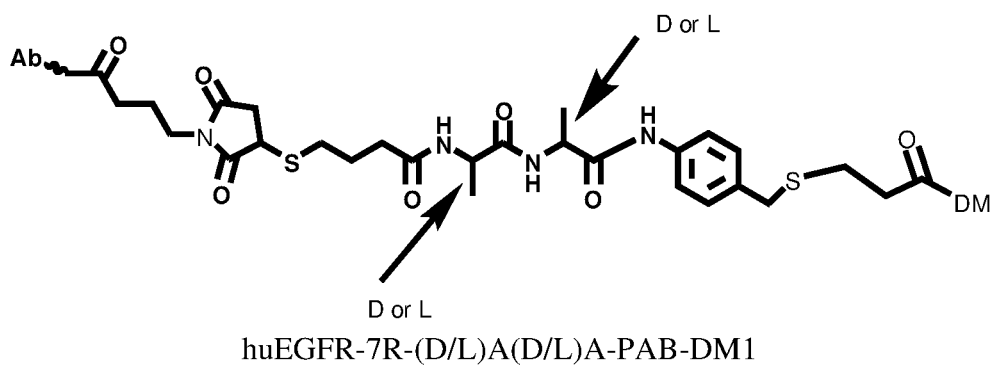
FIG. 25 shows the general structure of the huEGFR-7R-(D/L)A(D/L)A-PAB-DM1 (Ab-3c) conjugates comprising a human anti-EGF receptor antibody moiety (huEGFR-7R) as the cell-binding agent, the $L_2$ linker moiety, the Ala-Ala dipeptide moiety (either or both Ala can be D-Ala), the PAB ($L_1$) linker moiety, and the DM1 cytotoxic agent.
Figure 26A:
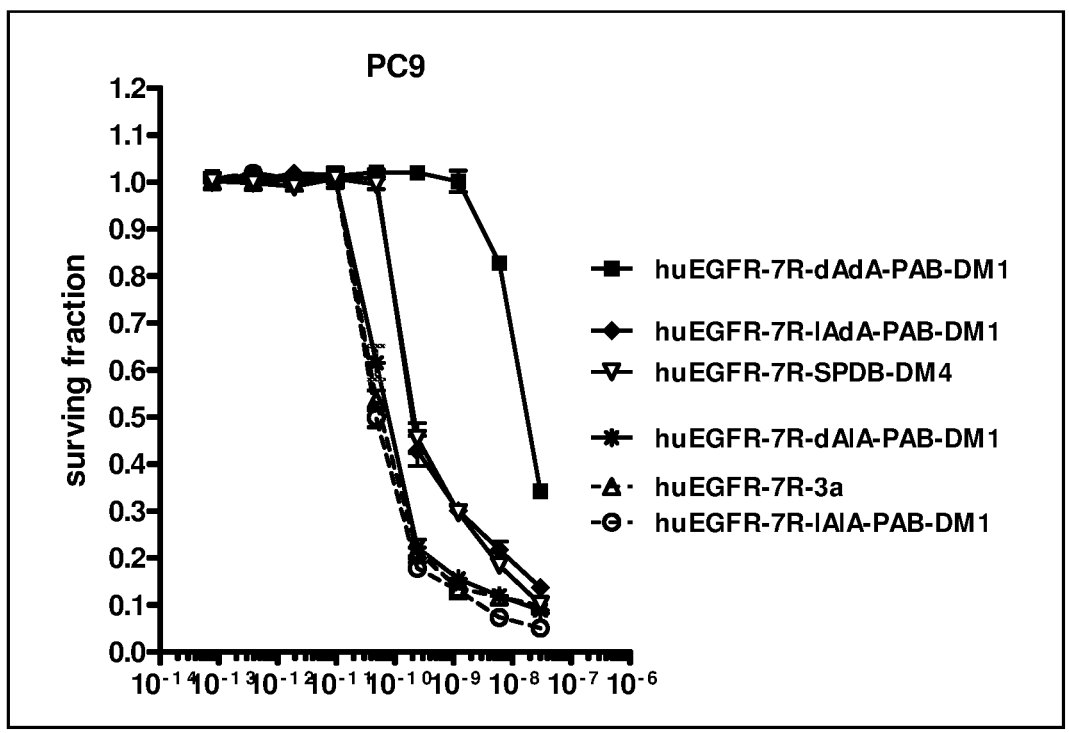
FIGS. 26A-26F show in vitro cytotoxicity data for conjugates comprising the Ala-Ala-PAB-DM1 moiety. Specifically, the fractions of surviving cells were plotted against concentrations of the various tested conjugates in human lung adenocarcinoma PC9 cells (FIG. 26A), SAS squamous cell carcinoma of head and neck (SCCHN) cell line (FIG. 26B), human oral squamous cell carcinoma cell line HSC2 (FIG. 26C), erlotinib-resistant non-small cell lung cancer (NSCLC) cell line H1975 (FIG. 26D), squamous cell carcinoma of lower gingiva originated CA922 cells (FIG. 26E), and squamous cell carcinoma cell line OSC-19 (FIG. 26F). "dA" stands for D-Ala. "1A" stands for L-Ala.
Figure 26B:
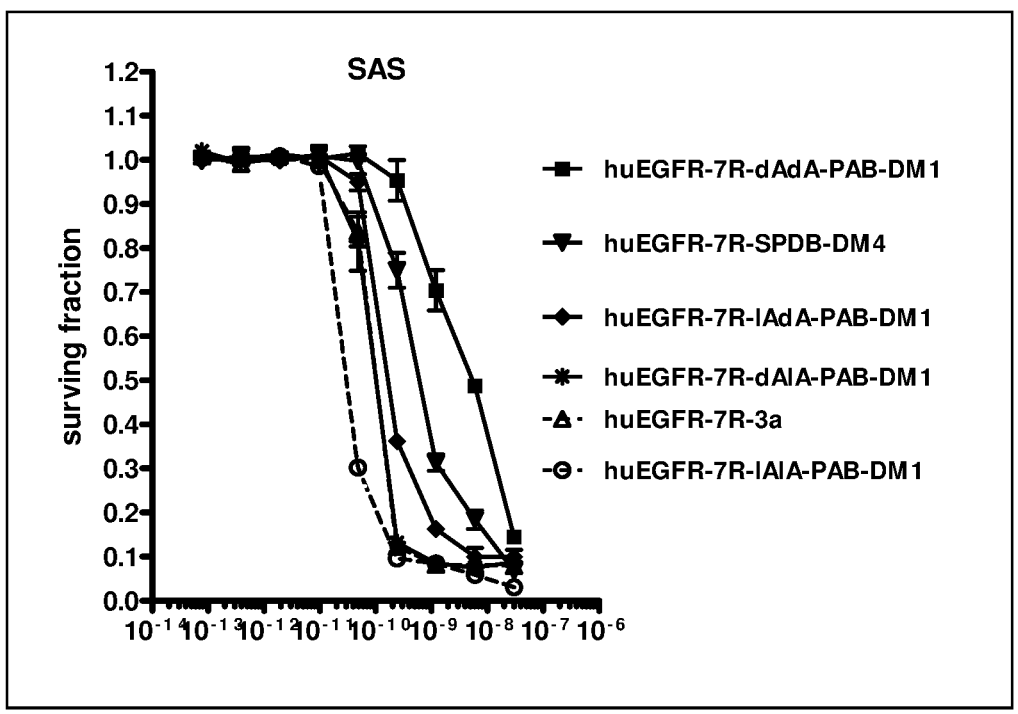
Figure 26C:
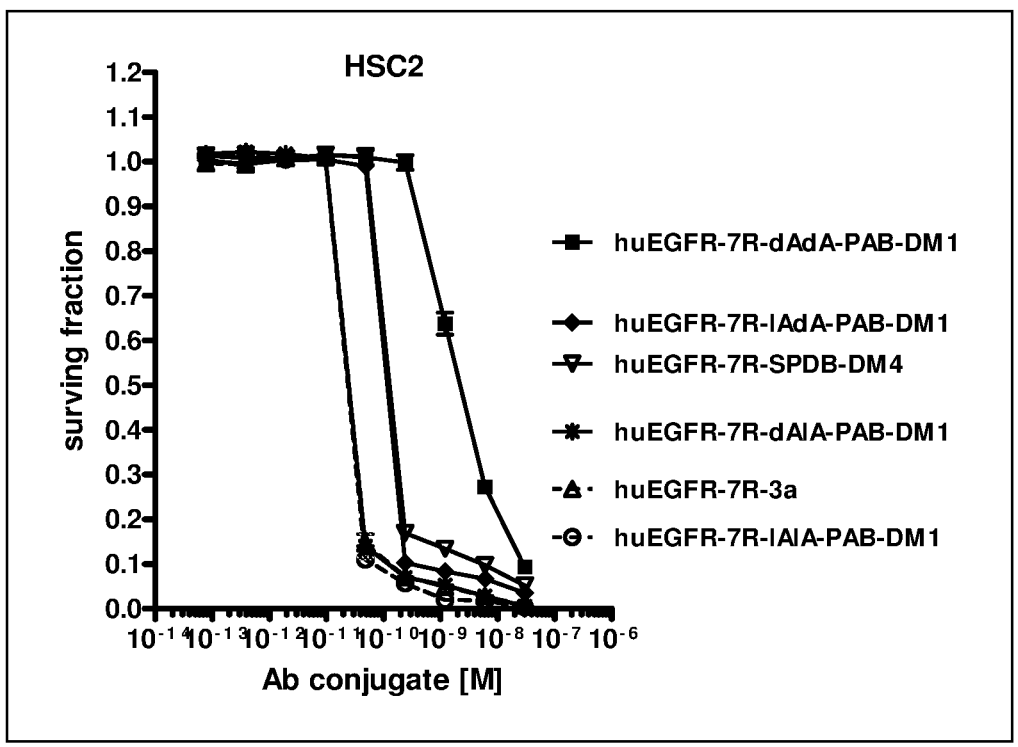
Figure 26D:
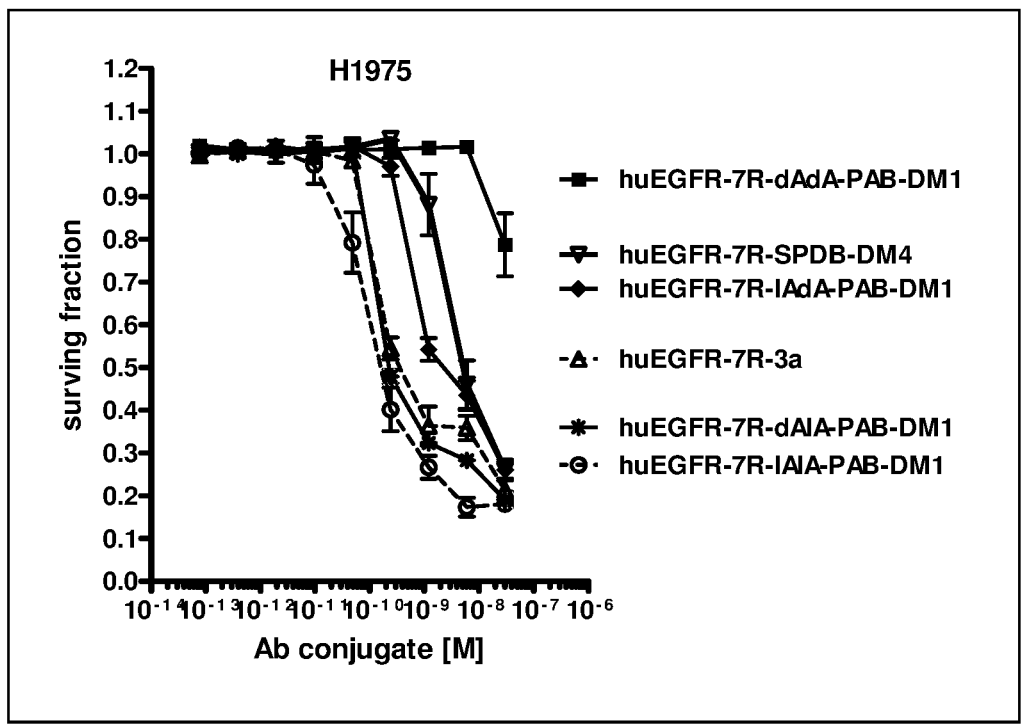
Figure 26E:
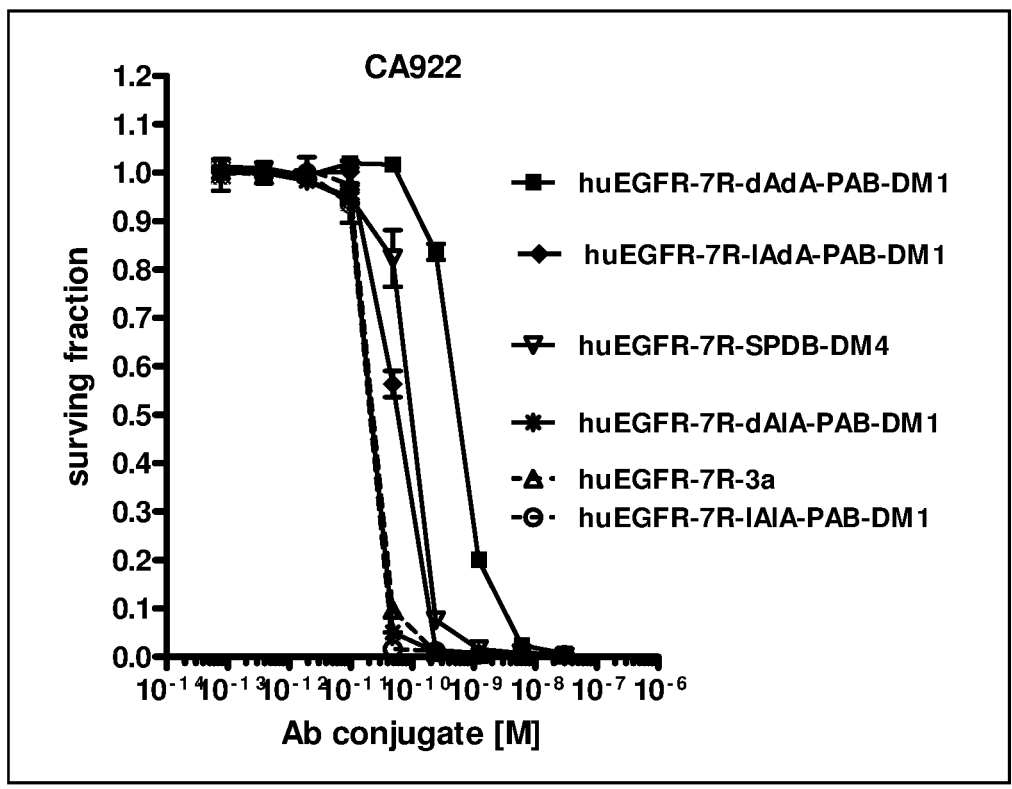
Figure 26F:
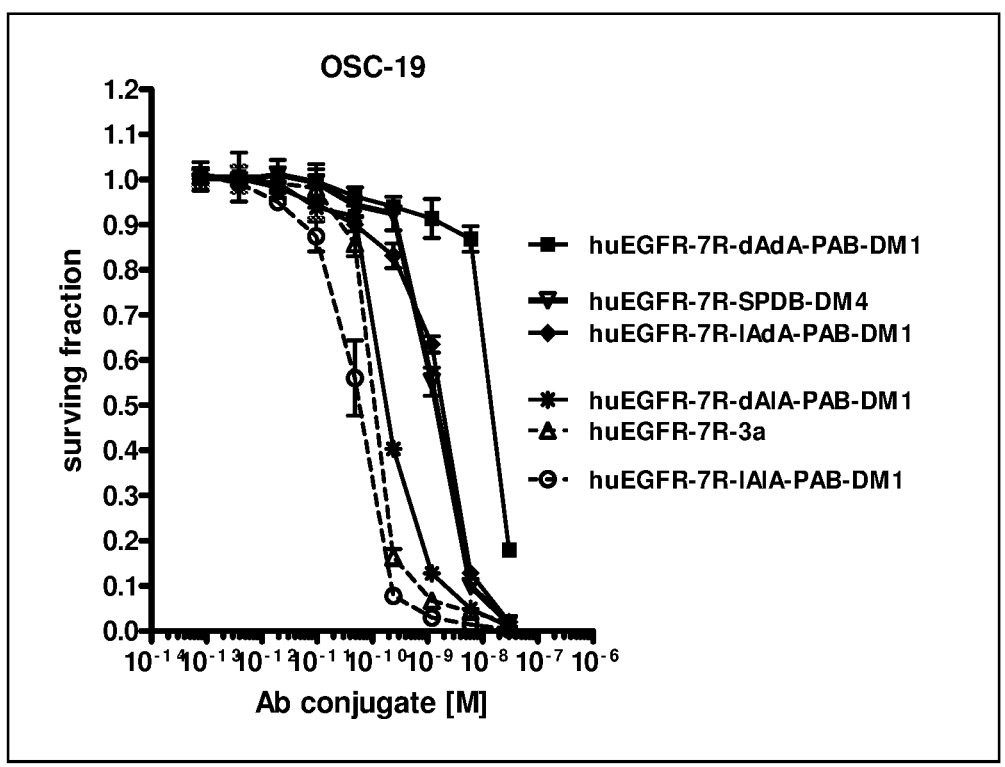

In another experiment, exemplary human anti-CD20 antibodies (huCD20-7 antibodies) and conjugates thereof were tested in a xenograft model using DOHH-2 follicular lymphoma cells implanted subcutaneous into SCID mice. Mice were randomized by body weight into treatment groups and treated once on day 11 post cell inoculation with 5 mg/kg of huCD20-7, huCD20-7-CX1-1-DM1, or huCD20-7-3a. The median tumor volume of the different treatment groups is plotted in FIG. 24. huCD20-7 antibody treatment resulted in a decrease in median tumor volume as compared to the PBS control with a % T/C of 11% on days 25. Dramatically enhanced efficacy was seen for huCD20-7-3a conjugates as compared to the unconjugated antibody with a % T/C of 1% on days 25. On study day 76, huCD20-7 treatment resulted in partial regression in 3 of 8 animals and complete regression in 1 of 8 animals. In contrast, huCD20-7-3a treatment resulted in partial regression in 7 of 8 animals and complete regression in 5 of 8 animals. No regressions were observed in the PBS control group. The results are summarized in Table 2 below.

TABLE 2

Activity of huCD20-7 Ab and maytansinoid conjugates thereof in xenograft model

|  | Dose | % T/C d25 | PR d76 | CR d76 | Conclusion |
|---|---|---|---|---|---|
| Vehicle (PBS) | — | — | — | — | — |
| huCD20-7 | 5 mg/kg | 11% | 3/8 | 1/8 | active |
| huCD20-7-CX1-1-DM1 | 5 mg/kg | 16% | 1/8 | 0/8 | active |
| huCD20-7-3a | 5 mg/kg | 1% | 7/8 | 5/8 | highly active |

PR - partial regression
CR - complete regression
% T/C - tumor growth reduction treatment/control
d25 - at Day 25
d76 - at Day 76
Structure of the huCD20-7-CX1-1-DM1 conjugate is shown below.

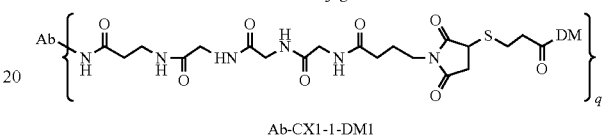

Ab-CX1-1-DM1

What is claimed is:

1. A cell-binding agent-cytotoxic agent conjugate represented by the following structural formula:

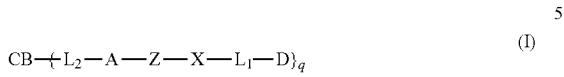
(I)

or a pharmaceutically acceptable salt thereof, wherein:
CB is an antibody and comprises a —S— group that is covalently linked to $L_2$;
$L_2$ is represented by:

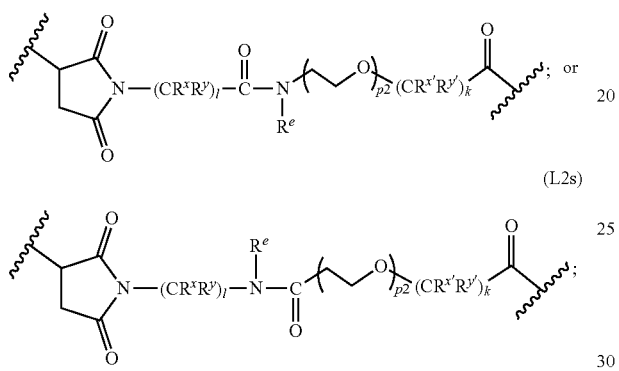

wherein:
$R^e$ is H, an alkyl, an alkenyl, an alkynyl, or —(CH$_2$—CH$_2$—O)$_n$—R$^k$;
$R^k$ is H or an alkyl;
p2 is an integer from 0 to 200;
$R^x$, $R^y$, $R^{x'}$, and $R^{y'}$, for each occurrence, are each independently H, $C_{1-4}$ alkyl, —OH, halogen or —O—($C_{1-4}$ alkyl); and
l, and k are each independently an integer from 1 to 10;
A is a peptide comprising 2 to 20 amino acids that is cleavable by a protease expressed in tumor tissue;
—Z—$L_1$-D is represented by one of the following structural formulas:

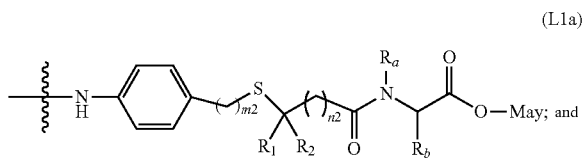
(L1a)

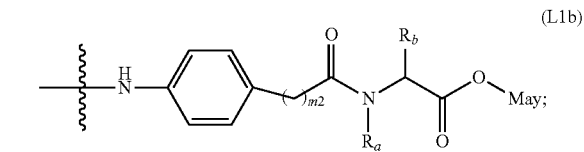
(L1b)

wherein May is represented by the following structural formula:

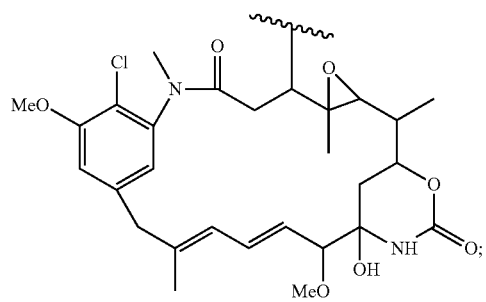 [SMILES: *C1CC(=O)N(C)c2cc(cc(OC)c2Cl)C/C(C)=C/C=C/C(OC)C2(O)CC(OC(=O)N2)C(C)C2OC12C]

$R_1$, $R_2$, $R_a$, and $R_b$ are each independently H or a $C_{1-4}$ alkyl; and m2 and n2 are each independently an integer from 1 to 10; and q is an integer from 1 to 20.

2. The conjugate of claim 1, wherein $R^x$, $R^y$, $R^{x'}$, and $R^{y'}$ are all H.

3. The conjugate of claim 2, wherein p2 for each occurrence is independently an integer from 2 to 24.

4. The conjugate of claim 3, wherein l and k are each independently an integer from 1 to 6.

5. The conjugate of claim 1, wherein A is selected from the group consisting of Val-Cit, Val-Lys, Phe-Lys, Lys-Lys, Ala-Lys, Phe-Cit, Leu-Cit, Lle-Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), β-Ala-Leu-Ala-Leu (SEQ ID NO: 2) and Gly-Phe-Leu-Gly (SEQ ID NO: 3), Val-Arg, Arg-Val, Arg-Arg, Val-D-Cit, Val-D-Lys, Val-D-Arg, D-Val-Cit, D-Val-Lys, D-Val-Arg, Ala-Ala, Ala-D-Ala, and D-Ala-Ala.

6. The conjugate of claim 1, wherein $R_a$ and $R_b$ are both methyl.

7. The conjugate of claim 6, wherein $R_1$ and $R_2$ are both H and n2 is 1.

8. The conjugate of claim 6, wherein $R_1$ and $R_2$ are both methyl and n2 is 2.

9. The conjugate of claim 1, wherein m2 is an integer from 1 to 3.

10. A pharmaceutical composition comprising the conjugate of claim 1 and a pharmaceutically acceptable carrier.

11. The conjugate of claim 1, wherein the conjugate is represented by the following structural formula:

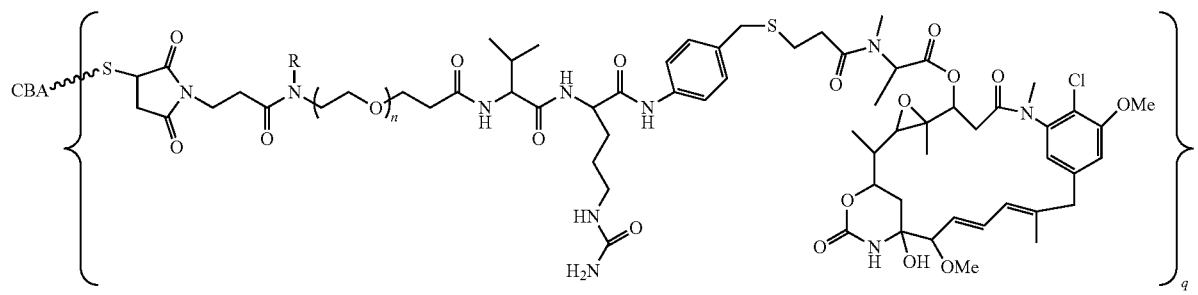

or a pharmaceutically acceptable salt thereof, wherein R is H or Me; and n is an integer from 2 to 100.

12. The conjugate of claim 11, wherein n is 4, 8 or 24.

13. A method of inhibiting abnormal cell growth or treating a proliferative disorder, an autoimmune disorder, destructive bone disorder, infectious disease, or fibrotic disease in a mammal comprising administering to said mammal a therapeutically effective amount of the conjugate of claim 1 and, optionally, a chemotherapeutic agent.

\* \* \* \* \*

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Ala Leu Ala Leu
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: bAla
<222> LOCATION: (1)..(1)

<400> SEQUENCE: 2

Ala Leu Ala Leu
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Gly Phe Leu Gly
1
```